US012378292B2

(12) United States Patent
Marchbank et al.

(10) Patent No.: US 12,378,292 B2
(45) Date of Patent: Aug. 5, 2025

(54) MODIFIED COMPLEMENT PROTEINS AND USES THEREOF

(71) Applicant: University of Newcastle Upon Tyne, Tyne and Wear (GB)

(72) Inventors: Kevin Marchbank, North Shields (GB); Yi Yang, Newcastle Upon Tyne (GB)

(73) Assignee: University of Newcastle Upon Tyne, Newcastle Upon Tyne (GB)

(*) Notice: Subject to any disclaimer, the term of this patent is extended or adjusted under 35 U.S.C. 154(b) by 1279 days.

(21) Appl. No.: 16/608,732

(22) PCT Filed: Apr. 25, 2018

(86) PCT No.: PCT/GB2018/051087
§ 371 (c)(1),
(2) Date: Oct. 25, 2019

(87) PCT Pub. No.: WO2018/197873
PCT Pub. Date: Nov. 1, 2018

(65) Prior Publication Data
US 2023/0101835 A1   Mar. 30, 2023

(30) Foreign Application Priority Data

Apr. 28, 2017 (GB) ...................................... 1706808
May 5, 2017 (GB) ...................................... 1707248

(51) Int. Cl.
*C07K 14/47* (2006.01)
*A61K 38/00* (2006.01)
*A61K 38/17* (2006.01)
*A61P 13/12* (2006.01)
*A61P 27/02* (2006.01)

(52) U.S. Cl.
CPC ...... *C07K 14/4702* (2013.01); *A61K 38/1709* (2013.01); *A61P 13/12* (2018.01); *A61P 27/02* (2018.01); *A61K 38/00* (2013.01); *C07K 2319/00* (2013.01)

(58) Field of Classification Search
None
See application file for complete search history.

(56) References Cited

U.S. PATENT DOCUMENTS

2006/0178308 A1  8/2006  Schwaeble et al.
2015/0110766 A1  4/2015  Lambris et al.
2019/0071477 A1  3/2019  Bao et al.

FOREIGN PATENT DOCUMENTS

| EP | 2516464 A1 | 10/2012 | |
|----|-----------|---------|--|
| WO | WO2013142362 | 9/2013 | |
| WO | WO-2017053732 A2 * | 3/2017 | ......... A61K 47/6911 |
| WO | WO 2017/114401 A1 | 7/2017 | |

OTHER PUBLICATIONS

Nichols et al. (Kidney International (2015) 88, 1314-1322) (Year: 2015).*
Dunne et al. (Front. Immunol. 11:601895, 2021) (Year: 2021).*
Józsi, Mihály, and Peter F. Zipfel. "Factor H family proteins and human diseases." Trends in Immunology 29.8 (2008): 380-387.
Zipfel, Peter F., et al. "The factor H protein family." Immunopharmacology 42.1-3 (1999): 53-60.
Skerka, Christine, et al. "Complement factor H related proteins (CFHRs)." Molecular immunology 56.3 (2013): 170-180.
Shaughnessy, Jutamas, et al. "A Novel Factor H-Fc Chimeric Immunotherapeutic Molecule against Neisseria gonorrhoeae." The Journal of Immunology 196.4 (2016): 1732-1740.
Clark et al., "Tissue-specific host recognition by complement factor H is mediated by differential activities of its glycosaminoglycan-binding regions", J. Immunol. 2013, 190, 2049-2057.
Clark et al., "Role of Factor H and Related Proteins in Regulating Complement Activation in the Macula, and relevance to age-related macular degeneration", J Clin Med. Jan. 2015; 4(1): 18-31.
Harris et al., "Decay-accelerating factor must bind both components of the complement alternative pathway C3 convertase to mediate efficient decay", J Immunol 178:352-359, 2007.
Isaacs et al., "Restoration of Complement-Enhanced Neutralization of Vaccinia Virus Virions by Novel Monoclonal Antibodies Raised against the Vaccinia Virus Complement Control Protein", Journal of Virology, Aug. 2003, p. 8256-8262.
Spiller et al., Dissecting the Regions of Virion-Associated Kaposi's Sarcoma-Associated Herpesvirus Complement Control Protein Required for Complement Regulation and Cell Binding, Journal of Virology, Apr. 2006, p. 4068-4078.
Tortajada et al. "The disease-protective complement factor H allotypic variant IIe62 shows increased binding affinity for C3b and enhanced cofactor activity", Hum Mol. Genet., 2009, 18(18) 3452-3461.
Xue et al., "Regulator dependent mechanisms of C3b processing by factor I allow differentiation of immune responses", Nat Struct Mol Biol 24(8) 643-651, 2017.
International Search Report and Written Opinion for International Application No. PCT/GB2018/051067, dated Nov. 11, 2018, 10 pages.
International Preliminary Report on Patentability for International Application No. PCT/GB2018/051067, dated Oct. 29, 2019, 6 pages.
Nichols et al., "An Extended mini-complement factor H molecule ameliorates experimental C3 glomerulopathy", *Kidney International*, vol. 88, No. 6, Jul. 29, 2015, pp. 1314-1322.

(Continued)

*Primary Examiner* — Sergio Coffa
(74) *Attorney, Agent, or Firm* — Morgan, Lewis & Bockius, LLP

(57) ABSTRACT

Certain embodiments of the present invention relate to regulation of the innate immune system and complement activation. In particular, but not exclusively certain embodiments relate to a complement regulator protein and pharmaceutical compositions thereof for use in the treatment of diseases associated with or mediated by the alternative complement pathway and methods of treating such diseases and other subject matter.

26 Claims, 24 Drawing Sheets
Specification includes a Sequence Listing.

(56) References Cited

OTHER PUBLICATIONS

Pangburn et al., "Polyanion-Induced Self-Association of Complement Factor H", The *Journal of Immunology*, vol. 182, No. 2, Jan. 5, 2009, pp. 1061-1068.

Giocoechea De Jorge et al., "Dimerization of complement factor H-related proteins modulates complement activation in vivo", *Proceedings of the National Academy of Sciences*, vol. 110, No. 12, Mar. 4, 2013, pp. 4685-4690.

Clark et al., "Identification of Factor H-like Protein 1 as the Predominant Complement Regulator in Bruch's Membrane: Implications for Age-Related Macular Degeneration", *The Journal of Immunology*, vol. 193, No. 10, Oct. 10, 2014, pp. 4962-4970.

Yang et al., "An Engineered Complement Factor H Construct for Treatment of C3 Glomerulopathy", *Journal of the American Society of Nephrology*, col. 29, No. 6, Mar. 27, 2018, pp. 1649-1661.

Saitou et al., "The Neighbor-joining Method: A New Method for Reconstructing Phylogenetic Trees", *Mol. Biol. Evol.* 4(4):406-425, 1987.

Aida et al., "Removal of endotoxin from protein solutions by phase separation using Triton X-114", *Journal of Immunological Methods*, 132 (1990) 191-195.

Hosgood et al., "First in Man Renal Transplantation After Ex Vivo Normothermic Perfusion", *Transplantation* 2011;92: 735-738.

Hosgood et al., "Successful Transplantation of Human Kidneys Deemed Intransplantable but Resuscitated by Ex Vivo Normothermic Machine Perfusion", *Am J Transplant* 16: 3062, Jun. 7, 2016.

Hosgood et al., "Ex Vivo normothermic perfusion for quality assessment of marginal donor kidney transplants", *Br J Surg* 102: 1433-12440, 2015.

Hebecker M, Alba-Dominguez M, Roumenina LT, Reuter S, Hyvärinen S, Dragon-Durey MA, Jokiranta TS, Sánchez-Corral P, Józsi M. An engineered construct combining complement regulatory and surface-recognition domains represents a minimal-size functional factor H. J Immunol. Jul. 15, 2013;191(2):912-21. doi: 10.4049/jimmunol. 1300269. Epub Jun. 14, 2013. PMID: 23772024.

Morgan HP, Schmidt CQ, Guariento M, Blaum BS, Gillespie D, Herbert AP, Kavanagh D, Mertens HD, Svergun DI, Johansson CM, Uhrin D, Barlow PN, Hannan JP. Structural basis for engagement by complement factor H of C3b on a self surface. Nat Struct Mol Biol. Apr. 2011;18(4):463-70. doi: 10.1038/nsmb.2018. Epub Feb. 13, 2011. PMID: 21317894; PMCID: PMC3512577.

Schmidt CQ, Bai H, Lin Z, Risitano AM, Barlow PN, Ricklin D, Lambris JD. Rational engineering of a minimized immune inhibitor with unique triple-targeting properties. J Immunol. Jun. 1, 2013;190(11):5712-21. doi: 10.4049/jimmunol.1203548. Epub Apr. 24, 2013. PMID: 23616575; PMCID: PMC3825029.

\* cited by examiner

Figure 9

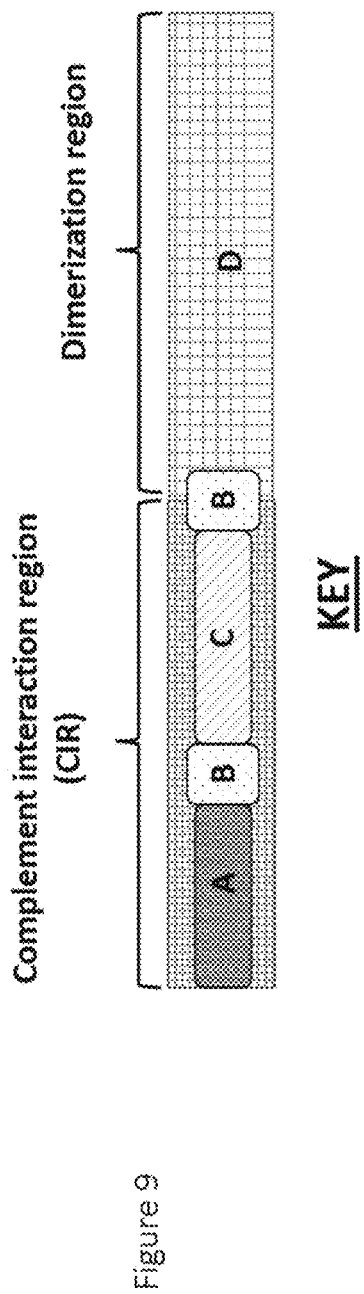

Complement interaction region (CIR) | Dimerization region

KEY

A) At least one FH fragment
A1 = FH CCPs 1-4 (SEQ ID NOs: 9-12)
A2 = FH CCPs 1-5 (SEQ ID NOs: 9-13)
A3 = FH CCPs 1-4 + 7 (SEQ ID NOs: 9-12 + 15)
A4 = FH CCPs 1-5 + 7 (SEQ ID NOs: 9-13 + 15)

B) Optional Linker molecule (independently selected)
B1 = Absent
B2 = SEQ. ID. NO. 30
B3 = SEQ. ID. NO. 31
B4 = SEQ. ID. NO. 32
B5 = SEQ. ID. NO. 33
B6 = GT
B7 = VD
B8 = VDT

C) Further fragment of CIR
C1 = Absent
C2 = FH CCPs 18-20 (SEQ ID NOs: 16-18)
C3 = FH CCPs 20 (SEQ ID NO: 18)
C4 = FHR2 CCPs 3-4
C5 = FHR3 CCPs 4-5
C6 = FHR4 CCPs 4-5
C7 = FHR5 CCPs 7-9 (SEQ ID NOs: 19-21)
C8 = FHR5 CCPs 8-9 (SEQ ID NOs: 20-21)
C9 = FHL-1 CCPs 6-7 (SEQ ID NO: 22-23)

D) Dimerization region
D1 = FHR1 CCPs 1-2 (SEQ ID NO: 24-25)
D2 = FHR2 CCPs 1-2
D3 = FHR5 CCPs 1-2

Factor H mature protein (SEQ. ID. NO. 1)
EDCNELPPRRNTEILTGSWSDQTYPEGTQAIYKCRPGYRSLGNVIMVCRKGEWVALNPLRKCQKRPCG
HPGDTPFGTFTLTGGNVFEYGVKAVYTCNEGYQLLGEINYRECDTDGWTNDIPICEVVKCLPVTAPENG
KIVSSAMEPDREYHFGQAVRFVCNSGYKIEGDEEMHCSDDGFWSKEKPKCVEISCKSPDVINGSPISQKI
IYKENERFQYKCNMGYEYSERGDAVCTESGWRPLPSCEEKSCDNPYIPNGDYSPLRIKHRTGDEITYQC
RNGFYPATRGNTAKCTSTGWIPAPRCTLKPCDYPDIKHGGLYHENMRRPYFPVAVGKYYSYYCDEHFET
PSGSYWDHIHCTQDGWSPAVPCLRKCYFPYLENGYNQNYGRKFVQGKSIDVACHPGYALPKAQTTVTC
MENGWSPTPRCIRVKTCSKSSIDIENGFISESQYTYALKEKAKYQCKLGYVTADGETSGSITCGKDGWSA
QPTCIKSCDIPVFMNARTKNDFTWFKLNDTLDYECHDGYESNTGSTTGSIVCGYNGWSDLPICYERECE
LPKIDVHLVPDRKKDQYKVGEVLKFSCKPGFTIVGPNSVQCYHFGLSPDLPICKEQVQSCGPPELLNGN
VKEKTKEEYGHSEVVEYYCNPRFLMKGPNKIQCVDGEWTTLPVCIVEESTCGDIPELEHGWAQLSPPY
YYGDSVEFNCSESFTMIGHRSITCIHGVWTQLPQCVAIDKLKKCKSSNLIIEEHLKNKKEFDHNSNIRYR
CRGKEGWIHTVCINGRWDPEVNCSMAQIQLCPPPPQIPNSHNMTTTLNYRDGEKVSVLCQENYLIQEG
EEITCKQGRWQSIPLCVEKIPCSQPPQIEHGTINSSRSSQESYAHGTKLSYTCEGGFRISEENETTCYMG
KWSSPPQCEGLPCKSPPEISHGVVAHMSDSYQYGEEVTYKCFEGFGIDGPAIAKCLGEKWSHPPSCIKT
DCLSLPSFENAIPMGEKKDVVKAGEQVTYTCATYYKMDGASNVTCINSRWTGRPTCRDTSCVNPPTVQ
NAYIVSRQMSKYPSGERVRYQCRSPYEMFGDEEVMCLNGNWTEPPQCKDSTGKCGPPPPIDNGDITSF
PLSVYAPASSVEYQCQNLYQLEGNKRITCRNGQWSEPPKCLHPCVISREIMENYNIALRWTAKQKLYSRT
GESVEFVCKRGYRLSSRSHTLRTTCWDGKLEYPTCAKR

FIG. 10

Factor H Related Protein 5 (FHR5) mature protein (SEQ. ID. NO. 2)
EGTLCDFPKIHHGFLYDEEDYNPFSQVPTGEVFYSCEYNFVSPSKSFWTRITCTEEGWSPTPKCLR
MCSFPFVKNGHSESSGLIHLEGDTVQIICNTGYSLQNNEKNISCVERGWSTPPICSFTKGECHVPILEA
NVDAQPKKESYKVGDVLKFSCRKNLIRVGSDSVQCYQFGWSPNFPTCKGQVRSCGPPPQLSNGEVK
EIRKEEYGHNEVEYDCNPNFIINGPKKIQCVDGEWTTLPTCVEQVKTCGYIPELEYGVQPSVPPYQ
HGVSVEVNCRNEYAMIGNNMITCINGIWTELPMCVATHQLKRCKIAGVNIKTLLKLSGKEFNHNSRIRY
RCSDIFRYRHSVCINGKWNPEVDCTEKREQFQPPPPQIPNAQNMTTVNYQDGEKVAVLCKENYLLP
EAKEIVCKDGRWQSLPRCVESTAYCGPPPSINNGDTTSFPLSVYPPGSTVTYRCQSFYKLQGSVTVT
CRNKQWSEPPRCLDPCVVSEENMKNNIQLKWRNDGKLYAKTGDAVEFQCKFPHKAMISSPPFRAIC
QEGKFEYPICE Factor H like Protein 1 (FHL-1) mature (SEQ. ID. NO. 3)
EDCNELPPRRNTEILTGSWSDQTYPEGTQAIYKCRPGYRSLGNVIMVCRKGEWVALNPLRKCQKRP
CGHPGDTPFGTFTLTGGNVFEYGKAVTCNEGYQLLGEINYRECDTDGWTNDIPICEVVKCLPVTA
PENGKIVSSAMEPDREYHFGQAVRFVCNSGYKIEGDEEMHCSDDGFWSKEKPKCVEISCKSPDVIN
GSPISQKIIYKENERFQYKCNMGYEYSERGDAVCTESGWRPLPSCEEKSCDNPYIPNGDYSPLRIKH
RTGDEITYQCRNGFYPATRGNTAKCTSTGWIPAPRCTLKPCDYPDIKHGGLYHENMRRPYFPVAVGK
YYSYYCDEHFETPSGSYWDHIHCTQDGWSPAVPCLRKCYFPYLENGYNQNYGRKFVQGKSIDVAC
HPGYALPKAQTTVTCMENGWSPTPRCIRVSFTL

FIG. 11

Factor H Related Protein 1 (FHR1) mature (SEQ. ID. NO. 4)

EATFCDFPKINHGILYDEEKYKPFSQVPTGEVFYYSCEYNFVSPSKSFWTRITCTEEGWSPTPKCLRLCFFPFVENGHSESSGQT
HLEGDTVQIICNTGYRLQNNENNISCVERGWSTPPKCRSTDTSCVNPPTVQNAHILSRQMSKYPSGERVRYECRSPYEMFGD
EEVMCLNGNWTEPPQCKDSTGKCGPPPIDNGDITSFPLSVYAPASSVEYQCQNLYQLEGNKRITCRNGQWSEPPKCLHPCV
ISREIMENYNIALRWTAKQKLYLRTGESAEFVCKRGYRLSSRSHTLRTTCWDGKLEYPTCAKR

FIG. 12

Factor H Precursor (SEQ. ID. NO. 5)

MRLLAKIICLMLWAICVAEDCNELPPRRNTEILTGSWSDQTYPEGTQAIYKCRPGYRSLGNVIMVCRKGEWVALNPLRKCQKRPCGHP
GDTPFGTFTLTGGNVFEYGVKAVYTCNEGYQLLGEINYRECDTDGWTNDIPICEVVKCLPVTAPENGKIVSSAMEPDREYHFGQAVRFV
CNSGYKIEGDEEMHCSDDGFWSKEKPKCVEISCKSPDVINGSPISQKIIYKENERFQYKCNMGYEYSERGDAVCTESGWRPLPSCEEKSC
DNPYIPNGDYSPLRIKHRTGDEITYQCRNGFYPATRGNTAKCTSTGWIPAPRCTLKPCDYPDIKHGGLYHENMRRPYFPVAVGKYYSYYC
DEHFETPSGSYWDHIHCTQDGWSPAVPCLRKCYFPYLENGYNQNYGRKFVQGKSIDVACHPGYALPKAQTTVTCMENGWSPTPRCIR
VKTCSKSSIDIENGFISESQYTVALKEKAKYQCKLGYTIADGETSGSITCGKDGWSAQPTCIKSCDIPVFMNARTKNDFTWFKLNDTLDYE
CHDGYESNTGSTTGSIVCGYNGWSDLPICYERECELPKIDVHLVPDRKKDQYKVGEVLKFSCKPGFTIVGPNSVQCYHFGLSPDLPICKE
QVQSCGPPPELLNGNVKEKTKEEYGHSEVEYYCNPRFLMKGPNKIQCVDGEWTTLPVCIVESTCGDIPELEHGWAQLSSPPYYYGD
SVEFNCSESFTMIGHRSITCIHGVWTQLPQCVAIDRLKKCKSSNLILEEHLKNKKEFDHNSNIRYRCRGKEGWIHTVCINGRWDPEVNC
SMAQIQLCPPPPQJPNSHNNMTTLNYRDGEKVSVLCQENYLIQEGEEITCKDGRWQSIPLCVEKIPCSQPPQIEHGTINSSRSSQESYAH
GTKLSYTCEGGFRISEENETTCYMGKWSSPPQCEGLPCKSPPEISHGVVAHMSDSYQYGEEVTYKCFEGFGIDGPAIAKCLGEKWSHPP
SCIKTDCLSLPSFENAIPMGEKKDVYKAGEQVTYTCATYYKMDGASNVTCINSRMTGRPTCRDTSCVNPPTVQNAYIVSRQMSKYPSG
ERVRYQCRSPYEMFGDEEVMCLNGNWTEPPQCKDSTGKCGPPPIDNGDITSFPLSVYAPASSVEYQCQNLYQLEGNKRITCRNGQW
SEPPKCLHPCVISREIMENYNIALRWTAKQKLYLRTGESVEFVCKRGYRLSSRSHTLRTTCWDGKLEYPTCAKR

FIG. 13

FHR5 Precursor (SEQ. ID. NO. 6)

MLLLFSVILISWVSTVGGEGTLCDFPKIHHGFLYDEEDYNPFSQVPTGEVFYYSCEYNFVSPSKSFWTRIT
CTEEGWSPTPKCLRMCSFPFVKNGHSESSGLIHLEGDTVQICNTGYSLQNNEKNISCVERGWSTPPICS
FTKGECHVPILEANVDAQPKKESYKVGDVLKFSCRKNLIRVGSDSVQCYQFGWSPNFPTCKGQVRSCG
PPPQLSNGEVKEIRKEEYGHNEVVEYDCNPNFIINGPKKIQCVDGEWTTLPTCVEQVKTCGYIPELEYGY
VQPSVPPYQHGVSVEVNCRNEYAMIGNNMITCINGIWTELPMCVATHQLKRCKIAGVNIKTLLKLSGK
EFNHNSRIRYRCSDIFRYRHSVCINGKWNPEVDCTEKREQFCPPPQIPNAQNMTTVNYQDGEKVAV
LCKENYLLPEAKEIVCKDGRWQSLPRCVESTAYCGPPPSINNGDTSFPLSVPPGSTVTYRCQSFYKLQG
SVTVTCRNKQWSEPPRCLDPCVVSEENMKNNIQLKWRNDGKLYAKTGDAVEFQCKFPHKAMISSPP
FRAICQEGKFEYPICE

FHL-1 Precursor (SEQ. ID. NO. 7)

MRLLAKIICLMLWAICVAEDCNELPPRRNTEILTGSWSDQTYPEGTQAIYKCRPGYRSLGNVIMVCRKGEWVALNPL
RKCQKRPCGHPGDTPFGTFTLTGGNVFEYGSYKAVYTCNEGYQLLGEINYRECDTDGWTNDIPICEVVKCLPVTAPEN
GKIVSSAMEPDREYHFGQAVRFVCNSGYKIEGDEEMHCSDDGFWSKEKPKCVEISCKSPDVINGSPISQKIIYKENER
FQYKCNMGYEYSERGDAVCTESGWRPLPSCEEKSCDNPYIPNGDYSPLRIKHRTGDEITYQCRNGFYPATRGNTAKC
TSTGWIPAPRCTLKPCDYPDIKHGGLIYHENMRRPYFPVAVGKYYSYYCDEHFETPSGSYWDHIHCTQDGWSPAVPC
LRKCYFPYLENGYNQNYGRKFVQGKSIDVACHPGYALPKAQTTVTCMENGWSPTPRCRVSFTL

FIG. 14

FHR1 Precursor protein (SEQ. ID. NO. 8)
MWLLVSVILISRISSVGGEATFCDFPKINHGILYDEEKYKPFSQVPTGEVFYYSCEYNFVSPSKSFWTRIT
CTEEGWSPTPKCLRLCFFPVENGHSESSGQTHLEGDTVQIICNTGYRLQNNENNISCVERGWSTPP
KCRSTDTSCVNPPTVQNAHILSRQMSKYPSGERVRYECRSPYEMFGDEEVMCLNGNWTEPPQCKD
STGKCGPPPPIDNGDITSFPLSVYAPASSVEYQCQNLYQLEGNKRITCRNGQWSEPPKCLHPCVISREI
MENYNIALRWTAKQKLYLRTGESAEFVCKRGYRLSSRSHTLRTTCWDGKLEYPTCAKR

FHL-1 CCP 6 (SEQ. ID. NO. 22):
PCDYPDIKHGGLYHENMRRPYFPVAVGKYYSYYCDEHFETPSGSYWDHIHCTQDGWSPAVPCL

FHL-1 CCP 7 (SEQ. ID. NO. 23):
RKCYFPYLENGYNQNYGRKFVQGKSIDVACHPGYALPKAQTTVTCMENGWSPTPRCIRVSFTL

FHR5 CCP 7 (SEQ. ID. NO. 19)
QFCPPPPQIPNAQNMTTTVNYQDGEKVAVLCKENYLPEAKEIVCKDGRWQSLPRCVE

FHR5 CCP 8 (SEQ. ID. NO. 20)
AYCGPPPSINNGDTTSFPLSVYPPGSTVTYRCQSFYKLQGSVTVTCRNKQWSEPPRCLD

FHR5 CCP 9 (SEQ. ID. NO. 21)
CVVSEENMNKNNIQLKWRNDGKLYAKTGDAVEFQCKFPNKAMISSPPFRAICQEGKFEYPICE

FIG. 15

FHR-1 N-terminal CCP domain 1 (SEQ. ID. NO. 24):

EATFCDFPKINHGILYDEEKYKPFSQVPTGEVFYYSCEYNFVSPSKSFWTRITCTEEGWSPTPKCL

FHR-1 N-terminal CCP domain 2 (SEQ. ID. NO. 25):

RLCFFPFVENGHSESSGQTHLEGDTVQIICNTGYRLQNNENNISCVERGWSTPPKCRSTDTS

Factor H CCP 1 (SEQ. ID. NO. 9):
EDCNELPPRRNTEILTGSWSDQTYPEGTQAIYKCRPGYRSLGNIIMVCRKGEWVALNPLRKCQK Factor H CCP 2 (SEQ. ID. NO. 10):
RPCGHPGDTPFGTFTLTGGNVFEYGVKAVYTCNEGYQLLGEINYRECDTDGWTNDIPICEV Factor H CCP 3 (SEQ. ID. NO. 11):
VKCLPVTAPENGKIVSSAMEPDREYHFGQAVRFVCNSGYKIEGDEEMHCSDDGFWSKEKPKCVE Factor H CCP 4 (SEQ. ID. NO. 12):
ISCKSPDVINGSPISQKIIYKENERFQYKCNMGYEYSERGDAVCTESGWRPLPSCEE

FIG. 16

Factor H CCP 5 (SEQ. ID. NO. 13):
KSCDNPYIPNGDYSPLRIKHRTGDEITYQCRNGFYPATRGNTAKCTSTGWIPAPRCTL Factor H CCP 6 (SEQ. ID. NO. 14):
PCDYPDIKHGGLYHENMRRPYFPVAVGKYYSYYCDEHFETPSGSYWDHIHCTQDGWSPAVPCL Factor H CCP 7 (SEQ. ID. NO. 15):
RKCYFPYLENGYNQNYGRKFVQGKSIDVACHPGYALPKAQTTVTCMENGWSPTPRCIR Factor H CCP 18 (SEQ. ID. NO. 16):
TSCVNPPTVQNAYIVSRQMSKYPSGERVRVQCKSPYEMFGDEEVMCLNGNWTEPPQCKDST Factor H CCP 19 (SEQ. ID. NO. 17):
GKCGPPPPIDNGDITSFPLSVYAPASSVEYQCQNLYQLEGNKRITCRNGQWSEPPKCLHPCVI Factor H CCP 20 (SEQ. ID. NO. 18):
SREIMENYNIALRWTAKQKLYSKTGESVEFVCKRGYRLSSRSHTLRTTCWDGKLEYPTCAKR

FIG. 17

FH^(1-5^18-20^R1-2) protein sequence (SEQ. ID. NO. 26):

EDCNELPPRRNTEILTGSWSDQTYPEGTQAIYKCRPCGHPGDTPFGTFTLTGG
NVFEYGVKAVYTCNEGYQLLGEINYRECDTDGWTNDIPICEVVKCLPVTAPENGKIVSSAMEPDREYHFGQAVRFVCNSGYKIE
GDEEMHCSDDGFWSKEKPKCVEISCKSPDVINGSPISQKIIYKENERFQYKCNMGYEYSERGDAVCTESGWRPLPSCEEKSC
DNPYIPNGDYSPLRIKHRTGDEITYQCRNGFYPATRGNTAKCTSTGWIPAPRCTSGSGGGVDTTSCVNPPTVQNAYIVSRQM
SKYPSGERVRYQCRSPYEMFGDEEVMCLNGNWTEPPQCKDSTGKCGPPPIDNGDITSFPLSVYAPASSVEYQCQNLYQLEG
NKRITCRNGQWSEPPKCLHPCVISREIMENYNIALRWTAKQKLYSRTGESVEFVCKRGYRLSSRSHTLRTTCWDGKLEYPTCA
KRGTEATFCDFPKINHGILYDEEKYKPFSQVPTGEVFYYSCEYNFVSPSKSFWTRITCTEEGWSPTPKCLRLCFFPFVENGHSE
SSGQTHLEGDTVQIICNTGYRLQNNENNISCVERGWSTPPKCRSTDTS

FH^(R1-2^1-5^18-20) protein sequence (SEQ. ID. NO. 27):

EATFCDFPKINHGILYDEEKYKPFSQVPTGEVFYYSCEYNFVSPSKSFWTRITCTEEGWSPTPKCLRLCFFPFVENGHSESSGQ
THLEGDTVQIICNTGYRLQNNENNISCVERGWSTPPKCRSTDTSVDEDCNELPPRRNTEILTGSWSDQTYPEGTQAIYKCRPG
YRSLGNIIMVCRKGEWVALNPLRKCQKPCGHPGDTPFGTFTLTGGNVFEYGVKAVYTCNEGYQLLGEINYRECDTDGWTNDI
PICEVVKCLPVTAPENGKIVSSAMEPDREYHFGQAVRFVCNSGYKIEGDEEMHCSDDGFWSKEKPKCVEISCKSPDVINGSPIS
QKIIYKENERFQYKCNMGYEYSERGDAVCTESGWRPLPSCEEKSCDNPYIPNGDYSPLRIKHRTGDEITYQCRNGFYPATRGN
TAKCTSTGWIPAPRCTSGSGGGVDTTSCVNPPTVQNAYIVSRQMSKYPSGERVRYQCRSPYEMFGDEEVMCLNGNWTEPPQ
CKDSTGKCGPPPIDNGDITSFPLSVYAPASSVEYQCQNLYQLEGNKRITCRNGQWSEPPKCLHPCVISREIMENYNIALRWTA
KQKLYSRTGESVEFVCKRGYRLSSRSHTLRTTCWDGKLEYPTCAKR

FIG. 18

FH1-5^L6-L7^R1-2    (SEQ. ID. NO. 28)

EDCNELPPRRNTEILTGSWSDQTYPEGTQAIYKCRPGYRSLGNIIMVCRKGEWVALNPLRKCQKRPCGHPGDTPFGTFTLTGG
NVFEYGVKAVYTCNEGYQLLGEINYRECDTDGWTNDIPICEVVKCLPVTAPENGKIVSSAMEPDREYHFGQAVRFVONSGYKIE
GDEEMHCSDDGFWSKEPKCVEISCKSPDVINGSPISQKIIYKENERFQYKCNMGYEYSERGDAVCTESGWRPLPSCEEKSCD
NPYIPNGDYSPLRIKHRTGDEITYQCRNGFYPATRGNTAKCTSTGWIPAPRCTSGSGGGVDTKHGGLYHENMRRPYFPVAVG
KYYSYYCDEHFETPSGSYWDHIHCTQDGWSPAVPCLRKCYFPYLENGYNQNYGRKFVQGKSIDVACHPGYALPKAQTTVTCM
ENGWSPTPRCIRVSFTLGTEATFCDFPKINHGILYDEEKYKPFSQVPTGEVFYSCEYNFVSPSKSFWTRITCTEEGWSPTPKCL
RLCFFPFVENGHSESSGQTHLEGDTVQIICNTGYRLQNNENNISCVERGWSTPPKCRSTDTS

FH R1-2^1-5^L6-L7   (SEQ. ID. NO. 29)

EATFCDFPKINHGILYDEEKYKPFSQVPTGEVFYSCEYNFVSPSKSFWTRITCTEEGWSPTPKCLRLCFFPFVENGHSES
SGQTHLEGDTVQIICNTGYRLQNNENNISCVERGWSTPPKCRSTDTSVDEDCNELPPRRNTEILTGSWSDQTYPEGTQAI
YKCRPGYRSLGNIIMVCRKGEWVALNPLRKCQKRPCGHPGDTPFGTFTLTGGNVFEYGVKAVYTCNEGYQLLGEINYRE
CDTDGWTNDIPICEVVKCLPVTAPENGKIVSSAMEPDREYHFGQAVRFVONSGYKIEGDEEMHCSDDGFWSKEPKCVE
ISCKSPDVINGSPISQKIIYKENERFQYKCNMGYEYSERGDAVCTESGWRPLPSCEEKSCDNPYIPNGDYSPLRIKHRTGD
EITYQCRNGFYPATRGNTAKCTSTGWIPAPRCTSGSGGGVDTKHGGLYHENMRRPYFPVAVGKYYSYYCDEHFETPSG
SYWDHIHCTQDGWSPAVPCLRKCYFPYLENGYNQNYGRKFVQGKSIDVACHPGYALPKAQTTVTCMENGWSPTPRCIR
VSFTL

SEQ. ID. NO. 30
SGSGGGG

SEQ. ID. NO. 31
SGSGGGGGT

SEQ. ID. NO. 32
SGSGGGGVD

SEQ. ID. NO. 33
SGSGGGGVDT

B.

SEQ. ID. NO. 34
5' GCTCTAGAATGTGGCTCCTGGTCAGTGTA 3'

SEQ. ID. NO. 35
5' CGGGTCGACGGAAGTGTCAGTGGACCTGC 3'

SEQ. ID. NO. 36
5' CGGGTCGACGAAGATTGCAATGAACTTCCTCC 3'

SEQ. ID. NO. 37
5' GGGGTACCCCCACCTCCTCCCGAAC 3'

SEQ. ID. NO. 38
5' GCTCTAGAATGTGGCTCCTGGTC 3'

SEQ. ID. NO. 39
5' GGGGTACCCCCACCTCC 3'

SEQ. ID. NO. 40
5' GGGGTACCGAAGCAACATTTGTGATTTCCA 3'

SEQ. ID. NO. 41
5' CTAGCTAGCTTAGGAAGTGTCAGTGGACCTGC 3'

SEQ. ID. NO. 42
5' CGGGTCGACCACCACCTCCTCATGTGTGAAT 3'

SEQ. ID. NO. 43
5' GGGGTACCTCTTTTGCACAAGTTGGATACTC 3'

SEQ. ID. NO. 44
5' CGCGTCGACCACCACCTC 3'

SEQ. ID. NO. 45
5' CTAGCTAGCTTAGGAAGTGTCAGTGGACC 3'

FIG. 20

FH1-5^18-28^R1-2 precursor protein sequence (SEQ. ID. NO. 46):

(MRLLAKIICLMLWAICVA)EDCNELPPRRNTEILTGSWSDQTYFEGTQAIYKCRPGYRSLGNIIMVCRKGEWVALNPLRKCQKRP
CGHPGDTPFGTFTLTGGNVFEYGVKAVYTCNEGYQLLGEINYRECDTDGWTNDIPICEVKCLPVTAPENGKIVSSAMEPDREY
HFGQAVRFVCNSGYKIEGDEEMHCSDDGFWSKEKPKCVEISCKSPDVINGSPISQKIIYKENERFQYKCNMGYESERGDAVC
TESGWRPLPSCEEKSCDNPYIPNGDYSPLRIKHRTGDEITYQCRNGFYPATRGNTAKCTSTGWIPAPRCTSGSGGGVDTTSG
VNPPTVQNAYIVSRQMSKYPSGERVYQCRSPYEMFGDEEVMCLNGNWTEPPQCKDSTGKCGPPPPIDNGDITSFPLSVYAP
ASSVEYQCQNLYQLEGNKRITCRNGQWSEPPKCLHPCVISREIMENYNIALRWTAKQKLYSRTGESVEFVCKRGYRLSSRSHT
LRTTCWDGKLEYPTCAKRGTEATFCDFPKINHGILYDEEKYKPFSQVPTGEVFYSCEYNFVSPSKSFWTRITCTEEGWSTPFK
CLRLCFFPFVENGHSESSGQTHLEGDTVQIICNTGYRLQNNENNISCVERGWSTPPKCRSTDTS

FH^R1-2^1.5^18-28 precursor protein sequence (SEQ. ID. NO. 47):

(MWILNSVILISRISSVGG)EATFCDFPKINHGILYDEEKYKPFSQVPTGEVFYSCEYNFVSPSKSFWTRITCTEEGWSPTPKCLRL
CFFPFVENGHSESSGQTHLEGDTVQIICNTGYRLQNNENNISCVERGWSTPPKCRSTDTSVDEDCNELPPRRNTEILTGSWSD
QTYFEGTQAIYKCRPGYRSLGNIIMVCRKGEWVALNPLRKCQKRPCGHPGDTPFGTFTLTGGNVFEYGVKAVYTCNEGYQLL
GEINYRECDTDGWTNDIPICEVKCLPVTAPENGKIVSSAMEPDREYHFGQAVRFVCNSGYKIEGDEEMHCSDDGFWSKEKPK
CVEISCKSPDVINGSPISQKIIYKENERFQYKCNMGYESERGDAVCTESGWRPLPSCEEKSCDNPYIPNGDYSPLRIKHRTGD
EITYQCRNGFYPATRGNTAKCTSTGWIPAPRCTSGSGGGVDTTSGVNPPTVQNAYIVSRQMSKYPSGERVYQCRSPYEMFG
DEEVMCLNGNWTEPPQCKDSTGKCGPPPPIDNGDITSFPLSVYAPASSVEYQCQNLYQLEGNKRITCRNGQWSEPPKCLHPC
VISREIMENYNIALRWTAKQKLYSRTGESVEFVCKRGYRLSSRSHTLRTTCWDGKLEYPTCAKR

FIG. 21

FH^(1-15^L17^R1-2) precursor protein (SEQ. ID. NO. 48)

(MRLLAKIICLMLWAICVA)EDONELPPRRNTEILTGSWSDQTYPEGTQAIYKCRPGYRSLGNIIMVCRKGEWVALNPLRKCQKR
PCGHPGDTPFGTFTLTGGNVFEYGVKAVYTCNEGYQLLGEINYRECDTDGWTNDPICEVVKCLPVTAPENGKIVSSAMEPDRE
YHFGQAVRFVCNSGYKIEGDEEMHCSDDGFWSKEKPKCVEISCKSPDVINGSPISQKIIYKENERFQYKCNMGYEYSERGDAVC
TESGWRPLPSCEEKSCDNPYIPNGDYSPLRIKHRTGDEITYQCRNGFYPATRGNTAKCTSTGWIPAPRCTSGSGGGVDTKHG
GLYHENMRRPYFPVAVGKYYSYYCDEHFETPSGSYWDHIHCTQDGWSPAVPCLRKCYFPYLENGYNQNYGRKFVQGKSIDVA
CHPGYALPKAQTTVTCMENGWSPTPRCIRVSFTLGTEATFCDFPKINHGILYDEEKYKPFSQVPTGEVFYYSCEYNFVSPSKSF
WTRITCTEEGWSPTPKCLRLCFFPFVENGHSESSGQTHLEGDTVQIICNTGYRLQNNENNISCVERGMSTPPKCRSTDTS

FH^(R1-2^L1-5^L6-L7) precursor protein (SEQ. ID. NO. 49)

(MWLLVSVILISRISSVGG)EATFCDFPKINHGILYDEEKYKPFSQVPTGEVFYYSCEYNFVSPSKSFWTRITCTEEGWSPTP
KCLRLCFFPFVENGHSESSGQTHLEGDTVQIICNTGYRLQNNENNISCVERGMSTPPKCRSTDTSVDEDCNELPPRRNT
EILTGSWSDQTYPEGTQAIYKCRPGYRSLGNIIMVCRKGEWVALNPLRKCQKRPCGHPGDTPFGTFTLTGGNVFEYGVK
AVYTCNEGYQLLGEINYRECDTDGWTNDPICEVVKCLPVTAPENGKIVSSAMEPDREYHFGQAVRFVCNSGYKIEGDEE
MHCSDDGFWSKEKPKCVEISCKSPDVINGSPISQKIIYKENERFQYKCNMGYEYSERGDAVCTESGWRPLPSCEEKSCD
NPYIPNGDYSPLRIKHRTGDEITYQCRNGFYPATRGNTAKCTSTGWIPAPRCTSGSGGGGTKHGGLYHENMRRPYFPV
AVGKYYSYYCDEHFETPSGSYWDHIHCTQDGWSPAVPCLRKCYFPYLENGYNQNYGRKFVQGKSIDVACHPGYALPKA
QTTVTCMENGWSPTPRCIRVSFTL

FIG. 22

SEQUENCE LISTING

<160> NUMBER OF SEQ ID NOS: 56

<210> SEQ ID NO 1
<211> LENGTH: 1213
<212> TYPE: PRT
<213> ORGANISM: Homo sapiens

<400> SEQUENCE: 1

```
Glu Asp Cys Asn Glu Leu Pro Pro Arg Arg Asn Thr Glu Ile Leu Thr
1               5                   10                  15

Gly Ser Trp Ser Asp Gln Thr Tyr Pro Glu Gly Thr Gln Ala Ile Tyr
            20                  25                  30

Lys Cys Arg Pro Gly Tyr Arg Ser Leu Gly Asn Val Ile Met Val Cys
        35                  40                  45

Arg Lys Gly Glu Trp Val Ala Leu Asn Pro Leu Arg Lys Cys Gln Lys
    50                  55                  60

Arg Pro Cys Gly His Pro Gly Asp Thr Pro Phe Gly Thr Phe Thr Leu
65                  70                  75                  80

Thr Gly Gly Asn Val Phe Glu Tyr Gly Val Lys Ala Val Tyr Thr Cys
                85                  90                  95

Asn Glu Gly Tyr Gln Leu Leu Gly Glu Ile Asn Tyr Arg Glu Cys Asp
            100                 105                 110

Thr Asp Gly Trp Thr Asn Asp Ile Pro Ile Cys Glu Val Val Lys Cys
        115                 120                 125

Leu Pro Val Thr Ala Pro Glu Asn Gly Lys Ile Val Ser Ser Ala Met
    130                 135                 140

Glu Pro Asp Arg Glu Tyr His Phe Gly Gln Ala Val Arg Phe Val Cys
145                 150                 155                 160

Asn Ser Gly Tyr Lys Ile Glu Gly Asp Glu Glu Met His Cys Ser Asp
                165                 170                 175

Asp Gly Phe Trp Ser Lys Glu Lys Pro Lys Cys Val Glu Ile Ser Cys
            180                 185                 190

Lys Ser Pro Asp Val Ile Asn Gly Ser Pro Ile Ser Gln Lys Ile Ile
        195                 200                 205

Tyr Lys Glu Asn Glu Arg Phe Gln Tyr Lys Cys Asn Met Gly Tyr Glu
    210                 215                 220

Tyr Ser Glu Arg Gly Asp Ala Val Cys Thr Glu Ser Gly Trp Arg Pro
225                 230                 235                 240

Leu Pro Ser Cys Glu Glu Lys Ser Cys Asp Asn Pro Tyr Ile Pro Asn
                245                 250                 255

Gly Asp Tyr Ser Pro Leu Arg Ile Lys His Arg Thr Gly Asp Glu Ile
            260                 265                 270

Thr Tyr Gln Cys Arg Asn Gly Phe Tyr Pro Ala Thr Arg Gly Asn Thr
        275                 280                 285

Ala Lys Cys Thr Ser Thr Gly Trp Ile Pro Ala Pro Arg Cys Thr Leu
    290                 295                 300

Lys Pro Cys Asp Tyr Pro Asp Ile Lys His Gly Gly Leu Tyr His Glu
305                 310                 315                 320
```

```
Asn Met Arg Arg Pro Tyr Phe Pro Val Ala Val Gly Lys Tyr Tyr Ser
            325                 330                 335

Tyr Tyr Cys Asp Glu His Phe Glu Thr Pro Ser Gly Ser Tyr Trp Asp
            340                 345                 350

His Ile His Cys Thr Gln Asp Gly Trp Ser Pro Ala Val Pro Cys Leu
            355                 360                 365

Arg Lys Cys Tyr Phe Pro Tyr Leu Glu Asn Gly Tyr Asn Gln Asn Tyr
            370                 375                 380

Gly Arg Lys Phe Val Gln Gly Lys Ser Ile Asp Val Ala Cys His Pro
385                 390                 395                 400

Gly Tyr Ala Leu Pro Lys Ala Gln Thr Thr Val Thr Cys Met Glu Asn
                    405                 410                 415

Gly Trp Ser Pro Thr Pro Arg Cys Ile Arg Val Lys Thr Cys Ser Lys
                    420                 425                 430

Ser Ser Ile Asp Ile Glu Asn Gly Phe Ile Ser Glu Ser Gln Tyr Thr
                    435                 440                 445

Tyr Ala Leu Lys Glu Lys Ala Lys Tyr Gln Cys Lys Leu Gly Tyr Val
            450                 455                 460

Thr Ala Asp Gly Glu Thr Ser Gly Ser Ile Thr Cys Gly Lys Asp Gly
465                 470                 475                 480

Trp Ser Ala Gln Pro Thr Cys Ile Lys Ser Cys Asp Ile Pro Val Phe
                    485                 490                 495

Met Asn Ala Arg Thr Lys Asn Asp Phe Thr Trp Phe Lys Leu Asn Asp
                    500                 505                 510

Thr Leu Asp Tyr Glu Cys His Asp Gly Tyr Glu Ser Asn Thr Gly Ser
            515                 520                 525

Thr Thr Gly Ser Ile Val Cys Gly Tyr Asn Gly Trp Ser Asp Leu Pro
530                 535                 540

Ile Cys Tyr Glu Arg Glu Cys Glu Leu Pro Lys Ile Asp Val His Leu
545                 550                 555                 560

Val Pro Asp Arg Lys Lys Asp Gln Tyr Lys Val Gly Glu Val Leu Lys
                    565                 570                 575

Phe Ser Cys Lys Pro Gly Phe Thr Ile Val Gly Pro Asn Ser Val Gln
                    580                 585                 590

Cys Tyr His Phe Gly Leu Ser Pro Asp Leu Pro Ile Cys Lys Glu Gln
            595                 600                 605

Val Gln Ser Cys Gly Pro Pro Pro Glu Leu Leu Asn Gly Asn Val Lys
            610                 615                 620

Glu Lys Thr Lys Glu Glu Tyr Gly His Ser Glu Val Val Glu Tyr Tyr
625                 630                 635                 640

Cys Asn Pro Arg Phe Leu Met Lys Gly Pro Asn Lys Ile Gln Cys Val
                    645                 650                 655

Asp Gly Glu Trp Thr Thr Leu Pro Val Cys Ile Val Glu Glu Ser Thr
                    660                 665                 670

Cys Gly Asp Ile Pro Glu Leu Glu His Gly Trp Ala Gln Leu Ser Ser
            675                 680                 685

Pro Pro Tyr Tyr Tyr Gly Asp Ser Val Glu Phe Asn Cys Ser Glu Ser
            690                 695                 700

Phe Thr Met Ile Gly His Arg Ser Ile Thr Cys Ile His Gly Val Trp
705                 710                 715                 720

Thr Gln Leu Pro Gln Cys Val Ala Ile Asp Lys Leu Lys Lys Cys Lys
                    725                 730                 735

Ser Ser Asn Leu Ile Ile Leu Glu Glu His Leu Lys Asn Lys Lys Glu
```

```
            740                 745                 750
Phe Asp His Asn Ser Asn Ile Arg Tyr Arg Cys Arg Gly Lys Glu Gly
            755                 760                 765

Trp Ile His Thr Val Cys Ile Asn Gly Arg Trp Asp Pro Glu Val Asn
            770                 775                 780

Cys Ser Met Ala Gln Ile Gln Leu Cys Pro Pro Pro Gln Ile Pro
785                 790                 795                 800

Asn Ser His Asn Met Thr Thr Thr Leu Asn Tyr Arg Asp Gly Glu Lys
                805                 810                 815

Val Ser Val Leu Cys Gln Glu Asn Tyr Leu Ile Gln Glu Gly Glu Glu
            820                 825                 830

Ile Thr Cys Lys Asp Gly Arg Trp Gln Ser Ile Pro Leu Cys Val Glu
            835                 840                 845

Lys Ile Pro Cys Ser Gln Pro Pro Gln Ile Glu His Gly Thr Ile Asn
850                 855                 860

Ser Ser Arg Ser Ser Gln Glu Ser Tyr Ala His Gly Thr Lys Leu Ser
865                 870                 875                 880

Tyr Thr Cys Glu Gly Gly Phe Arg Ile Ser Glu Glu Asn Glu Thr Thr
                885                 890                 895

Cys Tyr Met Gly Lys Trp Ser Ser Pro Pro Gln Cys Glu Gly Leu Pro
            900                 905                 910

Cys Lys Ser Pro Pro Glu Ile Ser His Gly Val Val Ala His Met Ser
            915                 920                 925

Asp Ser Tyr Gln Tyr Gly Glu Glu Val Thr Tyr Lys Cys Phe Glu Gly
            930                 935                 940

Phe Gly Ile Asp Gly Pro Ala Ile Ala Lys Cys Leu Gly Glu Lys Trp
945                 950                 955                 960

Ser His Pro Pro Ser Cys Ile Lys Thr Asp Cys Leu Ser Leu Pro Ser
                965                 970                 975

Phe Glu Asn Ala Ile Pro Met Gly Glu Lys Lys Asp Val Tyr Lys Ala
            980                 985                 990

Gly Glu Gln Val Thr Tyr Thr Cys Ala Thr Tyr Tyr Lys Met Asp Gly
            995                 1000                1005

Ala Ser Asn Val Thr Cys Ile Asn Ser Arg Trp Thr Gly Arg Pro
            1010                1015                1020

Thr Cys Arg Asp Thr Ser Cys Val Asn Pro Pro Thr Val Gln Asn
            1025                1030                1035

Ala Tyr Ile Val Ser Arg Gln Met Ser Lys Tyr Pro Ser Gly Glu
            1040                1045                1050

Arg Val Arg Tyr Gln Cys Arg Ser Pro Tyr Glu Met Phe Gly Asp
            1055                1060                1065

Glu Glu Val Met Cys Leu Asn Gly Asn Trp Thr Glu Pro Pro Gln
            1070                1075                1080

Cys Lys Asp Ser Thr Gly Lys Cys Gly Pro Pro Pro Ile Asp
            1085                1090                1095

Asn Gly Asp Ile Thr Ser Phe Pro Leu Ser Val Tyr Ala Pro Ala
            1100                1105                1110

Ser Ser Val Glu Tyr Gln Cys Gln Asn Leu Tyr Gln Leu Glu Gly
            1115                1120                1125

Asn Lys Arg Ile Thr Cys Arg Asn Gly Gln Trp Ser Glu Pro Pro
            1130                1135                1140

Lys Cys Leu His Pro Cys Val Ile Ser Arg Glu Ile Met Glu Asn
            1145                1150                1155
```

```
Tyr Asn Ile Ala Leu Arg Trp Thr Ala Lys Gln Lys Leu Tyr Ser
    1160                1165            1170

Arg Thr Gly Glu Ser Val Glu Phe Val Cys Lys Arg Gly Tyr Arg
    1175                1180            1185

Leu Ser Ser Arg Ser His Thr Leu Arg Thr Thr Cys Trp Asp Gly
    1190                1195            1200

Lys Leu Glu Tyr Pro Thr Cys Ala Lys Arg
    1205                1210

<210> SEQ ID NO 2
<211> LENGTH: 551
<212> TYPE: PRT
<213> ORGANISM: Homo sapiens

<400> SEQUENCE: 2

Glu Gly Thr Leu Cys Asp Phe Pro Lys Ile His His Gly Phe Leu Tyr
1               5                   10                  15

Asp Glu Glu Asp Tyr Asn Pro Phe Ser Gln Val Pro Thr Gly Glu Val
                20                  25                  30

Phe Tyr Tyr Ser Cys Glu Tyr Asn Phe Val Ser Pro Ser Lys Ser Phe
            35                  40                  45

Trp Thr Arg Ile Thr Cys Thr Glu Glu Gly Trp Ser Pro Thr Pro Lys
    50                  55                  60

Cys Leu Arg Met Cys Ser Phe Pro Phe Val Lys Asn Gly His Ser Glu
65                  70                  75                  80

Ser Ser Gly Leu Ile His Leu Glu Gly Asp Thr Val Gln Ile Ile Cys
                85                  90                  95

Asn Thr Gly Tyr Ser Leu Gln Asn Asn Glu Lys Asn Ile Ser Cys Val
            100                 105                 110

Glu Arg Gly Trp Ser Thr Pro Pro Ile Cys Ser Phe Thr Lys Gly Glu
        115                 120                 125

Cys His Val Pro Ile Leu Glu Ala Asn Val Asp Ala Gln Pro Lys Lys
    130                 135                 140

Glu Ser Tyr Lys Val Gly Asp Val Leu Lys Phe Ser Cys Arg Lys Asn
145                 150                 155                 160

Leu Ile Arg Val Gly Ser Asp Ser Val Gln Cys Tyr Gln Phe Gly Trp
                165                 170                 175

Ser Pro Asn Phe Pro Thr Cys Lys Gly Gln Val Arg Ser Cys Gly Pro
            180                 185                 190

Pro Pro Gln Leu Ser Asn Gly Glu Val Lys Glu Ile Arg Lys Glu Glu
        195                 200                 205

Tyr Gly His Asn Glu Val Val Glu Tyr Asp Cys Asn Pro Asn Phe Ile
    210                 215                 220

Ile Asn Gly Pro Lys Lys Ile Gln Cys Val Asp Gly Glu Trp Thr Thr
225                 230                 235                 240

Leu Pro Thr Cys Val Glu Gln Val Lys Thr Cys Gly Tyr Ile Pro Glu
                245                 250                 255

Leu Glu Tyr Gly Tyr Val Gln Pro Ser Val Pro Pro Tyr Gln His Gly
            260                 265                 270

Val Ser Val Glu Val Asn Cys Arg Asn Glu Tyr Ala Met Ile Gly Asn
        275                 280                 285

Asn Met Ile Thr Cys Ile Asn Gly Ile Trp Thr Glu Leu Pro Met Cys
    290                 295                 300

Val Ala Thr His Gln Leu Lys Arg Cys Lys Ile Ala Gly Val Asn Ile
```

```
                305                 310                 315                 320
Lys Thr Leu Leu Lys Leu Ser Gly Lys Glu Phe Asn His Asn Ser Arg
                325                 330                 335

Ile Arg Tyr Arg Cys Ser Asp Ile Phe Arg Tyr Arg His Ser Val Cys
                340                 345                 350

Ile Asn Gly Lys Trp Asn Pro Glu Val Asp Cys Thr Glu Lys Arg Glu
                355                 360                 365

Gln Phe Cys Pro Pro Pro Gln Ile Pro Asn Ala Gln Asn Met Thr
                370                 375                 380

Thr Thr Val Asn Tyr Gln Asp Gly Glu Lys Val Ala Val Leu Cys Lys
385                 390                 395                 400

Glu Asn Tyr Leu Leu Pro Glu Ala Lys Glu Ile Val Cys Lys Asp Gly
                405                 410                 415

Arg Trp Gln Ser Leu Pro Arg Cys Val Glu Ser Thr Ala Tyr Cys Gly
                420                 425                 430

Pro Pro Pro Ser Ile Asn Asn Gly Asp Thr Thr Ser Phe Pro Leu Ser
                435                 440                 445

Val Tyr Pro Pro Gly Ser Thr Val Thr Tyr Arg Cys Gln Ser Phe Tyr
                450                 455                 460

Lys Leu Gln Gly Ser Val Thr Val Thr Cys Arg Asn Lys Gln Trp Ser
465                 470                 475                 480

Glu Pro Pro Arg Cys Leu Asp Pro Cys Val Val Ser Glu Glu Asn Met
                485                 490                 495

Asn Lys Asn Asn Ile Gln Leu Lys Trp Arg Asn Asp Gly Lys Leu Tyr
                500                 505                 510

Ala Lys Thr Gly Asp Ala Val Glu Phe Gln Cys Lys Phe Pro His Lys
                515                 520                 525

Ala Met Ile Ser Ser Pro Pro Phe Arg Ala Ile Cys Gln Glu Gly Lys
                530                 535                 540

Phe Glu Tyr Pro Ile Cys Glu
545                 550

<210> SEQ ID NO 3
<211> LENGTH: 431
<212> TYPE: PRT
<213> ORGANISM: Homo sapiens

<400> SEQUENCE: 3

Glu Asp Cys Asn Glu Leu Pro Pro Arg Arg Asn Thr Glu Ile Leu Thr
1               5                   10                  15

Gly Ser Trp Ser Asp Gln Thr Tyr Pro Glu Gly Thr Gln Ala Ile Tyr
                20                  25                  30

Lys Cys Arg Pro Gly Tyr Arg Ser Leu Gly Asn Val Ile Met Val Cys
                35                  40                  45

Arg Lys Gly Glu Trp Val Ala Leu Asn Pro Leu Arg Lys Cys Gln Lys
                50                  55                  60

Arg Pro Cys Gly His Pro Gly Asp Thr Pro Phe Gly Thr Phe Thr Leu
65                  70                  75                  80

Thr Gly Gly Asn Val Phe Glu Tyr Gly Val Lys Ala Val Tyr Thr Cys
                85                  90                  95

Asn Glu Gly Tyr Gln Leu Leu Gly Glu Ile Asn Tyr Arg Glu Cys Asp
                100                 105                 110

Thr Asp Gly Trp Thr Asn Asp Ile Pro Ile Cys Glu Val Val Lys Cys
                115                 120                 125
```

```
Leu Pro Val Thr Ala Pro Glu Asn Gly Lys Ile Val Ser Ser Ala Met
            130                 135                 140

Glu Pro Asp Arg Glu Tyr His Phe Gly Gln Ala Val Arg Phe Val Cys
145                 150                 155                 160

Asn Ser Gly Tyr Lys Ile Glu Gly Asp Glu Met His Cys Ser Asp
                165                 170                 175

Asp Gly Phe Trp Ser Lys Glu Lys Pro Lys Cys Val Glu Ile Ser Cys
                180                 185                 190

Lys Ser Pro Asp Val Ile Asn Gly Ser Pro Ile Ser Gln Lys Ile Ile
                195                 200                 205

Tyr Lys Glu Asn Glu Arg Phe Gln Tyr Lys Cys Asn Met Gly Tyr Glu
            210                 215                 220

Tyr Ser Glu Arg Gly Asp Ala Val Cys Thr Glu Ser Gly Trp Arg Pro
225                 230                 235                 240

Leu Pro Ser Cys Glu Glu Lys Ser Cys Asp Asn Pro Tyr Ile Pro Asn
                245                 250                 255

Gly Asp Tyr Ser Pro Leu Arg Ile Lys His Arg Thr Gly Asp Glu Ile
                260                 265                 270

Thr Tyr Gln Cys Arg Asn Gly Phe Tyr Pro Ala Thr Arg Gly Asn Thr
            275                 280                 285

Ala Lys Cys Thr Ser Thr Gly Trp Ile Pro Ala Pro Arg Cys Thr Leu
290                 295                 300

Lys Pro Cys Asp Tyr Pro Asp Ile Lys His Gly Gly Leu Tyr His Glu
305                 310                 315                 320

Asn Met Arg Arg Pro Tyr Phe Pro Val Ala Val Gly Lys Tyr Tyr Ser
                325                 330                 335

Tyr Tyr Cys Asp Glu His Phe Glu Thr Pro Ser Gly Ser Tyr Trp Asp
                340                 345                 350

His Ile His Cys Thr Gln Asp Gly Trp Ser Pro Ala Val Pro Cys Leu
            355                 360                 365

Arg Lys Cys Tyr Phe Pro Tyr Leu Glu Asn Gly Tyr Asn Gln Asn Tyr
                370                 375                 380

Gly Arg Lys Phe Val Gln Gly Lys Ser Ile Asp Val Ala Cys His Pro
385                 390                 395                 400

Gly Tyr Ala Leu Pro Lys Ala Gln Thr Thr Val Thr Cys Met Glu Asn
                405                 410                 415

Gly Trp Ser Pro Thr Pro Arg Cys Ile Arg Val Ser Phe Thr Leu
                420                 425                 430

<210> SEQ ID NO 4
<211> LENGTH: 312
<212> TYPE: PRT
<213> ORGANISM: Homo sapiens

<400> SEQUENCE: 4

Glu Ala Thr Phe Cys Asp Phe Pro Lys Ile Asn His Gly Ile Leu Tyr
1               5                   10                  15

Asp Glu Glu Lys Tyr Lys Pro Phe Ser Gln Val Pro Thr Gly Glu Val
                20                  25                  30

Phe Tyr Tyr Ser Cys Glu Tyr Asn Phe Val Ser Pro Ser Lys Ser Phe
            35                  40                  45

Trp Thr Arg Ile Thr Cys Thr Glu Glu Gly Trp Ser Pro Thr Pro Lys
        50                  55                  60

Cys Leu Arg Leu Cys Phe Phe Pro Phe Val Glu Asn Gly His Ser Glu
65                  70                  75                  80
```

```
Ser Ser Gly Gln Thr His Leu Glu Gly Asp Thr Val Gln Ile Ile Cys
                85                  90                  95

Asn Thr Gly Tyr Arg Leu Gln Asn Asn Glu Asn Ile Ser Cys Val
            100                 105                 110

Glu Arg Gly Trp Ser Thr Pro Pro Lys Cys Arg Ser Thr Asp Thr Ser
            115                 120                 125

Cys Val Asn Pro Pro Thr Val Gln Asn Ala His Ile Leu Ser Arg Gln
130                 135                 140

Met Ser Lys Tyr Pro Ser Gly Glu Arg Val Arg Tyr Glu Cys Arg Ser
145                 150                 155                 160

Pro Tyr Glu Met Phe Gly Asp Glu Glu Val Met Cys Leu Asn Gly Asn
                165                 170                 175

Trp Thr Glu Pro Pro Gln Cys Lys Asp Ser Thr Gly Lys Cys Gly Pro
            180                 185                 190

Pro Pro Pro Ile Asp Asn Gly Asp Ile Thr Ser Phe Pro Leu Ser Val
            195                 200                 205

Tyr Ala Pro Ala Ser Ser Val Glu Tyr Gln Cys Gln Asn Leu Tyr Gln
210                 215                 220

Leu Glu Gly Asn Lys Arg Ile Thr Cys Arg Asn Gly Gln Trp Ser Glu
225                 230                 235                 240

Pro Pro Lys Cys Leu His Pro Cys Val Ile Ser Arg Glu Ile Met Glu
                245                 250                 255

Asn Tyr Asn Ile Ala Leu Arg Trp Thr Ala Lys Gln Lys Leu Tyr Leu
                260                 265                 270

Arg Thr Gly Glu Ser Ala Glu Phe Val Cys Lys Arg Gly Tyr Arg Leu
            275                 280                 285

Ser Ser Arg Ser His Thr Leu Arg Thr Thr Cys Trp Asp Gly Lys Leu
290                 295                 300

Glu Tyr Pro Thr Cys Ala Lys Arg
305                 310

<210> SEQ ID NO 5
<211> LENGTH: 1231
<212> TYPE: PRT
<213> ORGANISM: Homo sapiens

<400> SEQUENCE: 5

Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
            20                  25                  30

Leu Thr Gly Ser Trp Ser Asp Gln Thr Tyr Pro Glu Gly Thr Gln Ala
        35                  40                  45

Ile Tyr Lys Cys Arg Pro Gly Tyr Arg Ser Leu Gly Asn Val Ile Met
50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
            100                 105                 110

Thr Cys Asn Glu Gly Tyr Gln Leu Leu Gly Glu Ile Asn Tyr Arg Glu
            115                 120                 125

Cys Asp Thr Asp Gly Trp Thr Asn Asp Ile Pro Ile Cys Glu Val Val
```

```
                130               135               140
Lys Cys Leu Pro Val Thr Ala Pro Glu Asn Gly Lys Ile Val Ser Ser
145                 150               155               160

Ala Met Glu Pro Asp Arg Glu Tyr His Phe Gly Gln Ala Val Arg Phe
                    165               170               175

Val Cys Asn Ser Gly Tyr Lys Ile Glu Gly Asp Glu Met His Cys
                180               185               190

Ser Asp Asp Gly Phe Trp Ser Lys Glu Pro Lys Cys Val Glu Ile
                195               200               205

Ser Cys Lys Ser Pro Asp Val Ile Asn Gly Ser Pro Ile Ser Gln Lys
    210               215               220

Ile Ile Tyr Lys Glu Asn Glu Arg Phe Gln Tyr Lys Cys Asn Met Gly
225               230               235               240

Tyr Glu Tyr Ser Glu Arg Gly Asp Ala Val Cys Thr Glu Ser Gly Trp
                    245               250               255

Arg Pro Leu Pro Ser Cys Glu Glu Lys Ser Cys Asp Asn Pro Tyr Ile
                260               265               270

Pro Asn Gly Asp Tyr Ser Pro Leu Arg Ile Lys His Arg Thr Gly Asp
                275               280               285

Glu Ile Thr Tyr Gln Cys Arg Asn Gly Phe Tyr Pro Ala Thr Arg Gly
                290               295               300

Asn Thr Ala Lys Cys Thr Ser Thr Gly Trp Ile Pro Ala Pro Arg Cys
305               310               315               320

Thr Leu Lys Pro Cys Asp Tyr Pro Asp Ile Lys His Gly Gly Leu Tyr
                    325               330               335

His Glu Asn Met Arg Arg Pro Tyr Phe Pro Val Ala Val Gly Lys Tyr
                340               345               350

Tyr Ser Tyr Tyr Cys Asp Glu His Phe Glu Thr Pro Ser Gly Ser Tyr
                355               360               365

Trp Asp His Ile His Cys Thr Gln Asp Gly Trp Ser Pro Ala Val Pro
                370               375               380

Cys Leu Arg Lys Cys Tyr Phe Pro Tyr Leu Glu Asn Gly Tyr Asn Gln
385                 390               395               400

Asn Tyr Gly Arg Lys Phe Val Gln Gly Lys Ser Ile Asp Val Ala Cys
                    405               410               415

His Pro Gly Tyr Ala Leu Pro Lys Ala Gln Thr Thr Val Thr Cys Met
                420               425               430

Glu Asn Gly Trp Ser Pro Thr Pro Arg Cys Ile Arg Val Lys Thr Cys
                435               440               445

Ser Lys Ser Ser Ile Asp Ile Glu Asn Gly Phe Ile Ser Glu Ser Gln
    450               455               460

Tyr Thr Tyr Ala Leu Lys Glu Lys Ala Lys Tyr Gln Cys Lys Leu Gly
465                 470               475               480

Tyr Val Thr Ala Asp Gly Glu Thr Ser Gly Ser Ile Thr Cys Gly Lys
                    485               490               495

Asp Gly Trp Ser Ala Gln Pro Thr Cys Ile Lys Ser Cys Asp Ile Pro
                500               505               510

Val Phe Met Asn Ala Arg Thr Lys Asn Asp Phe Thr Trp Phe Lys Leu
                515               520               525

Asn Asp Thr Leu Asp Tyr Glu Cys His Asp Gly Tyr Glu Ser Asn Thr
                530               535               540

Gly Ser Thr Thr Gly Ser Ile Val Cys Gly Tyr Asn Gly Trp Ser Asp
545                 550               555               560
```

```
Leu Pro Ile Cys Tyr Glu Arg Glu Cys Glu Leu Pro Lys Ile Asp Val
                565                 570                 575

His Leu Val Pro Asp Arg Lys Asp Gln Tyr Lys Val Gly Glu Val
            580                 585                 590

Leu Lys Phe Ser Cys Lys Pro Gly Phe Thr Ile Val Gly Pro Asn Ser
        595                 600                 605

Val Gln Cys Tyr His Phe Gly Leu Ser Pro Asp Leu Pro Ile Cys Lys
    610                 615                 620

Glu Gln Val Gln Ser Cys Gly Pro Pro Glu Leu Leu Asn Gly Asn
625                 630                 635                 640

Val Lys Glu Lys Thr Lys Glu Glu Tyr Gly His Ser Glu Val Val Glu
                645                 650                 655

Tyr Tyr Cys Asn Pro Arg Phe Leu Met Lys Gly Pro Asn Lys Ile Gln
            660                 665                 670

Cys Val Asp Gly Glu Trp Thr Thr Leu Pro Val Cys Ile Val Glu Glu
        675                 680                 685

Ser Thr Cys Gly Asp Ile Pro Glu Leu Glu His Gly Trp Ala Gln Leu
    690                 695                 700

Ser Ser Pro Pro Tyr Tyr Tyr Gly Asp Ser Val Glu Phe Asn Cys Ser
705                 710                 715                 720

Glu Ser Phe Thr Met Ile Gly His Arg Ser Ile Thr Cys Ile His Gly
                725                 730                 735

Val Trp Thr Gln Leu Pro Gln Cys Val Ala Ile Asp Lys Leu Lys Lys
            740                 745                 750

Cys Lys Ser Ser Asn Leu Ile Ile Leu Glu Glu His Leu Lys Asn Lys
        755                 760                 765

Lys Glu Phe Asp His Asn Ser Asn Ile Arg Tyr Arg Cys Arg Gly Lys
    770                 775                 780

Glu Gly Trp Ile His Thr Val Cys Ile Asn Gly Arg Trp Asp Pro Glu
785                 790                 795                 800

Val Asn Cys Ser Met Ala Gln Ile Gln Leu Cys Pro Pro Pro Gln
                805                 810                 815

Ile Pro Asn Ser His Asn Met Thr Thr Thr Leu Asn Tyr Arg Asp Gly
            820                 825                 830

Glu Lys Val Ser Val Leu Cys Gln Glu Asn Tyr Leu Ile Gln Glu Gly
        835                 840                 845

Glu Glu Ile Thr Cys Lys Asp Gly Arg Trp Gln Ser Ile Pro Leu Cys
    850                 855                 860

Val Glu Lys Ile Pro Cys Ser Gln Pro Pro Gln Ile Glu His Gly Thr
865                 870                 875                 880

Ile Asn Ser Ser Arg Ser Ser Gln Glu Ser Tyr Ala His Gly Thr Lys
                885                 890                 895

Leu Ser Tyr Thr Cys Glu Gly Gly Phe Arg Ile Ser Glu Glu Asn Glu
            900                 905                 910

Thr Thr Cys Tyr Met Gly Lys Trp Ser Ser Pro Pro Gln Cys Glu Gly
        915                 920                 925

Leu Pro Cys Lys Ser Pro Pro Glu Ile Ser His Gly Val Val Ala His
    930                 935                 940

Met Ser Asp Ser Tyr Gln Tyr Gly Glu Glu Val Thr Tyr Lys Cys Phe
945                 950                 955                 960

Glu Gly Phe Gly Ile Asp Gly Pro Ala Ile Ala Lys Cys Leu Gly Glu
                965                 970                 975
```

Lys Trp Ser His Pro Pro Ser Cys Ile Lys Thr Asp Cys Leu Ser Leu
            980                 985                 990

Pro Ser Phe Glu Asn Ala Ile Pro Met Gly Glu Lys Lys Asp Val Tyr
        995                 1000                1005

Lys Ala Gly Glu Gln Val Thr Tyr Thr Cys Ala Thr Tyr Tyr Lys
    1010                1015                1020

Met Asp Gly Ala Ser Asn Val Thr Cys Ile Asn Ser Arg Trp Thr
    1025                1030                1035

Gly Arg Pro Thr Cys Arg Asp Thr Ser Cys Val Asn Pro Pro Thr
    1040                1045                1050

Val Gln Asn Ala Tyr Ile Val Ser Arg Gln Met Ser Lys Tyr Pro
    1055                1060                1065

Ser Gly Glu Arg Val Arg Tyr Gln Cys Arg Ser Pro Tyr Glu Met
    1070                1075                1080

Phe Gly Asp Glu Glu Val Met Cys Leu Asn Gly Asn Trp Thr Glu
    1085                1090                1095

Pro Pro Gln Cys Lys Asp Ser Thr Gly Lys Cys Gly Pro Pro Pro
    1100                1105                1110

Pro Ile Asp Asn Gly Asp Ile Thr Ser Phe Pro Leu Ser Val Tyr
    1115                1120                1125

Ala Pro Ala Ser Ser Val Glu Tyr Gln Cys Gln Asn Leu Tyr Gln
    1130                1135                1140

Leu Glu Gly Asn Lys Arg Ile Thr Cys Arg Asn Gly Gln Trp Ser
    1145                1150                1155

Glu Pro Pro Lys Cys Leu His Pro Cys Val Ile Ser Arg Glu Ile
    1160                1165                1170

Met Glu Asn Tyr Asn Ile Ala Leu Arg Trp Thr Ala Lys Gln Lys
    1175                1180                1185

Leu Tyr Ser Arg Thr Gly Glu Ser Val Glu Phe Val Cys Lys Arg
    1190                1195                1200

Gly Tyr Arg Leu Ser Ser Arg Ser His Thr Leu Arg Thr Thr Cys
    1205                1210                1215

Trp Asp Gly Lys Leu Glu Tyr Pro Thr Cys Ala Lys Arg
    1220                1225                1230

<210> SEQ ID NO 6
<211> LENGTH: 569
<212> TYPE: PRT
<213> ORGANISM: Homo sapiens

<400> SEQUENCE: 6

Met Leu Leu Leu Phe Ser Val Ile Leu Ile Ser Trp Val Ser Thr Val
1               5                   10                  15

Gly Gly Glu Gly Thr Leu Cys Asp Phe Pro Lys Ile His His Gly Phe
            20                  25                  30

Leu Tyr Asp Glu Glu Asp Tyr Asn Pro Phe Ser Gln Val Pro Thr Gly
        35                  40                  45

Glu Val Phe Tyr Tyr Ser Cys Glu Tyr Asn Phe Val Ser Pro Ser Lys
    50                  55                  60

Ser Phe Trp Thr Arg Ile Thr Cys Thr Glu Glu Gly Trp Ser Pro Thr
65                  70                  75                  80

Pro Lys Cys Leu Arg Met Cys Ser Phe Pro Phe Val Lys Asn Gly His
                85                  90                  95

Ser Glu Ser Ser Gly Leu Ile His Leu Glu Gly Asp Thr Val Gln Ile
            100                 105                 110

```
Ile Cys Asn Thr Gly Tyr Ser Leu Gln Asn Asn Glu Lys Asn Ile Ser
        115                 120                 125
Cys Val Glu Arg Gly Trp Ser Thr Pro Pro Ile Cys Ser Phe Thr Lys
    130                 135                 140
Gly Glu Cys His Val Pro Ile Leu Glu Ala Asn Val Asp Ala Gln Pro
145                 150                 155                 160
Lys Lys Glu Ser Tyr Lys Val Gly Asp Val Leu Lys Phe Ser Cys Arg
                165                 170                 175
Lys Asn Leu Ile Arg Val Gly Ser Asp Ser Val Gln Cys Tyr Gln Phe
            180                 185                 190
Gly Trp Ser Pro Asn Phe Pro Thr Cys Lys Gly Gln Val Arg Ser Cys
        195                 200                 205
Gly Pro Pro Pro Gln Leu Ser Asn Gly Glu Val Lys Glu Ile Arg Lys
    210                 215                 220
Glu Glu Tyr Gly His Asn Glu Val Val Glu Tyr Asp Cys Asn Pro Asn
225                 230                 235                 240
Phe Ile Ile Asn Gly Pro Lys Lys Ile Gln Cys Val Asp Gly Glu Trp
                245                 250                 255
Thr Thr Leu Pro Thr Cys Val Glu Gln Val Lys Thr Cys Gly Tyr Ile
            260                 265                 270
Pro Glu Leu Glu Tyr Gly Tyr Val Gln Pro Ser Val Pro Pro Tyr Gln
        275                 280                 285
His Gly Val Ser Val Glu Val Asn Cys Arg Asn Glu Tyr Ala Met Ile
    290                 295                 300
Gly Asn Asn Met Ile Thr Cys Ile Asn Gly Ile Trp Thr Glu Leu Pro
305                 310                 315                 320
Met Cys Val Ala Thr His Gln Leu Lys Arg Cys Lys Ile Ala Gly Val
                325                 330                 335
Asn Ile Lys Thr Leu Leu Lys Leu Ser Gly Lys Glu Phe Asn His Asn
            340                 345                 350
Ser Arg Ile Arg Tyr Arg Cys Ser Asp Ile Phe Arg Tyr Arg His Ser
        355                 360                 365
Val Cys Ile Asn Gly Lys Trp Asn Pro Glu Val Asp Cys Thr Glu Lys
    370                 375                 380
Arg Glu Gln Phe Cys Pro Pro Pro Gln Ile Pro Asn Ala Gln Asn
385                 390                 395                 400
Met Thr Thr Thr Val Asn Tyr Gln Asp Gly Glu Lys Val Ala Val Leu
                405                 410                 415
Cys Lys Glu Asn Tyr Leu Leu Pro Glu Ala Lys Glu Ile Val Cys Lys
            420                 425                 430
Asp Gly Arg Trp Gln Ser Leu Pro Arg Cys Val Glu Ser Thr Ala Tyr
        435                 440                 445
Cys Gly Pro Pro Pro Ser Ile Asn Asn Gly Asp Thr Thr Ser Phe Pro
    450                 455                 460
Leu Ser Val Tyr Pro Pro Gly Ser Thr Val Thr Tyr Arg Cys Gln Ser
465                 470                 475                 480
Phe Tyr Lys Leu Gln Gly Ser Val Thr Val Thr Cys Arg Asn Lys Gln
                485                 490                 495
Trp Ser Glu Pro Pro Arg Cys Leu Asp Pro Cys Val Val Ser Glu Glu
            500                 505                 510
Asn Met Asn Lys Asn Asn Ile Gln Leu Lys Trp Arg Asn Asp Gly Lys
        515                 520                 525
```

```
Leu Tyr Ala Lys Thr Gly Asp Ala Val Glu Phe Gln Cys Lys Phe Pro
530                 535                 540

His Lys Ala Met Ile Ser Ser Pro Pro Phe Arg Ala Ile Cys Gln Glu
545                 550                 555                 560

Gly Lys Phe Glu Tyr Pro Ile Cys Glu
                565

<210> SEQ ID NO 7
<211> LENGTH: 449
<212> TYPE: PRT
<213> ORGANISM: Homo sapiens

<400> SEQUENCE: 7

Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
            20                  25                  30

Leu Thr Gly Ser Trp Ser Asp Gln Thr Tyr Pro Glu Gly Thr Gln Ala
        35                  40                  45

Ile Tyr Lys Cys Arg Pro Gly Tyr Arg Ser Leu Gly Asn Val Ile Met
50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
            100                 105                 110

Thr Cys Asn Glu Gly Tyr Gln Leu Leu Gly Glu Ile Asn Tyr Arg Glu
        115                 120                 125

Cys Asp Thr Asp Gly Trp Thr Asn Asp Ile Pro Ile Cys Glu Val Val
130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
            180                 185                 190

Ser Asp Asp Gly Phe Trp Ser Lys Glu Lys Pro Lys Cys Val Glu Ile
        195                 200                 205

Ser Cys Lys Ser Pro Asp Val Ile Asn Gly Ser Pro Ile Ser Gln Lys
210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
                245                 250                 255

Arg Pro Leu Pro Ser Cys Glu Glu Lys Ser Cys Asp Asn Pro Tyr Ile
            260                 265                 270

Pro Asn Gly Asp Tyr Ser Pro Leu Arg Ile Lys His Arg Thr Gly Asp
        275                 280                 285

Glu Ile Thr Tyr Gln Cys Arg Asn Gly Phe Tyr Pro Ala Thr Arg Gly
290                 295                 300

Asn Thr Ala Lys Cys Thr Ser Thr Gly Trp Ile Pro Ala Pro Arg Cys
305                 310                 315                 320

Thr Leu Lys Pro Cys Asp Tyr Pro Asp Ile Lys His Gly Gly Leu Tyr
                325                 330                 335
```

```
His Glu Asn Met Arg Arg Pro Tyr Phe Pro Val Ala Val Gly Lys Tyr
                340                 345                 350

Tyr Ser Tyr Tyr Cys Asp Glu His Phe Glu Thr Pro Ser Gly Ser Tyr
            355                 360                 365

Trp Asp His Ile His Cys Thr Gln Asp Gly Trp Ser Pro Ala Val Pro
370                 375                 380

Cys Leu Arg Lys Cys Tyr Phe Pro Tyr Leu Glu Asn Gly Tyr Asn Gln
385                 390                 395                 400

Asn Tyr Gly Arg Lys Phe Val Gln Gly Lys Ser Ile Asp Val Ala Cys
                405                 410                 415

His Pro Gly Tyr Ala Leu Pro Lys Ala Gln Thr Thr Val Thr Cys Met
                420                 425                 430

Glu Asn Gly Trp Ser Pro Thr Pro Arg Cys Ile Arg Val Ser Phe Thr
                435                 440                 445

Leu

<210> SEQ ID NO 8
<211> LENGTH: 330
<212> TYPE: PRT
<213> ORGANISM: Homo sapiens

<400> SEQUENCE: 8

Met Trp Leu Leu Val Ser Val Ile Leu Ile Ser Arg Ile Ser Ser Val
1               5                   10                  15

Gly Gly Glu Ala Thr Phe Cys Asp Phe Pro Lys Ile Asn His Gly Ile
            20                  25                  30

Leu Tyr Asp Glu Glu Lys Tyr Lys Pro Phe Ser Gln Val Pro Thr Gly
        35                  40                  45

Glu Val Phe Tyr Tyr Ser Cys Glu Tyr Asn Phe Val Ser Pro Ser Lys
    50                  55                  60

Ser Phe Trp Thr Arg Ile Thr Cys Thr Glu Glu Gly Trp Ser Pro Thr
65                  70                  75                  80

Pro Lys Cys Leu Arg Leu Cys Phe Phe Pro Phe Val Glu Asn Gly His
                85                  90                  95

Ser Glu Ser Ser Gly Gln Thr His Leu Glu Gly Asp Thr Val Gln Ile
                100                 105                 110

Ile Cys Asn Thr Gly Tyr Arg Leu Gln Asn Asn Glu Asn Asn Ile Ser
                115                 120                 125

Cys Val Glu Arg Gly Trp Ser Thr Pro Pro Lys Cys Arg Ser Thr Asp
            130                 135                 140

Thr Ser Cys Val Asn Pro Pro Thr Val Gln Asn Ala His Ile Leu Ser
145                 150                 155                 160

Arg Gln Met Ser Lys Tyr Pro Ser Gly Glu Arg Val Arg Tyr Glu Cys
                165                 170                 175

Arg Ser Pro Tyr Glu Met Phe Gly Asp Glu Glu Val Met Cys Leu Asn
            180                 185                 190

Gly Asn Trp Thr Glu Pro Pro Gln Cys Lys Asp Ser Thr Gly Lys Cys
        195                 200                 205

Gly Pro Pro Pro Pro Ile Asp Asn Gly Asp Ile Thr Ser Phe Pro Leu
    210                 215                 220

Ser Val Tyr Ala Pro Ala Ser Ser Val Glu Tyr Gln Cys Gln Asn Leu
225                 230                 235                 240

Tyr Gln Leu Glu Gly Asn Lys Arg Ile Thr Cys Arg Asn Gly Gln Trp
                245                 250                 255
```

```
Ser Glu Pro Pro Lys Cys Leu His Pro Cys Val Ile Ser Arg Glu Ile
        260                 265                 270

Met Glu Asn Tyr Asn Ile Ala Leu Arg Trp Thr Ala Lys Gln Lys Leu
        275                 280                 285

Tyr Leu Arg Thr Gly Glu Ser Ala Glu Phe Val Cys Lys Arg Gly Tyr
        290                 295                 300

Arg Leu Ser Ser Arg Ser His Thr Leu Arg Thr Cys Trp Asp Gly
305                 310                 315                 320

Lys Leu Glu Tyr Pro Thr Cys Ala Lys Arg
                325                 330

<210> SEQ ID NO 9
<211> LENGTH: 64
<212> TYPE: PRT
<213> ORGANISM: Homo sapiens

<400> SEQUENCE: 9

Glu Asp Cys Asn Glu Leu Pro Pro Arg Arg Asn Thr Glu Ile Leu Thr
1               5                   10                  15

Gly Ser Trp Ser Asp Gln Thr Tyr Pro Glu Gly Thr Gln Ala Ile Tyr
                20                  25                  30

Lys Cys Arg Pro Gly Tyr Arg Ser Leu Gly Asn Ile Ile Met Val Cys
            35                  40                  45

Arg Lys Gly Glu Trp Val Ala Leu Asn Pro Leu Arg Lys Cys Gln Lys
        50                  55                  60

<210> SEQ ID NO 10
<211> LENGTH: 61
<212> TYPE: PRT
<213> ORGANISM: Homo sapiens

<400> SEQUENCE: 10

Arg Pro Cys Gly His Pro Gly Asp Thr Pro Phe Gly Thr Phe Thr Leu
1               5                   10                  15

Thr Gly Gly Asn Val Phe Glu Tyr Gly Val Lys Ala Val Tyr Thr Cys
                20                  25                  30

Asn Glu Gly Tyr Gln Leu Leu Gly Glu Ile Asn Tyr Arg Glu Cys Asp
            35                  40                  45

Thr Asp Gly Trp Thr Asn Asp Ile Pro Ile Cys Glu Val
        50                  55                  60

<210> SEQ ID NO 11
<211> LENGTH: 64
<212> TYPE: PRT
<213> ORGANISM: Homo sapiens

<400> SEQUENCE: 11

Val Lys Cys Leu Pro Val Thr Ala Pro Glu Asn Gly Lys Ile Val Ser
1               5                   10                  15

Ser Ala Met Glu Pro Asp Arg Glu Tyr His Phe Gly Gln Ala Val Arg
                20                  25                  30

Phe Val Cys Asn Ser Gly Tyr Lys Ile Glu Gly Asp Glu Glu Met His
            35                  40                  45

Cys Ser Asp Asp Gly Phe Trp Ser Lys Glu Lys Pro Lys Cys Val Glu
        50                  55                  60

<210> SEQ ID NO 12
<211> LENGTH: 57
```

```
<212> TYPE: PRT
<213> ORGANISM: Homo sapiens

<400> SEQUENCE: 12

Ile Ser Cys Lys Ser Pro Asp Val Ile Asn Gly Ser Pro Ile Ser Gln
1               5                   10                  15

Lys Ile Ile Tyr Lys Glu Asn Glu Arg Phe Gln Tyr Lys Cys Asn Met
                20                  25                  30

Gly Tyr Glu Tyr Ser Arg Gly Asp Ala Val Cys Thr Glu Ser Gly
            35                  40                  45

Trp Arg Pro Leu Pro Ser Cys Glu Glu
    50                  55

<210> SEQ ID NO 13
<211> LENGTH: 58
<212> TYPE: PRT
<213> ORGANISM: Homo sapiens

<400> SEQUENCE: 13

Lys Ser Cys Asp Asn Pro Tyr Ile Pro Asn Gly Asp Tyr Ser Pro Leu
1               5                   10                  15

Arg Ile Lys His Arg Thr Gly Asp Glu Ile Thr Tyr Gln Cys Arg Asn
                20                  25                  30

Gly Phe Tyr Pro Ala Thr Arg Gly Asn Thr Ala Lys Cys Thr Ser Thr
            35                  40                  45

Gly Trp Ile Pro Ala Pro Arg Cys Thr Leu
    50                  55

<210> SEQ ID NO 14
<211> LENGTH: 63
<212> TYPE: PRT
<213> ORGANISM: Homo sapiens

<400> SEQUENCE: 14

Pro Cys Asp Tyr Pro Asp Ile Lys His Gly Gly Leu Tyr His Glu Asn
1               5                   10                  15

Met Arg Arg Pro Tyr Phe Pro Val Ala Val Gly Lys Tyr Tyr Ser Tyr
                20                  25                  30

Tyr Cys Asp Glu His Phe Glu Thr Pro Ser Gly Ser Tyr Trp Asp His
            35                  40                  45

Ile His Cys Thr Gln Asp Gly Trp Ser Pro Ala Val Pro Cys Leu
    50                  55                  60

<210> SEQ ID NO 15
<211> LENGTH: 58
<212> TYPE: PRT
<213> ORGANISM: Homo sapiens

<400> SEQUENCE: 15

Arg Lys Cys Tyr Phe Pro Tyr Leu Glu Asn Gly Tyr Asn Gln Asn Tyr
1               5                   10                  15

Gly Arg Lys Phe Val Gln Gly Lys Ser Ile Asp Val Ala Cys His Pro
                20                  25                  30

Gly Tyr Ala Leu Pro Lys Ala Gln Thr Thr Val Thr Cys Met Glu Asn
            35                  40                  45

Gly Trp Ser Pro Thr Pro Arg Cys Ile Arg
    50                  55

<210> SEQ ID NO 16
```

```
<211> LENGTH: 61
<212> TYPE: PRT
<213> ORGANISM: Homo sapiens

<400> SEQUENCE: 16

Thr Ser Cys Val Asn Pro Pro Thr Val Gln Asn Ala Tyr Ile Val Ser
1               5                   10                  15

Arg Gln Met Ser Lys Tyr Pro Ser Gly Glu Arg Val Arg Tyr Gln Cys
                20                  25                  30

Arg Ser Pro Tyr Glu Met Phe Gly Asp Glu Val Met Cys Leu Asn
                35                  40                  45

Gly Asn Trp Thr Glu Pro Pro Gln Cys Lys Asp Ser Thr
    50                  55                  60

<210> SEQ ID NO 17
<211> LENGTH: 63
<212> TYPE: PRT
<213> ORGANISM: Homo sapiens

<400> SEQUENCE: 17

Gly Lys Cys Gly Pro Pro Pro Ile Asp Asn Gly Asp Ile Thr Ser
1               5                   10                  15

Phe Pro Leu Ser Val Tyr Ala Pro Ala Ser Ser Val Glu Tyr Gln Cys
                20                  25                  30

Gln Asn Leu Tyr Gln Leu Glu Gly Asn Lys Arg Ile Thr Cys Arg Asn
                35                  40                  45

Gly Gln Trp Ser Glu Pro Pro Lys Cys Leu His Pro Cys Val Ile
    50                  55                  60

<210> SEQ ID NO 18
<211> LENGTH: 62
<212> TYPE: PRT
<213> ORGANISM: Homo sapiens

<400> SEQUENCE: 18

Ser Arg Glu Ile Met Glu Asn Tyr Asn Ile Ala Leu Arg Trp Thr Ala
1               5                   10                  15

Lys Gln Lys Leu Tyr Ser Arg Thr Gly Glu Ser Val Glu Phe Val Cys
                20                  25                  30

Lys Arg Gly Tyr Arg Leu Ser Ser Arg Ser His Thr Leu Arg Thr Thr
                35                  40                  45

Cys Trp Asp Gly Lys Leu Glu Tyr Pro Thr Cys Ala Lys Arg
    50                  55                  60

<210> SEQ ID NO 19
<211> LENGTH: 58
<212> TYPE: PRT
<213> ORGANISM: Homo sapiens

<400> SEQUENCE: 19

Gln Phe Cys Pro Pro Pro Gln Ile Pro Asn Ala Gln Asn Met Thr
1               5                   10                  15

Thr Thr Val Asn Tyr Gln Asp Gly Glu Lys Val Ala Val Leu Cys Lys
                20                  25                  30

Glu Asn Tyr Leu Leu Pro Glu Ala Lys Glu Ile Val Cys Lys Asp Gly
                35                  40                  45

Arg Trp Gln Ser Leu Pro Arg Cys Val Glu
    50                  55
```

```
<210> SEQ ID NO 20
<211> LENGTH: 59
<212> TYPE: PRT
<213> ORGANISM: Homo sapiens

<400> SEQUENCE: 20

Ala Tyr Cys Gly Pro Pro Ser Ile Asn Asn Gly Asp Thr Thr Ser
1               5                   10                  15

Phe Pro Leu Ser Val Tyr Pro Pro Gly Ser Thr Val Thr Tyr Arg Cys
                20                  25                  30

Gln Ser Phe Tyr Lys Leu Gln Gly Ser Val Thr Val Thr Cys Arg Asn
            35                  40                  45

Lys Gln Trp Ser Glu Pro Pro Arg Cys Leu Asp
        50                  55

<210> SEQ ID NO 21
<211> LENGTH: 63
<212> TYPE: PRT
<213> ORGANISM: Homo sapiens

<400> SEQUENCE: 21

Cys Val Val Ser Glu Glu Asn Met Asn Lys Asn Asn Ile Gln Leu Lys
1               5                   10                  15

Trp Arg Asn Asp Gly Lys Leu Tyr Ala Lys Thr Gly Asp Ala Val Glu
                20                  25                  30

Phe Gln Cys Lys Phe Pro His Lys Ala Met Ile Ser Ser Pro Pro Phe
            35                  40                  45

Arg Ala Ile Cys Gln Glu Gly Lys Phe Glu Tyr Pro Ile Cys Glu
        50                  55                  60

<210> SEQ ID NO 22
<211> LENGTH: 63
<212> TYPE: PRT
<213> ORGANISM: Homo sapiens

<400> SEQUENCE: 22

Pro Cys Asp Tyr Pro Asp Ile Lys His Gly Gly Leu Tyr His Glu Asn
1               5                   10                  15

Met Arg Arg Pro Tyr Phe Pro Val Ala Val Gly Lys Tyr Tyr Ser Tyr
                20                  25                  30

Tyr Cys Asp Glu His Phe Glu Thr Pro Ser Gly Ser Tyr Trp Asp His
            35                  40                  45

Ile His Cys Thr Gln Asp Gly Trp Ser Pro Ala Val Pro Cys Leu
        50                  55                  60

<210> SEQ ID NO 23
<211> LENGTH: 63
<212> TYPE: PRT
<213> ORGANISM: Homo sapiens

<400> SEQUENCE: 23

Arg Lys Cys Tyr Phe Pro Tyr Leu Glu Asn Gly Tyr Asn Gln Asn Tyr
1               5                   10                  15

Gly Arg Lys Phe Val Gln Gly Lys Ser Ile Asp Val Ala Cys His Pro
                20                  25                  30

Gly Tyr Ala Leu Pro Lys Ala Gln Thr Thr Val Thr Cys Met Glu Asn
            35                  40                  45

Gly Trp Ser Pro Thr Pro Arg Cys Ile Arg Val Ser Phe Thr Leu
        50                  55                  60
```

<210> SEQ ID NO 24
<211> LENGTH: 66
<212> TYPE: PRT
<213> ORGANISM: Homo sapiens

<400> SEQUENCE: 24

```
Glu Ala Thr Phe Cys Asp Phe Pro Lys Ile Asn His Gly Ile Leu Tyr
1               5                   10                  15

Asp Glu Glu Lys Tyr Lys Pro Phe Ser Gln Val Pro Thr Gly Glu Val
                20                  25                  30

Phe Tyr Tyr Ser Cys Glu Tyr Asn Phe Val Ser Pro Ser Lys Ser Phe
            35                  40                  45

Trp Thr Arg Ile Thr Cys Thr Glu Glu Gly Trp Ser Pro Thr Pro Lys
    50                  55                  60

Cys Leu
65
```

<210> SEQ ID NO 25
<211> LENGTH: 62
<212> TYPE: PRT
<213> ORGANISM: Homo sapiens

<400> SEQUENCE: 25

```
Arg Leu Cys Phe Phe Pro Phe Val Glu Asn Gly His Ser Glu Ser Ser
1               5                   10                  15

Gly Gln Thr His Leu Glu Gly Asp Thr Val Gln Ile Ile Cys Asn Thr
                20                  25                  30

Gly Tyr Arg Leu Gln Asn Asn Glu Asn Asn Ile Ser Cys Val Glu Arg
            35                  40                  45

Gly Trp Ser Thr Pro Pro Lys Cys Arg Ser Thr Asp Thr Ser
    50                  55                  60
```

<210> SEQ ID NO 26
<211> LENGTH: 629
<212> TYPE: PRT
<213> ORGANISM: Homo sapiens

<400> SEQUENCE: 26

```
Glu Asp Cys Asn Glu Leu Pro Pro Arg Arg Asn Thr Glu Ile Leu Thr
1               5                   10                  15

Gly Ser Trp Ser Asp Gln Thr Tyr Pro Glu Gly Thr Gln Ala Ile Tyr
                20                  25                  30

Lys Cys Arg Pro Gly Tyr Arg Ser Leu Gly Asn Ile Ile Met Val Cys
            35                  40                  45

Arg Lys Gly Glu Trp Val Ala Leu Asn Pro Leu Arg Lys Cys Gln Lys
    50                  55                  60

Arg Pro Cys Gly His Pro Gly Asp Thr Pro Phe Gly Thr Phe Thr Leu
65                  70                  75                  80

Thr Gly Gly Asn Val Phe Glu Tyr Gly Val Lys Ala Val Tyr Thr Cys
                85                  90                  95

Asn Glu Gly Tyr Gln Leu Leu Gly Glu Ile Asn Tyr Arg Glu Cys Asp
            100                 105                 110

Thr Asp Gly Trp Thr Asn Asp Ile Pro Ile Cys Glu Val Val Lys Cys
        115                 120                 125

Leu Pro Val Thr Ala Pro Glu Asn Gly Lys Ile Val Ser Ser Ala Met
    130                 135                 140

Glu Pro Asp Arg Glu Tyr His Phe Gly Gln Ala Val Arg Phe Val Cys
```

-continued

```
            145                 150                 155                 160
        Asn Ser Gly Tyr Lys Ile Glu Gly Asp Glu Glu Met His Cys Ser Asp
                        165                 170                 175
        Asp Gly Phe Trp Ser Lys Glu Lys Pro Lys Cys Val Glu Ile Ser Cys
                        180                 185                 190
        Lys Ser Pro Asp Val Ile Asn Gly Ser Pro Ile Ser Gln Lys Ile Ile
                        195                 200                 205
        Tyr Lys Glu Asn Glu Arg Phe Gln Tyr Lys Cys Asn Met Gly Tyr Glu
            210                 215                 220
        Tyr Ser Glu Arg Gly Asp Ala Val Cys Thr Glu Ser Gly Trp Arg Pro
        225                 230                 235                 240
        Leu Pro Ser Cys Glu Glu Lys Ser Cys Asp Asn Pro Tyr Ile Pro Asn
                        245                 250                 255
        Gly Asp Tyr Ser Pro Leu Arg Ile Lys His Arg Thr Gly Asp Glu Ile
                        260                 265                 270
        Thr Tyr Gln Cys Arg Asn Gly Phe Tyr Pro Ala Thr Arg Gly Asn Thr
                        275                 280                 285
        Ala Lys Cys Thr Ser Thr Gly Trp Ile Pro Ala Pro Arg Cys Thr Ser
            290                 295                 300
        Gly Ser Gly Gly Gly Val Asp Thr Thr Ser Cys Val Asn Pro Pro
        305                 310                 315                 320
        Thr Val Gln Asn Ala Tyr Ile Val Ser Arg Gln Met Ser Lys Tyr Pro
                        325                 330                 335
        Ser Gly Glu Arg Val Arg Tyr Gln Cys Arg Ser Pro Tyr Glu Met Phe
                        340                 345                 350
        Gly Asp Glu Glu Val Met Cys Leu Asn Gly Asn Trp Thr Glu Pro Pro
                        355                 360                 365
        Gln Cys Lys Asp Ser Thr Gly Lys Cys Gly Pro Pro Pro Ile Asp
            370                 375                 380
        Asn Gly Asp Ile Thr Ser Phe Pro Leu Ser Val Tyr Ala Pro Ala Ser
        385                 390                 395                 400
        Ser Val Glu Tyr Gln Cys Gln Asn Leu Tyr Gln Leu Glu Gly Asn Lys
                        405                 410                 415
        Arg Ile Thr Cys Arg Asn Gly Gln Trp Ser Glu Pro Pro Lys Cys Leu
                        420                 425                 430
        His Pro Cys Val Ile Ser Arg Glu Ile Met Glu Asn Tyr Asn Ile Ala
                        435                 440                 445
        Leu Arg Trp Thr Ala Lys Gln Lys Leu Tyr Ser Arg Thr Gly Glu Ser
            450                 455                 460
        Val Glu Phe Val Cys Lys Arg Gly Tyr Arg Leu Ser Ser Arg Ser His
        465                 470                 475                 480
        Thr Leu Arg Thr Thr Cys Trp Asp Gly Lys Leu Glu Tyr Pro Thr Cys
                        485                 490                 495
        Ala Lys Arg Gly Thr Glu Ala Thr Phe Cys Asp Phe Pro Lys Ile Asn
                        500                 505                 510
        His Gly Ile Leu Tyr Asp Glu Glu Lys Tyr Lys Pro Phe Ser Gln Val
                        515                 520                 525
        Pro Thr Gly Glu Val Phe Tyr Tyr Ser Cys Glu Tyr Asn Phe Val Ser
                        530                 535                 540
        Pro Ser Lys Ser Phe Trp Thr Arg Ile Thr Cys Thr Glu Glu Gly Trp
        545                 550                 555                 560
        Ser Pro Thr Pro Lys Cys Leu Arg Leu Cys Phe Phe Pro Phe Val Glu
                        565                 570                 575
```

```
Asn Gly His Ser Glu Ser Ser Gly Gln Thr His Leu Glu Gly Asp Thr
            580                 585                 590

Val Gln Ile Ile Cys Asn Thr Gly Tyr Arg Leu Gln Asn Asn Glu Asn
            595                 600                 605

Asn Ile Ser Cys Val Glu Arg Gly Trp Ser Thr Pro Pro Lys Cys Arg
            610                 615                 620

Ser Thr Asp Thr Ser
625

<210> SEQ ID NO 27
<211> LENGTH: 628
<212> TYPE: PRT
<213> ORGANISM: Homo sapiens

<400> SEQUENCE: 27

Glu Ala Thr Phe Cys Asp Phe Pro Lys Ile Asn His Gly Ile Leu Tyr
1               5                   10                  15

Asp Glu Glu Lys Tyr Lys Pro Phe Ser Gln Val Pro Thr Gly Glu Val
            20                  25                  30

Phe Tyr Tyr Ser Cys Glu Tyr Asn Phe Val Ser Pro Ser Lys Ser Phe
            35                  40                  45

Trp Thr Arg Ile Thr Cys Thr Glu Glu Gly Trp Ser Pro Thr Pro Lys
    50                  55                  60

Cys Leu Arg Leu Cys Phe Phe Pro Phe Val Glu Asn Gly His Ser Glu
65                  70                  75                  80

Ser Ser Gly Gln Thr His Leu Glu Gly Asp Thr Val Gln Ile Ile Cys
            85                  90                  95

Asn Thr Gly Tyr Arg Leu Gln Asn Asn Glu Asn Asn Ile Ser Cys Val
            100                 105                 110

Glu Arg Gly Trp Ser Thr Pro Pro Lys Cys Arg Ser Thr Asp Thr Ser
            115                 120                 125

Val Asp Glu Asp Cys Asn Glu Leu Pro Pro Arg Arg Asn Thr Glu Ile
        130                 135                 140

Leu Thr Gly Ser Trp Ser Asp Gln Thr Tyr Pro Glu Gly Thr Gln Ala
145                 150                 155                 160

Ile Tyr Lys Cys Arg Pro Gly Tyr Arg Ser Leu Gly Asn Ile Ile Met
                165                 170                 175

Val Cys Arg Lys Gly Glu Trp Val Ala Leu Asn Pro Leu Arg Lys Cys
            180                 185                 190

Gln Lys Arg Pro Cys Gly His Pro Gly Asp Thr Pro Phe Gly Thr Phe
            195                 200                 205

Thr Leu Thr Gly Gly Asn Val Phe Glu Tyr Gly Val Lys Ala Val Tyr
    210                 215                 220

Thr Cys Asn Glu Gly Tyr Gln Leu Leu Gly Glu Ile Asn Tyr Arg Glu
225                 230                 235                 240

Cys Asp Thr Asp Gly Trp Thr Asn Asp Ile Pro Ile Cys Glu Val Val
                245                 250                 255

Lys Cys Leu Pro Val Thr Ala Pro Glu Asn Gly Lys Ile Val Ser Ser
            260                 265                 270

Ala Met Glu Pro Asp Arg Glu Tyr His Phe Gly Gln Ala Val Arg Phe
            275                 280                 285

Val Cys Asn Ser Gly Tyr Lys Ile Glu Gly Asp Glu Glu Met His Cys
    290                 295                 300

Ser Asp Asp Gly Phe Trp Ser Lys Glu Lys Pro Lys Cys Val Glu Ile
```

```
                305                 310                 315                 320
Ser Cys Lys Ser Pro Asp Val Ile Asn Gly Ser Pro Ile Ser Gln Lys
                325                 330                 335
Ile Ile Tyr Lys Glu Asn Glu Arg Phe Gln Tyr Lys Cys Asn Met Gly
                340                 345                 350
Tyr Glu Tyr Ser Glu Arg Gly Asp Ala Val Cys Thr Glu Ser Gly Trp
                355                 360                 365
Arg Pro Leu Pro Ser Cys Glu Glu Lys Ser Cys Asp Asn Pro Tyr Ile
            370                 375                 380
Pro Asn Gly Asp Tyr Ser Pro Leu Arg Ile Lys His Arg Thr Gly Asp
385                 390                 395                 400
Glu Ile Thr Tyr Gln Cys Arg Asn Gly Phe Tyr Pro Ala Thr Arg Gly
                405                 410                 415
Asn Thr Ala Lys Cys Thr Ser Thr Gly Trp Ile Pro Ala Pro Arg Cys
                420                 425                 430
Thr Ser Gly Ser Gly Gly Gly Gly Thr Thr Ser Cys Val Asn Pro
                435                 440                 445
Pro Thr Val Gln Asn Ala Tyr Ile Val Ser Arg Gln Met Ser Lys Tyr
    450                 455                 460
Pro Ser Gly Glu Arg Val Arg Tyr Gln Cys Arg Ser Pro Tyr Glu Met
465                 470                 475                 480
Phe Gly Asp Glu Glu Val Met Cys Leu Asn Gly Asn Trp Thr Glu Pro
                485                 490                 495
Pro Gln Cys Lys Asp Ser Thr Gly Lys Cys Gly Pro Pro Pro Pro Ile
            500                 505                 510
Asp Asn Gly Asp Ile Thr Ser Phe Pro Leu Ser Val Tyr Ala Pro Ala
            515                 520                 525
Ser Ser Val Glu Tyr Gln Cys Gln Asn Leu Tyr Gln Leu Glu Gly Asn
            530                 535                 540
Lys Arg Ile Thr Cys Arg Asn Gly Gln Trp Ser Glu Pro Pro Lys Cys
545                 550                 555                 560
Leu His Pro Cys Val Ile Ser Arg Glu Ile Met Glu Asn Tyr Asn Ile
                565                 570                 575
Ala Leu Arg Trp Thr Ala Lys Gln Lys Leu Tyr Ser Arg Thr Gly Glu
            580                 585                 590
Ser Val Glu Phe Val Cys Lys Arg Gly Tyr Arg Leu Ser Ser Arg Ser
            595                 600                 605
His Thr Leu Arg Thr Thr Cys Trp Asp Gly Lys Leu Glu Tyr Pro Thr
    610                 615                 620
Cys Ala Lys Arg
625

<210> SEQ ID NO 28
<211> LENGTH: 562
<212> TYPE: PRT
<213> ORGANISM: Homo sapiens

<400> SEQUENCE: 28

Glu Asp Cys Asn Glu Leu Pro Pro Arg Arg Asn Thr Glu Ile Leu Thr
1               5                   10                  15
Gly Ser Trp Ser Asp Gln Thr Tyr Pro Glu Gly Thr Gln Ala Ile Tyr
                20                  25                  30
Lys Cys Arg Pro Gly Tyr Arg Ser Leu Gly Asn Ile Ile Met Val Cys
            35                  40                  45
```

-continued

Arg Lys Gly Glu Trp Val Ala Leu Asn Pro Leu Arg Lys Cys Gln Lys
    50                  55                  60

Arg Pro Cys Gly His Pro Gly Asp Thr Pro Phe Gly Thr Phe Thr Leu
65                  70                  75                  80

Thr Gly Gly Asn Val Phe Glu Tyr Gly Val Lys Ala Val Tyr Thr Cys
                85                  90                  95

Asn Glu Gly Tyr Gln Leu Leu Gly Glu Ile Asn Tyr Arg Glu Cys Asp
            100                 105                 110

Thr Asp Gly Trp Thr Asn Asp Ile Pro Ile Cys Glu Val Lys Cys
        115                 120                 125

Leu Pro Val Thr Ala Pro Glu Asn Gly Lys Ile Val Ser Ser Ala Met
    130                 135                 140

Glu Pro Asp Arg Glu Tyr His Phe Gly Gln Ala Val Arg Phe Val Cys
145                 150                 155                 160

Asn Ser Gly Tyr Lys Ile Glu Gly Asp Glu Met His Cys Ser Asp
                165                 170                 175

Asp Gly Phe Trp Ser Lys Glu Lys Pro Lys Cys Val Glu Ile Ser Cys
            180                 185                 190

Lys Ser Pro Asp Val Ile Asn Gly Ser Pro Ile Ser Gln Lys Ile Ile
        195                 200                 205

Tyr Lys Glu Asn Glu Arg Phe Gln Tyr Lys Cys Asn Met Gly Tyr Glu
    210                 215                 220

Tyr Ser Glu Arg Gly Asp Ala Val Cys Thr Glu Ser Gly Trp Arg Pro
225                 230                 235                 240

Leu Pro Ser Cys Glu Glu Lys Ser Cys Asp Asn Pro Tyr Ile Pro Asn
                245                 250                 255

Gly Asp Tyr Ser Pro Leu Arg Ile Lys His Arg Thr Gly Asp Glu Ile
            260                 265                 270

Thr Tyr Gln Cys Arg Asn Gly Phe Tyr Pro Ala Thr Arg Gly Asn Thr
        275                 280                 285

Ala Lys Cys Thr Ser Thr Gly Trp Ile Pro Ala Pro Arg Cys Thr Ser
    290                 295                 300

Gly Ser Gly Gly Gly Gly Val Asp Thr Lys His Gly Gly Leu Tyr His
305                 310                 315                 320

Glu Asn Met Arg Arg Pro Tyr Phe Pro Val Ala Val Gly Lys Tyr Tyr
                325                 330                 335

Ser Tyr Tyr Cys Asp Glu His Phe Glu Thr Pro Ser Gly Ser Tyr Trp
            340                 345                 350

Asp His Ile His Cys Thr Gln Asp Gly Trp Ser Pro Ala Val Pro Cys
        355                 360                 365

Leu Arg Lys Cys Tyr Phe Pro Tyr Leu Glu Asn Gly Tyr Asn Gln Asn
    370                 375                 380

Tyr Gly Arg Lys Phe Val Gln Gly Lys Ser Ile Asp Val Ala Cys His
385                 390                 395                 400

Pro Gly Tyr Ala Leu Pro Lys Ala Gln Thr Thr Val Thr Cys Met Glu
                405                 410                 415

Asn Gly Trp Ser Pro Thr Pro Arg Cys Ile Arg Val Ser Phe Thr Leu
            420                 425                 430

Gly Thr Glu Ala Thr Phe Cys Asp Phe Pro Lys Ile Asn His Gly Ile
        435                 440                 445

Leu Tyr Asp Glu Glu Lys Tyr Lys Pro Phe Ser Gln Val Pro Thr Gly
    450                 455                 460

Glu Val Phe Tyr Tyr Ser Cys Glu Tyr Asn Phe Val Ser Pro Ser Lys

```
             465                 470                 475                 480
Ser Phe Trp Thr Arg Ile Thr Cys Thr Glu Glu Gly Trp Ser Pro Thr
                485                 490                 495

Pro Lys Cys Leu Arg Leu Cys Phe Phe Pro Phe Val Glu Asn Gly His
                500                 505                 510

Ser Glu Ser Ser Gly Gln Thr His Leu Glu Gly Asp Thr Val Gln Ile
                515                 520                 525

Ile Cys Asn Thr Gly Tyr Arg Leu Gln Asn Asn Glu Asn Asn Ile Ser
                530                 535                 540

Cys Val Glu Arg Gly Trp Ser Thr Pro Pro Lys Cys Arg Ser Thr Asp
545                 550                 555                 560

Thr Ser

<210> SEQ ID NO 29
<211> LENGTH: 561
<212> TYPE: PRT
<213> ORGANISM: Homo sapiens

<400> SEQUENCE: 29

Glu Ala Thr Phe Cys Asp Phe Pro Lys Ile Asn His Gly Ile Leu Tyr
1               5                   10                  15

Asp Glu Glu Lys Tyr Lys Pro Phe Ser Gln Val Pro Thr Gly Glu Val
                20                  25                  30

Phe Tyr Tyr Ser Cys Glu Tyr Asn Phe Val Ser Pro Ser Lys Ser Phe
            35                  40                  45

Trp Thr Arg Ile Thr Cys Thr Glu Glu Gly Trp Ser Pro Thr Pro Lys
50                  55                  60

Cys Leu Arg Leu Cys Phe Phe Pro Phe Val Glu Asn Gly His Ser Glu
65                  70                  75                  80

Ser Ser Gly Gln Thr His Leu Glu Gly Asp Thr Val Gln Ile Ile Cys
                85                  90                  95

Asn Thr Gly Tyr Arg Leu Gln Asn Asn Glu Asn Asn Ile Ser Cys Val
                100                 105                 110

Glu Arg Gly Trp Ser Thr Pro Pro Lys Cys Arg Ser Thr Asp Thr Ser
            115                 120                 125

Val Asp Glu Asp Cys Asn Glu Leu Pro Pro Arg Arg Asn Thr Glu Ile
130                 135                 140

Leu Thr Gly Ser Trp Ser Asp Gln Thr Tyr Pro Glu Gly Thr Gln Ala
145                 150                 155                 160

Ile Tyr Lys Cys Arg Pro Gly Tyr Arg Ser Leu Gly Asn Ile Ile Met
                165                 170                 175

Val Cys Arg Lys Gly Glu Trp Val Ala Leu Asn Pro Leu Arg Lys Cys
                180                 185                 190

Gln Lys Arg Pro Cys Gly His Pro Gly Asp Thr Pro Phe Gly Thr Phe
            195                 200                 205

Thr Leu Thr Gly Gly Asn Val Phe Glu Tyr Gly Val Lys Ala Val Tyr
210                 215                 220

Thr Cys Asn Glu Gly Tyr Gln Leu Leu Gly Glu Ile Asn Tyr Arg Glu
225                 230                 235                 240

Cys Asp Thr Asp Gly Trp Thr Asn Asp Ile Pro Ile Cys Glu Val Val
                245                 250                 255

Lys Cys Leu Pro Val Thr Ala Pro Glu Asn Gly Lys Ile Val Ser Ser
                260                 265                 270

Ala Met Glu Pro Asp Arg Glu Tyr His Phe Gly Gln Ala Val Arg Phe
```

```
                275                 280                 285
Val Cys Asn Ser Gly Tyr Lys Ile Glu Gly Asp Glu Met His Cys
    290                 295                 300

Ser Asp Asp Gly Phe Trp Ser Lys Glu Lys Pro Lys Cys Val Glu Ile
305                 310                 315                 320

Ser Cys Lys Ser Pro Asp Val Ile Asn Gly Ser Pro Ile Ser Gln Lys
                325                 330                 335

Ile Ile Tyr Lys Glu Asn Glu Arg Phe Gln Tyr Lys Cys Asn Met Gly
            340                 345                 350

Tyr Glu Tyr Ser Glu Arg Gly Asp Ala Val Cys Thr Glu Ser Gly Trp
        355                 360                 365

Arg Pro Leu Pro Ser Cys Glu Lys Ser Cys Asp Asn Pro Tyr Ile
370                 375                 380

Pro Asn Gly Asp Tyr Ser Pro Leu Arg Ile Lys His Arg Thr Gly Asp
385                 390                 395                 400

Glu Ile Thr Tyr Gln Cys Arg Asn Gly Phe Tyr Pro Ala Thr Arg Gly
                405                 410                 415

Asn Thr Ala Lys Cys Thr Ser Thr Gly Trp Ile Pro Ala Pro Arg Cys
            420                 425                 430

Thr Ser Gly Ser Gly Gly Gly Gly Thr Lys His Gly Gly Leu Tyr
        435                 440                 445

His Glu Asn Met Arg Arg Pro Tyr Phe Pro Val Ala Val Gly Lys Tyr
    450                 455                 460

Tyr Ser Tyr Tyr Cys Asp Glu His Phe Glu Thr Pro Ser Gly Ser Tyr
465                 470                 475                 480

Trp Asp His Ile His Cys Thr Gln Asp Gly Trp Ser Pro Ala Val Pro
                485                 490                 495

Cys Leu Arg Lys Cys Tyr Phe Pro Tyr Leu Glu Asn Gly Tyr Asn Gln
            500                 505                 510

Asn Tyr Gly Arg Lys Phe Val Gln Gly Lys Ser Ile Asp Val Ala Cys
        515                 520                 525

His Pro Gly Tyr Ala Leu Pro Lys Ala Gln Thr Thr Val Thr Cys Met
    530                 535                 540

Glu Asn Gly Trp Ser Pro Thr Pro Arg Cys Ile Arg Val Ser Phe Thr
545                 550                 555                 560

Leu

<210> SEQ ID NO 30
<211> LENGTH: 7
<212> TYPE: PRT
<213> ORGANISM: Homo sapiens

<400> SEQUENCE: 30

Ser Gly Ser Gly Gly Gly Gly
1               5

<210> SEQ ID NO 31
<211> LENGTH: 9
<212> TYPE: PRT
<213> ORGANISM: Homo sapiens

<400> SEQUENCE: 31

Ser Gly Ser Gly Gly Gly Gly Gly Thr
1               5

<210> SEQ ID NO 32
```

```
<211> LENGTH: 9
<212> TYPE: PRT
<213> ORGANISM: Homo sapiens

<400> SEQUENCE: 32

Ser Gly Ser Gly Gly Gly Gly Val Asp
1               5

<210> SEQ ID NO 33
<211> LENGTH: 10
<212> TYPE: PRT
<213> ORGANISM: Homo sapiens

<400> SEQUENCE: 33

Ser Gly Ser Gly Gly Gly Gly Val Asp Thr
1               5                   10

<210> SEQ ID NO 34
<211> LENGTH: 29
<212> TYPE: DNA
<213> ORGANISM: Homo sapiens

<400> SEQUENCE: 34
gctctagaat gtggctcctg gtcagtgta                                  29

<210> SEQ ID NO 35
<211> LENGTH: 29
<212> TYPE: DNA
<213> ORGANISM: Homo sapiens

<400> SEQUENCE: 35
cgcgtcgacg gaagtgtcag tggacctgc                                  29

<210> SEQ ID NO 36
<211> LENGTH: 32
<212> TYPE: DNA
<213> ORGANISM: Homo sapiens

<400> SEQUENCE: 36
cgcgtcgacg aagattgcaa tgaacttcct cc                              32

<210> SEQ ID NO 37
<211> LENGTH: 25
<212> TYPE: DNA
<213> ORGANISM: Homo sapiens

<400> SEQUENCE: 37
ggggtacccc cacctcctcc cgaac                                      25

<210> SEQ ID NO 38
<211> LENGTH: 23
<212> TYPE: DNA
<213> ORGANISM: Homo sapiens

<400> SEQUENCE: 38
gctctagaat gtggctcctg gtc                                        23

<210> SEQ ID NO 39
<211> LENGTH: 17
<212> TYPE: DNA
<213> ORGANISM: Homo sapiens

<400> SEQUENCE: 39
ggggtacccc cacctcc                                               17
```

<210> SEQ ID NO 40
<211> LENGTH: 32
<212> TYPE: DNA
<213> ORGANISM: Homo sapiens

<400> SEQUENCE: 40
ggggtaccga agcaacattt tgtgattttc ca                                32

<210> SEQ ID NO 41
<211> LENGTH: 32
<212> TYPE: DNA
<213> ORGANISM: Homo sapiens

<400> SEQUENCE: 41
ctagctagct taggaagtgt cagtggacct gc                                32

<210> SEQ ID NO 42
<211> LENGTH: 30
<212> TYPE: DNA
<213> ORGANISM: Homo sapiens

<400> SEQUENCE: 42
cgcgtcgaca ccacctcctc atgtgtgaat                                   30

<210> SEQ ID NO 43
<211> LENGTH: 32
<212> TYPE: DNA
<213> ORGANISM: Homo sapiens

<400> SEQUENCE: 43
ggggtacctc ttttttgcaca agttggatac tc                               32

<210> SEQ ID NO 44
<211> LENGTH: 17
<212> TYPE: DNA
<213> ORGANISM: Homo sapiens

<400> SEQUENCE: 44
cgcgtcgaca ccacctc                                                 17

<210> SEQ ID NO 45
<211> LENGTH: 29
<212> TYPE: DNA
<213> ORGANISM: Homo sapiens

<400> SEQUENCE: 45
ctagctagct taggaagtgt cagtggacc                                    29

<210> SEQ ID NO 46
<211> LENGTH: 647
<212> TYPE: PRT
<213> ORGANISM: Homo sapiens

<400> SEQUENCE: 46

Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
                20                  25                  30

Leu Thr Gly Ser Trp Ser Asp Gln Thr Tyr Pro Glu Gly Thr Gln Ala
            35                  40                  45

Ile Tyr Lys Cys Arg Pro Gly Tyr Arg Ser Leu Gly Asn Ile Ile Met

-continued

```
            50                  55                  60
Val Cys Arg Lys Gly Glu Trp Val Ala Leu Asn Pro Leu Arg Lys Cys
 65                  70                  75                  80

Gln Lys Arg Pro Cys Gly His Pro Gly Asp Thr Pro Phe Gly Thr Phe
                 85                  90                  95

Thr Leu Thr Gly Gly Asn Val Phe Glu Tyr Gly Val Lys Ala Val Tyr
                100                 105                 110

Thr Cys Asn Glu Gly Tyr Gln Leu Leu Gly Glu Ile Asn Tyr Arg Glu
                115                 120                 125

Cys Asp Thr Asp Gly Trp Thr Asn Asp Ile Pro Ile Cys Glu Val Val
            130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
                180                 185                 190

Ser Asp Asp Gly Phe Trp Ser Lys Glu Lys Pro Lys Cys Val Glu Ile
            195                 200                 205

Ser Cys Lys Ser Pro Asp Val Ile Asn Gly Ser Pro Ile Ser Gln Lys
            210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
                245                 250                 255

Arg Pro Leu Pro Ser Cys Glu Glu Lys Ser Cys Asp Asn Pro Tyr Ile
                260                 265                 270

Pro Asn Gly Asp Tyr Ser Pro Leu Arg Ile Lys His Arg Thr Gly Asp
            275                 280                 285

Glu Ile Thr Tyr Gln Cys Arg Asn Gly Phe Tyr Pro Ala Thr Arg Gly
            290                 295                 300

Asn Thr Ala Lys Cys Thr Ser Thr Gly Trp Ile Pro Ala Pro Arg Cys
305                 310                 315                 320

Thr Ser Gly Ser Gly Gly Gly Val Asp Thr Thr Ser Cys Val Asn
                325                 330                 335

Pro Pro Thr Val Gln Asn Ala Tyr Ile Val Ser Arg Gln Met Ser Lys
                340                 345                 350

Tyr Pro Ser Gly Glu Arg Val Arg Tyr Gln Cys Arg Ser Pro Tyr Glu
                355                 360                 365

Met Phe Gly Asp Glu Glu Val Met Cys Leu Asn Gly Asn Trp Thr Glu
            370                 375                 380

Pro Pro Gln Cys Lys Asp Ser Thr Gly Lys Cys Gly Pro Pro Pro
385                 390                 395                 400

Ile Asp Asn Gly Asp Ile Thr Ser Phe Pro Leu Ser Val Tyr Ala Pro
                405                 410                 415

Ala Ser Ser Val Glu Tyr Gln Cys Gln Asn Leu Tyr Gln Leu Glu Gly
                420                 425                 430

Asn Lys Arg Ile Thr Cys Arg Asn Gly Gln Trp Ser Glu Pro Pro Lys
            435                 440                 445

Cys Leu His Pro Cys Val Ile Ser Arg Glu Ile Met Glu Asn Tyr Asn
            450                 455                 460

Ile Ala Leu Arg Trp Thr Ala Lys Gln Lys Leu Tyr Ser Arg Thr Gly
465                 470                 475                 480
```

```
Glu Ser Val Glu Phe Val Cys Lys Arg Gly Tyr Arg Leu Ser Ser Arg
                485                 490                 495

Ser His Thr Leu Arg Thr Thr Cys Trp Asp Gly Lys Leu Glu Tyr Pro
            500                 505                 510

Thr Cys Ala Lys Arg Gly Thr Glu Ala Thr Phe Cys Asp Phe Pro Lys
        515                 520                 525

Ile Asn His Gly Ile Leu Tyr Asp Glu Glu Lys Tyr Lys Pro Phe Ser
    530                 535                 540

Gln Val Pro Thr Gly Glu Val Phe Tyr Tyr Ser Cys Glu Tyr Asn Phe
545                 550                 555                 560

Val Ser Pro Ser Lys Ser Phe Trp Thr Arg Ile Thr Cys Thr Glu Glu
                565                 570                 575

Gly Trp Ser Pro Thr Pro Lys Cys Leu Arg Leu Cys Phe Phe Pro Phe
            580                 585                 590

Val Glu Asn Gly His Ser Glu Ser Ser Gly Gln Thr His Leu Glu Gly
        595                 600                 605

Asp Thr Val Gln Ile Ile Cys Asn Thr Gly Tyr Arg Leu Gln Asn Asn
    610                 615                 620

Glu Asn Asn Ile Ser Cys Val Glu Arg Gly Trp Ser Thr Pro Pro Lys
625                 630                 635                 640

Cys Arg Ser Thr Asp Thr Ser
                645

<210> SEQ ID NO 47
<211> LENGTH: 646
<212> TYPE: PRT
<213> ORGANISM: Homo sapiens

<400> SEQUENCE: 47

Met Trp Leu Leu Val Ser Val Ile Leu Ile Ser Arg Ile Ser Ser Val
1               5                   10                  15

Gly Gly Glu Ala Thr Phe Cys Asp Phe Pro Lys Ile Asn His Gly Ile
            20                  25                  30

Leu Tyr Asp Glu Glu Lys Tyr Lys Pro Phe Ser Gln Val Pro Thr Gly
        35                  40                  45

Glu Val Phe Tyr Tyr Ser Cys Glu Tyr Asn Phe Val Ser Pro Ser Lys
    50                  55                  60

Ser Phe Trp Thr Arg Ile Thr Cys Thr Glu Glu Gly Trp Ser Pro Thr
65                  70                  75                  80

Pro Lys Cys Leu Arg Leu Cys Phe Phe Pro Phe Val Glu Asn Gly His
                85                  90                  95

Ser Glu Ser Ser Gly Gln Thr His Leu Glu Gly Asp Thr Val Gln Ile
            100                 105                 110

Ile Cys Asn Thr Gly Tyr Arg Leu Gln Asn Asn Glu Asn Asn Ile Ser
        115                 120                 125

Cys Val Glu Arg Gly Trp Ser Thr Pro Pro Lys Cys Arg Ser Thr Asp
    130                 135                 140

Thr Ser Val Asp Glu Asp Cys Asn Glu Leu Pro Pro Arg Arg Asn Thr
145                 150                 155                 160

Glu Ile Leu Thr Gly Ser Trp Ser Asp Gln Thr Tyr Pro Glu Gly Thr
                165                 170                 175

Gln Ala Ile Tyr Lys Cys Arg Pro Gly Tyr Arg Ser Leu Gly Asn Ile
            180                 185                 190

Ile Met Val Cys Arg Lys Gly Glu Trp Val Ala Leu Asn Pro Leu Arg
```

```
            195                 200                 205
Lys Cys Gln Lys Arg Pro Cys Gly His Pro Gly Asp Thr Pro Phe Gly
210                 215                 220

Thr Phe Thr Leu Thr Gly Gly Asn Val Phe Glu Tyr Gly Val Lys Ala
225                 230                 235                 240

Val Tyr Thr Cys Asn Glu Gly Tyr Gln Leu Leu Gly Glu Ile Asn Tyr
                    245                 250                 255

Arg Glu Cys Asp Thr Asp Gly Trp Thr Asn Asp Ile Pro Ile Cys Glu
                260                 265                 270

Val Val Lys Cys Leu Pro Val Thr Ala Pro Glu Asn Gly Lys Ile Val
            275                 280                 285

Ser Ser Ala Met Glu Pro Asp Arg Glu Tyr His Phe Gly Gln Ala Val
290                 295                 300

Arg Phe Val Cys Asn Ser Gly Tyr Lys Ile Glu Gly Asp Glu Glu Met
305                 310                 315                 320

His Cys Ser Asp Asp Gly Phe Trp Ser Lys Glu Lys Pro Lys Cys Val
                    325                 330                 335

Glu Ile Ser Cys Lys Ser Pro Asp Val Ile Asn Gly Ser Pro Ile Ser
                340                 345                 350

Gln Lys Ile Ile Tyr Lys Glu Asn Glu Arg Phe Gln Tyr Lys Cys Asn
            355                 360                 365

Met Gly Tyr Glu Tyr Ser Glu Arg Gly Asp Ala Val Cys Thr Glu Ser
370                 375                 380

Gly Trp Arg Pro Leu Pro Ser Cys Glu Lys Ser Cys Asp Asn Pro
385                 390                 395                 400

Tyr Ile Pro Asn Gly Asp Tyr Ser Pro Leu Arg Ile Lys His Arg Thr
                    405                 410                 415

Gly Asp Glu Ile Thr Tyr Gln Cys Arg Asn Gly Phe Tyr Pro Ala Thr
                420                 425                 430

Arg Gly Asn Thr Ala Lys Cys Thr Ser Thr Gly Trp Ile Pro Ala Pro
            435                 440                 445

Arg Cys Thr Ser Gly Ser Gly Gly Gly Gly Thr Thr Ser Cys Val
450                 455                 460

Asn Pro Pro Thr Val Gln Asn Ala Tyr Ile Val Ser Arg Gln Met Ser
465                 470                 475                 480

Lys Tyr Pro Ser Gly Glu Arg Val Arg Tyr Gln Cys Arg Ser Pro Tyr
                    485                 490                 495

Glu Met Phe Gly Asp Glu Glu Val Met Cys Leu Asn Gly Asn Trp Thr
                500                 505                 510

Glu Pro Pro Gln Cys Lys Asp Ser Thr Gly Lys Cys Gly Pro Pro Pro
            515                 520                 525

Pro Ile Asp Asn Gly Asp Ile Thr Ser Phe Pro Leu Ser Val Tyr Ala
530                 535                 540

Pro Ala Ser Ser Val Glu Tyr Gln Cys Gln Asn Leu Tyr Gln Leu Glu
545                 550                 555                 560

Gly Asn Lys Arg Ile Thr Cys Arg Asn Gly Gln Trp Ser Glu Pro Pro
                    565                 570                 575

Lys Cys Leu His Pro Cys Val Ile Ser Arg Glu Ile Met Glu Asn Tyr
                580                 585                 590

Asn Ile Ala Leu Arg Trp Thr Ala Lys Gln Lys Leu Tyr Ser Arg Thr
            595                 600                 605

Gly Glu Ser Val Glu Phe Val Cys Lys Arg Gly Tyr Arg Leu Ser Ser
610                 615                 620
```

Arg Ser His Thr Leu Arg Thr Thr Cys Trp Asp Gly Lys Leu Glu Tyr
625                 630                 635                 640

Pro Thr Cys Ala Lys Arg
                645

<210> SEQ ID NO 48
<211> LENGTH: 580
<212> TYPE: PRT
<213> ORGANISM: Homo sapiens

<400> SEQUENCE: 48

Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
                20                  25                  30

Leu Thr Gly Ser Trp Ser Asp Gln Thr Tyr Pro Glu Gly Thr Gln Ala
            35                  40                  45

Ile Tyr Lys Cys Arg Pro Gly Tyr Arg Ser Leu Gly Asn Ile Ile Met
    50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
            100                 105                 110

Thr Cys Asn Glu Gly Tyr Gln Leu Leu Gly Glu Ile Asn Tyr Arg Glu
    115                 120                 125

Cys Asp Thr Asp Gly Trp Thr Asn Asp Ile Pro Ile Cys Glu Val Val
130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
            180                 185                 190

Ser Asp Asp Gly Phe Trp Ser Lys Glu Lys Pro Lys Cys Val Glu Ile
    195                 200                 205

Ser Cys Lys Ser Pro Asp Val Ile Asn Gly Ser Pro Ile Ser Gln Lys
210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
                245                 250                 255

Arg Pro Leu Pro Ser Cys Glu Glu Lys Ser Cys Asp Asn Pro Tyr Ile
            260                 265                 270

Pro Asn Gly Asp Tyr Ser Pro Leu Arg Ile Lys His Arg Thr Gly Asp
    275                 280                 285

Glu Ile Thr Tyr Gln Cys Arg Asn Gly Phe Tyr Pro Ala Thr Arg Gly
290                 295                 300

Asn Thr Ala Lys Cys Thr Ser Thr Gly Trp Ile Pro Ala Pro Arg Cys
305                 310                 315                 320

Thr Ser Gly Ser Gly Gly Gly Val Asp Thr Lys His Gly Gly Leu
                325                 330                 335

Tyr His Glu Asn Met Arg Arg Pro Tyr Phe Pro Val Ala Val Gly Lys

```
                340             345             350
Tyr Tyr Ser Tyr Tyr Cys Asp Glu His Phe Glu Thr Pro Ser Gly Ser
            355             360             365

Tyr Trp Asp His Ile His Cys Thr Gln Asp Gly Trp Ser Pro Ala Val
            370             375             380

Pro Cys Leu Arg Lys Cys Tyr Phe Pro Tyr Leu Glu Asn Gly Tyr Asn
385             390             395             400

Gln Asn Tyr Gly Arg Lys Phe Val Gln Gly Lys Ser Ile Asp Val Ala
            405             410             415

Cys His Pro Gly Tyr Ala Leu Pro Lys Ala Gln Thr Thr Val Thr Cys
            420             425             430

Met Glu Asn Gly Trp Ser Pro Thr Pro Arg Cys Ile Arg Val Ser Phe
            435             440             445

Thr Leu Gly Thr Glu Ala Thr Phe Cys Asp Phe Pro Lys Ile Asn His
            450             455             460

Gly Ile Leu Tyr Asp Glu Glu Lys Tyr Lys Pro Phe Ser Gln Val Pro
465             470             475             480

Thr Gly Glu Val Phe Tyr Tyr Ser Cys Glu Tyr Asn Phe Val Ser Pro
            485             490             495

Ser Lys Ser Phe Trp Thr Arg Ile Thr Cys Thr Glu Gly Trp Ser
            500             505             510

Pro Thr Pro Lys Cys Leu Arg Leu Cys Phe Phe Pro Phe Val Glu Asn
            515             520             525

Gly His Ser Glu Ser Ser Gly Gln Thr His Leu Glu Gly Asp Thr Val
            530             535             540

Gln Ile Ile Cys Asn Thr Gly Tyr Arg Leu Gln Asn Asn Glu Asn Asn
545             550             555             560

Ile Ser Cys Val Glu Arg Gly Trp Ser Thr Pro Pro Lys Cys Arg Ser
            565             570             575

Thr Asp Thr Ser
            580

<210> SEQ ID NO 49
<211> LENGTH: 579
<212> TYPE: PRT
<213> ORGANISM: Homo sapiens

<400> SEQUENCE: 49

Met Trp Leu Leu Val Ser Val Ile Leu Ile Ser Arg Ile Ser Ser Val
1               5               10              15

Gly Gly Glu Ala Thr Phe Cys Asp Phe Pro Lys Ile Asn His Gly Ile
            20              25              30

Leu Tyr Asp Glu Glu Lys Tyr Lys Pro Phe Ser Gln Val Pro Thr Gly
            35              40              45

Glu Val Phe Tyr Tyr Ser Cys Glu Tyr Asn Phe Val Ser Pro Ser Lys
            50              55              60

Ser Phe Trp Thr Arg Ile Thr Cys Thr Glu Glu Gly Trp Ser Pro Thr
65              70              75              80

Pro Lys Cys Leu Arg Leu Cys Phe Phe Pro Phe Val Glu Asn Gly His
            85              90              95

Ser Glu Ser Ser Gly Gln Thr His Leu Glu Gly Asp Thr Val Gln Ile
            100             105             110

Ile Cys Asn Thr Gly Tyr Arg Leu Gln Asn Asn Glu Asn Asn Ile Ser
            115             120             125
```

```
Cys Val Glu Arg Gly Trp Ser Thr Pro Pro Lys Cys Arg Ser Thr Asp
    130                 135                 140
Thr Ser Val Asp Glu Asp Cys Asn Glu Leu Pro Pro Arg Arg Asn Thr
145                 150                 155                 160
Glu Ile Leu Thr Gly Ser Trp Ser Asp Gln Thr Tyr Pro Glu Gly Thr
                165                 170                 175
Gln Ala Ile Tyr Lys Cys Arg Pro Gly Tyr Arg Ser Leu Gly Asn Ile
                180                 185                 190
Ile Met Val Cys Arg Lys Gly Glu Trp Val Ala Leu Asn Pro Leu Arg
                195                 200                 205
Lys Cys Gln Lys Arg Pro Cys Gly His Pro Gly Asp Thr Pro Phe Gly
    210                 215                 220
Thr Phe Thr Leu Thr Gly Gly Asn Val Phe Glu Tyr Gly Val Lys Ala
225                 230                 235                 240
Val Tyr Thr Cys Asn Glu Gly Tyr Gln Leu Leu Gly Glu Ile Asn Tyr
                245                 250                 255
Arg Glu Cys Asp Thr Asp Gly Trp Thr Asn Asp Ile Pro Ile Cys Glu
                260                 265                 270
Val Val Lys Cys Leu Pro Val Thr Ala Pro Glu Asn Gly Lys Ile Val
    275                 280                 285
Ser Ser Ala Met Glu Pro Asp Arg Glu Tyr His Phe Gly Gln Ala Val
    290                 295                 300
Arg Phe Val Cys Asn Ser Gly Tyr Lys Ile Glu Gly Asp Glu Glu Met
305                 310                 315                 320
His Cys Ser Asp Asp Gly Phe Trp Ser Lys Glu Lys Pro Lys Cys Val
                325                 330                 335
Glu Ile Ser Cys Lys Ser Pro Asp Val Ile Asn Gly Ser Pro Ile Ser
                340                 345                 350
Gln Lys Ile Ile Tyr Lys Glu Asn Glu Arg Phe Gln Tyr Lys Cys Asn
    355                 360                 365
Met Gly Tyr Glu Tyr Ser Glu Arg Gly Asp Ala Val Cys Thr Glu Ser
    370                 375                 380
Gly Trp Arg Pro Leu Pro Ser Cys Glu Glu Lys Ser Cys Asp Asn Pro
385                 390                 395                 400
Tyr Ile Pro Asn Gly Asp Tyr Ser Pro Leu Arg Ile Lys His Arg Thr
                405                 410                 415
Gly Asp Glu Ile Thr Tyr Gln Cys Arg Asn Gly Phe Tyr Pro Ala Thr
                420                 425                 430
Arg Gly Asn Thr Ala Lys Cys Thr Ser Thr Gly Trp Ile Pro Ala Pro
                435                 440                 445
Arg Cys Thr Ser Gly Ser Gly Gly Gly Gly Thr Lys His Gly Gly
    450                 455                 460
Leu Tyr His Glu Asn Met Arg Arg Pro Tyr Phe Pro Val Ala Val Gly
465                 470                 475                 480
Lys Tyr Tyr Ser Tyr Tyr Cys Asp Glu His Phe Glu Thr Pro Ser Gly
                485                 490                 495
Ser Tyr Trp Asp His Ile His Cys Thr Gln Asp Gly Trp Ser Pro Ala
                500                 505                 510
Val Pro Cys Leu Arg Lys Cys Tyr Phe Pro Tyr Leu Glu Asn Gly Tyr
    515                 520                 525
Asn Gln Asn Tyr Gly Arg Lys Phe Val Gln Gly Lys Ser Ile Asp Val
    530                 535                 540
Ala Cys His Pro Gly Tyr Ala Leu Pro Lys Ala Gln Thr Thr Val Thr
```

```
                545                 550                 555                 560
Cys Met Glu Asn Gly Trp Ser Pro Thr Pro Arg Cys Ile Arg Val Ser
                    565                 570                 575

Phe Thr Leu

<210> SEQ ID NO 50
<211> LENGTH: 8
<212> TYPE: PRT
<213> ORGANISM: Artificial Sequence
<220> FEATURE:
<223> OTHER INFORMATION: linker sequence H6GT

<400> SEQUENCE: 50

His His His His His His Gly Thr
1               5

<210> SEQ ID NO 51
<211> LENGTH: 9
<212> TYPE: PRT
<213> ORGANISM: Artificial Sequence
<220> FEATURE:
<223> OTHER INFORMATION: linker sequence SGSG4GT

<400> SEQUENCE: 51

Ser Gly Ser Gly Gly Gly Gly Gly Thr
1               5

<210> SEQ ID NO 52
<211> LENGTH: 10
<212> TYPE: PRT
<213> ORGANISM: Artificial Sequence
<220> FEATURE:
<223> OTHER INFORMATION: SGSG4VDT

<400> SEQUENCE: 52

Ser Gly Ser Gly Gly Gly Gly Val Asp Thr
1               5                   10

<210> SEQ ID NO 53
<211> LENGTH: 31
<212> TYPE: DNA
<213> ORGANISM: Homo sapiens

<400> SEQUENCE: 53
ggggtaccac cttgaaacct tgtgattatc c                              31

<210> SEQ ID NO 54
<211> LENGTH: 30
<212> TYPE: DNA
<213> ORGANISM: Homo sapiens

<400> SEQUENCE: 54
ctagctagct cagagggtaa agctgacacg                                30

<210> SEQ ID NO 55
<211> LENGTH: 33
<212> TYPE: DNA
<213> ORGANISM: Homo sapiens

<400> SEQUENCE: 55
acgcgtcgac accttgaaac cttgtgatta tcc                            33

<210> SEQ ID NO 56
<211> LENGTH: 29
```

-continued

```
<212> TYPE: DNA
<213> ORGANISM: Homo sapiens

<400> SEQUENCE: 56
ggggtaccga gggtaaagct gacacggat                                29
```

MODIFIED COMPLEMENT PROTEINS AND USES THEREOF

FIELD OF INVENTION

Certain embodiments of the present invention relate to regulation of the innate immune system and complement activation. In particular, but not exclusively certain embodiments relate to a complement regulator protein and pharmaceutical compositions thereof for use in the treatment of diseases associated with or mediated by the alternative complement pathway and methods of treating such diseases and other subject matter.

Work resulting in this invention was funded by Kidney Research UK.

BACKGROUND

The complement system is a part of the innate immune system which is involved in response to and clearance of foreign pathogens, such as microbes as well as abnormal host cells. The complement system and its inappropriate activation plays an important role in a number disease states and disorders associated with autoimmunity, inflammation and biocompatibility as well as a number of other pathologies.

The complement system consists of several blood proteins and can be activated by one of three pathways, the lectin pathway, the classical pathway and the alternative pathway. The alternative pathway is constantly active in a so called "tick over" state. When a pathogen such as a microbe or abnormal cell is present that does not express, display or contain inhibitors or regulator proteins of the alternative pathway, this leads to an amplification loop causing rapid and acute activation of the alternative pathway.

Initiation of the alternative pathway occurs by a spontaneous hydrolysis of fluid-phase C3 to C3($H_2O$) a partially active form of C3b known as a C3b-like molecule (also known as iC3) which has a C3a part still attached. Conversion to the C3b-like state allows the binding of fluid-phase factor B, forming a complex. This complex is then cleaved by fluid phase factor D to yield the factor B fragments Ba and Bb. Bb remains bound to the C3($H_2O$) forming enzymatically active C3($H_2O$) Bb also known as the initiation C3 convertase. C3($H_2O$) Bb cleaves further C3 molecules into two fragments C3b and C3a. This cleavage exposes an internal thioester-containing domain (TED) of C3b which allows C3b to covalently bind to a target such as the surface of a foreign cell or any nearby nucleophile. C3b bound to a target at a surface, binds with factor B and is further cleaved by factor D to form the C3 convertase C3bBb (also known as the amplification C3 convertase) which is able to cleave further C3 molecules to C3b and C3a fragments. This initiates the amplification process by formation of more C3b molecules resulting in further C3bBb and further C3b which binds to a target forming a positive feedback loop. This opsonisation by C3b can lead to a number of responses such as inflammation, phagocytosis and membrane attack of a targeted cell. The relatively short-lived reactivity of surface bound C3b means that that alternative pathway activation is limited to a localised environment.

As this process is spontaneous the deposition of C3b on host cells must be regulated to prevent damage to host cells and tissues. Most host cells are protected by proteins of the regulator of complement activation (RCA) family such as the cell surface-bound RCA proteins, decay accelerating factor (DAF (A000571); also called CD55), membrane co-factor protein (MCP (A000568); also called CD46) and complement receptor 1 (CR1; also called CD35), which act through several mechanisms. The RCA family also includes the soluble protein Complement Factor H (FH).

FH is one the principle regulators of the alternative pathway. FH is a single-chain, 150-kDa glycoprotein composed of 20 domains. These are termed short consensus repeats (SCRs) or complement control protein (CCPs) domains. Each of these autonomously folding globular domains is composed of approximately 60 amino acids held together by four conserved cysteine residues. FH regulates complement activation by (i) inhibiting the assembly of the alternative pathway C3 convertase enzymes via competition with factor B for C3b binding; (ii) facilitating the disassembly of the C3 convertases by displacing bound factor Bb ('decay accelerating activity'); and (iii) acting as a cofactor for the serine protease factor I in the cleavage and inactivation of C3b ('cofactor activity'). These complement regulatory activities are partly mediated by the N-terminal CCP domains, while the C-terminal CCP domains and some of the central CCP domains are believed to be responsible for target recognition. One of the important targets for factor H binding in the vicinity of C3b on host cells are polyanionic surface molecules, such as glycosaminoglycans and sialic acid, which increase the affinity of factor H for C3b. Thus, in addition to its regulatory activities in the fluid-phase, FH is also able to control complement activation on host surfaces. In contrast, host-like polyanionic molecules are normally not present on the surface of pathogens, rendering them susceptible to complement attack. The FH protein is member of a family of highly related proteins that includes the five Complement Factor H Related proteins, FHR1, FHR2, FHR3, FHR4, FHR5, the spliced variant factor H-like protein 1 (FHL-1) and FH. Each single gene of the family members (CFHR1, CFHR2, CFHR3, CFHR4, CFHR5 and factor H) is located on a distinct segment on human chromosome 1q32 within the RCA gene cluster.

The incorrect functioning of FH, which may occur due polymorphisms or mutations of the FH encoding gene, and subsequent dysfunctional regulation of the alternative pathway has been associated with a number of diseases such as age-related macular degeneration (AMD), atypical haemolytic uremic syndrome (aHUS), paroxysomal nocturnal haemoglobinuria (PNH), C3 Glomerulopathies and lupus nephritis. Complement regulation has also been associated with a wide range of diseases and disorders such as for example autoimmune disease, asthma and inflammation related diseases.

FH has also been associated with the attenuation of oxidative stress. FH CCP domains 7 and 20 have been demonstrated to be able to bind to the common lipid peroxidation product malondialdehyde (MDA), which is associated with many pathological processes such as AMD. FH is able to bind MDA-modified proteins and block the uptake of these proteins by macrophages and help prevent MDA induced inflammatory responses.

Prior art therapeutics have been directed at complement regulation but suffer from a number of disadvantages. Eculizumab (used for the treatment of PNH and aHUS) inhibits complement at a later stage and has been associated with side effects such as residual anaemia and increased susceptibility to infection. Another alternative treatment of aHUS has been plasma transfusion which has the disadvantages of requiring large amounts of plasma to be used which can lead to high costs, circulatory overload and may lead to the need for dialysis. A further disadvantage is the risk of functional FH polymorphisms which can mean that the function of 'normal FH' may be affected and lead to worsening of a patient by unknown mechanisms related to mixed FH variants in donated plasma.

Truncated forms of FH (referred to as mini-FH or mini-CFH) have been developed as described in WO2013142362. These truncated forms of FH are composed of certain CCP domains of FH which retain the functional binding and activity of a full-size FH held together by a flexible linker. Even though these mini-FH proteins were seen as promising therapeutics, the half-life of the mini-FH proteins, for example in plasma or serum, was short (about 6 to 9 hours) meaning that the mini-FH molecules were not as effective as expected.

It is an aim of certain embodiments of the present invention to at least partly mitigate the above-mentioned problems.

It is an aim of certain embodiments of the present invention to provide a complement regulator protein with improved serum stability and/or improved serum half-life.

It is an aim of certain embodiments of the present invention to provide a complement regulator protein with reduced risk of functional FH polymorphisms.

It is an aim of certain embodiments of the present invention to provide a treatment for complement-related disorders.

BRIEF SUMMARY OF CERTAIN EMBODIMENTS

According to a first aspect of the present invention, there is provided a recombinant complement regulator protein, comprising;
a) at least one complement interaction region operable to regulate complement and bind the complement regulator protein to at least one target, the complement interaction region comprising;
   (i) at least one Factor H (FH) fragment; and
b) at least one dimerization region operable to dimerize the complement regulator protein.

In certain embodiments, the at least one FH fragment comprises at least one FH complement control protein domain (CCP). Aptly, the at least one FH fragment is not a full-length FH protein.

As used herein, the term "FH fragment" refers to a peptide molecule having an amino acid sequence derived from an FH protein. The peptide may have an amino acid sequence which is derived from a plurality of fragments of the FH protein which are not necessarily contiguous in a wild-type FH protein.

In certain embodiments, the at least one FH fragment comprises one or more of a FH CCP1 domain (SEQ ID NO: 9), a FH CCP2 domain (SEQ ID NO: 10), a FH CCP3 domain (SEQ ID NO: 11), a FH CCP4 domain (SEQ ID NO: 12), a FH CCP5 domain (SEQ ID NO: 13), a FH CCP6 domain (SEQ ID NO: 14) and/or a FH CCP7 domain (SEQ ID NO: 15).

In certain embodiments, the at least one FH fragment comprises a FH CCP1 domain (SEQ ID NO: 9), a FH CCP2 domain (SEQ ID NO: 10), a FH CCP3 domain (SEQ ID NO: 11) and a FH CCP4 domain (SEQ ID NO: 12).

In certain embodiments, the at least one FH fragment comprises a FH CCP1 domain (SEQ ID NO: 9), a FH CCP2 domain (SEQ ID NO: 10), a FH CCP3 domain (SEQ ID NO: 11), a FH CCP4 domain (SEQ ID NO: 12) and a FH CCP5 domain (SEQ ID NO: 13).

In certain embodiments, the dimerization region comprises at least one Factor H Related protein (FHR) CCP domain.

In certain embodiments, the at least one FHR CCP domain of the dimerization region is selected from a complement Factor H Related Protein 1 (FHR1) CCP1 domain (SEQ ID NO: 24), a FHR1 CCP2 domain (SEQ ID NO: 25), and combinations thereof.

In certain embodiments, the dimerization region comprises a FHR1 CCP1 domain (SEQ ID NO: 24) and a FHR1 CCP2 domain (SEQ ID NO: 25).

In certain embodiments, the at least one complement interaction region further comprises at least one further FH fragment operable to bind the complement regulator protein to the at least one target and/or at least one further target. In certain embodiments, the at least one further FH fragment comprises at least one further FH CCP domain.

In certain embodiments, the at least one further FH fragment comprises one or more of a FH CCP18 domain (SEQ ID NO: 16), a FH CCP19 domain (SEQ ID NO: 17) and/or a FH CCP20 domain (SEQ ID NO: 18). In certain embodiments, the at least one further FH fragment comprises a FH CCP18 domain (SEQ ID NO: 16), a FH CCP19 domain (SEQ ID NO: 17) and a FH CCP20 domain (SEQ ID NO: 18).

In certain embodiments, the at least one complement interaction region further comprises at least one Factor H Related protein (FHR) fragment operable to bind the complement regulator protein to the at least one target and/or at least one further target.

As used herein, the term "FHR fragment" refers to a peptide molecule having an amino acid sequence derived from an FHR protein. The peptide may have an amino acid sequence which is derived from a plurality of fragments of the FHR protein which are not necessarily contiguous in a wild-type FHR protein.

In certain embodiments, the at least one FHR fragment comprises at least one FHR5 CCP domain. In certain embodiments, the at least one FHR5 CCP domain comprises one or more of a FHR5 CCP7 domain (SEQ ID NO: 19), a FHR5 CCP8 domain (SEQ ID NO: 20), and/or a FHR5 CCP9 domain (SEQ ID NO: 21). In certain embodiments, the at least one FHR fragment comprises a FHR5 CCP7 domain (SEQ ID NO: 19), a FHR5 CCP8 domain (SEQ ID NO: 20), and a FHR5 CCP9 domain (SEQ ID NO: 21).

In certain embodiments, the at least one FHR fragment comprises a FHR5 CCP8 domain (SEQ ID NO: 20) and a FHR5 CCP9 domain (SEQ ID NO: 21).

In certain embodiments, the at least one complement interaction region further comprises at least one complement Factor H-Like protein (FHL) fragment operable to bind the complement regulator protein to the at least one target and/or at least one further target.

In certain embodiments, the at least one FHL fragment comprises at least one FHL-1 CCP domain. In certain embodiments, the at least one FHL-1 CCP domain comprises one or more of a FHL-1 CCP6 domain (SEQ ID NO: 22) and/or a FHL-1 CCP7 domain (SEQ ID NO: 23). In certain embodiments, the at least one FHL CCP domain comprises a FHL-1 CCP6 domain (SEQ ID NO: 22) and a FHL-1 CCP7 domain (SEQ ID NO: 23).

In certain embodiments, the at least one FH fragment is derived from human FH. In certain embodiments, the at least one further FH fragment is derived from human FH. In certain embodiments, the at least one FH fragment and/or further FH fragment are derived from human FH.

In certain embodiments, the at least one FHR fragment of the complement interaction region is derived from one or more human FHRs. In certain embodiments, the at least one FHR CCP domain of the dimerization region is derived from one or more human FHRs.

In certain embodiments, the at least one FHR fragment of the complement interaction region and/or the at least one FHR CCP domain of the dimerization region are each derived from one or more human FHRs.

In certain embodiments, the at least one FHL fragment is derived from human FHL-1.

In certain embodiments, the complement regulator protein further comprises at least one linker molecule. In certain embodiments, the complement regulator protein further comprises at least one further linker molecule.

In certain embodiments, the at least one linker and/or further linker molecules are independently selected from one or more linker molecules comprising: an amino acid sequence as set forth in SEQ ID NO:30; an amino acid sequence as set forth in SEQ ID NO: 31; an amino acid sequence as set forth in SEQ ID NO: 32; an amino acid sequence as set forth in SEQ ID NO: 33; Glycine and Threonine (GT); Valine and Aspartic acid (VD); and/or Valine, Aspartic acid and Threonine (VDT).

In certain embodiments, the complement regulator protein comprises from N-terminal to C-terminal, a FH CCP1 domain (SEQ ID NO: 9), a FH CCP2 domain (SEQ ID NO: 10), a FH CCP3 domain (SEQ ID NO: 11), a FH CCP4 domain (SEQ ID NO: 12), a FH CCP5 domain (SEQ ID NO: 13), optionally at least one linker molecule, a FH CCP18 domain (SEQ ID NO: 16), a FH CCP19 domain (SEQ ID NO: 17), a FH CCP20 domain (SEQ ID NO: 18), optionally at least one linker molecule, a FHR1 CCP1 domain (SEQ ID NO: 24) and a FHR1 CCP2 domain (SEQ ID NO: 25). Aptly, each of the aforesaid domains are derived from a human protein.

In certain embodiments, the complement regulator protein comprises an amino acid sequence which has at least 80% sequence identity to the amino acid sequence as set forth in SEQ ID NO: 26, and optionally at least 90%, e.g. 95%, 96%, 97%, 98% or 99% sequence identity to the amino acid sequence as set forth in SEQ ID NO: 26.

In certain embodiments, the complement regulator protein comprises from N-terminal to C-terminal, a FHR1 CCP1 domain (SEQ ID NO: 24), a FHR1 CCP2 domain (SEQ ID NO: 25), optionally at least one linker molecule, a FH CCP1 domain (SEQ ID NO: 9), a FH CCP2 domain (SEQ ID NO: 10), a FH CCP3 domain (SEQ ID NO: 11), a FH CCP4 domain (SEQ ID NO: 12), a FH CCP5 domain (SEQ ID NO: 13), optionally at least one linker molecule, a FH CCP18 domain (SEQ ID NO: 16), a FH CCP19 domain (SEQ ID NO: 17) and a FH CCP20 domain (SEQ ID NO: 18).

In certain embodiments, the complement regulator protein comprises an amino acid sequence which has at least 80% sequence identity to the amino acid sequence as set forth in SEQ ID NO: 27 and optionally at least 90%, e.g. 95%, 96%, 97%, 98% or 99% sequence identity to the amino acid sequence as set forth in SEQ ID NO: 27.

In certain embodiments, the complement regulator protein comprises from N-terminal to C-terminal, a FH CCP1 domain (SEQ ID NO: 9), a FH CCP2 domain (SEQ ID NO: 10), a FH CCP3 domain (SEQ ID NO: 11), a FH CCP4 domain (SEQ ID NO: 12), a FH CCP5 domain (SEQ ID NO: 13), optionally at least one linker molecule, a FHL-1 CCP6 domain (SEQ ID NO: 22), a FHL-1 CCP7 domain (SEQ ID NO: 23), optionally at least one linker molecule, a FHR1 CCP1 domain (SEQ ID NO: 24) and a FHR1 CCP2 domain (SEQ ID NO: 25). Aptly, each of the aforesaid domains are derived from a human protein.

In certain embodiments, the complement regulator protein comprises an amino acid sequence which has at least 80% sequence identity to the amino acid sequence as set forth in SEQ ID NO: 28 and optionally at least 90%, e.g. 95%, 96%, 97%, 98% or 99% sequence identity to the amino acid sequence as set forth in SEQ ID NO: 28.

In certain embodiments, the complement regulator protein comprises from N-terminal to C-terminal, a FHR1 CCP1 domain (SEQ ID NO: 24), a FHR1 CCP2 domain (SEQ ID NO: 25), optionally at least one linker molecule, a FH CCP1 domain (SEQ ID NO: 9), a FH CCP2 domain (SEQ ID NO: 10), a FH CCP3 domain (SEQ ID NO: 11), a FH CCP4 domain (SEQ ID NO: 12), a FH CCP5 domain (SEQ ID NO: 13), optionally at least one linker molecule, a FHL-1 CCP6 domain (SEQ ID NO: 22) and a FHL-1 CCP7 domain (SEQ ID NO: 23). Aptly, each of the aforesaid domains are derived from a human protein.

In certain embodiments, the complement regulator protein comprises an amino acid sequence which has at least 80% sequence identity to the amino acid sequence as set forth in SEQ ID NO: 29 optionally at least 90%, e.g. 95%, 96%, 97%, 98% or 99% sequence identity to the amino acid sequence as set forth in SEQ ID NO: 29.

In certain embodiments, at least a portion of one or more regions and/or fragments are glycosylated.

In certain embodiments, the at least one target and/or further target comprises one or more of at least one polyanionic cell surface marker, at least one complement activation/inactivation component, at least one oxidation end product, at least one immune cell adhesion related molecule, at least one apoptotic cell related molecule and/or at least one acute phase response related molecule.

In certain embodiments, the at least one polyanionic cell surface marker is selected from one or more of N-linked glycosyl units with sialic acid end-groups and/or one or more glycosaminoglycans (GAGs); optionally selected from heparin, heparan sulphate, chondroitin sulphate, dermatan sulphate, keratan sulphate and hyaluronan.

In certain embodiments, the at least one complement activation/inactivation component is selected from one or more of C3b, iC3b, C3dg, C3d and/or Factor I.

In certain embodiments, the at least one oxidation end product is selected from one or more of malondialdehyde (MDA), 4-hydroxynonenal (4-HNE), carboxyethylpyrrole (CEP), oxidized phosphatidylserine (OxPS), oxidized cardiolipin (OxCL) and phosphocholine (PC).

In certain embodiments, the complement regulator protein comprises a multimer. Aptly a dimer.

According to a second aspect of the present invention, there is provided a complement regulator protein, comprising the general formula:

$$X_1\text{-}L_1\text{-}X_2\text{-}L_2\text{-}Y_1 \qquad \text{Formula I}$$

wherein:
  $X_1$ is a molecule selected from a molecule comprising:
    (i) FH CCP domains 1 (SEQ ID NO: 9), 2 (SEQ ID NO: 10), 3 (SEQ ID NO: 11) and 4 (SEQ ID NO: 12); (ii) FH CCP domains 1 (SEQ ID NO: 9), 2 (SEQ ID NO: 10), 3 (SEQ ID NO: 11), 4 (SEQ ID NO: 12) and 5 (SEQ ID NO: 13); (iii) FH CCP domains 1 (SEQ ID NO: 9), 2 (SEQ ID NO: 10), 3 (SEQ ID NO: 11), 4 (SEQ ID NO: 12), and 7 (SEQ ID NO: 15); and (iv) FH CCP domains 1 (SEQ ID NO: 9), 2

(SEQ ID NO: 10), 3 (SEQ ID NO: 11), 4 (SEQ ID NO: 12), 5 (SEQ ID NO: 13) and 7 (SEQ ID NO: 15);

$L_1$ is at least one linker molecule or is absent;

$X_2$ is a molecule selected from a molecule comprising: (i) FH CCP domains 18 (SEQ ID NO: 16), 19 (SEQ ID NO: 17) and 20 (SEQ ID NO: 18); (ii) FH CCP domain 19 (SEQ ID NO: 17) and 20 (SEQ ID NO: 18); (iii) FHL-1 CCP domains 6 (SEQ ID NO: 22) and 7 (SEQ ID NO: 23); (iv) FHR2 CCP domains 3 and 4; (v) FHR3 CCP domains 4 and 5; (vi) FHR4 CCP domains 8 and 9; (vii) FHR5 CCP domains 7 (SEQ ID NO: 19), 8 (SEQ ID NO: 20) and 9 (SEQ ID NO: 21); and (viii) FHR5 CCP domains 8 (SEQ ID NO: 20) and 9 (SEQ ID NO: 21); or is absent;

$L_2$ is at least one linker molecule or is absent; and $Y_1$ is a molecule selected from a molecule comprising: (i) FHR1 CCP domains 1 (SEQ ID NO: 24) and 2 (SEQ ID NO: 25) (ii) FHR2 CCP domains 1 and 2; and (ii) FHR5 CCP domains 1 and 2.

According to a third aspect of the present invention, there is provided a complement regulator protein comprising the general formula:

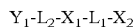

$$Y_1\text{-}L_2\text{-}X_1\text{-}L_1\text{-}X_2 \quad \text{Formula II}$$

wherein:

$X_1$ is a molecule selected from a molecule comprising: (i) FH CCP domains 1 (SEQ ID NO: 9), 2 (SEQ ID NO: 10), 3 (SEQ ID NO: 11) and 4 (SEQ ID NO: 12); (ii) FH CCP domains 1 (SEQ ID NO: 9), 2 (SEQ ID NO: 10), 3 (SEQ ID NO: 11), 4 (SEQ ID NO: 12) and 5 (SEQ ID NO: 13); (iii) FH CCP domains 1 (SEQ ID NO: 9), 2 (SEQ ID NO: 10), 3 (SEQ ID NO: 11), 4 (SEQ ID NO: 12), and 7 (SEQ ID NO: 15); and (iv) FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15);

$L_1$ is at least one linker molecule or is absent;

$X_2$ is a molecule selected from a molecule comprising: (i) FH CCP domains 18 (SEQ ID NO: 16), 19 (SEQ ID NO: 17) and 20 (SEQ ID NO: 18); (ii) FH CCP domain 19 (SEQ ID NO: 17) and 20 (SEQ ID NO: 18); (iii) FHL-1 CCP domains 6 (SEQ ID NO: 22) and 7 (SEQ ID NO: 23; (iv) FHR2 CCP domains 3 and 4; (v) FHR3 CCP domains 4 and 5; (vi) FHR4 CCP domains 8 and 9; (vii) FHR5 CCP domains 7 (SEQ ID NO: 19), 8 (SEQ ID NO: 20) and 9 (SEQ ID NO: 21); and (viii) FHR5 CCP domains 8 (SEQ ID NO: 20) and 9 (SEQ ID NO: 21); or is absent;

$L_2$ is at least one linker molecule or is absent; and $Y_1$ is a molecule selected from a molecule comprising: (i) FHR1 CCP domains 1 (SEQ ID NO: 24) and 2 (SEQ ID NO: 25); (ii) FHR2 CCP domains 1 and 2; and (iii) FHR5 CCP domains 1 and 2

According to a fourth aspect of the present invention there is provided a complement regulator protein comprising the general formula:

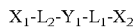

$$X_1\text{-}L_2\text{-}Y_1\text{-}L_1\text{-}X_2 \quad \text{Formula III}$$

wherein:

$X_1$ is a molecule selected from a molecule comprising: (i) FH CCP domains 1 (SEQ ID NO: 9), 2 (SEQ ID NO: 10), 3 (SEQ ID NO: 11) and 4 (SEQ ID NO: 12); (ii) FH CCP domains 1 (SEQ ID NO: 9), 2 (SEQ ID NO: 10), 3 (SEQ ID NO: 11), 4 (SEQ ID NO: 12) and 5 (SEQ ID NO: 13); (iii) FH CCP domains 1 (SEQ ID NO: 9), 2 (SEQ ID NO: 10), 3 (SEQ ID NO: 11), 4 (SEQ ID NO: 12), and 7 (SEQ ID NO: 15); and (iv) FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15);

$L_1$ is at least one linker molecule or is absent;

$X_2$ is a molecule selected from a molecule comprising: (i) FH CCP domains 18 (SEQ ID NO: 16), 19 (SEQ ID NO: 17) and 20 (SEQ ID NO: 18); (ii) FH CCP domain 19 (SEQ ID NO: 17) and 20 (SEQ ID NO: 18); (iii) FHL-1 CCP domains 6 (SEQ ID NO: 22) and 7 (SEQ ID NO: 23); (iv) FHR2 CCP domains 3 and 4; (v) FHR3 CCP domains 4 and 5; (vi) FHR4 CCP domains 8 and 9; (vii) FHR5 CCP domains 7 (SEQ ID NO: 19), 8 (SEQ ID NO: 20) and 9 (SEQ ID NO: 21); and (viii) FHR5 CCP domains 8 (SEQ ID NO: 20) and 9 (SEQ ID NO: 21); or is absent;

$L_2$ is at least one linker molecule or is absent; and $Y_1$ is a molecule selected from a molecule comprising: (i) FHR1 CCP domains 1 (SEQ ID NO: 24) and 2 (SEQ ID NO: 25); (ii) FHR2 CCP domains 1 and 2; and (iii) FHR5 CCP domains 1 and 2.

In certain embodiments, $X_1$, $X_2$, and/or $Y_1$ are derived from or are fragments of human FH, at least one human FHR and/or human FHL.

In certain embodiments, at least a portion of one or more of $X_1$, $X_2$, and/or $Y_1$ are glycosylated.

In certain embodiments, wherein $L_1$ and $L_2$ are present, $L_1$ and $L_2$ are independently selected from one or more linker molecules comprising: an amino acid sequence as set forth in SEQ ID NO: 30; an amino acid sequence as set forth in SEQ ID NO: 31; an amino acid sequence as set forth in SEQ ID NO: 32; an amino acid sequence as set forth in SEQ ID NO: 33; an amino acid sequence as set forth in SEQ ID NO: 34; Glycine and Threonine (GT); Valine and Aspartic acid (VD) and/or; Valine, Aspartic acid and Threonine (VDT).

In certain embodiments, the complement regulator protein comprises from N-terminal to C-terminal, a FH CCP1 domain (SEQ ID NO: 9), a FH CCP2 domain (SEQ ID NO: 10), a FH CCP3 domain (SEQ ID NO: 11), a FH CCP4 domain (SEQ ID NO: 12), a FH CCP5 domain (SEQ ID NO: 13), optionally at least one linker molecule, a FH CCP18 domain (SEQ ID NO: 16), a FH CCP19 domain (SEQ ID NO: 17), a FH CCP20 domain (SEQ ID NO: 18), optionally at least one linker molecule, a FHR1 CCP1 domain (SEQ ID NO: 24) and a FHR1 CCP2 domain (SEQ ID NO: 25).

In certain embodiments, the complement regulator protein comprises an amino acid sequence, which has at least 80% sequence identity to the amino acid sequence as set forth in SEQ ID NO: 26, and optionally at least 90%, e.g. 95%, 96%, 97%, 98% or 99% sequence identity to the amino acid sequence as set forth in SEQ ID NO: 26.

In certain embodiments, the complement regulator protein comprises from N-terminal to C-terminal, a FHR1 CCP1 domain (SEQ ID NO: 24), a FHR1 CCP2 domain (SEQ ID NO: 25), optionally at least one linker molecule, a FH CCP1 domain (SEQ ID NO: 9), a FH CCP2 domain (SEQ ID NO: 10), a FH CCP3 domain (SEQ ID NO: 11), a FH CCP4 domain (SEQ ID NO: 12), a FH CCP5 domain (SEQ ID NO: 13), optionally at least one linker molecule, a FH CCP18 domain (SEQ ID NO: 16), a FH CCP19 domain (SEQ ID NO: 17) and a FH CCP20 domain (SEQ ID NO: 18).

In certain embodiments, the complement regulator protein comprises an amino acid sequence which has at least 80% sequence identity to the amino acid sequence as set forth in SEQ ID NO: 27 and optionally at least 90%, e.g. 95%, 96%, 97%, 98% or 99% sequence identity to the amino acid sequence as set forth in SEQ ID NO: 27.

In certain embodiments, the complement regulator protein comprises from N-terminal to C-terminal, a FH CCP1 domain (SEQ ID NO: 9), a FH CCP2 domain (SEQ ID NO: 10), a FH CCP3 domain (SEQ ID NO: 11), a FH CCP4 domain (SEQ ID NO: 12), a FH CCP5 domain (SEQ ID NO: 13), optionally at least one linker molecule, a FHL-1 CCP6 domain (SEQ ID NO: 22), a FHL-1 CCP7 (SEQ ID NO: 23) domain, optionally at least one linker molecule, a FHR1 CCP1 domain (SEQ ID NO: 24) and a FHR1 CCP2 domain (SEQ ID NO: 25).

In certain embodiments, the complement regulator protein comprises an amino acid sequence which has at least 80% sequence identity to the amino acid sequence as set forth in SEQ ID NO: 28 and optionally at least 90%, e.g. 95%, 96%, 97%, 98% or 99% sequence identity to the amino acid sequence as set forth in SEQ ID NO: 28.

In certain embodiments, the complement regulator protein comprises from N-terminal to C-terminal, a FHR1 CCP1 domain (SEQ ID NO: 24), a FHR1 CCP2 domain (SEQ ID NO: 24), optionally at least one linker molecule, a FH CCP1 domain (SEQ ID NO: 9), a FH CCP2 domain (SEQ ID NO: 10), a FH CCP3 domain (SEQ ID NO: 11), a FH CCP4 domain (SEQ ID NO: 12), a FH CCP5 domain (SEQ ID NO: 13), optionally at least one linker molecule, a FHL-1 CCP6 domain (SEQ ID NO: 22) and a FHL-1 CCP7 domain (SEQ ID NO: 23).

In certain embodiments, the complement regulator protein comprises an amino acid sequence which has at least 80% sequence identity to the amino acid sequence as set forth in SEQ ID NO: 29 optionally at least 90%, e.g. 95%, 96%, 97%, 98% or 99% sequence identity to the amino acid sequence as set forth in SEQ ID NO: 29.

According to a fifth aspect of the present invention, there is provided, a dimer comprising at least one complement regulator protein as described herein.

According to a sixth aspect of the present invention, there is provided a pharmaceutical composition comprising a complement regulator protein as described herein and a pharmaceutically acceptable carrier. Compositions may be for use in the treatment and/or prophylaxis of a disease associated with or mediated by the alternative complement pathway as described herein. Further provided in the present disclosure is a kit including such a composition.

In a further aspect of the present invention, there is provided a complement regulator protein as described herein and compositions thereof for use as a medicament.

In a further aspect of the present invention, there is provided a complement regulator protein as described herein and compositions thereof are for use in the treatment of a disease associated with or mediated by the alternative complement pathway.

In certain embodiments, the disease associated with or mediated by the alternative complement pathway is selected from one or more of rheumatoid arthritis, ischemia reperfusion, myocardial infarction, adult respiratory distress syndrome, organ transplant rejection, a renal disease, an eye disease and/or lupus nephritis.

In certain embodiments, the renal disease is selected from haemolytic uremic syndrome, IgA nephropathy (Berger's disease), C3 Glomerulopathy; optionally C3 glomerulonephritis; mesangiocapillary glomerulonephritis and/or dense deposit disease.

In certain embodiments, the eye disease is selected from autoimmune uveitis, diabetic retinopathy and/or age related macular degeneration.

In certain embodiments, the complement regulator proteins and compositions thereof as described herein are for use in the treatment of age related macular degeneration.

In certain embodiments, the complement regulator proteins and compositions thereof as described herein are for use in the treatment of haemolytic uremic syndrome. Aptly, atypical haemolytic uremic syndrome.

Aptly, the complement regulator protein comprising an amino acid sequence as set forth in SEQ ID NO: 26 or SEQ ID NO: 26 is for use in the treatment of a renal disease as described herein.

Aptly, the complement regulator protein comprising an amino acid sequence as set forth in SEQ ID NO: 28 or SEQ ID NO: 29 is for use in the treatment of an eye disease as described herein.

According to a seventh aspect of the present invention, there is provided a method of treating and/or preventing a disease associated with or mediated by the alternative complement pathway in a subject in need thereof, the method comprising;

administering a pharmaceutically effective amount of a pharmaceutical composition comprising a recombinant complement regulator protein and pharmaceutically acceptable carrier, wherein the recombinant complement regulator protein, comprises;
a) at least one complement interaction region operable to regulate complement and bind the complement regulator protein to at least one target, the complement interaction region comprising;
    (i) at least one FH fragment; and
b) at least one dimerization region operable to dimerize the complement regulator protein.

Aptly, the disease associated with or mediated by the alternative complement pathway is a disease associated with or mediated by the alternative complement pathway as described herein.

Aptly, the recombinant complement regulator protein is a recombinant regulator protein as described herein.

According to an eighth aspect of the present invention, there is provided a method of treating and/or preventing atypical haemolytic uremic anaemia in a subject in need thereof, the method comprising;

administering a pharmaceutically effective amount of a pharmaceutical composition comprising a recombinant complement regulator protein and pharmaceutically acceptable carrier, wherein the recombinant complement regulator protein, comprises;
a) at least one complement interaction region operable to regulate complement and bind the complement regulator protein to at least one target, the complement interaction region comprising;
    (i) at least one FH fragment; and
b) at least one dimerization region operable to dimerize the complement regulator protein.

Aptly, the recombinant complement regulator protein is a recombinant complement regulator protein as described herein.

According to a ninth aspect of the present invention, there is provided a method of treating and/or preventing age related macular degeneration in a subject in need thereof, the method comprising;

administering a pharmaceutically effective amount of a pharmaceutical composition comprising a recombinant complement regulator protein and pharmaceutically acceptable carrier, wherein the recombinant complement regulator protein, comprises;

a) at least one complement interaction region operable to regulate complement and bind the complement regulator protein to at least one target, the complement interaction region comprising;
   (i) at least one FH fragment; and
b) at least one dimerization region operable to dimerize the complement regulator protein.

Aptly, the recombinant complement regulator protein is a recombinant complement regulator protein as described herein.

According to a tenth aspect of the present invention, there is provided a method for producing a recombinant complement regulator protein as described herein, comprising the steps of;
   transfecting a host cell with a vector comprising a nucleic acid encoding the complement regulator protein;
   culturing the host cell expressing the protein; and
   inducing the host cell to express the protein; and
   isolating the protein.

Aptly, the method further comprises the step of purifying the isolated complement regulator protein.

According to a further aspect of the present invention, there is provided a nucleic acid molecule encoding a recombinant regulator protein as described herein.

According to a further aspect of the present invention, there is provided a use of a complement regulator protein as described herein for development and/or commercialisation of treatments and/or preventative methods for a disease associated with or mediated by the alternative complement pathway as described herein.

BRIEF DESCRIPTION OF DRAWINGS

Certain embodiments of the present invention will now be described hereinafter, by way of example only, with reference to the accompanying drawings in which.

Figure 2:
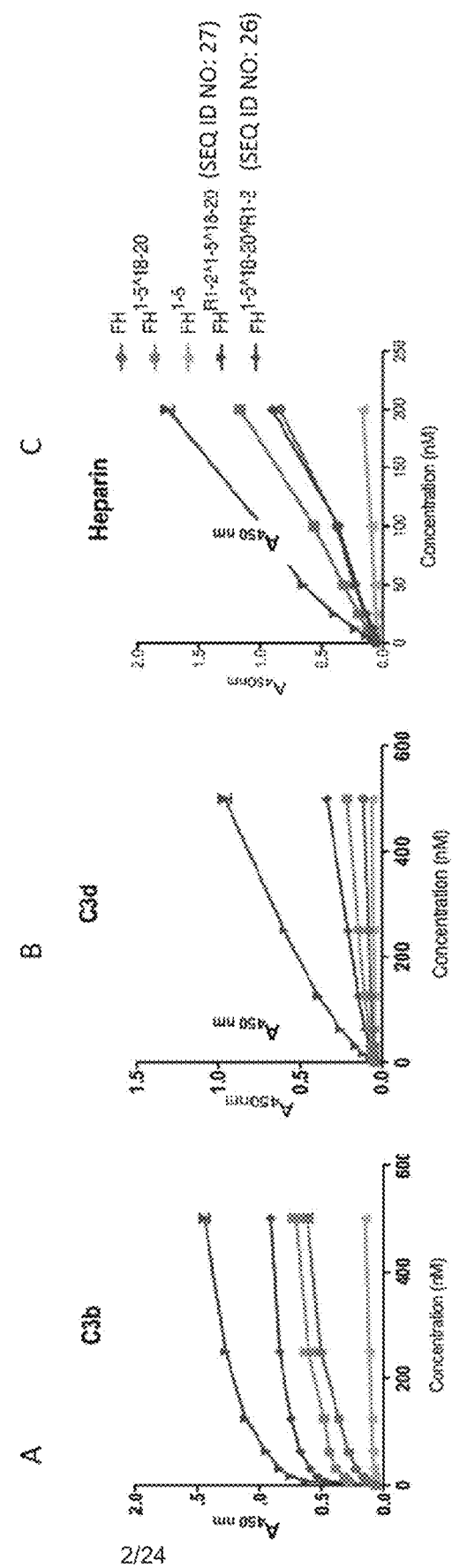
Figure 3:
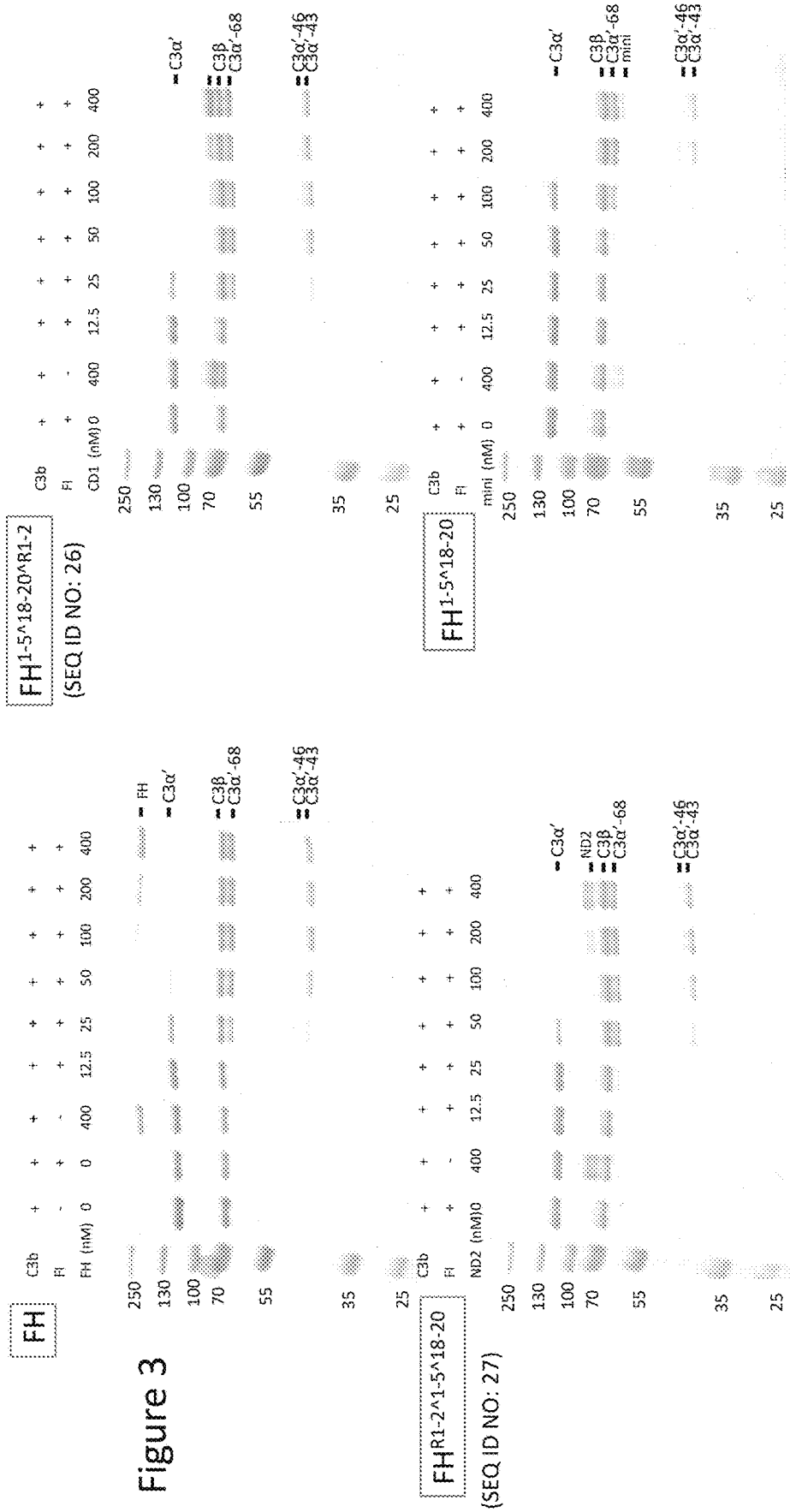
Figure 4:
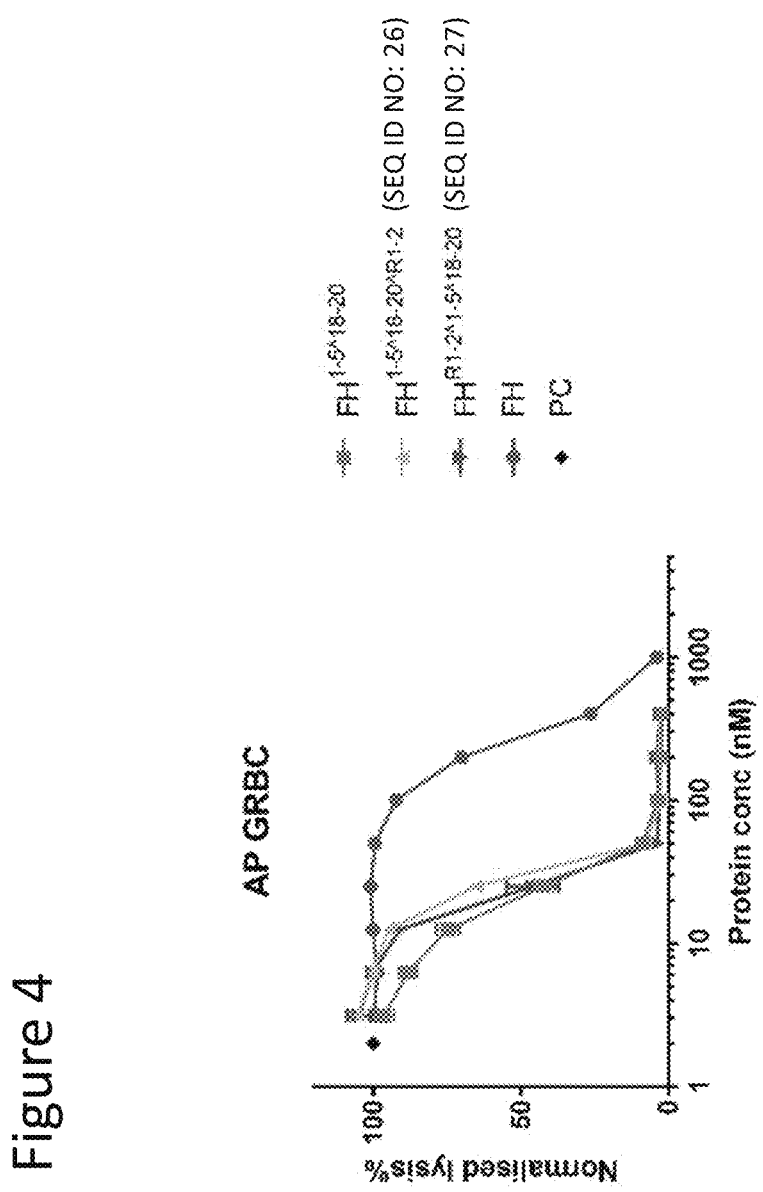
Figure 5:
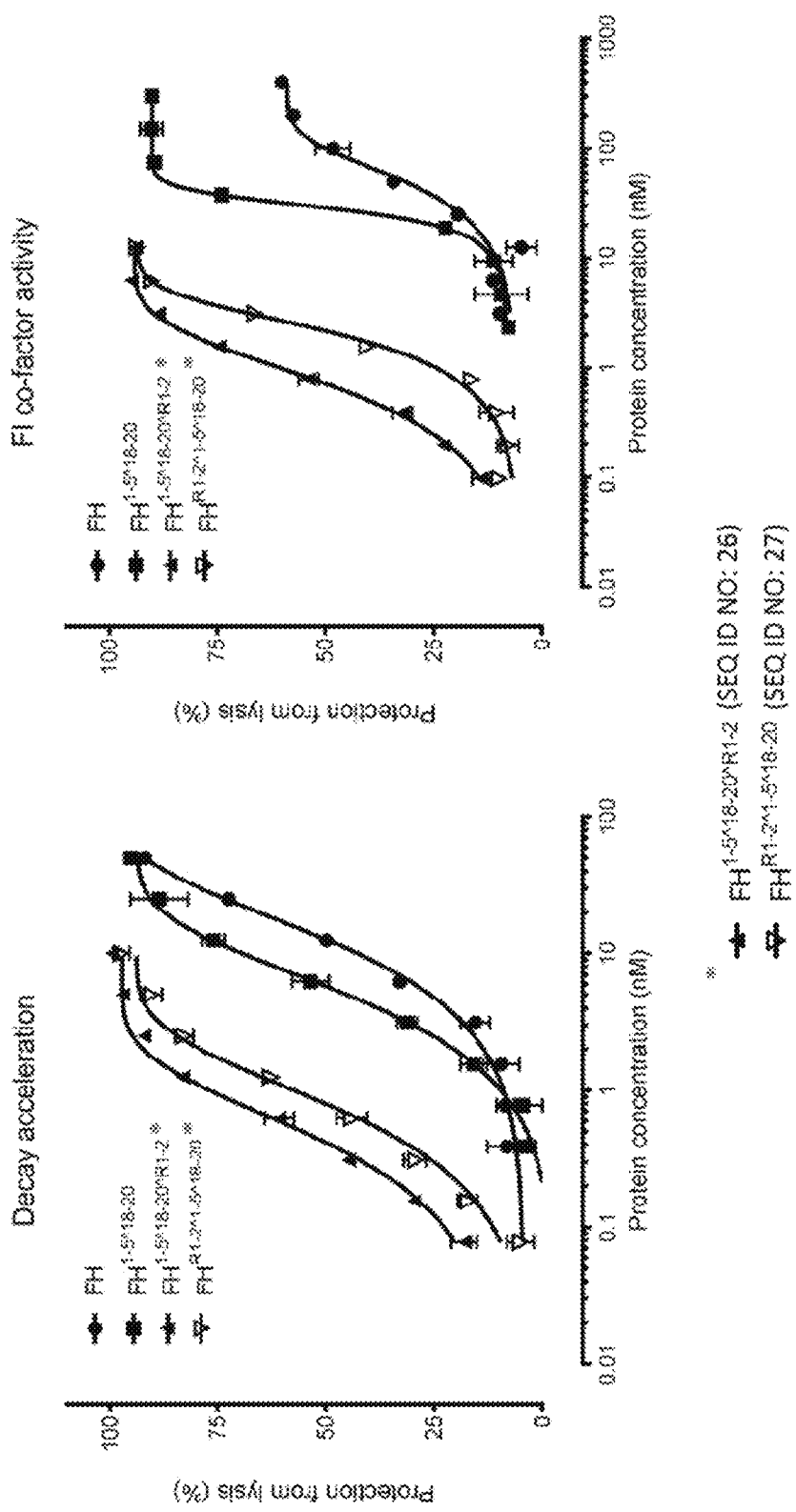
Figure 6:
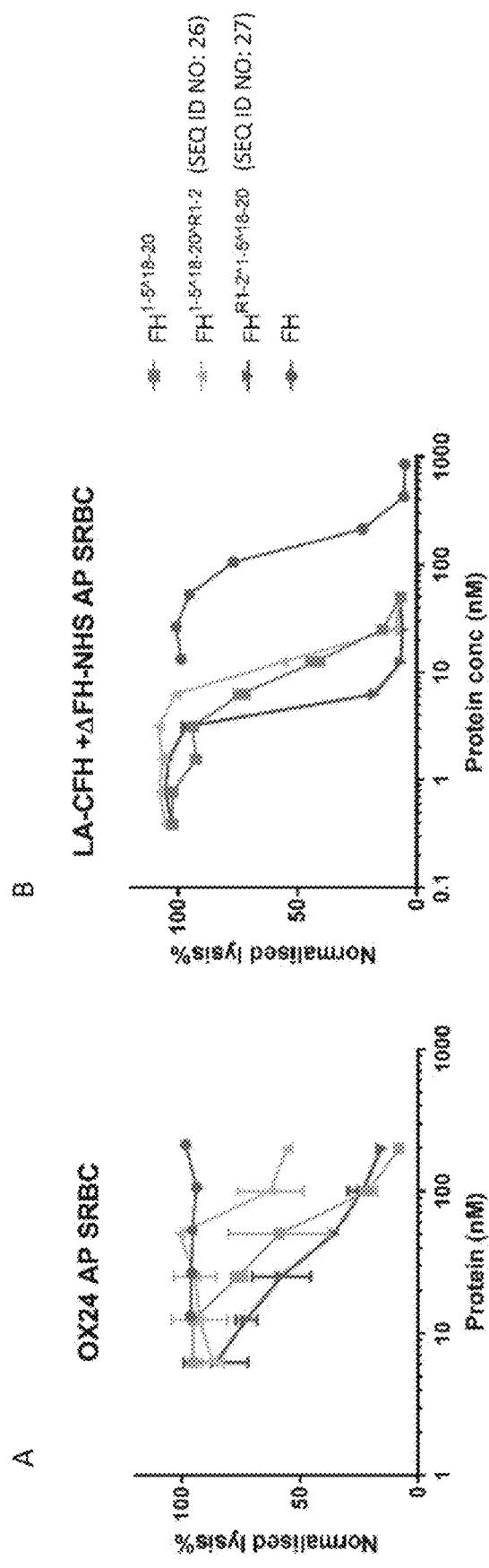
Figure 7:
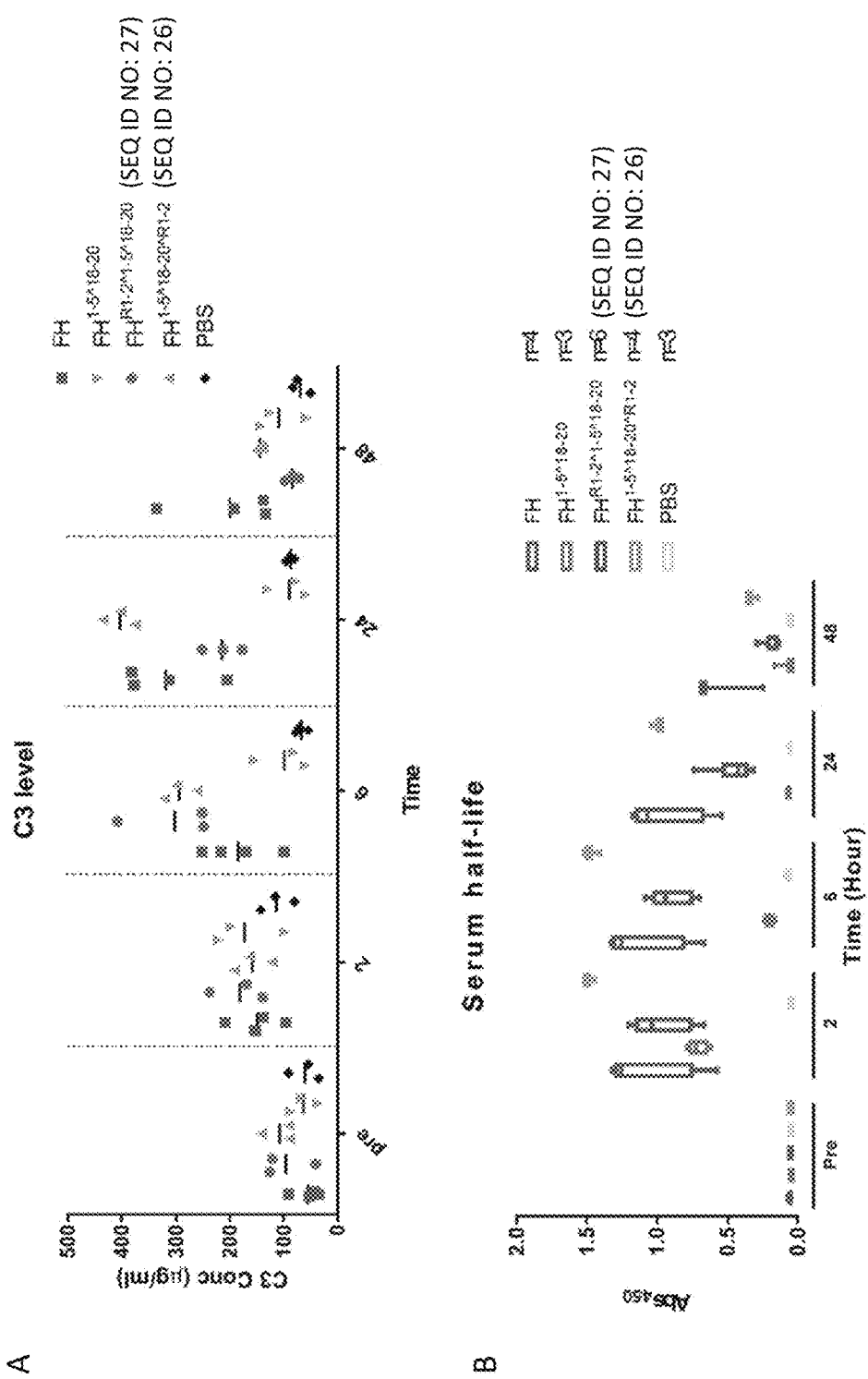
Figure 8:
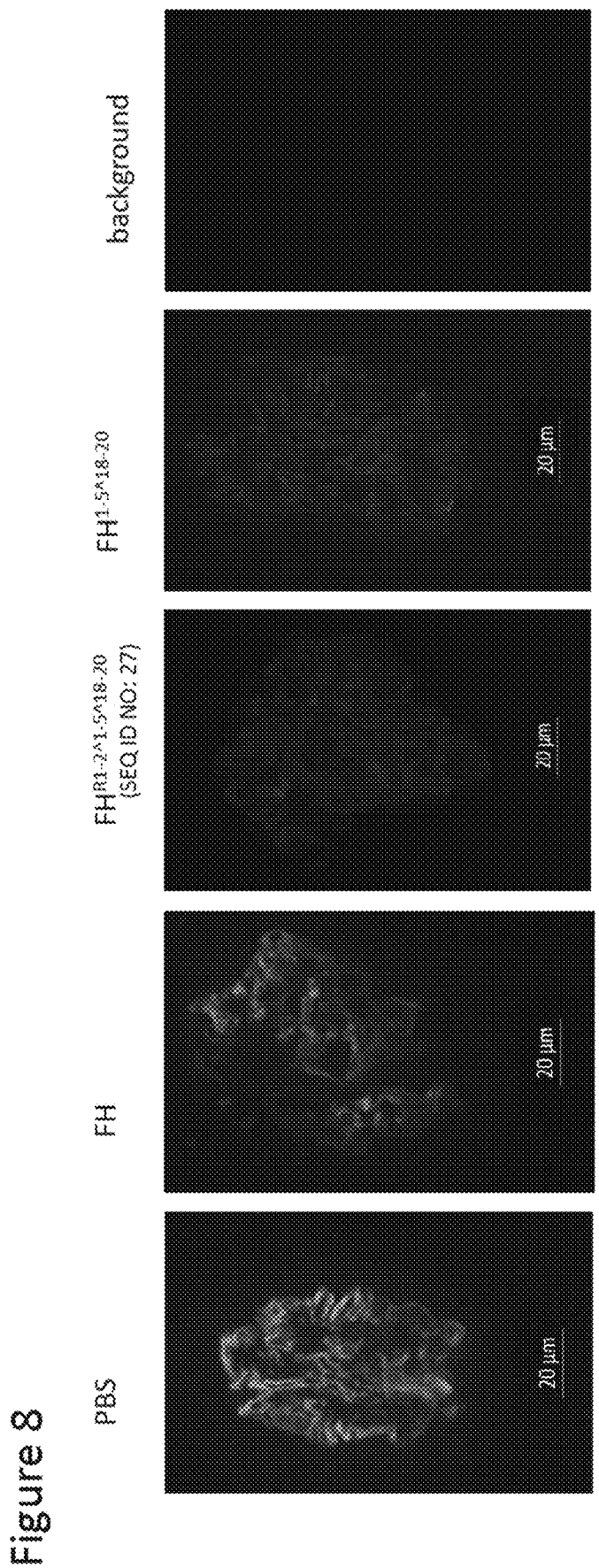
Figure 23:
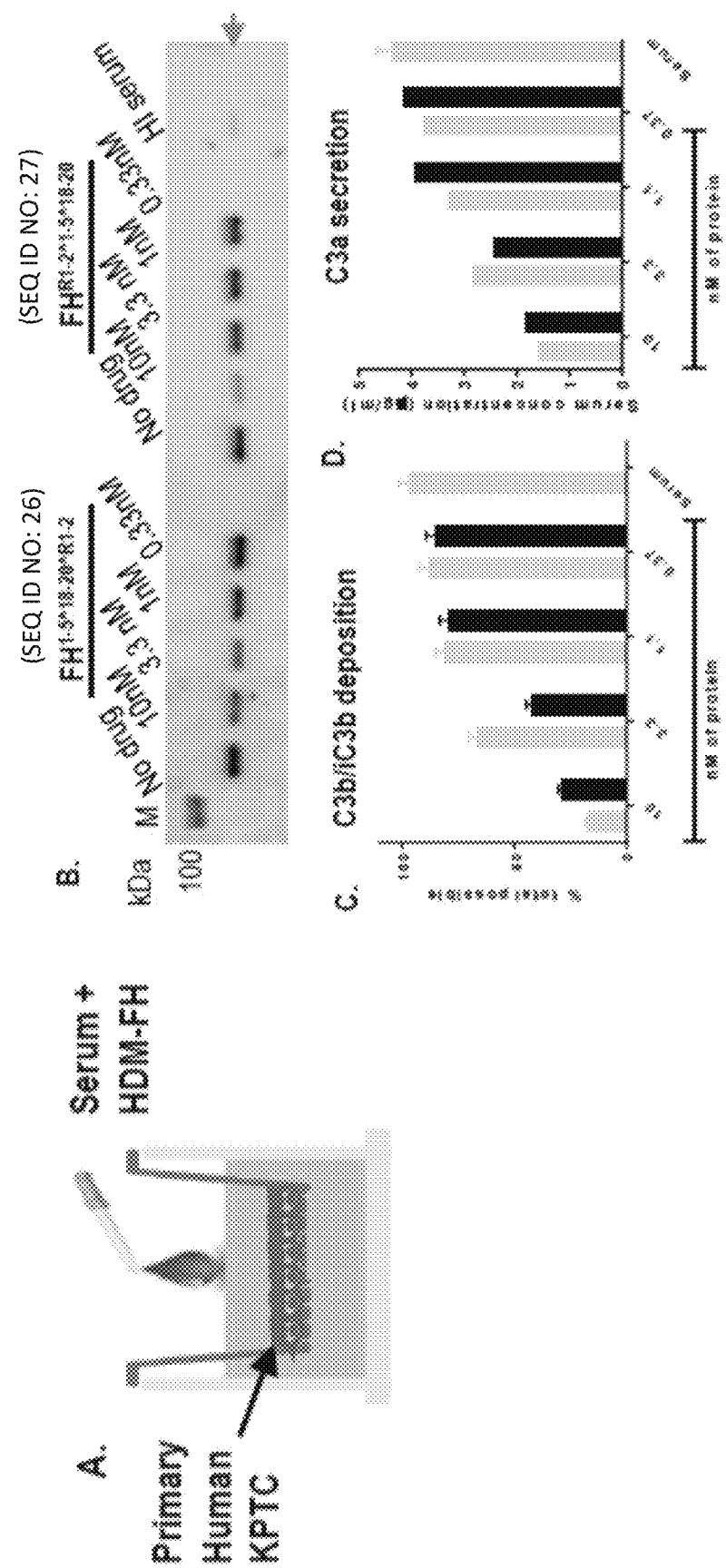
Figure 24:
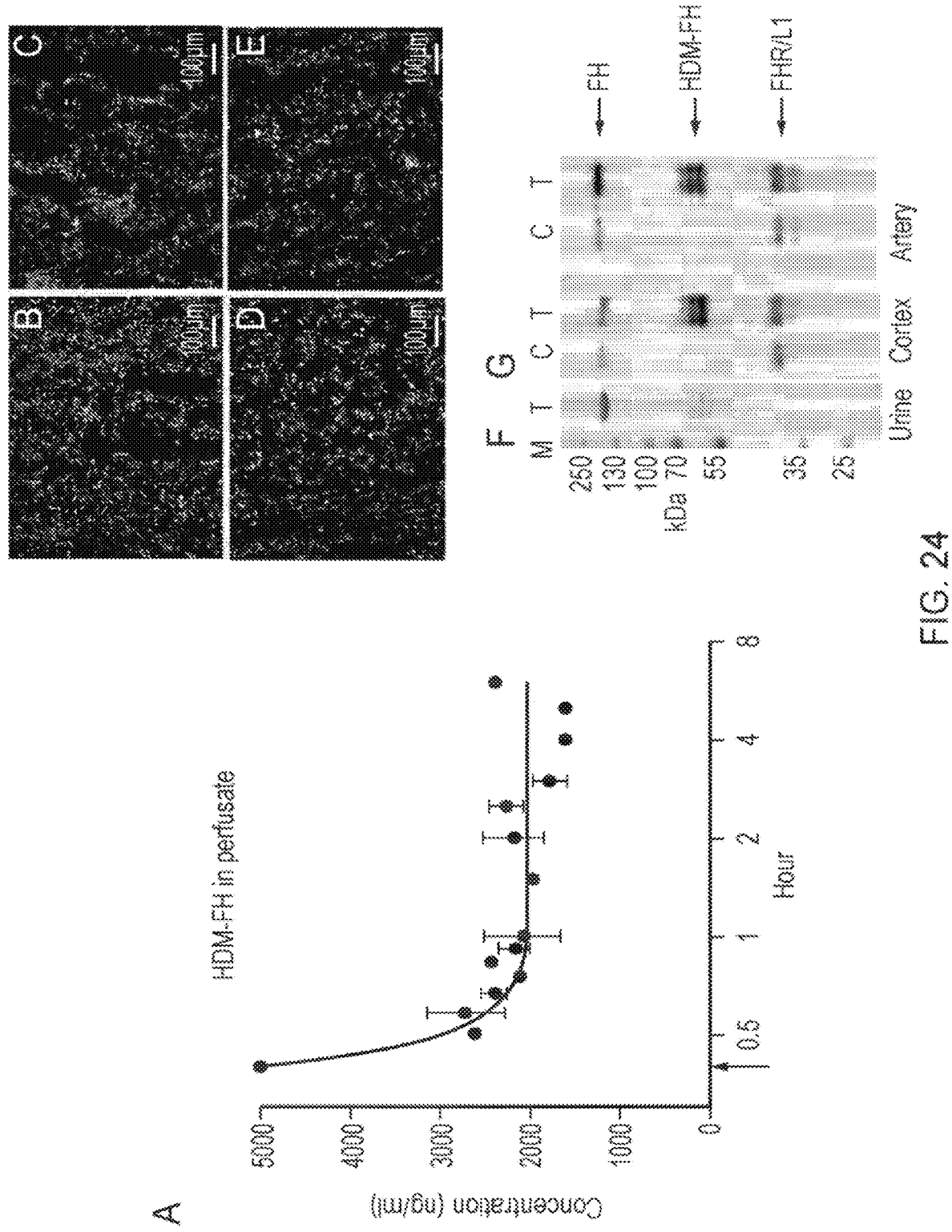
Figure 25:
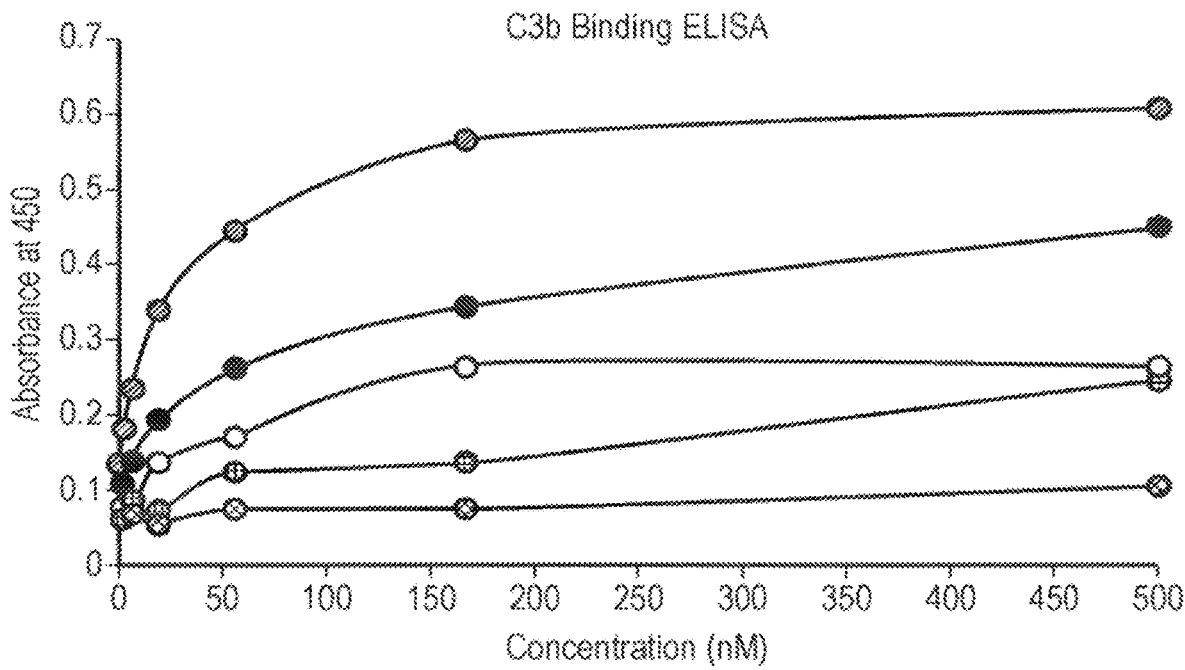
Figure 26:
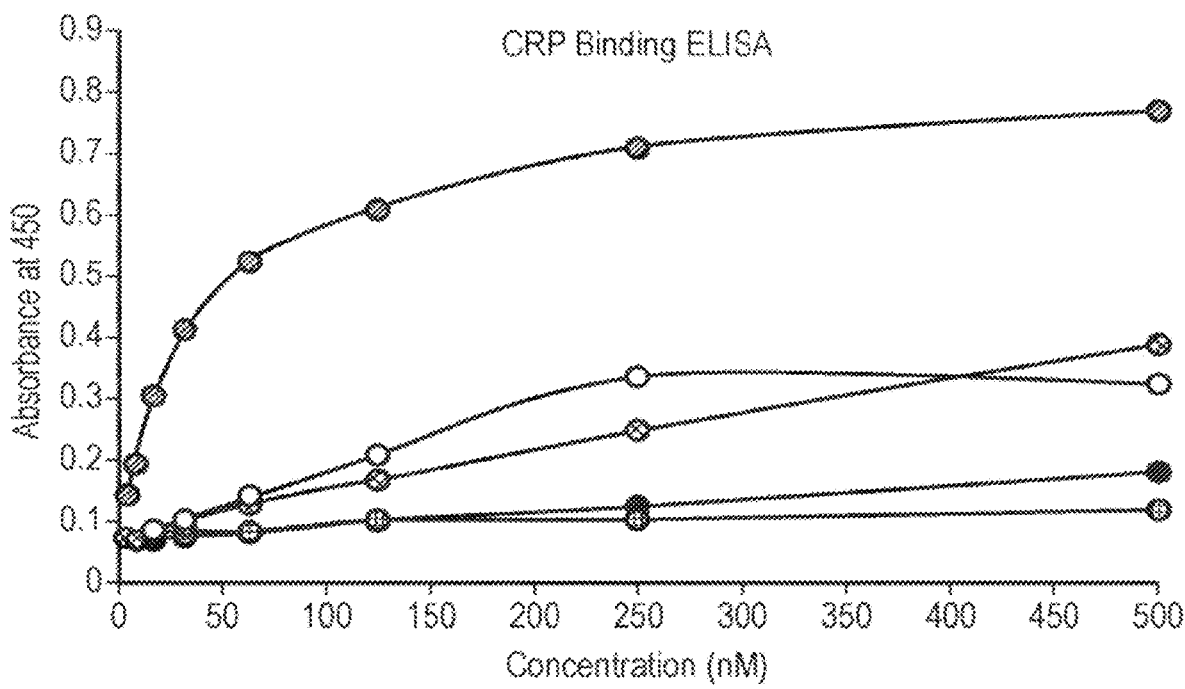

The proteins are represented from N-terminal to C-terminal (left to right). The FH CCP domains are labelled 1 to 20 and FHR-1 CCP domains are labelled R1 to R5. FHL-1 CCP domains are labelled L6 and L7. Glycosylation sites are indicated by the forked structures located on the top of modules. Linker amino acid residues are shown by the text within the rounded boxes;

FIG. 2 illustrates binding properties of a full-length FH protein, $FH^{1-5\wedge 18-20}$, FH CCP domains 1-5, $FH^{R1-2\wedge 1-5\wedge 18-20}$ (SEQ ID NO: 27) and $FH^{1-5\wedge 18-20\wedge R1-2}$ (SEQ ID NO: 26) to plate immobilised A) C3b, B) C3d and C) Heparin. Binding was detected by Enzyme-linked immunosorbent assay (ELISA) and quantified by measuring absorbance at 450 nm;

FIG. 3 illustrates fluid phase cofactor activity of A) FH, B) $FH^{1-5\wedge 18-20\wedge R1-2}$ (SEQ ID NO: 26), C) $FH^{R1-2\wedge 1-5\wedge 18-20}$ (SEQ ID NO: 27) and D) $FH^{1-5\wedge 18-20}$. Increasing concentrations of the complement regulator proteins were incubated in solution at 37° C. for 1 hour with C3b and Factor I (FI). C3b breakdown was analysed by SDS-PAGE and Coomassie staining. Reduced intensity of C3α'-110 kDa band and the increased intensity or presence of C3α'-68 kDa, -46 kDa and -43 kDa bands are indicative of C3b proteolytic inactivation;

FIG. 4 illustrates protection of a "non-self" surface by FH, $FH^{1-5\wedge 18-20}$, $FH^{R1-2\wedge 1-5\wedge 18-20}$ (SEQ ID NO: 27) and $FH^{1-5\wedge 18-20\wedge R1-2}$ (SEQ ID NO: 26) and PC. Guinea pig erythrocytes (red blood cells) suspended in 25% (v/v) of Normal Human Serum (NHS) were incubated with either FH, $FH^{1-5\wedge 18-20}$, $FH^{R1-2\wedge 1-5\wedge 18-20}$ (SEQ ID NO: 27) or $FH^{1-5\wedge 18-20\wedge R1-2}$ (SEQ ID NO: 26) at the concentrations indicated on the graph. Complement activation was restricted to the alternative pathway by the addition of $MgCl_2$ and ethylene glycol-bis(β-aminoethyl ether)-N,N,N',N'-tetra acetic acid (EGTA) to a final concentration of 7 and 10 mM respectively. The amount of lysis was quantified by measuring absorbance at 405 nm ($A_{405}$), and the reading in the absence of FH reagent was utilized to normalise the data;

FIG. 5 illustrates complement regulation activity at cell membranes for FH, $FH^{1-5\wedge 18-20}$, $FH^{R1-2\wedge 1-5\wedge 18-20}$ (SEQ ID NO: 27) and $FH^{1-5\wedge 18-20\wedge R1-2}$ (SEQ ID NO: 26). A) Shows decay acceleration activity of complement regulator proteins on surface bound alternative pathway C3 convertase. C3 convertases were reconstituted on the surface of C3b coated sheep red blood cells (SRBC) by incubation with purified Factor B (42 µg/ml) and Factor D (0.4 µg/ml). B) Shows Factor I (FI) cofactor activity of C3b pre-coated SRBC exposed to a concentration gradient of a complement regulator proteins with 2.5 µg/ml of FI. Data was processed and normalised using 100% lysis determined in water, and 0% lysis of diluted serum in diluted in buffer alone;

FIG. 6 illustrates protection of SRBCs from lysis in human sera with deregulated complement alternative pathway by plasma purified FH, $FH^{1-5\wedge 18-20}$, $FH^{R1-2\wedge 1-5\wedge 18-20}$ (SEQ ID NO: 27) and $FH^{1-5\wedge 18-20\wedge R1-2}$ (SEQ ID NO: 26). A) Shows the effects on alternative pathway mediated lysis of SRBCs of increasing concentration of plasma purified $FH^{1-5^{\wedge}18-20}$, $FH^{R1-2^{\wedge}1-5^{\wedge}18-20}$ (SEQ ID NO: 27) and $FH^{1-5^{\wedge}18-20^{\wedge}R1-2}$ (SEQ ID NO: 26) respectively, in alternative pathway deregulated (OX24 spiked) NHS (which acts as an autoantibody model serum). B) Shows effect of increasing concentration of plasma purified FH, $FH^{1-5^{\wedge}18-20}$, $FH^{R1-2^{\wedge}1-5^{\wedge}18-20}$ (SEQ ID NO: 27) and $FH^{1-5^{\wedge}18-20^{\wedge}R1-2}$ (SEQ ID NO: 26) respectively, on SRBC lysis in FH depleted serum supplemented with the recombinant mutant human FH S1191A+V1197L (an aHUS model serum). SRBC lysis was measured by haemoglobin release detected by measuring absorbance at 405 nm ($A_{405}$). Data were normalized against SRBC lysis with deregulated serum in the absence of FH reagent (100% lysis);

FIG. 7 illustrates the therapeutic effectiveness of FH, $FH^{1-5^{\wedge}18-20}$, $FH^{R1-2^{\wedge}1-5^{\wedge}18-20}$ (SEQ ID NO: 27) and $FH^{1-5^{\wedge}18-20^{\wedge}R1-2}$ (SEQ ID NO: 26) and PBS (control) in Cfh$^{-/-}$ (Factor H gene) mouse model. A) Shows plasma C3 levels after the injection of 3 nmoles of plasma purified FH or FH, $FH^{R1-2^{\wedge}1-5^{\wedge}18-20}$ (SEQ ID NO: 27) and $FH^{1-5^{\wedge}18-20^{\wedge}R1-2}$ (SEQ ID NO: 26) or 6 nmoles of $FH^{1-5^{\wedge}18-20}$ over a time period of 48 hours compared with the PBS treatment. B) Shows the serum half-life of 3 nmoles of plasma purified FH or FH, $FH^{R1-2^{\wedge}1-5^{\wedge}18-20}$ (SEQ ID NO: 27) and $FH^{1-5^{\wedge}18-20^{\wedge}R1-2}$ (SEQ ID NO: 26) or 6 nmoles of $FH^{1-5^{\wedge}18-20}$ over a time period of 48 hours compared with the PBS treatment;

FIG. 8 illustrates reduction in levels of glomerular C3 after 48 hours in Cfh$^{-/-}$ mice administered FH, $FH^{1-5^{\wedge}18-20}$, $FH^{R1-2^{\wedge}1-5^{\wedge}18-20}$ (SEQ ID NO: 27) and $FH^{1-5^{\wedge}18-20^{\wedge}R1-2}$ (SEQ ID NO: 26) compared with PBS. Mouse kidney sections were imaged using florescent microscopy at a magnification of ×40. C3 was detected by staining with Fluorescein isothiocyanate (FITC) conjugated goat polyclonal anti-mouse C3 antibody. Cells were also stained with 4'6-diamidino-2-phenylindole (DAPI);

FIG. 9 illustrates the modular structure of certain embodiments of complement regulator proteins as described herein. The complement regulator comprises a complement interaction region and a dimerization region. The complement interaction region comprises at least one FH fragment (A), an optional linker (B) and the complement interaction region may further comprise a further fragment (C). An optional linker links the complement interaction region to the dimerization region (D). A key below shows the different fragments that may be combined to form a complement regulator protein as described herein (the diagram is for representative purposes and is not to scale);

FIG. 10 illustrates human mature FH amino acid sequence (SEQ ID NO: 1);

FIG. 11 illustrates human mature FHR5 amino acid sequence (SEQ ID NO: 2) and human mature FHL-1 amino acid sequence (SEQ ID NO: 3);

FIG. 12 illustrates human mature FHR1 amino acid sequence (SEQ ID NO: 4);

FIG. 13 illustrates human FH precursor amino acid sequence (SEQ ID NO: 5);

FIG. 14 illustrates human FHR5 precursor amino acid sequence (SEQ ID NO: 6) and human FHL-1 precursor amino acid sequence (SEQ ID NO: 7);

FIG. 15 illustrates human FHR1 precursor amino acid sequence (SEQ ID NO: 8) and various sequences of certain embodiments;

FIG. 16 illustrates various sequences of certain embodiments of the present invention;

FIG. 17 illustrates various sequences of certain embodiments of the present invention;

FIG. 18 illustrates various sequences of certain embodiments of the present invention;

FIG. 19 illustrates various sequences of certain embodiments of the present invention;

FIG. 20 illustrates various sequences of certain embodiments of the present invention. A. shows various amino acid sequences and B. shows various nucleic acid sequences;

FIG. 21 illustrates various sequences of certain embodiments of the present invention. Precursor amino acids which are cleaved upon expression of the protein are shown in brackets in bold;

FIG. 22 illustrates various sequences of certain embodiments of the present invention. Precursor amino acids which are cleaved upon expression of the protein are shown in brackets in bold;

FIG. 23 illustrates that HDM-FH constructs reduce C3 deposition on kidney proximal tubule cells (KTPC) cells in vitro. (A) Diagram of primary human proximal tubule cells on the transwell system. (B) 10 nM of FH1-5^18-20^R1-2 (SEQ ID NO: 26) and FHR1-2^1-5^18-20 (SEQ ID NO: 27) when added to human serum (1:4 dilution) reduce C3 deposition and appearance of C3 breakdown fragments (arrow) on human proximal tubule epithelial cells by between 80-90% according to densitometry. (C) beta chain of C3 comparing serum only to serum plus drugs and serum plus drugs after 1 hour incubation. (D) Analysis of endpoint C3a generation using the Quidel MicroVue human C3a ELISA kit confirms a ~80% reduction in complement activation on the cell surface (less C3a released from cell surface into the fluid phase);

FIG. 24 illustrates the successful application of HDM-FH in the EVNP system. (A) HDM-FH constructs were injected (5 μg/ml) into the renal artery at 20 mins (indicated by arrow) and perfusate sampled. Drug is rapidly absorbed onto kidney vascular and is not excreted in urine. (B), (C), treated kidney and (D), (E), control. HDM-FH is shown in red (glomerulus) & Nuclei are shown in blue (DAPI stain). ×20 magnification of cortex. (F) SDS-PAGE of OX24 affinity purified proteins from urine (1 L). Approximately, 1% of the drug is lost over 6 hrs into urine, endogenous FH is 10 fold more abundant in the urine. (G) Western analysis of tissue lysates from the cortex and artery of a HDM-FH treated (T) or control (C) untreated kidney confirms the presence of significant quantities of HDM-FH, at least double endogenous FH by densitometry analysis. Marker (M) is shown;

FIG. 25 illustrates a C3b Binding ELISA of FH (blue), ND-FHL1 (grey), CD-FHL1 (yellow), FH1-5 (light blue) and Mini-FH (green); and FIG. 26 illustrates a CRP Binding ELISA of FH (blue), ND-FHL1 (grey), CD-FHL1 (yellow), FH1-5 (light blue) and Mini-FH (green).

DETAILED DESCRIPTION OF CERTAIN EMBODIMENTS OF THE INVENTION

The practice of embodiments of the present invention will employ, unless otherwise indicated, conventional techniques of molecular biology, microbiology, recombinant DNA technology and immunology, which are within the skill of those working in the art.

Most general molecular biology, microbiology recombinant DNA technology and immunological techniques can be found in Sambrook et al, Molecular Cloning, A Laboratory Manual (2001) Cold Harbor-Laboratory Press, Cold Spring Harbor, N.Y. or Ausubel et al., Current protocols in molecular biology (1990) John Wiley and Sons, N.Y. Unless defined otherwise, all technical and scientific terms used herein have the same meaning as commonly understood by one of ordinary skill in the art to which this disclosure belongs. For example, the Concise Dictionary of Biomedicine and Molecular Biology, Juo, Pei-Show, 2nd ed., 2002, CRC Press; The Dictionary of Cell and Molecular Biology, 3rd ed., Academic Press; and the Oxford University Press, provide a person skilled in the art with a general dictionary of many of the terms used in this disclosure.

Units, prefixes and symbols are denoted in their Système International de Unitese (SI) accepted form. Numeric ranges are inclusive of the numbers defining the range. Unless other indicated, amino acid sequences are written left to right in amino to carboxy orientation. All amino acid residues in peptides of embodiments of the invention are preferably of the L-configuration. However, D-configuration amino acids may also be present.

Certain embodiments of the present invention provide a recombinant complement regulator protein, compositions (such as pharmaceutical compositions) comprising the recombinant complement regulator protein, and methods of treating diseases which are associated with or mediated by the alternative complement pathway by administering such a composition. Aptly, the recombinant complement regulator protein in general exhibits regulation, binding and dimerization activity.

In certain embodiments, the recombinant complement regulator protein comprises a regulation activity which provides alternative complement pathway regulation. Aptly, the recombinant complement regulator protein comprises a binding activity which binds the complement regulator protein to a plurality of different targets.

Aptly, the recombinant complement regulator protein comprises a dimerization activity which dimerizes the protein.

Each of the aforementioned activities may be associated with a single region and/or fragment of the complement regulator or may be associated with a number of separate regions and/or fragments. In certain embodiments, wherein the complement regulator comprises more than one region and/or fragment, the complement regulator may be a fusion protein and/or regions and/or fragments may be linked by a linker.

Certain embodiments may provide a protein that dimerizes. Aptly, dimerization may have a number of advantages. For example, dimerization may help improve half-life of a recombinant complement regulator protein as described herein. In certain embodiments, dimerization may help to improve stability of the protein.

Thus, according to a first aspect of the present invention, there is provided a recombinant complement regulator protein, comprising;
   a) at least one complement interaction region operable to regulate complement and bind the complement regulator protein to at least one target, the complement interaction region comprising;
      (i) at least one first Factor H (FH) fragment; and
   b) at least one dimerization region operable to dimerize the complement regulator protein.

As used herein the terms "complement regulator protein" and "recombinant complement regulator protein" refer to a protein that possesses the type of complement regulating activity found in the family of mammalian proteins known as the regulator of complement activation (RCA) family, also referred to herein as "RCA proteins", which regulate complement activity through the alternative complement pathway.

Herein, the term "recombinant" refers to a protein that has been produced by artificial methods (i.e., deliberately produced or modified by human). In other words, the term "recombinant regulator protein" excludes naturally occurring recombinant regulator proteins such as endogenous factor H.

RCA proteins impair the generation of new C3b by accelerating the decay of the C3 convertases or act as cofactors for factor I (FI) in degrading existing C3b. Regulation activity may include but is not limited to (i) inhibiting the assembly of the alternative pathway C3 convertase enzymes via competition with factor B for C3b binding; (ii) facilitating the disassembly of the C3 convertases by displacing bound factor Bb ('decay accelerating activity'); and (iii) acting as a cofactor for the serine protease factor I in the cleavage and inactivation of C3b ('cofactor activity'). RCA proteins include but are not limited to cell surface-bound proteins such as decay accelerating factor (DAF), membrane cofactor protein (MCP) and complement receptor 1 (CR1), as well as the soluble FH protein which controls the steady-state alternative pathway activation in circulation and on surfaces to which it binds and FH related proteins (FHRs) such as Factor H Related Protein 1 (FHR1), Factor H Related Protein 2 (FHR2), Factor H Related Protein 3 (FHR3), Factor H Related Protein 4 (FHR4), Factor H Related Protein 5 (FHR5), and Factor H Like Protein 1 (FHL-1).

As used herein the terms "polypeptide" and "protein" are terms that are used interchangeably to refer to a polymer of amino acids, without regard to the length of the polymer. Typically, polypeptides and proteins have a polymer length that is greater than that of "peptides."

In certain embodiments, the at least one FH fragment exhibits both complement regulating activity and binding activity.

In certain embodiments, the at least one FH fragment comprises one or more FH CCP domains or fragments thereof. In certain embodiments, the at least one FH fragment comprises one or more domains selected from FH CCP domains 1 (SEQ ID NO: 9), 2 (SEQ ID NO: 10), 3 (SEQ ID NO: 11), 4 (SEQ ID NO: 12), 5 (SEQ ID NO: 13), 6 (SEQ ID NO: 14) and/or 7 (SEQ ID NO: 15). In certain embodiments the at least one FH fragment comprises FH CCP domains 1 (SEQ ID NO: 9), 2 (SEQ ID NO: 10), 3 (SEQ ID NO: 11) and 4 (SEQ ID NO: 12). In certain embodiments, the at least one FH fragment comprises FH CCP domains 1 (SEQ ID NO: 9), 2 (SEQ ID NO: 10), 3 (SEQ ID NO: 11), 4 (SEQ ID NO: 12) and 5 (SEQ ID NO: 13). In certain embodiments, the at least one FH fragment comprises FH CCP domains 1 (SEQ ID NO: 9), 2 (SEQ ID NO: 10), 3 (SEQ ID NO: 11), 4 (SEQ ID NO: 12) and 7 (SEQ ID NO: 15). In certain embodiments, the at least one FH fragment comprises FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15). In certain embodiments, the at least one FH fragment consists essentially of FH CCP domains 1 (SEQ ID NO: 9), 2 (SEQ ID NO: 10), 3 (SEQ ID NO: 11), 4 (SEQ ID NO: 12) and optionally 7 (SEQ ID NO: 15). In certain embodiments, the at least one FH fragment consists essentially of FH CCP domains 1 (SEQ ID NO: 9), 2 (SEQ ID NO: 10), 3 (SEQ ID NO: 11), 4 (SEQ ID NO: 12), 5 (SEQ ID NO: 13) and optionally 7 (SEQ ID NO: 15).

In certain embodiments, the at least one FH fragment is a first FH fragment and the at least one complement interaction region further comprises at least one further FH fragment wherein the at least one further FH fragment is operable to bind the complement regulator protein to at least one target and optionally at least one further target.

In certain embodiments, the at least one complement interaction region further comprises at least one Factor H related (FHR) protein fragment wherein the at least one FHR fragment is operable to bind the complement regulator protein to the at least one target and/or at least one further target.

In certain embodiments, the at least one complement interaction region further comprises at least one complement Factor H-like protein (FHL) fragment wherein the at least one FHL fragment is operable to bind the complement regulator protein to at least one target and/or at least one further target. Thus, in certain embodiments, the at least one further FH fragment, the at least one FHR fragment and/or the at least one complement FHL fragment exhibit binding activity e.g. to at least one target.

Without being bound by theory, FH CCP domain 7 (SEQ ID NO: 15) and/or FHL-1 CCP domains 6 (SEQ ID NO: 22) and/or 7 (SEQ ID NO: 23) may help to localise the complement regulator protein to the eye. It is considered that these domains contain recognition and binding sites for targets associated with eye related cells such as the Bruch's membrane cells and inner choroid cells.

Targets associated with eye related cells may include but are not limited to heparan sulphate and dermatan sulphate. Thus, inclusion of these aforementioned CCP domains may improve avidity and/or binding of a complement regulator protein as described herein to targets associated with eye related cells. Without being bound by theory inclusion of these aforementioned CCP domains may help provide a recombinant complement regulator protein with improved efficiency for use in the treatment of eye diseases.

In certain embodiments, the Factor H CCP domain 7 (SEQ ID NO: 15) and/or FHL-1 CCP domain 7 (SEQ ID NO: 23) comprises tyrosine (Y) at a position corresponding to amino acid 402 of full length Factor H mature protein (as set forth in SEQ ID NO: 1). The Y402 polymorphism (i.e., amino acid number 34 of SEQ ID NO: 15 or 23) leads to improved binding to heparan sulphate in retinal pigment epithelium as compared to other polymorphisms such as the 402H polymorphism which is associated with AMD. Aptly, the CCP7 domain described herein comprises the Y402 polymorphism.

Without being bound by theory, the C-terminal CCP domains of FHR proteins (such as FHR5 CCP domains 7 (SEQ ID NO; 19), 8 (SEQ ID NO: 20) and/or 9 (SEQ ID NO: 21) or FH CCP domains 18 (SEQ ID NO: 16), 19 (SEQ ID NO: 17) and/or 20 (SEQ ID NO: 18)) may help localise the complement regulator protein to the kidney(s). Thus, inclusion of FHR C-terminal CCP domains may help to improve avidity and/or binding to targets associated with kidney related cells. Without being bound by theory inclusion of these aforementioned CCP domains may help provide a recombinant complement regulator protein with improved efficiency for use in the treatment of renal diseases.

Thus, in certain embodiments the complement regulator protein comprises:
  a) at least one complement interaction region operable to regulate complement and bind the complement regulator protein to at least one target, the complement interaction region comprising;
    (i) at least one first FH fragment;
    (ii) at least one further FH fragment operable to bind the complement regulator protein to the at least one target and/or at least one further target; and
b) at least one dimerization region operable to dimerize the complement regulator protein.

In certain embodiments, the at least one FH and/or further FH fragment are derived from or are fragments of complement Factor H (FH) and/or a fragment of at least one FH CCP domain. Aptly a fragment of a protein retains at least one function of the protein.

In certain embodiments, the at least one further FH fragment comprises one or more of FH CCP domains 18 (SEQ ID NO: 16), 19 (SEQ ID NO: 17) and 20 (SEQ ID NO: 18) or a fragment thereof. In certain embodiments, the further FH fragment comprises FH CCP domains 18 (SEQ ID NO: 16), 19 (SEQ ID NO: 17) and 20 (SEQ ID NO: 18). In certain embodiments the further FH fragment consists essentially of FH CCP domains 18 (SEQ ID NO: 16), 19 (SEQ ID NO: 17) and 20 (SEQ ID NO: 18).

In certain embodiments, the amino acid sequence of the at least one FH fragment and/or further FH fragment may comprise one or more conservative substitutions as compared to the amino acid sequence of a corresponding fragment comprising wild-type naturally occurring FH CCP domains as described herein.

In certain embodiments, the at least one FH fragment comprises an amino acid sequence which is at least 80% identical to an amino acid sequence of one or more of FH CCP domains 1 (SEQ ID NO: 9), 2 (SEQ ID NO: 10), 3 (SEQ ID NO: 11), 4 (SEQ ID NO: 12), 5 (SEQ ID NO: 13), 6 (SEQ ID NO: 14) and/or 7 (SEQ ID NO: 15). For example, the at least one FH fragment comprises an amino acid sequence at least 85% identical to an amino acid sequence of one or more of FH CCP domains 1 (SEQ ID NO: 9), 2 (SEQ ID NO: 10), 3 (SEQ ID NO: 11), 4 (SEQ ID NO: 12), 5 (SEQ ID NO: 13), 6 (SEQ ID NO: 14) and/or 7 (SEQ ID NO: 15) e.g. at least 90% identical to an amino acid sequence of one or more of FH CCP domains 1 (SEQ ID NO: 9), 2 (SEQ ID NO: 10), 3 (SEQ ID NO: 11), 4 (SEQ ID NO: 12), 5 (SEQ ID NO: 13), 6 (SEQ ID NO: 14) and/or 7 (SEQ ID NO: 15), e.g. at least 95% identical to an amino acid sequence of one or more of FH CCP domains 1 (SEQ ID NO: 9), 2 (SEQ ID NO: 10), 3 (SEQ ID NO: 11), 4 (SEQ ID NO: 12), 5 (SEQ ID NO: 13), 6 (SEQ ID NO: 14) and/or 7 (SEQ ID NO: 15), e.g. at least 96, 97, 98, 99 or 100% identical. Aptly, the FH CCP domains are human.

In certain embodiments, the at least one further FH fragment comprises an amino acid sequence which is at least 80% identical to an amino acid sequence of one or more of FH CCP domains 18 (SEQ ID NO: 16), 19 (SEQ ID NO: 17) and/or 20 (SEQ ID NO: 18). For example, the at least one further FH fragment comprises an amino acid sequence at least 85% identical to an amino acid sequence of one or more of FH CCP domains 18 (SEQ ID NO: 16), 19 (SEQ ID NO: 17) and/or 20 (SEQ ID NO: 16) e.g. at least 90% identical to an amino acid sequence of one or more of FH CCP domains 18 (SEQ ID NO: 16), 19 (SEQ ID NO: 17) and/or 20 (SEQ ID NO: 18), e.g. at least 95% identical to an amino acid sequence of one or more of FH CCP domains 18 (SEQ ID NO: 16), 19 (SEQ ID NO: 17) and/or 20 (SEQ ID NO: 18), e.g. at least 96, 97, 98, 99 or 100% identical. Aptly, the FH CCP domains are human.

In certain embodiments, the at least one FH fragment and at least one further FH fragment comprise FH CCP domains 1 (SEQ ID NO: 9), 2 (SEQ ID NO: 10), 3 (SEQ ID NO: 11) and 4 (SEQ ID NO: 12) and FH CCP domains 18 (SEQ ID NO: 16), 19 (SEQ ID NO: 17) and 20 (SEQ ID NO: 18) respectively or comprise an amino acid molecule having an amino acid sequence which is at least 80% (e.g. 85%, 90% or 95%) identical to an amino acid molecule comprising FH CCP domains 1 (SEQ ID NO: 9), 2 (SEQ ID NO: 10), 3 (SEQ ID NO: 11) and 4 (SEQ ID NO: 12) and FH CCP domains 18 (SEQ ID NO: 16), 19 (SEQ ID NO: 17) and 20 (SEQ ID NO: 18) respectively.

In certain embodiments, the at least one FH and at least one further FH fragments comprise FH CCP domains 1 (SEQ ID NO: 9), 2 (SEQ ID NO: 10), 3 (SEQ ID NO: 11), 4 (SEQ ID NO: 12), and 5 (SEQ ID NO: 13) and FH CCP domains 18 (SEQ ID NO: 16), 19 (SEQ ID NO: 17) and 20 (SEQ ID NO: 18) respectively or comprise an amino acid molecule having an amino acid sequence which is at least 80% (e.g. 85%, 90% or 95%) identical to an amino acid molecule comprising FH CCP domains 1 (SEQ ID NO: 9), 2 (SEQ ID NO: 10), 3 (SEQ ID NO: 11), 4 (SEQ ID NO: 12), and 5 (SEQ ID NO: 13) and FH CCP domains 18 (SEQ ID NO: 16), 19 (SEQ ID NO: 17) and 20 (SEQ ID NO: 18) respectively.

In certain embodiments, the at least one FH and at least one further FH fragments comprise FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15) and FH CCP domains 18 (SEQ ID NO: 16), 19 (SEQ ID NO: 17) and 20 (SEQ ID NO: 18) respectively or comprise an amino acid molecule having an amino acid sequence which is at least 80% (e.g. 85%, 90% or 95%) identical to an amino acid molecule comprising FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15) and FH CCP domains 18 (SEQ ID NO: 16), 19 (SEQ ID NO: 17) and 20 (SEQ ID NO: 18) respectively.

In certain embodiments, the at least one FH and at least one further FH fragments comprise FH CCP domains 1 (SEQ ID NO: 9), 2 (SEQ ID NO: 10), 3 (SEQ ID NO: 11), 4 (SEQ ID NO: 12) and 7 (SEQ ID NO: 15) and FH CCP domains 18 (SEQ ID NO: 16), 19 (SEQ ID NO: 17) and 20 (SEQ ID NO: 18) respectively or comprise an amino acid molecule having an amino acid sequence which is at least 80% (e.g. 85%, 90% or 95%) identical to an amino acid molecule comprising FH CCP domains 1 (SEQ ID NO: 9), 2 (SEQ ID NO: 10), 3 (SEQ ID NO: 11), 4 (SEQ ID NO: 12) and 7 (SEQ ID NO: 15) and FH CCP domains 18 (SEQ ID NO: 16), 19 (SEQ ID NO: 17) and 20 (SEQ ID NO: 18) respectively.

In certain embodiments, the complement regulator protein comprises:
a) at least one complement interaction region operable to regulate complement and bind the complement regulator protein to at least one target, the complement interaction region comprising;
   (i) at least one FH fragment;
   (ii) at least one FHR fragment operable to bind the complement regulator protein to the at least one target and/or at least one further target;
b) at least one dimerization region operable to dimerize the complement regulator protein.

In certain embodiments, the at least one FHR fragment is derived from or fragment of one or more of FHR2, FHR3, FHR4 and/or FHR5. In certain embodiments, the at least one FHR fragment comprises at least one FHR5 CCP domain or fragment thereof. In certain embodiments, the at least one FHR5 CCP domain comprises one or more of FHR5 CCP7 (SEQ ID NO: 19), FHR5 CCP8 (SEQ ID NO: 20) and/or FHR CCP9 (SEQ ID NO: 21).

In certain embodiments, the at least one FHR fragment comprises FHR5 CCP7 (SEQ ID NO: 19), FHR5 CCP8 (SEQ ID NO: 20) and FHR CCP9 (SEQ ID NO: 21). In certain embodiments, the at least one FHR fragment comprises FHR5 CCP8 (SEQ ID NO: 20) and FHR CCP9 (SEQ ID NO: 21).

In certain embodiments, the amino acid sequence of the at least one FHR fragment may comprise one or more conservative substitutions as compared to the amino acid sequence of a corresponding fragment comprising wild-type naturally occurring FHR5 CCP domains as described herein.

In certain embodiments, the at least one FHR fragment comprises an amino acid sequence which is at least 80% identical to an amino acid sequence of FHR5 CCP domains 7 (SEQ ID NO: 19), 8 (SEQ ID NO: 20) and/or 9 (SEQ ID NO: 21). For example, the at least one FHR fragment comprises an amino acid sequence at least 85% identical to an amino acid sequence of FHR5 CCP domains 7 (SEQ ID NO: 19), 8 (SEQ ID NO: 20) and/or 9 (SEQ ID NO: 21) e.g. at least 90% identical to an amino acid sequence of FHR5 CCP domains 7 (SEQ ID NO: 19), 8 (SEQ ID NO: 20) and/or 9 (SEQ ID NO: 21), e.g. at least 95% identical to an amino acid sequence of FHR5 CCP domains 7 (SEQ ID NO: 19), 8 (SEQ ID NO: 20) and/or 9 (SEQ ID NO: 21), e.g. at least 96, 97, 98, 99 or 100% identical. Aptly, the FHR CCP domains are human.

In certain embodiments, the at least one FH and at least one FHR fragment comprise FH CCP domains 1 (SEQ ID NO: 9), 2 (SEQ ID NO: 10), 3 (SEQ ID NO: 11) and 4 (SEQ ID NO: 12) and FHR5 CCP domains 8 (SEQ ID NO: 20) and 9 (SEQ ID NO: 21) respectively or comprise an amino acid molecule having an amino acid sequence which is at least 80% (e.g. 85%, 90% or 95%) identical to an amino acid molecule comprising FH CCP domains 1 (SEQ ID NO: 9), 2 (SEQ ID NO: 10), 3 (SEQ ID NO: 11) and 4 (SEQ ID NO: 12) and FHR5 CCP domains 8 (SEQ ID NO: 20) and 9 (SEQ ID NO: 21) respectively.

In certain embodiments, the at least one FH and at least one FHR fragment comprise FH CCP domains 1 (SEQ ID NO: 9), 2 (SEQ ID NO: 10), 3 (SEQ ID NO: 11), 4 (SEQ ID NO: 12), and 5 (SEQ ID NO: 13) and FHR5 CCP domains 8 (SEQ ID NO: 20) and 9 (SEQ ID NO: 21) respectively or comprise an amino acid molecule having an amino acid sequence which is at least 80% (e.g. 85%, 90% or 95%) identical to an amino acid molecule comprising FH CCP domains 1 (SEQ ID NO: 9), 2 (SEQ ID NO: 10), 3 (SEQ ID NO: 11), 4 (SEQ ID NO: 12), and 5 (SEQ ID NO: 13) and FHR5 CCP domains 8 (SEQ ID NO: 20) and 9 (SEQ ID NO: 21) respectively.

In certain embodiments, the at least one FH and at least one FHR fragments comprise FH CCP domains 1 (SEQ ID NO: 9), 2 (SEQ ID NO: 10), 3 (SEQ ID NO: 11), 4 (SEQ ID NO: 12), 5 (SEQ ID NO: 9) and 7 (SEQ ID NO: 15) and FHR5 CCP domains 8 (SEQ ID NO: 20) and 9 (SEQ ID NO: 21) respectively or comprise an amino acid molecule having an amino acid sequence which is at least 80% (e.g. 85%, 90% or 95%) identical to an amino acid molecule comprising FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15) and FHR5 CCP domains 8 (SEQ ID NO: 20) and 9 (SEQ ID NO: 21) respectively.

In certain embodiments, the at least one FH and at least one further FH fragments comprise FH CCP domains 1 (SEQ ID NO: 9), 2 (SEQ ID NO: 10), 3 (SEQ ID NO: 11), 4 (SEQ ID NO: 12) and 7 (SEQ ID NO: 15) and FHR5 CCP domains 8 (SEQ ID NO: 20) and 9 (SEQ ID NO: 21) respectively or comprise an amino acid molecule having an amino acid sequence which is at least 80% (e.g. 85%, 90% or 95%) identical to an amino acid molecule comprising FH CCP domains 1 (SEQ ID NO: 9), 2 (SEQ ID NO: 10), 3 (SEQ ID NO: 11), 4 (SEQ ID NO: 12) and 7 (SEQ ID NO: 15) and FHR5 CCP domains 8 (SEQ ID NO: 20) and 9 (SEQ ID NO: 21) respectively.

In certain embodiments, the complement regulator protein comprises:
  a) at least one complement interaction region operable to regulate complement and bind the complement regulator protein to at least one target, the complement interaction region comprising;
    (i) at least one FH fragment;
    (ii) at least one FHL fragment operable to bind the complement regulator protein to the at least one target and/or at least one further target; and
  b) at least one dimerization region operable to dimerize the complement regulator protein.

In certain embodiments, the at least one FHL fragment is derived from or a fragment of FHL-1. In certain embodiments, the at least one FHL fragment comprises one or more of FHL-1 CCP domains 6 (SEQ ID NO: 22) and/or 7 (SEQ ID NO: 23) or a fragment thereof. In certain embodiments, the at least one FHL fragment comprises FHL-1 CCP domains 6 (SEQ ID NO: 22) and 7 (SEQ ID NO: 23). Aptly the FHL CCP domains are human.

FHL-1 (also known in the art as reconectin) is a protein encoded by the FH gene but produced by alternative splicing of the RNA transcript. Without being bound by theory wild-type FHL-1 has an N-terminal amino acid residue sequence identical to FH CCP domains 1 to 7 and at least four further amino acid residues, in comparison to wild-type FH, at its C-terminal. FHL-1 may be involved in cell adhesion as well as showing complement binding and regulation activity. FHL-1 is a plasma protein and may have some similar as well as additional and/or differing activities or functionalities as that of FH.

In certain embodiments, the at least one FHL fragment comprises an amino acid sequence which is at least 80% identical to an amino acid sequence of FHL-1 CCP domains 6 (SEQ ID NO: 22) and/or 7 (SEQ ID NO: 23). For example, the at least one FHL fragment comprises an amino acid sequence at least 85% identical to an amino acid sequence of FHL-1 CCP domains 6 (SEQ ID NO: 22) and/or 7 (SEQ ID NO: 23) e.g. at least 90% identical to an amino acid sequence of FHL-1 CCP domains 6 (SEQ ID NO: 22) and/or 7 (SEQ ID NO: 23), e.g. at least 95% identical to an amino acid sequence of FHL-1 CCP domains 6 (SEQ ID NO: 22) and/or 7 (SEQ ID NO: 23), e.g. at least 96, 97, 98, 99 or 100% identical. Aptly, the FHL-1 CCP domains are human.

In certain embodiments, the at least one FH and at least one FHL fragment comprise FH CCP domains 1 (SEQ ID NO: 9), 2 (SEQ ID NO: 10), 3 (SEQ ID NO: 11) and 4 (SEQ ID NO: 12) and FHL-1 CCP domains 6 (SEQ ID NO: 22) and 7 (SEQ ID NO: 23) respectively or comprise an amino acid molecule having an amino acid sequence which is at least 80% (e.g. 85%, 90% or 95%) identical to an amino acid molecule comprising FH CCP domains 1 (SEQ ID NO: 9), 2 (SEQ ID NO:10), 3 (SEQ ID NO: 11) and 4 (SEQ ID NO: 12) and FHL-1 CCP domains 6 (SEQ ID NO: 22) and 7 (SEQ ID NO: 23) respectively.

In certain embodiments, the at least one FH and at least one FHL fragment comprise FH CCP domains 1 (SEQ ID NO: 9), 2 (SEQ ID NO: 10), 3 (SEQ ID NO: 11), 4 (SEQ ID NO: 12) and 5 (SEQ ID NO: 13) and FHL-1 CCP domains 6 (SEQ ID NO: 22) and 7 (SEQ ID NO: 23) respectively or comprise an amino acid molecule having an amino acid sequence which is at least 80% (e.g. 85%, 90% or 95%) identical to an amino acid molecule comprising FH CCP domains 1 (SEQ ID NO: 9), 2 (SEQ ID NO: 10), 3 (SEQ ID NO: 11), 4 (SEQ ID NO: 12) and 5 (SEQ ID NO: 13) and FHL-1 CCP domains 6 (SEQ ID NO: 22) and 7 (SEQ ID NO: 23) respectively.

In certain embodiments, the at least one FH and at least one FHL fragments comprise FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15) and FHL-1 CCP domains 6 (SEQ ID NO: 22) and 7 (SEQ ID NO: 23) respectively or comprise an amino acid molecule having an amino acid sequence which is at least 80% (e.g. 85%, 90% or 95%) identical to an amino acid molecule comprising FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15) and FHL-1 CCP domains 6 (SEQ ID NO: 22) and 7 (SEQ ID NO: 23) respectively.

In certain embodiments, the at least one FH and at least one FHL fragments comprise FH CCP domains 1 (SEQ ID NO: 9), 2 (SEQ ID NO: 10), 3 (SEQ ID NO: 11), 4 (SEQ ID NO: 12) and 7 (SEQ ID NO: 15) and FHL-1 CCP domains 6 (SEQ ID NO: 22) and 7 (SEQ ID NO: 23) respectively or comprise an amino acid molecule having an amino acid sequence which is at least 80% (e.g. 85%, 90% or 95%) identical to an amino acid molecule comprising FH CCP domains 1 (SEQ ID NO: 9), 2 (SEQ ID NO: 10), 3 (SEQ ID NO: 11), 4 (SEQ ID NO: 12) and 7 (SEQ ID NO: 15) and FHL-1 CCP domains 6 (SEQ ID NO: 22) and 7 (SEQ ID NO: 23) respectively.

As used herein the terms "complement control protein (CCP) domain or module", "complement control protein (CCP), "short consensus repeat" (SCR) and "sushi domain" are used interchangeably and refer to domains found in all RCAs that contribute to their ability to regulate complement activation and bind to targets in the blood or on host cell surfaces to which they bind. CCP domains typically are composed of about 60 amino acids, with four cysteine residues disulphide bonded in a 1-3 2-4 arrangement and a hydrophobic core built around an almost invariant tryptophan residue. CCP domains are numbered from the N-termini of a protein of which they make up, for example the N-terminal CCP domain is numbered CCP1, the next CCP domain located further from the N-termini of the protein towards to the C-termini of the protein is CCP2 and so forth.

As there is overlap between binding sites and regulating activity of the FH, FHR and FHL-1 CCP domains it will be understood by those skilled in the art that the at least one FH fragment and/or further FH fragment, FHR fragment and/or FHL fragment of complement interaction region are not limited to just regulatory activity or just binding activity but may provide sites for both regulation and binding of certain targets.

In certain embodiments, the at least one complement interaction region, allows the complement regulator protein to bind to at least one target. The binding of certain embodiments of the complement regulators of the present invention may be multifunctional. That is to say, certain embodiments of the complement regulator proteins of the present invention are able to bind to a plurality of different targets.

In certain embodiments, the complement regulator protein is able to bind to one or more of:
  at least one polyanionic cell surface marker; and/or
  at least one complement activation/inactivation component; and/or
  at least one lipid peroxidation end product; and/or
  at least one immune cell adhesion related molecule; and/or
  at least one apoptotic cell related molecule; and/or
  at least one acute phase related molecule.

In certain embodiments, the at least one target and/or further target comprises at least one polyanionic cell surface marker. In certain embodiments, the at least one target and/or further target comprises at least one complement activation/inactivation component.

In certain embodiments, the at least one target and/or further target comprises at least one lipid peroxidation end product. In certain embodiments, the at least one target and/or further target comprises at least one immune cell adhesion related molecule. In certain embodiments, the at least one target and/or further target comprises at least one apoptotic cell related molecule.

In certain embodiments, the at least one target and/or further target comprises at least one acute phase related molecule.

Cell surface markers are proteins or molecules located on or near the surface of cells that serve as markers of specific cell types and/or certain cell conditions. The presence of cell surface markers can also determine if a cell type expresses the specific receptor important for a biological response. Markers therefore may allow proteins such as certain embodiments of proteins of the present invention to distinguish between self or host cells and foreign cells. They also may allow for proteins such as certain embodiments of proteins of the present invention to distinguish between normal and abnormal cells, such as for example non-toxic and/or non-cancerous cells and toxic and/or cancerous cells.

As used herein the term "host" and "self" are used interchangeably to describe cells or tissues belonging to a particular organism, as compared to foreign and/or abnormal cells, e.g., of invading microorganisms, or cancerous cells, which the immune system is designed to recognize as "other" or "non-self".

Polyanionic markers are markers that have a plurality of negatively charged (anionic) groups. For example, polyanionic cell surface markers may include but are not limited to N-linked glycosyl units with sialic acid end-groups and/or one or more glycosaminoglycans (GAGs) such as heparin, heparan sulphate, chondroitin sulphate, dermatan sulphate, keratan sulphate and hyaluronan.

Complement activation/inactivation components may include but are not limited to complement proteins or fragments thereof that include a thioester-containing domain (TED) such as for example C3b, iC3b, C3dg, C3d and C3. Complement activation/inactivation components may also include complement proteins such as Factor I.

Lipid peroxidation is the oxidative degeneration of lipids in a cell. It may be initiated by oxidative stress and the presence of free radicals such as reactive oxygen species. Lipids are oxidised to lipid free radicals and further oxidised to lipid peroxidyl free radicals. The reaction may be referred to as a chain reaction as it is propagated by each free radical produced reacting with a non-free radical to produce a further free radical and is terminated by neutralisation of these free radicals for example by a reaction between two free radicals. The end products of lipid peroxidation include but are not limited to malondialdehyde (MDA), malondialdehyde-acetaldehyde (MAA), 4-hydroxynonenal (4-HNE), carboxyethylpyrrole (CEP), oxidized phosphatidylserine (OxPS) and oxidized cardiolipin (OxCL). These end products may be mutagenic and cause damage to the cell as well as causing inflammatory responses in the cell or a tissue. These end products have also been linked to inflammatory diseases and other diseases such as age-related macular degeneration (AMD). By binding to these end products, the recombinant complement regulatory protein of certain embodiments can help to reduce or inhibit the inflammatory responses that may be caused by lipid peroxidation end products.

As used herein the term "immune cell adhesion related molecules" refers to proteins, peptides, lipids, nucleotides and/or carbohydrates that are involved in the adhesion of immune cells, such as, for example, monocytes, leukocytes, T cells, B-cells or other immune cells that will be known by those skilled in the art, to one or more targets such as membranes, extracellular matrix components or membrane proteins. Examples of immune cell related adhesion molecules includes, but is not limited to one or more of integrin proteins, selectin proteins, (such as L-selectin), Annexin II, immunoglobulin proteins, fibromodulin and cluster differentiation proteins (CDs) such as CD4, CD45 and CD24.

As used herein the term "apoptotic cell related molecules" refers to molecules such as proteins, peptides, lipids, nucleotides and/or carbohydrates that induce apoptosis in a cell and/or are present in a cell inducing and/or undergoing apoptosis. Apoptotic cell related molecules include but are not limited to caspases, phosphatidylserine, Annexin I, calreticulin, annexin V and Tumour Necrosis Factor (TNF) receptor proteins.

As used herein the term "acute phase proteins" refers to a group of plasmatic proteins whose plasma concentration increases or decreases in response to one or more of tissue injury, acute infections, burns, or chronic inflammation in a human or a non-human mammal. Acute phase proteins include, but are not limited to, serum amyloid A (SAA) proteins, alpha-1 acid glycoprotein, alpha-1 antitrypsin, haptoglobins, fibrinogen, C-reactive protein, ferritin, ceruloplasmin and complement factors.

In certain embodiments, the at least one dimerization region comprises at least one CCP domain or fragment thereof. That is to say, the dimerization region may comprise 1, 2, 3, 4, 5, 6, 7, 8, 9, 10, 12, 13, 14, 15, 16, 17, 18, 19, 20 or more CCP domains. In certain embodiments, the dimerization region comprises two CCP domains.

In certain embodiments, the at least one dimerization region comprises at least one CCP domain derived from or is a fragment of a complement Factor H Related protein (FHR).

FHR proteins are proteins that share features in common with FH. FHR proteins are made up of CCP domains and may have similar functions as FH such as cofactor and decay accelerating activity and target binding. According to the CCP domains FHR proteins can be divided into two major groups.

FHR1, 2 and 5 form Group 1. FHR1 is composed of 5 CCP domains, FHR2 is composed of 4 CCP domains and FHR5 is composed of 9 CCP domains. Group 1 FHRs are found circulating in plasma as dimers. Sometimes as homodimers (e.g. FHR1-FHR1 dimer) or as heterodimers (e.g. FHR1-FHR2 dimer).

In certain embodiments, the dimerization region comprises one or more CCPs derived from or that are fragments of FHR1, FHR2 and/or FHR5. Aptly, the FHR1, FHR2 and/or FHR5 are human. In certain embodiments, the dimerization region comprises one or more CCPs derived from or are fragments of FHR1 e.g. human FHR1.

In certain embodiments, the dimerization region comprises one or more CCPs derived from or are fragments of FHR2 e.g. human FHR2. In certain embodiments, the dimerization region comprises one or more CCPs derived from or are fragments of FHR5 e.g. human FHR5.

In certain embodiments, the dimerization region comprises FHR1 CCP1 (SEQ ID NO: 24) and FHR1 CCP2 (SEQ ID NO: 25). Aptly, the FHR1 CCP1 and CCP2 are human. In certain embodiments, the dimerization region comprises an amino acid molecule which comprises a sequence which has at least 80% (e.g. 85%, 90%, 95%, 96%, 97%, 98% or 99%) sequence identity to a sequence of human FHR1 CCP1 (SEQ ID NO: 24) and CCP2 (SEQ ID NO: 25).

Without being bound by theory, dimerization of certain embodiments of the recombinant complement regulator proteins as described herein increases the hydrodynamic radius. This increase in hydrodynamic radius may decrease kidney filtration due to the protein being larger than the glomerular boundary (approximately 50 to 60 kDa) and therefore increase serum half-life of the proteins. Dimerization may also help to increase avidity (the overall strength of binding between a binding protein and its target(s)). Improved avidity may help to improve complement regulation activity.

The at least one complement interaction region and fragments thereof and at least one dimerization region may be joined together in any order. For example, certain embodiments of the present invention comprise a complement regulator protein comprising, from N-terminal to C-terminal, at least one dimerization region, at least one first FH fragment and at least one further FH fragment. Certain embodiments comprise a complement regulator protein comprising from N-terminal to C-terminal at least at least one first FH fragment, at least one further FH fragment and at least one dimerization region.

According to a further aspect of the present invention, there is provided a recombinant complement regulator protein comprising a general formula selected from:

$X_1$-$L_1$-$X_2$-$L_2$-$Y_1$ Formula I

Or $Y_1$-$L_1$-$X_1$-$L_2$-$X_2$ Formula II

Or $X_1$-$L_1$-$Y_1$-$L_2$-$X_2$ Formula III wherein:

- $X_1$ is a molecule selected from a molecule comprising: (i) FH CCP domains 1 (SEQ ID NO: 9), 2 (SEQ ID NO: 10), 3 (SEQ ID NO: 11) and 4 (SEQ ID NO: 12); (ii) FH CCP domains 1 (SEQ ID NO: 9), 2 (SEQ ID NO: 10), 3 (SEQ ID NO: 11), 4 (SEQ ID NO: 12) and 5 (SEQ ID NO: 13); (iii) FH CCP domains 1 (SEQ ID NO: 9), 2 (SEQ ID NO: 10), 3 (SEQ ID NO: 11), 4 (SEQ ID NO: 12), and 7 (SEQ ID NO: 15); and (iv) FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15);
- $L_1$ is at least one linker molecule or is absent;
- $X_2$ is a molecule selected from a molecule comprising: (i) FH CCP domains 18 (SEQ ID NO: 16), 19 (SEQ ID NO: 17) and 20 (SEQ ID NO: 18); (ii) FH CCP domain 19 (SEQ ID NO: 17) and 20 (SEQ ID NO: 18); (iii) FHL-1 CCP domains 6 (SEQ ID NO: 22) and 7 (SEQ ID NO: 23); (iv) FHR2 CCP domains 3 and 4; (v) FHR3 CCP domains 4 and 5; (vi) FHR4 CCP domains 8 and 9; (vii) FHR5 CCP domains 7 (SEQ ID NO: 19), 8 (SEQ ID NO: 20) and 9 (SEQ ID NO: 21); and (viii) FHR5 CCP domains 8 (SEQ ID NO: 20) and 9 (SEQ ID NO: 21); or is absent;
- $L_2$ is at least one linker molecule or is absent; and
- $Y_1$ is a molecule selected from a molecule comprising: (i) FHR1 CCP domains 1 (SEQ ID NO: 24) and 2 (SEQ ID NO: 25); (ii) FHR2 CCP domains 1 and 2; or (iii) FHR5 CCP domains 1 and 2.

In certain embodiments, $X_1$ is a molecule comprising FH CCP domains 1 (SEQ ID NO: 9), 2 (SEQ ID NO: 10), 3 (SEQ ID NO: 11) and 4 (SEQ ID NO: 12).

In certain embodiments, $X_1$ is a molecule comprising FH CCP domains 1 (SEQ ID NO: 9), 2 (SEQ ID NO: 10), 3 (SEQ ID NO: 11), 4 (SEQ ID NO: 12) and 5 (SEQ ID NO: 13). In certain embodiments, $X_1$ is a molecule comprising FH CCP domains 1 (SEQ ID NO: 9), 2 (SEQ ID NO: 10), 3 (SEQ ID NO: 11), 4 (SEQ ID NO: 12) and 7 (SEQ ID NO: 15). In certain embodiments, $X_1$ is a molecule comprising FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15).

In certain embodiments, $X_2$ is a molecule comprising FH CCP domains 18 (SEQ ID NO: 16), 19 (SEQ ID NO: 17) and 20 (SEQ ID NO: 18). In certain embodiments, $X_2$ is a molecule comprising FH CCP domain 19 (SEQ ID NO: 17) and 20 (SEQ ID NO: 18). In certain embodiments, $X_2$ is a molecule comprising FHL-1 CCP domains 6 (SEQ ID NO: 22) and 7 (SEQ ID NO: 23). In certain embodiments, $X_2$ is a molecule comprising FHR2 CCP domains 3 and 4. In certain embodiments, $X_2$ is a molecule comprising FHR3 CCP domains 4 and 5. In certain embodiments, $X_2$ is a molecule comprising FHR4 CCP domains 8 and 9. In certain embodiments, $X_2$ is a molecule comprising FHR5 CCP domains 7 (SEQ ID NO: 19), 8 (SEQ ID NO: 20) and 9 (SEQ ID NO: 21). In certain embodiments, $X_2$ is a molecule comprising FHR5 CCP domains 8 (SEQ ID NO: 20) and 9 (SEQ ID NO: 21).

In certain embodiments $Y_1$ is a molecule comprising FHR1 CCP domains 1 (SEQ ID NO: 24) and 2 (SEQ ID NO: 25). In certain embodiments $Y_1$ is a molecule comprising FHR2 CCP domains 1 and 2. In certain embodiments $Y_1$ is or a molecule comprising FHR5 CCP domains 1 and 2.

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11) and 4 (SEQ ID NO: 12); at least one linker; and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11) and 4 (SEQ ID NO:12); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 5 (SEQ ID NO: 13); at least one linker; and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 5 (SEQ ID NO: 13); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 7 (SEQ ID NO: 15); at least one linker; and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 7 (SEQ ID NO: 15); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15); at least one linker; and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), and 4 (SEQ ID NO: 12); FH CCP domains 18 (SEQ ID NO: 16), 19 (SEQ ID NO: 17) and 20 (SEQ ID NO: 18); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), and 4 (SEQ ID NO: 12); at least one linker; FH CCP domains 18 (SEQ ID NO: 16), 19 (SEQ ID NO: 17) and 20 (SEQ ID NO: 18); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), and 4 (SEQ ID NO: 12); FH CCP domains 18 (SEQ ID NO: 16), 19 (SEQ ID NO: 17) and 20 (SEQ ID NO: 18); at least one linker; and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), and 4 (SEQ ID NO: 12); at least one linker; FH CCP domains 18 (SEQ ID NO: 16), 19 (SEQ ID NO: 17) and 20 (SEQ ID NO: 18); at least one further linker; and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 5 (SEQ ID NO: 15); FH CCP domains 18 (SEQ ID NO: 16), 19 (SEQ ID NO: 17) and 20 (SEQ ID NO: 18); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 5 (SEQ ID NO: 13); at least one linker; FH CCP domains 18 (SEQ ID NO: 16), 19 (SEQ ID NO: 17) and 20 (SEQ ID NO: 18); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 5 (SEQ ID NO: 15); FH CCP domains 18 (SEQ ID NO: 16), 19 (SEQ ID NO: 17) and 20 (SEQ ID NO: 18); at least one linker; and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 5 (SEQ ID NO: 15); at least one linker; FH CCP domains 18 (SEQ ID NO: 16), 19 (SEQ ID NO: 17) and 20 (SEQ ID NO: 18); at least one further linker; and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 7 (SEQ ID NO: 15); FH CCP domains 18 (SEQ ID NO: 16), 19 (SEQ ID NO: 17) and 20 (SEQ ID NO: 18); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 7 (SEQ ID NO: 15); at least one linker; FH CCP domains 18 (SEQ ID NO: 16), 19 (SEQ ID NO: 17) and 20 (SEQ ID NO: 18); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 7 (SEQ ID NO: 15); FH CCP domains 18 (SEQ ID NO: 16), 19 (SEQ ID NO: 17) and 20 (SEQ ID NO: 18); at least one linker and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 7 (SEQ ID NO: 15); at least one linker; FH CCP domains 18 (SEQ ID NO: 16), 19 (SEQ ID NO: 17) and 20 (SEQ ID NO: 18); at least one further linker; and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15); FH CCP domains 18 (SEQ ID NO: 16), 19 (SEQ ID NO: 17) and 20 (SEQ ID NO: 18); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15); at least one linker; FH CCP domains 18 (SEQ ID NO: 16), 19 (SEQ ID NO: 17) and 20 (SEQ ID NO: 18); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15); FH CCP domains 18 (SEQ ID NO: 16), 19 (SEQ ID NO: 17) and 20 (SEQ ID NO: 18); at least one linker; and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12), 5 (SEQ ID NO: 13)

and 7 (SEQ ID NO: 15); at least one linker; FH CCP domains 18 (SEQ ID NO: 16), 19 (SEQ ID NO: 17) and 20 (SEQ ID NO: 18); at least one further linker; and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), and 4 (SEQ ID NO: 12); FH CCP domain 19 (SEQ ID NO: 17) and 20 (SEQ ID NO: 18); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), and 4 (SEQ ID NO: 12); at least one linker; FH CCP domain 19 (SEQ ID NO: 17) and 20 (SEQ ID NO: 18); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), and 4 (SEQ ID NO: 12); FH CCP domain 19 (SEQ ID NO: 17) and 20 (SEQ ID NO: 18); at least one linker; and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), and 4 (SEQ ID NO: 12); at least one linker; FH CCP domain 19 (SEQ ID NO: 17) and 20 (SEQ ID NO: 18); at least one further linker; and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 5 (SEQ ID NO: 13); FH CCP domain 19 (SEQ ID NO: 17) and 20 (SEQ ID NO: 18); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 5 (SEQ ID NO: 13); at least one linker; FH CCP domain 19 (SEQ ID NO: 17) and 20 (SEQ ID NO: 18); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 5 (SEQ ID NO: 13); FH CCP domain 19 (SEQ ID NO: 17) and 20 (SEQ ID NO: 18); at least one linker; and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 5 (SEQ ID NO: 13); at least one linker; FH CCP domain 19 (SEQ ID NO: 17) and 20 (SEQ ID NO: 18); at least one further linker; and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 7 (SEQ ID NO: 15); FH CCP domain 19 (SEQ ID NO: 17) and 20 (SEQ ID NO: 18); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 7 (SEQ ID NO: 15); at least one linker; FH CCP domain 19 (SEQ ID NO: 17) and 20 (SEQ ID NO: 18); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 7 (SEQ ID NO: 15); FH CCP domain 19 (SEQ ID NO: 17) and 20 (SEQ ID NO: 18); at least one linker; and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 7 (SEQ ID NO: 15); at least one linker; FH CCP domain 19 (SEQ ID NO: 17) and 20 (SEQ ID NO: 18); at least one further linker; and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15); FH CCP domain 19 (SEQ ID NO: 17) and 20 (SEQ ID NO: 18); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15); at least one linker; FH CCP domain 19 (SEQ ID NO: 17) and 20 (SEQ ID NO: 18); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15); FH CCP domain 19 (SEQ ID NO: 17) and 20 (SEQ ID NO: 18); at least one linker; and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15); at least one linker; FH CCP domain 19 (SEQ ID NO: 17) and 20 (SEQ ID NO: 18); at least one further linker; and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11) and 4 (SEQ ID NO: 12); FHL-1 CCP domains 6 (SEQ ID NO: 22) and 7 (SEQ ID NO: 23); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11) and 4 (SEQ ID NO: 12); at least one linker; FHL-1 CCP domains 6 (SEQ ID NO: 22) and 7 (SEQ ID NO: 23); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11) and 4 (SEQ ID NO: 12); FHL-1 CCP domains 6 (SEQ ID NO: 22) and 7 (SEQ ID NO: 23); at least one linker; and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11) and 4 (SEQ ID NO: 12); at least one linker; FHL-1 CCP domains 6 (SEQ ID NO: 22) and 7 (SEQ ID NO: 23); at least one further linker; and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 5 (SEQ ID NO: 13); FHL-1 CCP domains 6 (SEQ ID NO: 22) and 7 (SEQ ID NO: 23); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 5 (SEQ ID NO: 13); at least one linker; FHL-1 CCP domains 6 (SEQ ID NO: 22) and 7 (SEQ ID NO: 23); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 5 (SEQ ID NO: 13); FHL-1 CCP domains 6 (SEQ ID NO: 22) and 7 (SEQ ID NO: 23); at least one linker; and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 5 (SEQ ID NO: 13); at least one linker; FHL-1 CCP domains 6 (SEQ ID NO: 22) and 7 (SEQ ID NO: 23); at least one further linker; and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 7 (SEQ ID NO: 15); FHL-1 CCP domains 6 (SEQ ID NO: 22) and 7 (SEQ ID NO: 23); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 7 (SEQ ID NO: 15); at least one linker; FHL-1 CCP domains 6 (SEQ ID NO: 22) and 7 (SEQ ID NO: 23); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 7 (SEQ ID NO: 15); FHL-1 CCP domains 6 (SEQ ID NO: 22) and 7 (SEQ ID NO: 23); at least one linker; and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 7 (SEQ ID NO: 15); at least one linker; FHL-1 CCP domains 6 (SEQ ID NO: 22) and 7 (SEQ ID NO: 23); at least one further linker; and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15); FHL-1 CCP domains 6 (SEQ ID NO: 22) and 7 (SEQ ID NO: 23); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15); at least one linker; FHL-1 CCP domains 6 (SEQ ID NO: 22) and 7 (SEQ ID NO: 23); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15); FHL-1 CCP domains 6 (SEQ ID NO: 22) and 7 (SEQ ID NO: 23); at least one linker; and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15); at least one linker; FHL-1 CCP domains 6 (SEQ ID NO: 22) and 7 (SEQ ID NO: 23); at least one further linker; and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11) and 4 (SEQ ID NO: 12); FHR5 CCP domains 7 (SEQ ID NO: 19), 8 (SEQ ID NO: 20) and 9 (SEQ ID NO: 21); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11) and 4 (SEQ ID NO: 12); at least one linker; FHR5 CCP domains 7 (SEQ ID NO: 19), 8 (SEQ ID NO: 20) and 9 (SEQ ID NO: 21); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11) and 4 (SEQ ID NO: 12); FHR5 CCP domains 7 (SEQ ID NO: 19), 8 (SEQ ID NO: 20) and 9 (SEQ ID NO: 21); at least one linker; and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11) and 4 (SEQ ID NO: 12); at least one linker; FHR5 CCP domains 7 (SEQ ID NO: 19), 8 (SEQ ID NO: 20) and 9 (SEQ ID NO: 21); at least one further linker; and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 5 (SEQ ID NO: 13); FHR5 CCP domains 7 (SEQ ID NO: 19), 8 (SEQ ID NO: 20) and 9 (SEQ ID NO: 21); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 5 (SEQ ID NO: 13); at least one linker; FHR5 CCP domains 7 (SEQ ID NO: 19), 8 (SEQ ID NO: 20) and 9 (SEQ ID NO: 21); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 5 (SEQ ID NO: 13); FHR5 CCP domains 7 (SEQ ID NO: 19), 8 (SEQ ID NO: 20) and 9 (SEQ ID NO: 21); at least one linker; and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 5 (SEQ ID NO: 13); at least one linker; FHR5 CCP domains 7 (SEQ ID NO: 19), 8 (SEQ ID NO: 20) and 9 (SEQ ID NO: 21); at least one further linker; and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 7 (SEQ ID NO: 15); FHR5 CCP domains 7 (SEQ ID NO: 19), 8 (SEQ ID NO: 20) and 9 (SEQ ID NO: 21); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 7 (SEQ ID NO: 15); at least one linker; FHR5 CCP domains 7 (SEQ ID NO: 19), 8 (SEQ ID NO: 20) and 9 (SEQ ID NO: 21); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 7 (SEQ ID NO: 15); FHR5 CCP domains 7 (SEQ ID NO: 19), 8 (SEQ ID NO: 20) and 9 (SEQ ID NO: 21); at least one linker; and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 7 (SEQ ID NO: 15); at least one linker; FHR5 CCP domains 7 (SEQ ID NO: 19), 8 (SEQ ID NO: 20) and 9 (SEQ ID NO: 21); at least one further linker; and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15); FHR5 CCP domains 7 (SEQ ID NO: 19), 8 (SEQ ID NO: 20) and 9 (SEQ ID NO: 21); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15); at least one linker; FHR5 CCP domains 7 (SEQ ID NO: 19), 8 (SEQ ID NO: 20) and 9 (SEQ ID NO: 21); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15); FHR5 CCP domains 7 (SEQ ID NO: 19), 8 (SEQ ID NO: 20) and 9 (SEQ ID NO: 21); at least one linker; and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15); at least one linker; FHR5 CCP domains 7 (SEQ ID NO: 19), 8 (SEQ ID NO: 20) and 9 (SEQ ID NO: 21); at least one further linker; and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11) and 4 (SEQ ID NO: 12); FHR5 CCP domains 8 (SEQ ID NO: 20) and 9 (SEQ ID NO: 21); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11) and 4 (SEQ ID NO: 12); at least one linker; FHR5 CCP domains 8 (SEQ ID NO: 20) and 9 (SEQ ID NO: 21); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11) and 4 (SEQ ID NO: 12); FHR5 CCP domains 8 (SEQ ID NO: 20) and 9 (SEQ ID NO: 21); at least one linker; and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11) and 4 (SEQ ID NO: 12); at least one linker; FHR5 CCP domains 8 (SEQ ID NO: 20) and 9 (SEQ ID NO: 21); at least one further linker; and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 5 (SEQ ID NO: 13); FHR5 CCP domains 8 (SEQ ID NO: 20) and 9 (SEQ ID NO: 21); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 5 (SEQ ID NO:

13); at least one linker; FHR5 CCP domains 8 (SEQ ID NO: 20) and 9 (SEQ ID NO: 21); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 5 (SEQ ID NO: 13); FHR5 CCP domains 8 (SEQ ID NO: 20) and 9 (SEQ ID NO: 21); at least one linker; and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 5 (SEQ ID NO: 13); at least one linker; FHR5 CCP domains 8 (SEQ ID NO: 20) and 9 (SEQ ID NO: 21); at least one further linker; and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 7 (SEQ ID NO: 15); FHR5 CCP domains 8 (SEQ ID NO: 20) and 9 (SEQ ID NO: 21); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 7 (SEQ ID NO: 15); at least one linker; FHR5 CCP domains 8 (SEQ ID NO: 20) and 9 (SEQ ID NO: 21); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 7 (SEQ ID NO: 15); FHR5 CCP domains 8 (SEQ ID NO: 20) and 9 (SEQ ID NO: 21); at least one linker; and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12) and 7 (SEQ ID NO: 15); at least one linker; FHR5 CCP domains 8 (SEQ ID NO: 20) and 9 (SEQ ID NO: 21); at least one further linker; and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15); FHR5 CCP domains 8 (SEQ ID NO: 20) and 9 (SEQ ID NO: 21); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15); at least one linker; FHR5 CCP domains 8 (SEQ ID NO: 20) and 9 (SEQ ID NO: 21); and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15); FHR5 CCP domains 8 (SEQ ID NO: 20) and 9 (SEQ ID NO: 21); at least one linker; and FHR1 CCP domains 1 (SEQ ID NO: 24) and 2 (SEQ ID NO: 25).

In certain embodiments, there is provided a complement regulator protein comprising from N-terminal to C-terminal: FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15); at least one linker; FHR5 CCP domains 8 (SEQ ID NO: 20) and 9 (SEQ ID NO: 21); at least one further linker; and FHR1 CCP domains 1 (SEQ ID NO: 24) and 2 (SEQ ID NO: 25).

In certain embodiments, there is provided a complement regulator protein comprising from N-terminal to C-terminal: FHR1 CCP domains 1 (SEQ ID NO: 24) and 2 (SEQ ID NO: 25); at least one linker; and FH CCP domains 1 (SEQ ID NO: 9), 2 (SEQ ID NO: 10), 3 (SEQ ID NO: 11) and 4 (SEQ ID NO: 12).

In certain embodiments, there is provided a complement regulator protein comprising from N-terminal to C-terminal: FHR1 CCP domains 1 (SEQ ID NO: 24) and 2 (SEQ ID NO: 25); and FH CCP domains 1 (SEQ ID NO: 9), 2 (SEQ ID NO: 10), 3 (SEQ ID NO: 11) and 4 (SEQ ID NO: 12).

In certain embodiments, there is provided a complement regulator protein comprising from N-terminal to C-terminal: FHR1 CCP domains 1 (SEQ ID NO: 24) and 2 (SEQ ID NO: 25); at least one linker; and FH CCP domains 1 (SEQ ID NO: 9), 2 (SEQ ID NO: 10), 3 (SEQ ID NO: 11), 4 (SEQ ID NO: 12) and 5 (SEQ ID NO: 13).

In certain embodiments, there is provided a complement regulator protein comprising from N-terminal to C-terminal: FHR1 CCP domains 1 (SEQ ID NO: 24) and 2 (SEQ ID NO: 25); and FH CCP domains 1 (SEQ ID NO: 9), 2 (SEQ ID NO: 10), 3 (SEQ ID NO: 11), 4 (SEQ ID NO: 12) and 5 (SEQ ID NO: 13).

In certain embodiments, there is provided a complement regulator protein comprising from N-terminal to C-terminal: FHR1 CCP domains 1 (SEQ ID NO: 24) and 2 (SEQ ID NO: 25); at least one linker; and FH CCP domains 1 (SEQ ID NO: 9), 2 (SEQ ID NO: 10), 3 (SEQ ID NO: 11), 4 (SEQ ID NO: 12) and 7 (SEQ ID NO: 15).

In certain embodiments, there is provided a complement regulator protein comprising from N-terminal to C-terminal: FHR1 CCP domains 1 (SEQ ID NO: 24) and 2 (SEQ ID NO: 25); and FH CCP domains 1 (SEQ ID NO: 9), 2 (SEQ ID NO: 10), 3 (SEQ ID NO: 11), 4 (SEQ ID NO: 12) and 7 (SEQ ID NO: 15).

In certain embodiments, there is provided a complement regulator protein comprising from N-terminal to C-terminal: FHR1 CCP domains 1 (SEQ ID NO: 24) and 2 (SEQ ID NO: 25); at least one linker; and FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15).

In certain embodiments, there is provided a complement regulator protein comprising from N-terminal to C-terminal: FHR1 CCP domains 1 (SEQ ID NO: 24) and 2 (SEQ ID NO: 25); and FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15).

In certain embodiments, there is provided a complement regulator protein comprising from N-terminal to C-terminal: FHR1 CCP domains 1 (SEQ ID NO: 24) and 2 (SEQ ID NO: 25); FH CCP domains 1 (SEQ ID NO: 9), 2 (SEQ ID NO: 10), 3 (SEQ ID NO: 11) and 4 (SEQ ID NO: 12); FH CCP domains 18 (SEQ ID NO: 16), 19 (SEQ ID NO: 17) and 20 (SEQ ID NO: 18).

In certain embodiments, there is provided a complement regulator protein comprising from N-terminal to C-terminal:

FHR1 CCP domains 1 (SEQ ID NO: 24) and 2 (SEQ ID NO: 25); at least one linker; FH CCP domains 1 (SEQ ID NO: 9), 2 (SEQ ID NO: 10), 3 (SEQ ID NO: 11) and 4 (SEQ ID NO: 12); FH CCP domains 18 (SEQ ID NO: 16), 19 (SEQ ID NO: 17) and 20 (SEQ ID NO: 18).

In certain embodiments, there is provided a complement regulator protein comprising from N-terminal to C-terminal: FHR1 CCP domains 1 (SEQ ID NO: 24) and 2 (SEQ ID NO: 25); FH CCP domains 1 (SEQ ID NO: 9), 2 (SEQ ID NO: 10), 3 (SEQ ID NO: 11) and 4 (SEQ ID NO: 12); at least one linker; and FH CCP domains 18 (SEQ ID NO: 16), 19 (SEQ ID NO: 17) and 20 (SEQ ID NO: 18).

In certain embodiments, there is provided a complement regulator protein comprising from N-terminal to C-terminal: FHR1 CCP domains 1 (SEQ ID NO: 24) and 2 (SEQ ID NO: 25); at least one linker; FH CCP domains 1 (SEQ ID NO: 9), 2 (SEQ ID NO: 10), 3 (SEQ ID NO: 11) and 4 (SEQ ID NO: 12); at least one further linker; FH CCP domains 18 (SEQ ID NO: 16), 19 (SEQ ID NO: 17) and 20 (SEQ ID NO: 18).

In certain embodiments, there is provided a complement regulator protein comprising from N-terminal to C-terminal: FHR1 CCP domains 1 (SEQ ID NO: 24) and 2 (SEQ ID NO: 25); FH CCP domains 1 (SEQ ID NO: 9), 2 (SEQ ID NO: 10), 3 (SEQ ID NO: 11), 4 (SEQ ID NO: 12) and 5 (SEQ ID NO: 13); FH CCP domains 18 (SEQ ID NO: 16), 19 (SEQ ID NO: 17) and 20 (SEQ ID NO: 18).

In certain embodiments, there is provided a complement regulator protein comprising from N-terminal to C-terminal: FHR1 CCP domains 1 (SEQ ID NO: 24) and 2 (SEQ ID NO: 25); at least one linker; FH CCP domains 1 (SEQ ID NO: 9), 2 (SEQ ID NO: 10), 3 (SEQ ID NO: 11), 4 (SEQ ID NO: 12) and 5 (SEQ ID NO: 13); FH CCP domains 18 (SEQ ID NO: 16), 19 (SEQ ID NO: 17) and 20 (SEQ ID NO: 18).

In certain embodiments, there is provided a complement regulator protein comprising from N-terminal to C-terminal: FHR1 CCP domains 1 (SEQ ID NO: 24) and 2 (SEQ ID NO: 25); FH CCP domains 1 (SEQ ID NO: 9), 2 (SEQ ID NO: 10), 3 (SEQ ID NO: 11), 4 (SEQ ID NO: 12) and 5 (SEQ ID NO: 13); at least one linker; and FH CCP domains 18 (SEQ ID NO: 16), 19 (SEQ ID NO: 17) and 20 (SEQ ID NO: 18).

In certain embodiments, there is provided a complement regulator protein comprising from N-terminal to C-terminal: FHR1 CCP domains 1 (SEQ ID NO: 24) and 2 (SEQ ID NO: 25); at least one linker; FH CCP domains 1 (SEQ ID NO: 9), 2 (SEQ ID NO: 10), 3 (SEQ ID NO: 11), 4 (SEQ ID NO: 12) and 5 (SEQ ID NO: 13); at least one further linker; FH CCP domains 18 (SEQ ID NO: 16), 19 (SEQ ID NO: 17) and 20 (SEQ ID NO: 18).

In certain embodiments, there is provided a complement regulator protein comprising from N-terminal to C-terminal: FHR1 CCP domains 1 (SEQ ID NO: 24) and 2 (SEQ ID NO: 25); FH CCP domains 1 (SEQ ID NO: 9), 2 (SEQ ID NO: 10), 3 (SEQ ID NO: 11), 4 (SEQ ID NO: 12) and 7 (SEQ ID NO: 15); and FH CCP domains 18 (SEQ ID NO: 16), 19 (SEQ ID NO: 17) and 20 (SEQ ID NO: 18).

In certain embodiments, there is provided a complement regulator protein comprising from N-terminal to C-terminal: FHR1 CCP domains 1 (SEQ ID NO: 24) and 2 (SEQ ID NO: 25); at least one linker; FH CCP domains 1 (SEQ ID NO: 9), 2 (SEQ ID NO: 10), 3 (SEQ ID NO: 11), 4 (SEQ ID NO: 12) and 7 (SEQ ID NO: 15); and FH CCP domains 18 (SEQ ID NO: 16), 19 (SEQ ID NO: 17) and 20 (SEQ ID NO: 18).

In certain embodiments, there is provided a complement regulator protein comprising from N-terminal to C-terminal: FHR1 CCP domains 1 (SEQ ID NO: 24) and 2 (SEQ ID NO: 25); FH CCP domains 1 (SEQ ID NO: 9), 2 (SEQ ID NO: 10), 3 (SEQ ID NO: 11), 4 (SEQ ID NO: 12) and 7 (SEQ ID NO: 15); at least one linker; and FH CCP domains 18 (SEQ ID NO: 16), 19 (SEQ ID NO: 17) and 20 (SEQ ID NO: 18).

In certain embodiments, there is provided a complement regulator protein comprising from N-terminal to C-terminal: FHR1 CCP domains 1 (SEQ ID NO: 24) and 2 (SEQ ID NO: 25); at least one linker; FH CCP domains 1 (SEQ ID NO: 9), 2 (SEQ ID NO: 10), 3 (SEQ ID NO: 11), 4 (SEQ ID NO: 12) and 7 (SEQ ID NO: 15); at least one further linker; and FH CCP domains 18 (SEQ ID NO: 16), 19 (SEQ ID NO: 17) and 20 (SEQ ID NO: 18).

In certain embodiments, there is provided a complement regulator protein comprising from N-terminal to C-terminal: FHR1 CCP domains 1 (SEQ ID NO: 24) and 2 (SEQ ID NO: 25); FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15); and FH CCP domains 18 (SEQ ID NO: 16), 19 (SEQ ID NO: 17) and 20 (SEQ ID NO: 18).

In certain embodiments, there is provided a complement regulator protein comprising from N-terminal to C-terminal: FHR1 CCP domains 1 (SEQ ID NO: 24) and 2 (SEQ ID NO: 25); at least one linker; FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15); and FH CCP domains 18 (SEQ ID NO: 16), 19 (SEQ ID NO: 17) and 20 (SEQ ID NO: 18).

In certain embodiments, there is provided a complement regulator protein comprising from N-terminal to C-terminal: FHR1 CCP domains 1 (SEQ ID NO: 24) and 2 (SEQ ID NO: 25); FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15); at least one linker; and FH CCP domains 18 (SEQ ID NO: 16), 19 (SEQ ID NO: 17) and 20 (SEQ ID NO: 18).

In certain embodiments, there is provided a complement regulator protein comprising from N-terminal to C-terminal: FHR1 CCP domains 1 (SEQ ID NO: 24) and 2 (SEQ ID NO: 25); at least one linker; FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15); at least one further linker; and FH CCP domains 18 (SEQ ID NO: 16), 19 (SEQ ID NO: 17) and 20 (SEQ ID NO: 18).

In certain embodiments, there is provided a complement regulator protein comprising from N-terminal to C-terminal: FHR1 CCP domains 1 (SEQ ID NO: 24) and 2 (SEQ ID NO: 25); FH CCP domains 1 (SEQ ID NO: 9), 2 (SEQ ID NO: 10), 3 (SEQ ID NO: 11) and 4 (SEQ ID NO: 12); and FH CCP domain 19 (SEQ ID NO: 17) and 20 (SEQ ID NO: 18).

In certain embodiments, there is provided a complement regulator protein comprising from N-terminal to C-terminal: FHR1 CCP domains 1 (SEQ ID NO: 24) and 2 (SEQ ID NO: 25); at least one linker; FH CCP domains 1 (SEQ ID NO: 9), 2 (SEQ ID NO: 10), 3 (SEQ ID NO: 11) and 4 (SEQ ID NO: 12); and FH CCP domain 19 (SEQ ID NO: 17) and 20 (SEQ ID NO: 18).

In certain embodiments, there is provided a complement regulator protein comprising from N-terminal to C-terminal: FHR1 CCP domains 1 (SEQ ID NO: 24) and 2 (SEQ ID NO: 25); FH CCP domains 1 (SEQ ID NO: 9), 2 (SEQ ID NO: 10), 3 (SEQ ID NO: 11) and 4 (SEQ ID NO: 12); at least one linker; and FH CCP domain 19 (SEQ ID NO: 17) and 20 (SEQ ID NO: 18).

In certain embodiments, there is provided a complement regulator protein comprising from N-terminal to C-terminal: FHR1 CCP domains 1 (SEQ ID NO: 24) and 2 (SEQ ID NO: 25); at least one linker; FH CCP domains 1 (SEQ ID NO: 9), 2 (SEQ ID NO: 10), 3 (SEQ ID NO: 11) and 4 (SEQ ID NO:

12); at least one further linker; and FH CCP domain 19 (SEQ ID NO: 17) and 20 (SEQ ID NO: 18).

In certain embodiments, there is provided a complement regulator protein comprising from N-terminal to C-terminal: FHR1 CCP domains 1 (SEQ ID NO: 24) and 2 (SEQ ID NO: 25); FH CCP domains 1 (SEQ ID NO: 9), 2 (SEQ ID NO: 10), 3 (SEQ ID NO: 11), 4 (SEQ ID NO: 12) and 5 (SEQ ID NO: 13); and FH CCP domain 19 (SEQ ID NO: 17) and 20 (SEQ ID NO: 18).

In certain embodiments, there is provided a complement regulator protein comprising from N-terminal to C-terminal: FHR1 CCP domains 1 (SEQ ID NO: 24) and 2 (SEQ ID NO: 25); at least one linker; FH CCP domains 1 (SEQ ID NO: 9), 2 (SEQ ID NO: 10), 3 (SEQ ID NO: 11), 4 (SEQ ID NO: 12) and 5 (SEQ ID NO: 13); and FH CCP domain 19 (SEQ ID NO: 17) and 20 (SEQ ID NO: 18).

In certain embodiments, there is provided a complement regulator protein comprising from N-terminal to C-terminal: FHR1 CCP domains 1 (SEQ ID NO: 24) and 2 (SEQ ID NO: 25); FH CCP domains 1 (SEQ ID NO: 9), 2 (SEQ ID NO: 10), 3 (SEQ ID NO: 11), 4 (SEQ ID NO: 12) and 5 (SEQ ID NO: 13); at least one linker; and FH CCP domain 19 (SEQ ID NO: 17) and 20 (SEQ ID NO: 18).

In certain embodiments, there is provided a complement regulator protein comprising from N-terminal to C-terminal: FHR1 CCP domains 1 (SEQ ID NO: 24) and 2 (SEQ ID NO: 25); at least one linker; FH CCP domains 1 (SEQ ID NO: 9), 2 (SEQ ID NO: 10), 3 (SEQ ID NO: 11), 4 (SEQ ID NO: 12) and 5 (SEQ ID NO: 13); at least one further linker; and FH CCP domain 19 (SEQ ID NO: 17) and 20 (SEQ ID NO: 18).

In certain embodiments, there is provided a complement regulator protein comprising from N-terminal to C-terminal: FHR1 CCP domains 1 (SEQ ID NO: 24) and 2 (SEQ ID NO: 25); FH CCP domains 1 (SEQ ID NO: 9), 2 (SEQ ID NO: 10), 3 (SEQ ID NO: 11), 4 (SEQ ID NO: 12) and 7 (SEQ ID NO: 15); and FH CCP domain 19 (SEQ ID NO: 17) and 20 (SEQ ID NO: 18).

In certain embodiments, there is provided a complement regulator protein comprising from N-terminal to C-terminal: FHR1 CCP domains 1 (SEQ ID NO: 24) and 2 (SEQ ID NO: 25); at least one linker; FH CCP domains FH CCP domains 1 (SEQ ID NO: 9), 2 (SEQ ID NO: 10), 3 (SEQ ID NO: 11), 4 (SEQ ID NO: 12) and 7 (SEQ ID NO: 15); and FH CCP domain 19 (SEQ ID NO: 17) and 20 (SEQ ID NO: 18).

In certain embodiments, there is provided a complement regulator protein comprising from N-terminal to C-terminal: FHR1 CCP domains 1 (SEQ ID NO: 24) and 2 (SEQ ID NO: 25); FH CCP domains 1 (SEQ ID NO: 9), 2 (SEQ ID NO: 10), 3 (SEQ ID NO: 11), 4 (SEQ ID NO: 12) and 7 (SEQ ID NO: 15); at least one linker; and FH CCP domain 19 (SEQ ID NO: 17) and 20 (SEQ ID NO: 18).

In certain embodiments, there is provided a complement regulator protein comprising from N-terminal to C-terminal: FHR1 CCP domains 1 (SEQ ID NO: 24) and 2 (SEQ ID NO: 25); at least one linker; FH CCP domains 1 (SEQ ID NO: 9), 2 (SEQ ID NO: 10), 3 (SEQ ID NO: 11), 4 (SEQ ID NO: 12) and 7 (SEQ ID NO: 15); at least one further linker; and FH CCP domain 19 (SEQ ID NO: 17) and 20 (SEQ ID NO: 18).

In certain embodiments, there is provided a complement regulator protein comprising from N-terminal to C-terminal: FHR1 CCP domains 1 (SEQ ID NO: 24) and 2 (SEQ ID NO: 25); FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15); and FH CCP domain 19 (SEQ ID NO: 17) and 20 (SEQ ID NO: 18).

In certain embodiments, there is provided a complement regulator protein comprising from N-terminal to C-terminal: FHR1 CCP domains 1 (SEQ ID NO: 24) and 2 (SEQ ID NO: 25); at least one linker; FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15); and FH CCP domain 19 (SEQ ID NO: 17) and 20 (SEQ ID NO: 18).

In certain embodiments, there is provided a complement regulator protein comprising from N-terminal to C-terminal: FHR1 CCP domains 1 (SEQ ID NO: 24) and 2 (SEQ ID NO: 25); FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15); at least one linker; and FH CCP domain 19 (SEQ ID NO: 17) and 20 (SEQ ID NO: 18).

In certain embodiments, there is provided a complement regulator protein comprising from N-terminal to C-terminal: FHR1 CCP domains 1 (SEQ ID NO: 24) and 2 (SEQ ID NO: 25); at least one linker; FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15); at least one further linker; and FH CCP domain 19 (SEQ ID NO: 17) and 20 (SEQ ID NO: 18).

In certain embodiments, there is provided a complement regulator protein comprising from N-terminal to C-terminal: FHR1 CCP domains 1 (SEQ ID NO: 24) and 2 (SEQ ID NO: 25); FH CCP domains 1 (SEQ ID NO: 9), 2 (SEQ ID NO: 10), 3 (SEQ ID NO: 11) and 4 (SEQ ID NO: 12); and FHL-1 CCP domains 6 (SEQ ID NO: 22) and 7 (SEQ ID NO: 23).

In certain embodiments, there is provided a complement regulator protein comprising from N-terminal to C-terminal: FHR1 CCP domains 1 (SEQ ID NO: 24) and 2 (SEQ ID NO: 25); at least one linker; FH CCP domains 1 (SEQ ID NO: 9), 2 (SEQ ID NO: 10), 3 (SEQ ID NO: 11) and 4 (SEQ ID NO: 12); and FHL-1 CCP domains 6 (SEQ ID NO: 22) and 7 (SEQ ID NO: 23).

In certain embodiments, there is provided a complement regulator protein comprising from N-terminal to C-terminal: FHR1 CCP domains 1 (SEQ ID NO: 24) and 2 (SEQ ID NO: 25); FH CCP domains 1 (SEQ ID NO: 9), 2 (SEQ ID NO: 10), 3 (SEQ ID NO: 11) and 4 (SEQ ID NO: 12); at least one linker; and FHL-1 CCP domains 6 (SEQ ID NO: 22) and 7 (SEQ ID NO: 23).

In certain embodiments, there is provided a complement regulator protein comprising from N-terminal to C-terminal: FHR1 CCP domains 1 (SEQ ID NO: 24) and 2 (SEQ ID NO: 25); at least one linker; FH CCP domains 1 (SEQ ID NO: 9), 2 (SEQ ID NO: 10), 3 (SEQ ID NO: 11) and 4 (SEQ ID NO: 12); at least one further linker; and FHL-1 CCP domains 6 (SEQ ID NO: 22) and 7 (SEQ ID NO: 23).

In certain embodiments, there is provided a complement regulator protein comprising from N-terminal to C-terminal: FHR1 CCP domains 1 (SEQ ID NO: 24) and 2 (SEQ ID NO: 25); FH CCP domains 1 (SEQ ID NO: 9), 2 (SEQ ID NO: 10), 3 (SEQ ID NO: 11), 4 (SEQ ID NO: 12) and 5 (SEQ ID NO: 13); and FHL-1 CCP domains 6 (SEQ ID NO: 22) and 7 (SEQ ID NO: 23).

In certain embodiments, there is provided a complement regulator protein comprising from N-terminal to C-terminal: FHR1 CCP domains 1 (SEQ ID NO: 24) and 2 (SEQ ID NO: 25); at least one linker; FH CCP domains 1 (SEQ ID NO: 9), 2 (SEQ ID NO: 10), 3 (SEQ ID NO: 11), 4 (SEQ ID NO: 12) and 5 (SEQ ID NO: 13); and FHL-1 CCP domains 6 (SEQ ID NO: 22) and 7 (SEQ ID NO: 23).

In certain embodiments, there is provided a complement regulator protein comprising from N-terminal to C-terminal: FHR1 CCP domains 1 (SEQ ID NO: 24) and 2 (SEQ ID NO: 25); FH CCP domains 1 (SEQ ID NO: 9), 2 (SEQ ID NO: 10), 3 (SEQ ID NO: 11), 4 (SEQ ID NO: 12) and 5 (SEQ ID NO: 13); at least one linker; and FHL-1 CCP domains 6 (SEQ ID NO: 22) and 7 (SEQ ID NO: 23).

In certain embodiments, there is provided a complement regulator protein comprising from N-terminal to C-terminal: FHR1 CCP domains 1 (SEQ ID NO: 24) and 2 (SEQ ID NO: 25); at least one linker; FH CCP domains 1 (SEQ ID NO: 9), 2 (SEQ ID NO: 10), 3 (SEQ ID NO: 11), 4 (SEQ ID NO: 12) and 5 (SEQ ID NO: 13); at least one further linker; and FHL-1 CCP domains 6 (SEQ ID NO: 22) and 7 (SEQ ID NO: 23).

In certain embodiments, there is provided a complement regulator protein comprising from N-terminal to C-terminal: FHR1 CCP domains 1 (SEQ ID NO: 24) and 2 (SEQ ID NO: 25); FH CCP domains 1 (SEQ ID NO: 9), 2 (SEQ ID NO: 10), 3 (SEQ ID NO: 11), 4 (SEQ ID NO: 12) and 7 (SEQ ID NO: 15); and FHL-1 CCP domains 6 (SEQ ID NO: 22) and 7 (SEQ ID NO: 23).

In certain embodiments, there is provided a complement regulator protein comprising from N-terminal to C-terminal: FHR1 CCP domains 1 (SEQ ID NO: 24) and 2 (SEQ ID NO: 25); at least one linker; FH CCP domains FH CCP domains 1 (SEQ ID NO: 9), 2 (SEQ ID NO: 10), 3 (SEQ ID NO: 11), 4 (SEQ ID NO: 12) and 7 (SEQ ID NO: 15); and FHL-1 CCP domains 6 (SEQ ID NO: 22) and 7 (SEQ ID NO: 23).

In certain embodiments, there is provided a complement regulator protein comprising from N-terminal to C-terminal: FHR1 CCP domains 1 (SEQ ID NO: 24) and 2 (SEQ ID NO: 25); FH CCP domains 1 (SEQ ID NO: 9), 2 (SEQ ID NO: 10), 3 (SEQ ID NO: 11), 4 (SEQ ID NO: 12) and 7 (SEQ ID NO: 15); at least one linker; and FHL-1 CCP domains 6 (SEQ ID NO: 22) and 7 (SEQ ID NO: 23).

In certain embodiments, there is provided a complement regulator protein comprising from N-terminal to C-terminal: FHR1 CCP domains 1 (SEQ ID NO: 24) and 2 (SEQ ID NO: 25); at least one linker; FH CCP domains 1 (SEQ ID NO: 9), 2 (SEQ ID NO: 10), 3 (SEQ ID NO: 11), 4 (SEQ ID NO: 12) and 7 (SEQ ID NO: 15); at least one further linker; and FHL-1 CCP domains 6 (SEQ ID NO: 22) and 7 (SEQ ID NO: 23).

In certain embodiments, there is provided a complement regulator protein comprising from N-terminal to C-terminal: FHR1 CCP domains 1 (SEQ ID NO: 24) and 2 (SEQ ID NO: 25); FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15); and FHL-1 CCP domains 6 (SEQ ID NO: 22) and 7 (SEQ ID NO: 23).

In certain embodiments, there is provided a complement regulator protein comprising from N-terminal to C-terminal: FHR1 CCP domains 1 (SEQ ID NO: 24) and 2 (SEQ ID NO: 25); at least one linker; FH CCP domains FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15); and FHL-1 CCP domains 6 (SEQ ID NO: 22) and 7 (SEQ ID NO: 23).

In certain embodiments, there is provided a complement regulator protein comprising from N-terminal to C-terminal: FHR1 CCP domains 1 (SEQ ID NO: 24) and 2 (SEQ ID NO: 25); FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15); at least one linker; and FHL-1 CCP domains 6 (SEQ ID NO: 22) and 7 (SEQ ID NO: 23).

In certain embodiments, there is provided a complement regulator protein comprising from N-terminal to C-terminal: FHR1 CCP domains 1 (SEQ ID NO: 24) and 2 (SEQ ID NO: 25); at least one linker; FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15); at least one further linker; and FHL-1 CCP domains 6 (SEQ ID NO: 22) and 7 (SEQ ID NO: 23).

In certain embodiments, there is provided a complement regulator protein comprising from N-terminal to C-terminal: FHR1 CCP domains 1 (SEQ ID NO: 24) and 2 (SEQ ID NO: 25); FH CCP domains 1 (SEQ ID NO: 9), 2 (SEQ ID NO: 10), 3 (SEQ ID NO: 11) and 4 (SEQ ID NO: 12); and FHR5 CCP domains 7 (SEQ ID NO: 19), 8 (SEQ ID NO: 20) and 9 (SEQ ID NO: 21).

In certain embodiments, there is provided a complement regulator protein comprising from N-terminal to C-terminal: FHR1 CCP domains 1 (SEQ ID NO: 24) and 2 (SEQ ID NO: 25); at least one linker; FH CCP domains 1 (SEQ ID NO: 9), 2 (SEQ ID NO: 10), 3 (SEQ ID NO: 11) and 4 (SEQ ID NO: 12); and FHR5 CCP domains 7 (SEQ ID NO: 19), 8 (SEQ ID NO: 20) and 9 (SEQ ID NO: 21).

In certain embodiments, there is provided a complement regulator protein comprising from N-terminal to C-terminal: FHR1 CCP domains 1 (SEQ ID NO: 24) and 2 (SEQ ID NO: 25); FH CCP domains 1 (SEQ ID NO: 9), 2 (SEQ ID NO: 10), 3 (SEQ ID NO: 11) and 4 (SEQ ID NO: 12); at least one linker; and FHR5 CCP domains 7 (SEQ ID NO: 19), 8 (SEQ ID NO: 20) and 9 (SEQ ID NO: 21).

In certain embodiments, there is provided a complement regulator protein comprising from N-terminal to C-terminal: FHR1 CCP domains 1 (SEQ ID NO: 24) and 2 (SEQ ID NO: 25); at least one linker; FH CCP domains 1 (SEQ ID NO: 9), 2 (SEQ ID NO: 10), 3 (SEQ ID NO: 11) and 4 (SEQ ID NO: 12); at least one further linker; and FHR5 CCP domains 7 (SEQ ID NO: 19), 8 (SEQ ID NO: 20) and 9 (SEQ ID NO: 21).

In certain embodiments, there is provided a complement regulator protein comprising from N-terminal to C-terminal: FHR1 CCP domains 1 (SEQ ID NO: 24) and 2 (SEQ ID NO: 25); FH CCP domains 1 (SEQ ID NO: 9), 2 (SEQ ID NO: 10), 3 (SEQ ID NO: 11), 4 (SEQ ID NO: 12) and 5 (SEQ ID NO: 13); and FHR5 CCP domains 7 (SEQ ID NO: 19), 8 (SEQ ID NO: 20) and 9 (SEQ ID NO: 21).

In certain embodiments, there is provided a complement regulator protein comprising from N-terminal to C-terminal: FHR1 CCP domains 1 (SEQ ID NO: 24) and 2 (SEQ ID NO: 25); at least one linker; FH CCP domains 1 (SEQ ID NO: 9), 2 (SEQ ID NO: 10), 3 (SEQ ID NO: 11), 4 (SEQ ID NO: 12) and 5 (SEQ ID NO: 13); and FHR5 CCP domains 7 (SEQ ID NO: 19), 8 (SEQ ID NO: 20) and 9 (SEQ ID NO: 21).

In certain embodiments, there is provided a complement regulator protein comprising from N-terminal to C-terminal: FHR1 CCP domains 1 (SEQ ID NO: 24) and 2 (SEQ ID NO: 25); FH CCP domains 1 (SEQ ID NO: 9), 2 (SEQ ID NO: 10), 3 (SEQ ID NO: 11), 4 (SEQ ID NO: 12) and 5 (SEQ ID NO: 13); at least one linker; and FHR5 CCP domains 7 (SEQ ID NO: 19), 8 (SEQ ID NO: 20) and 9 (SEQ ID NO: 21).

In certain embodiments, there is provided a complement regulator protein comprising from N-terminal to C-terminal: FHR1 CCP domains 1 (SEQ ID NO: 24) and 2 (SEQ ID NO: 25); at least one linker; FH CCP domains 1 (SEQ ID NO: 9), 2 (SEQ ID NO: 10), 3 (SEQ ID NO: 11), 4 (SEQ ID NO: 12) and 5 (SEQ ID NO: 13); at least one further linker; and FHR5 CCP domains 7 (SEQ ID NO: 19), 8 (SEQ ID NO: 20) and 9 (SEQ ID NO: 21).

In certain embodiments, there is provided a complement regulator protein comprising from N-terminal to C-terminal: FHR1 CCP domains 1 (SEQ ID NO: 24) and 2 (SEQ ID NO: 25); FH CCP domains 1 (SEQ ID NO: 9), 2 (SEQ ID NO: 10), 3 (SEQ ID NO: 11), 4 (SEQ ID NO: 12) and 7 (SEQ ID NO: 15); and FHR5 CCP domains 7 (SEQ ID NO: 19), 8 (SEQ ID NO: 20) and 9 (SEQ ID NO: 21).

In certain embodiments, there is provided a complement regulator protein comprising from N-terminal to C-terminal: FHR1 CCP domains 1 (SEQ ID NO: 24) and 2 (SEQ ID NO: 25); at least one linker; FH CCP domains FH CCP domains 1 (SEQ ID NO: 9), 2 (SEQ ID NO: 10), 3 (SEQ ID NO: 11), 4 (SEQ ID NO: 12) and 7 (SEQ ID NO: 15); and FHR5 CCP domains 7 (SEQ ID NO: 19), 8 (SEQ ID NO: 20) and 9 (SEQ ID NO: 21).

In certain embodiments, there is provided a complement regulator protein comprising from N-terminal to C-terminal: FHR1 CCP domains 1 (SEQ ID NO: 24) and 2 (SEQ ID NO: 25); FH CCP domains 1 (SEQ ID NO: 9), 2 (SEQ ID NO: 10), 3 (SEQ ID NO: 11), 4 (SEQ ID NO: 12) and 7 (SEQ ID NO: 15); at least one linker; and FHR5 CCP domains 7 (SEQ ID NO: 19), 8 (SEQ ID NO: 20) and 9 (SEQ ID NO: 21).

In certain embodiments, there is provided a complement regulator protein comprising from N-terminal to C-terminal: FHR1 CCP domains 1 (SEQ ID NO: 24) and 2 (SEQ ID NO: 25); at least one linker; FH CCP domains 1 (SEQ ID NO: 9), 2 (SEQ ID NO: 10), 3 (SEQ ID NO: 11), 4 (SEQ ID NO: 12) and 7 (SEQ ID NO: 15); at least one further linker; and FHR5 CCP domains 7 (SEQ ID NO: 19), 8 (SEQ ID NO: 20) and 9 (SEQ ID NO: 21).

In certain embodiments, there is provided a complement regulator protein comprising from N-terminal to C-terminal: FHR1 CCP domains 1 (SEQ ID NO: 24) and 2 (SEQ ID NO: 25); FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15); and FHR5 CCP domains 7 (SEQ ID NO: 19), 8 (SEQ ID NO: 20) and 9 (SEQ ID NO: 21).

In certain embodiments, there is provided a complement regulator protein comprising from N-terminal to C-terminal: FHR1 CCP domains 1 (SEQ ID NO: 24) and 2 (SEQ ID NO: 25); at least one linker; FH CCP domains FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15); and FHR5 CCP domains 7 (SEQ ID NO: 19), 8 (SEQ ID NO: 20) and 9 (SEQ ID NO: 21).

In certain embodiments, there is provided a complement regulator protein comprising from N-terminal to C-terminal: FHR1 CCP domains 1 (SEQ ID NO: 24) and 2 (SEQ ID NO: 25); FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15); at least one linker; and FHR5 CCP domains 7 (SEQ ID NO: 19), 8 (SEQ ID NO: 20) and 9 (SEQ ID NO: 21).

In certain embodiments, there is provided a complement regulator protein comprising from N-terminal to C-terminal: FHR1 CCP domains 1 (SEQ ID NO: 24) and 2 (SEQ ID NO: 25); at least one linker; FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15); at least one further linker; and FHR5 CCP domains 7 (SEQ ID NO: 19), 8 (SEQ ID NO: 20) and 9 (SEQ ID NO: 21).

In certain embodiments, there is provided a complement regulator protein comprising from N-terminal to C-terminal: FHR1 CCP domains 1 (SEQ ID NO: 24) and 2 (SEQ ID NO: 25); FH CCP domains 1 (SEQ ID NO: 9), 2 (SEQ ID NO: 10), 3 (SEQ ID NO: 11) and 4 (SEQ ID NO: 12); and FHR5 CCP domains 8 (SEQ ID NO: 20) and 9 (SEQ ID NO: 21).

In certain embodiments, there is provided a complement regulator protein comprising from N-terminal to C-terminal: FHR1 CCP domains 1 (SEQ ID NO: 24) and 2 (SEQ ID NO: 25); at least one linker; FH CCP domains 1 (SEQ ID NO: 9), 2 (SEQ ID NO: 10), 3 (SEQ ID NO: 11) and 4 (SEQ ID NO: 12); and FHR5 CCP domains 8 (SEQ ID NO: 20) and 9 (SEQ ID NO: 21).

In certain embodiments, there is provided a complement regulator protein comprising from N-terminal to C-terminal: FHR1 CCP domains 1 (SEQ ID NO: 24) and 2 (SEQ ID NO: 25); FH CCP domains 1 (SEQ ID NO: 9), 2 (SEQ ID NO: 10), 3 (SEQ ID NO: 11) and 4 (SEQ ID NO: 12); at least one linker; and FHR5 CCP domains 8 (SEQ ID NO: 20) and 9 (SEQ ID NO: 21).

In certain embodiments, there is provided a complement regulator protein comprising from N-terminal to C-terminal: FHR1 CCP domains 1 (SEQ ID NO: 24) and 2 (SEQ ID NO: 25); at least one linker; FH CCP domains 1 (SEQ ID NO: 9), 2 (SEQ ID NO: 10), 3 (SEQ ID NO: 11) and 4 (SEQ ID NO: 12); at least one further linker; and FHR5 CCP domains 8 (SEQ ID NO: 20) and 9 (SEQ ID NO: 21).

In certain embodiments, there is provided a complement regulator protein comprising from N-terminal to C-terminal: FHR1 CCP domains 1 (SEQ ID NO: 24) and 2 (SEQ ID NO: 25); FH CCP domains 1 (SEQ ID NO: 9), 2 (SEQ ID NO: 10), 3 (SEQ ID NO: 11), 4 (SEQ ID NO: 12) and 5 (SEQ ID NO: 13); and FHR5 CCP domains 8 (SEQ ID NO: 20) and 9 (SEQ ID NO: 21).

In certain embodiments, there is provided a complement regulator protein comprising from N-terminal to C-terminal: FHR1 CCP domains 1 (SEQ ID NO: 24) and 2 (SEQ ID NO: 25); at least one linker; FH CCP domains 1 (SEQ ID NO: 9), 2 (SEQ ID NO: 10), 3 (SEQ ID NO: 11), 4 (SEQ ID NO: 12) and 5 (SEQ ID NO: 13); and FHR5 CCP domains 8 (SEQ ID NO: 20) and 9 (SEQ ID NO: 21).

In certain embodiments, there is provided a complement regulator protein comprising from N-terminal to C-terminal: FHR1 CCP domains 1 (SEQ ID NO: 24) and 2 (SEQ ID NO: 25); FH CCP domains 1 (SEQ ID NO: 9), 2 (SEQ ID NO: 10), 3 (SEQ ID NO: 11), 4 (SEQ ID NO: 12) and 5 (SEQ ID NO: 13); at least one linker; and FHR5 CCP domains 8 (SEQ ID NO: 20) and 9 (SEQ ID NO: 21).

In certain embodiments, there is provided a complement regulator protein comprising from N-terminal to C-terminal: FHR1 CCP domains 1 (SEQ ID NO: 24) and 2 (SEQ ID NO: 25); at least one linker; FH CCP domains 1 (SEQ ID NO: 9), 2 (SEQ ID NO: 10), 3 (SEQ ID NO: 11), 4 (SEQ ID NO: 12) and 5 (SEQ ID NO: 13); at least one further linker; and FHR5 CCP domains 8 (SEQ ID NO: 20) and 9 (SEQ ID NO: 21).

In certain embodiments, there is provided a complement regulator protein comprising from N-terminal to C-terminal: FHR1 CCP domains 1 (SEQ ID NO: 24) and 2 (SEQ ID NO: 25); FH CCP domains 1 (SEQ ID NO: 9), 2 (SEQ ID NO: 10), 3 (SEQ ID NO: 11), 4 (SEQ ID NO: 12) and 7 (SEQ ID NO: 15); and FHR5 CCP domains 8 (SEQ ID NO: 20) and 9 (SEQ ID NO: 21).

In certain embodiments, there is provided a complement regulator protein comprising from N-terminal to C-terminal: FHR1 CCP domains 1 (SEQ ID NO: 24) and 2 (SEQ ID NO: 25); at least one linker; FH CCP domains FH CCP domains 1 (SEQ ID NO: 9), 2 (SEQ ID NO: 10), 3 (SEQ ID NO: 11), 4 (SEQ ID NO: 12) and 7 (SEQ ID NO: 15); and FHR5 CCP domains 8 (SEQ ID NO: 20) and 9 (SEQ ID NO: 21).

In certain embodiments, there is provided a complement regulator protein comprising from N-terminal to C-terminal: FHR1 CCP domains 1 (SEQ ID NO: 24) and 2 (SEQ ID NO: 25); FH CCP domains 1 (SEQ ID NO: 9), 2 (SEQ ID NO: 10), 3 (SEQ ID NO: 11), 4 (SEQ ID NO: 12) and 7 (SEQ ID NO: 15); at least one linker; and FHR5 CCP domains 8 (SEQ ID NO: 20) and 9 (SEQ ID NO: 21).

In certain embodiments, there is provided a complement regulator protein comprising from N-terminal to C-terminal: FHR1 CCP domains 1 (SEQ ID NO: 24) and 2 (SEQ ID NO: 25); at least one linker; FH CCP domains 1 (SEQ ID NO: 9), 2 (SEQ ID NO: 10), 3 (SEQ ID NO: 11), 4 (SEQ ID NO: 12) and 7 (SEQ ID NO: 15); at least one further linker; and FHR5 CCP domains 8 (SEQ ID NO: 20) and 9 (SEQ ID NO: 21).

In certain embodiments, there is provided a complement regulator protein comprising from N-terminal to C-terminal: FHR1 CCP domains 1 (SEQ ID NO: 24) and 2 (SEQ ID NO: 25); FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15); and FHR5 CCP domains 8 (SEQ ID NO: 20) and 9 (SEQ ID NO: 21).

In certain embodiments, there is provided a complement regulator protein comprising from N-terminal to C-terminal: FHR1 CCP domains 1 (SEQ ID NO: 24) and 2 (SEQ ID NO: 25); at least one linker; FH CCP domains FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15); and FHR5 CCP domains 8 (SEQ ID NO: 20) and 9 (SEQ ID NO: 21).

In certain embodiments, there is provided a complement regulator protein comprising from N-terminal to C-terminal: FHR1 CCP domains 1 (SEQ ID NO: 24) and 2 (SEQ ID NO: 25); FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15); at least one linker; and FHR5 CCP domains 8 (SEQ ID NO: 20) and 9 (SEQ ID NO: 21).

In certain embodiments, there is provided a complement regulator protein comprising from N-terminal to C-terminal: FHR1 CCP domains 1 (SEQ ID NO: 24) and 2 (SEQ ID NO: 25); at least one linker; FH CCP domains 1 (SEQ ID NO: 9), 2 (SEQ ID NO: 10), 3 (SEQ ID NO: 1), 4 (SEQ ID NO: 12), 5 (SEQ ID NO: 13) and 7 (SEQ ID NO: 15); at least one further linker; and FHR5 CCP domains 8 (SEQ ID NO: 20) and 9 (SEQ ID NO: 21).

In certain embodiments, the at least one FH and/or further FH fragments are derived from or a fragment of human FH, including but not limited to the human FH represented herein by SEQ ID NO: 1. Factor H has significant sequence conservation across species, especially for the CCP domains 1~4 and the CCP domains 19-20. In certain embodiments, the FH CCP domains may be derived from or are fragments of one or more homologs of human FH.

In certain embodiments, the FHR fragment of the complement interaction region is derived from or is a fragment of human FHR5 represented herein by SEQ ID NO: 2. In certain embodiments, the FHR5 CCP domains may be derived from or are fragments of one or more homologs of human FHR5.

In certain embodiments, the FHL fragment of the complement interaction region is derived from or is a fragment of human FHL-1 represented herein by SEQ ID NO: 3. In certain embodiments, the FHL-1 CCP domains may be derived from or are fragments of one or more homologs of human FHL-1.

In certain embodiments, the dimerization region CCP domains are derived from or are fragments of human FHR1 represented herein by SEQ ID NO: 4. In certain embodiments, the FHR1 CCP domains may be derived from or are fragments of one or more homologs of human FHR1.

The sequences represented by SEQ ID NO: 1, SEQ ID NO: 2, SEQ ID NO: 3 and SEQ ID NO: 4 are the amino acid residue sequences for mature processed human FH, FHR5, FHL-1 and FHR1 proteins respectively. That is to say, any signal peptides or pro and/or pre-protein amino acid residues have been cleaved from the protein. The sequences of human FH, human FHR5, human FHL-1 and human FHR1 pre-proteins are represented herein by SEQ ID NO: 5, SEQ ID NO: 6, SEQ ID NO: 7 and SEQ ID NO: 8 respectively. Pre- and/or pro-sequences may be shown as negative amino acid residue positions.

As used herein the term "homologous proteins" and "homologue" refer to proteins that have distinct similarity in primary, secondary, and/or tertiary structure. Protein homology can refer to the similarity in linear amino acid sequence when proteins are aligned. Homologous search of protein sequences can be done using BLASTP and PSI-BLAST from NCBI BLAST. Using this information, protein sequences can be grouped. A phylogenetic tree can be built using the amino acid residue sequences. Amino acid residue sequences can be entered in a program such as the Vector NTI Advance suite and a Guide Tree can be created using the Neighbour Joining (NJ) method (Saitou and Nei, Mol Biol Evol, 4:406-425, 1987). The tree construction can be calculated using Kimura's correction for sequence distance and ignoring positions with gaps. A program such as AlignX can display the calculated distance values in parenthesis following the molecule name displayed on the phylogenetic tree.

Understanding the homology between molecules can help reveal the evolutionary history of the molecules as well as information about their function; if a newly sequenced protein is homologous to an already characterized protein, there is a strong indication of the new protein's biochemical function. The most fundamental relationship between two entities is homology; two molecules are said to be homologous if they have been derived from a common ancestor. Homologous molecules, or homologs, can be divided into two classes, paralogs and orthologs. Paralogs are homologs that are present within one species. Paralogs often differ in their detailed biochemical functions. Orthologs are homologs that are present within different species and have very similar or identical functions.

In certain embodiments, the at least one FH and/or further FH fragments are derived from or are fragments of orthologs of human FH. In certain embodiments, the FHR fragment of the complement interaction region is derived from or a fragment of an ortholog of a human FHR protein such as human FHR5. In certain embodiments, the at least one FHL fragment is derived from or is a fragment of an ortholog of a human FHL protein such as human FHL-1. In certain embodiments, the CCP domains of the dimerization region are derived from or are fragments of orthologs of human FHR1.

Typically, greater than 30% amino acid sequence identity between two polypeptides (preferably, over a specified region) is considered to be an indication of functional equivalence and thus an indication that two or more proteins are homologous.

In certain embodiments, proteins that are homologues of FH have a degree of sequence identity with the human FH of SEQ ID NO: 1 of greater than 30%. In other embodiments, homologues have degrees of identity of greater than 70%, 80%, 90%, 95%, 98% or 99%, respectively with the protein sequence of SEQ ID NO: 1.

In certain embodiments, proteins that are homologues of the FHR5 have a degree of sequence identity with the human FHR5 of SEQ ID NO: 2 of greater than 30%. In other embodiments, homologues have degrees of identity of greater than 70%, 80%, 90%, 95%, 98% or 99%, respectively with the protein sequence of SEQ ID NO: 2.

In certain embodiments, proteins that are homologues of the FHL-1 have a degree of sequence identity with the human FHL-1 of SEQ ID NO: 3 of greater than 30%. In other embodiments, homologues have degrees of identity of greater than 70%, 80%, 90%, 95%, 98% or 99%, respectively with the protein sequence of SEQ ID NO: 3.

In certain embodiments, proteins that are homologues of the FHR1 have a degree of sequence identity with the human FHR1 of SEQ ID NO: 4 of greater than 30%. In other embodiments, homologues have degrees of identity of greater than 70%, 80%, 90%, 95%, 98% or 99%, respectively with the protein sequence of SEQ ID NO: 4.

"Percent (%) amino acid sequence identity" as used herein is defined as the percentage of amino acid residues in a candidate sequence that are identical with the amino acid residues in a specific complement regulator protein, after aligning the sequences and introducing gaps, if necessary, to achieve the maximum percent sequence identity, and not considering any conservative substitutions as part of the sequence identity.

In certain embodiments, FH CCP domain 1 comprises an amino acid sequence as set forth in SEQ ID NO: 9. In certain embodiments, FH CCP domain 2 comprises an amino acid sequence as set forth in SEQ ID NO: 10. In certain embodiments, FH CCP domain 3 comprises an amino acid sequence as set forth in SEQ ID NO: 11. In certain embodiments, FH CCP domain 4 comprises an amino acid sequence as set forth in SEQ ID NO: 12. In certain embodiments, FH CCP domain 5 comprises an amino acid sequence as set forth in SEQ ID NO: 13. In certain embodiments, FH CCP domain 6 comprises an amino acid sequence as set forth in SEQ ID NO: 14. In certain embodiments, FH CCP domain 7 has an amino acid sequence as set forth in SEQ ID NO: 15. In certain embodiments, FH CCP domain 18 comprises an amino acid sequence as set forth in SEQ ID NO: 16. In certain embodiments, FH CCP domain 19 comprises an amino acid sequence as set forth in SEQ ID NO: 17. In certain embodiments, FH CCP domain 20 comprises an amino acid sequence as set forth in SEQ ID NO: 18.

In certain embodiments, FHR5 CCP domain 7 comprises an amino acid sequences as set forth in SEQ ID NO: 19. In certain embodiments, FHR5 CCP domain 8 comprises an amino acid sequences as set forth in SEQ ID NO: 20. In certain embodiments, FHR5 CCP domain 9 comprises an amino acid sequences as set forth in SEQ ID NO: 21. In certain embodiments, FHL-1 CCP domain 6 comprises an amino acid sequences as set forth in SEQ ID NO: 22.

In certain embodiments, FHL-1 CCP domain 7 comprises an amino acid sequences as set forth in SEQ ID NO: 23. In certain embodiments, FHR1 CCP domain 1 comprises an amino acid sequences as set forth in SEQ ID NO: 24. In certain embodiments, FHR1 CCP domain 2 comprises an amino acid sequences as set forth in SEQ ID NO: 25.

In certain embodiments of the present invention there is provided a complement regulator protein comprising from N-terminal to C-terminal; FH CCP1 (SEQ ID NO: 9), FH CCP2 (SEQ ID NO: 10), FH CCP3 (SEQ ID NO: 11), FH CCP4 (SEQ ID NO: 12), FH CCP5 (SEQ ID NO: 13), optionally at least one linker molecule, FH CCP18 (SEQ ID NO: 16), FH CCP19 (SEQ ID NO: 17), FH CCP20 (SEQ ID NO: 18), optionally at least one linker molecule, FHR1 CCP1 (SEQ ID NO: 24) and FHR1 CCP2 (SEQ ID NO: 25). Aptly the FH CCP domains are human FH CCP domains. Aptly the FHR1 domains are human FHR1 CCP domains.

In certain embodiments, there is provided a complement regulator protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% sequence identity to the sequence as set forth in SEQ ID NO: 26.

In certain embodiments of the present invention there is provided a complement regulator protein comprising from N-terminal to C-terminal; FHR1 CCP1 (SEQ ID NO: 24), FHR1 CCP2 (SEQ ID NO: 25), optionally at least one linker molecule, FH CCP1 (SEQ ID NO: 9), FH CCP2 (SEQ ID NO: 10), FH CCP3 (SEQ ID NO: 11), FH CCP4 (SEQ ID NO: 12), FH CCP5 (SEQ ID NO: 13), optionally at least one linker molecule and FH CCP18 (SEQ ID NO: 16), FH CCP19 (SEQ ID NO: 17) and FH CCP20 (SEQ ID NO: 18). Aptly the FH CCP domains are human FH CCP domains. Aptly the FHR1 domains are human FHR1 CCP domains.

In certain embodiments, there is provided a complement regulator protein comprising at least 80%, 81%, 82%, 83%, 84%, 85%, 86%, 87%, 88%, 89%, 90%, 91%, 92%, 93%, 94%, 95%, 96%, 97%, 98%, 99% sequence identity to the sequence as set forth in SEQ ID NO: 27.

In certain embodiments of the present invention there is provided a complement regulator protein comprising from N-terminal to C-terminal; FH CCP1 (SEQ ID NO: 9), FH CCP2 (SEQ ID NO: 10), FH CCP3 (SEQ ID NO: 11), FH CCP4 (SEQ ID NO: 12), FH CCP5 (SEQ ID NO: 13), optionally at least one linker, FHL-1 CCP6 (SEQ ID NO: 22), FHL-1 CCP7 (SEQ ID NO: 23), optionally at least one linker molecule and FHR1 CCP1 (SEQ ID NO: 24) and FHR1 CCP2 (SEQ ID NO: 25). Aptly the FH CCP domains are human FH CCP domains. Aptly the FHR1 domains are human FHR1 CCP domains. Aptly the FHL-1 CCP domains are human.

In certain embodiments, there is provided a complement regulator protein comprising at least 80%, 81%, 82%, 83%, 84%, 85%, 86%, 87%, 88%, 89%, 90%, 91%, 92%, 93%, 94%, 95%, 96%, 97%, 98%, 99% sequence identity to the sequence as set forth in SEQ ID NO: 28.

In certain embodiments of the present invention there is provided a complement regulator protein comprising from N-terminal to C-terminal; FHR1 CCP1 (SEQ ID NO: 24), FHR1 CCP2 (SEQ ID NO: 25), optionally at least one linker molecule, FH CCP1 (SEQ ID NO: 9), FH CCP2 (SEQ ID NO: 10), FH CCP3 (SEQ ID NO: 11), FH CCP4 (SEQ ID NO: 12), FH CCP5 (SEQ ID NO: 13), optionally at least one linker molecule and FHL-1 CCP6 (SEQ ID NO: 22), FHL-1 CCP7 (SEQ ID NO: 23). Aptly the FH CCP domains are human FH CCP domains. Aptly the FHR1 domains are human FHR1 CCP domains. Aptly the FHL-1 CCP domains are human.

In certain embodiments, there is provided a complement regulator protein comprising at least 80%, 81%, 82%, 83%, 84%, 85%, 86%, 87%, 88%, 89%, 90%, 91%, 92%, 93%, 94%, 95%, 96%, 97%, 98%, 99% sequence identity to the sequence as set forth in SEQ ID NO: 29.

In certain embodiments, the complement regulator protein comprises at least one post-translationally modification. As used herein "post-translational modification" refers to any chemical modification of a polypeptide after it is produced. Post-translational modifications may involve attaching at least one moiety to the polypeptide chain, certain post-translational modifications may involve cleavage of the polypeptide chain, proteolytic processing, the formation of disulfide bonds, and the like. Non-limiting examples of post-translational modifications include, glycosylation, phosphorylation, acylation, acetylation, methylation, sulfonation, prenylation, isoprenylation, ubiquitination, biotinylation, formylation, citrullination, myristolation, ribosylation, sumoylation, gamma carboxylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, demethylation, formation of covalent cross-links, formation of cystine, formation of pyroglutamate, GPI anchor formation, hydroxylation, iodination, methylation, oxidation, proteolytic processing, racemization, selenoylation, sulfation and transfer-RNA mediated addition of amino acids to proteins such as arginylation.

In certain embodiments, there is provided a recombinant complement regulator protein comprising an amino acid sequence as set forth in SEQ ID NO: 46 that is proteolytically cleaved to the amino acid sequences as set forth in SEQ ID NO: 26.

In certain embodiments, there is provided a recombinant complement regulator protein comprising an amino acid sequence as set forth in SEQ ID NO: 47 that is proteolytically cleaved to the amino acid sequences as set forth in SEQ ID NO: 27.

In certain embodiments, there is provided a recombinant complement regulator protein comprising an amino acid sequence as set forth in SEQ ID NO: 48 that is proteolytically cleaved to the amino acid sequences as set forth in SEQ ID NO: 28.

In certain embodiments, there is provided a recombinant complement regulator protein comprising an amino acid sequence as set forth in SEQ ID NO: 49 that is proteolytically cleaved to the amino acid sequences as set forth in SEQ ID NO: 29.

In certain embodiments, at least one CCP domain of the proteins of the present invention include CCP domains which differ from a naturally occurring CCP domains (or fragments thereof). For example, one or more amino acid residues may have been deleted (e.g., a truncated version of the protein, such as a peptide or fragment), inserted, inverted, substituted and/or derivatized (e.g., by glycosylation, phosphorylation, acetylation, myristoylation, prenylation, palmitation, amidation and/or addition of glycosylphosphatidyl inositol).

In certain embodiments, the CCP domains may contain no more than 2, 3, 4, 5, 6, 7, 8, 9, or 10 conservative amino acid substitutions as compared to a native CCP polypeptide sequences. The term "conservative substitution" as used herein refers to substitutions of amino acid residues of a complement regulator protein that have no effect on activity or properties of the complement regulator protein. Conservative substitutions may be naturally occurring or non-naturally occurring.

In certain embodiments, the complement regulator proteins of the present invention or one or more CCP domains thereof are glycosylated. As used herein, "glycosylation" refers to the chemical attachment of at least one saccharide moiety to a molecule such as a protein. Glycosylation can be N-linked or O-linked. N-linked glycosylation involves the attachment of at least one saccharide moiety to at least one amide group nitrogen of at least one amino acid residue of a protein. O-linked glycosylation involves the attachment of at least one saccharide moiety to at least one oxygen atom of at least one amino acid residue of a protein. Saccharide moieties include but are not limited to one or more of mannose, fucose, N-acetylglucosamine, galactose, glucose, xylitol, N-Glycolylneuraminic acid and siacilic acid.

In certain embodiments, the at least one dimerization region is glycosylated. In certain embodiments, at least one CCP domain of the dimerization domain is glycosylated.

In certain embodiments, wherein the complement regulator protein comprises at least one FHR CCP domain, at least one FHR CCP is glycosylated. Aptly the at least one CCP domain is a fragment of FHR1, FHR2, FHR3 and/or FHR5. In certain embodiments, wherein the complement regulator protein comprises FHR1 CCP domains 1 (SEQ ID NO: 24) and 2 (SEQ ID NO: 25), FHR1 CCP domain 2 (SEQ ID NO: 25) is glycosylated. In certain embodiments, wherein $X_3$ is or wherein the complement regulator protein comprises FH CCP domains 18 (SEQ ID NO: 16), 19 (SEQ ID NO: 17) and 20 (SEQ ID NO: 18), FH CCP domain 18 (SEQ ID NO: 16) is glycosylated.

Without being bound by theory glycosylation may help with trafficking of a protein, cell signalling responses to a protein and may help to reduce or prevent an antigenic response to a protein or recombinant protein in a host cell or tissue.

In certain embodiments, the complement regulator proteins of the present invention are fusion proteins.

The term "fusion polypeptide" or "fusion protein" as used herein refers to a protein having a plurality of polypeptides, proteins and or protein fragments, unjoined in their native or not joined in the same order or state, as in a native protein, that are joined to form a single continuous polypeptide. The polypeptides forming the fusion protein may be linked C-terminus to N-terminus, they can also be linked C-terminus to C-terminus, N-terminus to N-terminus, or N-terminus to C-terminus. The polypeptides of the fusion protein can be in any order and may include more than one of either or all of the constituent polypeptides. The term incudes but is not limited to conservatively modified variants, polymorphic variants, mutants and, interspecies homologs.

These polypeptides can be joined directly together, or linker molecules (e.g., heterologous amino acid residues) can be situated between them. As such, polypeptides that are fused together may be connected directly or indirectly (i.e., via a linker molecule or the like).

The term "linker", "linker molecule" or "linked" as used herein refers to a covalent linkage between two or more polypeptides in a fusion protein. The polypeptides may be joined for example via a peptide bond, either directly to each other or via one or more additional amino acids. The composition and length of the linker may be determined in accordance with methods well known in the art and may be tested for efficacy. The linker is generally from about 1 to about 30 amino acids long, in some embodiments about 2 to about 15 amino acids long. Aptly longer or shorter linkers may be used. Aptly the linker may be dispensed with entirely.

In certain embodiments, the complement regulator protein comprises at least one linker for operably linking one or more of any of the fragments of the complement interaction region to each other and/or for operably linking the complement interaction region to the dimerization region.

In certain embodiments, the complement regulator protein comprises at least one further linker for operably linking one or more of any of the fragments of complement interaction region to each other and/or for operably linking the complement interaction region to the dimerization. For example, the complement regulator protein may comprise at least one linker operable to link one or more fragments of the complement interaction region and at least one further linker operable to link the complement interaction region to the dimerization region.

In certain embodiments, the complement regulator protein comprises at least two, three, four, five or more linker molecules.

The term "operably linked" as used herein refers to a first moiety joined to a second moiety, wherein the moieties are so arranged that the both moieties are able to maintain their intended function and/or show a synergistic effect.

In certain embodiments, the at least one linker and/or further linker are a naturally occurring linkers. In certain embodiments, the at least one linker and/or further linker are heterologous linkers.

As used herein the term "heterologous" refers to a peptide, polypeptide, protein or nucleic acid that is not normally linked or fused to a naturally occurring complement regulator protein and is not normally expressed in association with complement regulator proteins.

In certain embodiments, the at least one linker and/or further linker may be peptidic, non-peptidic or partially peptidic.

In certain embodiments, the at least one linker and/or further linker are independently selected from one or more linker molecules comprising: an amino acid sequence as set forth in SEQ ID NO: 30; an amino acid sequence as set forth in SEQ ID NO: 31; an amino acid sequence as set forth in SEQ ID NO: 32; an amino acid sequence as set forth in SEQ ID NO: 33; an amino acid sequence as set forth in SEQ ID NO: 34; Glycine and Threonine (GT); Valine and Aspartic acid (VD) and/or Valine, Aspartic acid and Threonine (VDT).

In certain embodiments, the at least one linker and/or further linker comprises one or more amino acid residues that are transcribed and translated from nucleic acid residues that are at least a portion of one or more restriction sites that may be introduced into a nucleic acid molecule encoding one or more protein regions and/or fragments as described herein.

The introduction of one or more restrictions sites may allow for ligation of nucleic acids encoding one or more regions and/or fragments of one or more complement regulator proteins to form a single nucleic acid molecule encoding a recombinant complement regulator protein as described herein.

As used herein the terms "restriction endonuclease" and "restriction enzyme" refer to enzymes (e.g. bacterial enzymes), each of which cut double-stranded DNA at or near a specific nucleotide residue sequence (a cognate restriction site). Examples include, but are not limited to, KpnI, BamHI, EcoRV, HindIII, HincII, NcoI, SalI, and NotI. Other suitable restriction enzymes will be known by those skilled in the art. As used herein the term "restriction" means cleavage of a nucleic acid molecule by a restriction enzyme at its cognate restriction site. As used herein the term "restriction site" refers to a particular nucleic acid sequence, such as a DNA sequence recognized by its cognate restriction enzymes.

Therefore, the amino acid residues introduced by a restriction site are dependent on the restriction enzyme used in the production of a recombinant complement regulator protein as described herein.

For example, in certain embodiments wherein the restriction site introduced is cognate with the restriction enzyme KpnI the at least one linker and/or further linker may comprise the amino acid residues Glycine and Threonine (GT).

In certain embodiments, the at least one linker and/or further linker molecule comprise the amino acid sequence GT. In certain embodiments, the at least one linker and/or further molecule linker comprise the amino acid sequence VD (Valine and Aspartic acid). In certain embodiments, the at least one linker and/or further linker molecule comprise the amino acid sequence VDT (Valine, Aspartic acid and Threonine).

In certain embodiments, the at least one linker and/or further linker molecule comprises the sequence identified herein as SEQ ID NO: 30 and one or more further amino acid residues introduced by one or more restriction sites as described herein.

In certain embodiments, the at least one linker and/or further linker molecule comprises the sequence identified herein as SEQ ID NO: 31. In certain embodiments, the at least one linker and/or further linker molecule comprises the sequence identified herein as SEQ ID NO: 32. In certain embodiments, the at least one linker and/or further linker molecule comprises the sequence identified herein as SEQ ID NO: 33.

In certain embodiments, the at least one linker and/or further linker molecule are independently selected from one or more linkers as described herein.

In certain embodiments, the complement regulator proteins may be or form multimers, e.g. dimers.

The complement regulator proteins of certain embodiments may be manufactured either by standard synthetic methods, recombinant expression systems, or any other state of the art method. Thus, the complement regulator proteins as described herein may be synthesized in a number of ways, including, for example, a method which comprises:

(a) synthesizing the protein by means of solid-phase or liquid-phase methodology, either stepwise or by fragment assembly, and isolation and purifying of the final protein product; or (b) expressing a nucleic acid construct that encodes the protein in a host cell, and recovering the expression product from the host cell or culture medium; or (c) effecting cell-free in vitro expression of a nucleic acid construct that encodes the protein, and recovering the expression product;

or any combination of methods of (a), (b), and (c) to obtain fragments of the proteins, subsequently ligating the fragments to obtain the protein, reproducing and/or propagating the protein and recovering the protein.

In one aspect of the present invention there is provided a nucleic acid molecule encoding a recombinant complement regulator protein as described herein. Aptly the nucleic acid sequences may be DNA or RNA. Aptly the sequences may be double stranded DNA. Aptly the sequences may be single stranded DNA.

Aptly the nucleic acid molecules are isolated and/or purified. Aptly the nucleic acid molecules are substantially free or free from material which it may be associated with.

In one aspect of the present invention there is provided a nucleic acid molecule encoding a protein having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% sequence identity to the amino acid sequence as set forth in SEQ ID NO: 26, 27, 28 or 29.

In one aspect of the present invention there is provided a nucleic acid molecule encoding a protein having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% sequence identity to the amino acid sequence as set forth in SEQ ID NO: 46, 47, 48 or 49.

In certain embodiments, the nucleic acid molecule may be incorporated into a recombinant replicable vector. Aptly the vector is used to replicate the nucleic acid molecule in a compatible host cell.

Thus, in a further aspect of the present invention there is provided a method of producing a complement regulator protein as described herein comprising the steps of introducing a nucleic acid encoding the complement regulator protein into a replicable vector, introducing the vector into a compatible host cell and culturing the host cell under conditions to bring about the replication of the vector. Aptly the host cell expresses the complement regulator protein.

Aptly the method further comprises a step of purifying the isolated complement regulator protein.

The proteins of the present disclosure may be formulated as pharmaceutical compositions prepared for storage or administration for use in the treatment and/or prevention of a diseases associated with or mediated by the complement pathway as described herein. Aptly associated with or mediated by the alternative complement pathway. Such a composition typically comprises a therapeutically effective amount of a complement regulator protein, in the appropriate form, in a pharmaceutically acceptable carrier.

The therapeutically effective amount of a complement regulator protein as described herein will depend on the route of administration, the type of animal being treated, and the physical characteristics of the specific animal under consideration. These factors and their relationship to determining this amount are well known to skilled practitioners in the medical arts. This amount and the method of administration can be tailored to achieve optimal efficacy, and may depend on such factors as weight, diet, concurrent medication and other factors, well known to those skilled in the medical arts. The proteins of the present disclosure may be particularly useful for treatment of humans.

An effective dosage and treatment protocol may be determined by conventional means, starting with a low dose in laboratory animals and then increasing the dosage while monitoring the effects, and systematically varying the dosage regime as well. Numerous factors may be taken into consideration by a clinician when determining an optimal dosage for a given subject. Such considerations are known to the person skilled in the art.

The term "pharmaceutically acceptable carrier" includes any of the standard pharmaceutical carriers. Pharmaceutically acceptable carriers for therapeutic use are well known in the pharmaceutical art, and are described, for example, in Remington's Pharmaceutical Sciences, Mack Publishing Co. (A. R. Gennaro edit. 1985). For example, sterile saline and phosphate-buffered saline at slightly acidic or physiological pH may be used. pH buffering agents may be phosphate, citrate, acetate, tris/hydroxymethyl)aminomethane (TRIS), N-Tris (hydroxymethyl)methyl-3-aminopropanesulphonic acid (TAPS), ammonium bicarbonate, diethanolamine, histidine, arginine, lysine, or acetate or mixtures thereof. The term further encompasses any agents listed in the US Pharmacopeia for use in animals, including humans.

"Treatment" is an approach for obtaining beneficial or desired clinical results. For the purposes of the present disclosure, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" is an intervention performed with the intention of preventing the development or altering the pathology of a disorder. Accordingly, "treatment" refers to both therapeutic treatment and prophylactic or preventative measures in certain embodiments. Those in need of treatment include those already with the disorder as well as those in which the disorder is to be prevented. By treatment is meant inhibiting or reducing an increase in pathology or symptoms when compared to the absence of treatment, and is not necessarily meant to imply complete cessation of the relevant condition.

The pharmaceutical compositions for use in the treatment of a disease associated with or mediated by the alternative complement pathway can be in unit dosage form. In such form, the composition is divided into unit doses containing appropriate quantities of the active component, the unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms. It may be provided in single dose injectable form, for example in the form of a pen. In certain embodiments, packaged forms include a label or insert with instructions for use. Compositions may be formulated for any suitable route and means of administration. Pharmaceutically acceptable carriers or diluents include those used in formulations suitable for oral, rectal, nasal, topical (including buccal and sublingual), vaginal or parenteral (including subcutaneous, intramuscular, intravenous, intradermal, intraocular and transdermal) administration. The formulations may conveniently be presented in unit dosage form and may be prepared by any of the methods well known in the art of pharmacy.

As used herein an "effective" amount or a "therapeutically effective amount" of a protein refers to a nontoxic but sufficient amount of the complement regulator protein to provide the desired effect. The amount that is "effective" will vary from subject to subject, depending on the age and general condition of the individual, mode of administration, and the like. An appropriate "effective" amount in any individual case may be determined by one of ordinary skill in the art using routine experimentation.

The terms "patient", "subject" and "individual" may be used interchangeably and refer to either a humans or non-human mammals. Aptly, the subject is a human.

In one embodiment, the complement regulator protein is for use as a medicament.

In one embodiment, the complement regulator protein is for use in the treatment of a disease associated with or mediated by the complement pathway. Aptly the complement regulator protein is for use in the treatment of a disease associated with or mediated by the alternative complement pathway.

Certain embodiments of the complement regulator proteins and compositions thereof as described herein may function to inhibit in vivo complement activation in the alternative complement pathway and inflammatory responses that accompany it, such as recruitment and/or activation of; macrophages; neutrophils; platelets; mast cells; and direct activation of local and endogenous cells. In certain embodiments, the complement regulator proteins described herein and compositions thereof may therefore be used for treatment of a disease or condition that is associated with or mediated by excessive or uncontrolled activation of the complement system and diseases or conditions associated with or mediated by excessive or uncontrolled activation of the alternative complement pathway.

In some embodiments, the complement regulator proteins and compositions thereof are for use in treating diseases involving local inflammation processes. In some embodiments, the complement regulator proteins and compositions thereof are for use in treating one or more diseases associated with FH deficiencies (for example a decrease in host FH level, decrease in host FH activity, or lack of wild type or protective host FH), including, for example chronic inflammation such as rheumatoid arthritis, ischemia reperfusion (such as renal ischemia reperfusion or intestinal ischemia reperfusion), organ transplant rejection, myocardial infarction, edema, tissue damage, adult respiratory distress syndrome, renal diseases, eye diseases and/or lupus nephritis.

In some embodiments, the complement regulator proteins and compositions thereof are for use in treating eye diseases. In certain embodiments, the eye disease is selected from autoimmune uveitis, diabetic retinopathy and/or age related macular degeneration. In certain embodiments, the eye disease is age related macular degeneration.

In some embodiments, the complement regulator protein and compositions thereof are for use in treating renal diseases. In certain embodiments, the renal disease is selected from one or more of atypical haemolytic uremic syndrome (aHUS), IgA nephropathy (Berger's disease), C3 Glomerulopathy; optionally C3 glomerulonephritis, mesangiocapillary glomerulonephritis and/or dense deposit disease. Aptly the renal disease is aHUS.

Other diseases and disorders that may be associated with or mediated by the alternative complement pathway will be apparent to those skilled in the art and may include but are not limited to: (1) tissue damage due to ischemia-reperfusion following one or more of acute myocardial infarction, aneurysm, stroke, haemorrhagic shock, crush injury, multiple organ failure, hypovolemic shock intestinal ischemia, spinal cord injury, and traumatic brain injury; (2) inflammatory disorders, as a consequence of, for example, burns, endotoxemia and septic shock, adult respiratory distress syndrome, cardiopulmonary bypass, haemodialysis, anaphylactic shock, severe asthma, angioedema, Crohn's disease, sickle cell anaemia, poststreptococcal glomerulonephritis, membranous nephritis, and pancreatitis; (3) disorders associated with transplant rejection, e.g., hyperacute xenograft rejection; (4) pregnancy related diseases, such as recurrent foetal loss and pre-eclampsia, and (5) adverse drug reactions, e.g., drug allergy, IL-2 induced vascular leakage syndrome and radiographic contrast media allergy (6) autoimmune disorders including, but not limited to, myasthenia gravis, Alzheimer's disease, multiple sclerosis, emphysema, obesity, rheumatoid arthritis, systemic lupus erythematosus, myasthenia gravis, insulin-dependent diabetes mellitus, acute disseminated encephalomyelitis, Addison's disease, antiphospholipid antibody syndrome, autoimmune hepatitis, Goodpasture's syndrome, Graves' disease, Guillain-Barre syndrome, Hashimoto's disease, idiopathic thrombocytopenia purpura, pemphigus, Sjögren's syndrome, and Takayasu's arteritis.

In a further aspect of the present invention there is provided method of treating and/or preventing a disease associated with or mediated by the alternative complement pathway as described herein in a subject in need thereof, the method comprising;
   administering a pharmaceutically effective amount of a pharmaceutical composition comprising a recombinant complement regulator protein, wherein the complement regulator protein comprises;
   a) at least one complement interaction region operable to regulate complement and bind the complement regulator protein to at least one target, the complement interaction region comprising;
      (i) at least one FH fragment; and
   b) at least one dimerization region operable to dimerize the complement regulator protein.

Aptly the complement regulator protein is a complement regulator protein as described herein.

In certain embodiments, the complement regulator protein comprises an amino acid sequence as set forth in sequences SEQ ID NO: 26 or SEQ ID NO: 27. In certain embodiments, the complement regulator protein comprises an amino acid sequence as set forth in sequences SEQ ID NO: 28 or SEQ ID NO: 29.

In certain embodiments, the complement regulator protein comprises a sequence as set forth in sequences SEQ ID NO: 28 or SEQ ID NO: 29 and compositions thereof are for use in the treatment and methods of treating eye diseases as described above In certain embodiments, the complement regulator protein comprises a sequence as set forth in sequences SEQ ID NO: 46 or SEQ ID NO: 47 and compositions thereof are for use in the treatment and methods of treating renal diseases as described above.

In certain embodiments, the complement regulator protein comprises a sequence as set forth in sequences SEQ ID NO: 48 or SEQ ID NO: 49 and compositions thereof are for use in the treatment and methods of treating eye diseases as described above.

Certain embodiments of the complement regulator proteins as described herein and compositions thereof are for use in the treatment of macular degeneration. Aptly for use in the treatment of age related macular degeneration (AMD).

AMD is clinically characterized by progressive loss of central vision which occurs as a result of damage to the photoreceptor cells in an area of the retina called the macula. AMD has been broadly classified into two clinical states: a wet form and a dry form, with the dry form making up to 80-90% of total cases. The dry form is characterized clinically by the presence of macular drusen, which are localized deposits between the retinal pigment epithelium (RPE) and the Bruch's membrane, and by geographic atrophy characterized by RPE cell death with overlying photoreceptor atrophy. Wet AMD, which accounts for approximately 90% of serious vision loss, is associated with neovascularization in the area of the macular and leakage of these new vessels. The accumulation of blood and fluid can cause retina detachment followed by rapid photoreceptor degeneration and loss of vision. It is generally accepted that the wet form of AMD is preceded by and arises from the dry form. Analysis of the contents of drusen in AMD patients has shown a large number of inflammatory proteins including amyloid proteins, coagulation factors, and a large number of proteins of the complement pathways. Genetic variations in the FH substantially raises the risk of age-related macular degeneration (AMD), suggesting that uncontrolled complement activation underlies the pathogenesis of AMD.

In another aspect of the present invention there is provided a method of treating and/or preventing age related macular degeneration in a subject in need thereof, the method comprising;
   administering a pharmaceutically effective amount of a pharmaceutical composition comprising a recombinant complement regulator protein, wherein the recombinant complement regulator protein comprises;
   a) at least one complement interaction region operable to regulate complement and bind the complement regulator protein to at least one target, the complement interaction region comprising;
(i) at least one FH fragment; and
b) at least one dimerization region operable to dimerize the complement regulator protein.

Aptly the complement regulator protein is a complement regulator protein as described herein.

In certain embodiments of the present invention there is provided methods of treating and/or preventing one or more symptoms or pathologies of AMD, including, but not limited to, formation of ocular drusen, inflammation in the eye or eye tissue, loss of photoreceptor cells, loss of vision (including for example visual acuity and visual field), neovascularization (such as choroidal neovascularization (CNV)), and retinal detachment. In certain embodiments related symptoms or pathologies of AMD may be treated, such as photoreceptor degeneration, RPE degeneration, retinal degeneration, chorioretinal degeneration, cone degeneration, retinal dysfunction, retinal damage in response to light exposure (such as constant light exposure), damage of the Bruch's membrane, loss of RPE function, loss of integrity of the histoarchitecture of the cells and/or extracellular matrix of the normal macular, loss of function of the cells in the macula, photoreceptor dystrophy, mucopolysaccharidoses, rod-cone dystrophies, cone-rod dystrophies, anterior and posterior uvitis, and diabetic neuropathy.

In addition to macular degeneration, other eye diseases may be treated by methods of the present invention, for example, retinitis pigmentosa, diabetic retinopathy, and other eye diseases that involve a local inflammatory process.

In certain embodiments, the method of treating and/or preventing an eye disease such as AMD comprises administering a pharmaceutically effective amount of a pharmaceutical composition comprising a recombinant complement regulator protein, wherein the recombinant complement regulator protein comprises:
a) at least one complement interaction region operable to regulate complement and bind the complement regulator protein to at least one target, the complement interaction region comprising a FH CCP1 domain (SEQ ID NO: 9), a FH CCP2 domain (SEQ ID NO: 10), a FH CCP3 domain (SEQ ID NO: 11), a FH CCP4 domain (SEQ ID NO: 12) and a FH CCP5 domain (SEQ ID NO: 13); and
b) at least one dimerization region operable to dimerize the complement regulator protein, the dimerization region of the complement regulator protein comprises a FHR1 CCP1 domain (SEQ ID NO: 24) and a FHR1 CCP2 domain (SEQ ID NO: 25);
wherein the at least one complement interaction region further comprises at least one further FH fragment operable to bind the complement regulator protein to the at least one target and/or at least one further target, wherein the further FH fragment comprises FHL-1 CCP domains 6 (SEQ ID NO: 22) and 7 (SEQ ID NO: 23).

Aptly, the recombinant regulator protein forms a dimer (e.g. homodimer). Aptly, the recombinant regulatory protein targets AMD (or other eye disease) specific C3b, GAGs, heparin or other ligands to reduce inflammation or other damage to retinal epithelial cells. For example, FHL-1 CCP domains 6 (SEQ ID NO: 22) and 7 (SEQ ID NO: 23) (also referred herein as SCR 6-7) are capable of binding to GAG receptors within the retina that contain heparin sulphates (HS) on their surface. As discussed above, the CCP domain 7 (SEQ ID NO: 23) typically comprises the 402Y polymorphism.

Certain embodiments of the complement regulator proteins as described herein and compositions thereof are for use in the treatment of haemolytic uremic anaemia. Aptly, the complement regulator proteins are for use in the treatment of atypical haemolytic uremic anaemia (aHUS).

HUS is a disease consisting of microangiopathic haemolytic anaemia, thrombocytopenia, and acute renal failure, caused by continuous platelet degradation in the periphery and platelet thrombin in the microcirculation of the kidney.

Typical (or infection-induced) HUS such as diarrheal forms of HUS (D-HUS) are most commonly associated with bacterial infections. For example, infection by *Escherichia coli* (*E. coli*) with somatic (O) antigen 157 and flagella (H) antigen. The *E. coli* produces toxins such as Shiga toxin and/or verotoxin. HUS is a systemic disease caused by damage arising from the circulating toxins which bind to endothelial receptors, particularly in the renal, gastrointestinal and central nervous systems. Thrombin and fibrin are deposited in the microvasculature. This may occur early in the disease, prior even to the development of HUS and may be why antibiotics are commonly not beneficial. Erythrocytes are damaged as they pass through partially occluded small vessels and subsequent haemolysis occurs. Platelets are sequestered but without the cascade of clotting factors as in disseminated intravascular coagulation (DIC). Other pathogens may induce HUS, for example bacteria such as *Streptococcus pneumoniae* and *Shigella dysenteriae* type 1 and viruses such as HIV and Coxsackievirus.

Atypical HUS can be caused by exposure to certain medications (e.g., cyclosporin, tacrolimus) genetic mutations in the complement pathway (i.e. FH or FHR proteins) and systemic conditions, including but not limited to lupus, cancer and pregnancy. aHUS is characterized by low levels of circulating red blood cells due to their destruction (haemolytic anaemia), low platelet count (thrombocytopenia) and inability of the kidneys to process waste products from the blood and excrete them into the urine (acute kidney failure, also known as uraemia). aHUS differs from typical HUS in that most cases of aHUS are genetic, although some may be acquired due to autoantibodies or occur for unknown reasons (idiopathic). There is considerable evidence that the non-diarrheal form of HUS (D-HUS) is associated with alternations and mutations of FH. In addition, autoantibodies to FH have been reported in aHUS and HUS patients. Targeting FH to complement activation sites may have therapeutic effects on an individual suffering from HUS or aHUS. aHUS may become chronic, and affected individuals may experience repeated episodes of the disorder. Unlike individuals with typical HUS, who usually recover from the initial episode and usually respond well to supportive treatment, individuals with aHUS are much more likely to develop chronic serious complications such as severe high blood pressure (hypertension) and kidney (renal) failure. The signs and symptoms of aHUS result from the formation of microthrombi in various small blood vessels of the body. These microthrombi reduce or prevent proper blood flow to various organs of the body, especially the kidneys. aHUS may involve multiple factors, including but not limited to genetic, environmental and/or immunologic factors.

Thus, in one aspect of the present invention there is provided a method of treating and/or preventing atypical haemolytic uremic anaemia in a subject in need thereof, the method comprising;
administering a pharmaceutically effective amount of a pharmaceutical composition comprising a recombinant complement regulator protein, wherein the complement regulator protein comprises;

a) at least one complement interaction region operable to regulate complement and bind the complement regulator protein to at least one target, the complement interaction region comprising;
   (i) at least one FH fragment; and
b) at least one dimerization region operable to dimerize the complement regulator protein.

In one aspect of the present invention, the complement regulator protein inhibits complement activation on the surface of a cell, tissue or organ ex vivo. In certain embodiments, the complement regulator protein is administered to a (donor) cell, tissue or organ ex vivo prior to transplantation of the (donor) cell, tissue or organ to a patient in need thereof.

The (donor) cell, tissue or organ may be from a different species to the patient in need thereof (i.e., xenotransplantation). For example, the (donor) cell, tissue or organ may be derived from a pig and the patient in need thereof human. Alternatively, the (donor) cell, tissue or organ may be derived from the same species to the patient in need thereof (i.e., allotransplantation). In certain embodiments, the (donor) cell, tissue or organ is derived from a human and the patient in need thereof is a different human.

The cell, tissue or organ may be any cell, tissue or organ that is capable of being used for allografts. For example, the cell, tissue or organ may be (or may be derived from) skin, cornea, heart, liver, pancreas, bone or bone marrow, ligament or tendon. Aptly, the cell, tissue or organ is (or is derived from) kidney.

In certain embodiments, the complement regulator protein is administered to a cell, tissue or organ ex vivo by injection. For example, the complement regulator protein may be administered to a stem cell or a population of stem cells prior to transplantation. The complement regulator protein may be administered to a kidney prior to transplantation. For example, where the organ is a kidney, the complement regulator protein may be administered via the renal artery.

In certain embodiments, the complement regulator protein is administered to an organ through which warm oxygenated red-blood cells are circulated ex vivo. For example, the organ (such as a kidney) may be comprised in an Ex-vivo Normothermic Perfusion (EVNP) system.

In certain embodiments, the complement regulator protein is absorbed onto the vasculature of an organ such as kidney upon administration. Typically, the complement regulator protein reduces C3 deposition on the surface of the organ such as a kidney thereby reducing the risk of the organ being rejected by the patient in need thereof and/or reducing the need for the patient to take immunosuppressive drugs.

In certain embodiments, the at least one FH fragment of the complement regulator protein comprises a FH CCP1 domain (SEQ ID NO: 9), a FH CCP2 domain (SEQ ID NO: 10), a FH CCP3 domain (SEQ ID NO: 11), a FH CCP4 domain (SEQ ID NO: 12) and a FH CCP5 domain (SEQ ID NO: 13). Aptly, the dimerization region of the complement regulator protein comprises a FHR1 CCP1 domain (SEQ ID NO: 24) and a FHR1 CCP2 domain (SEQ ID NO: 25). Aptly, the complement regulator protein comprises at least one further FH fragment comprising a FH CCP18 domain (SEQ ID NO: 16), a FH CCP19 domain (SEQ ID NO: 17) and a FH CCP20 domain (SEQ ID NO: 18). Aptly, the complement regulator protein forms a dimer (e.g., a homodimer).

Aptly the complement regulator protein is a complement regulator protein as described herein.

Example 1

Figure 1:
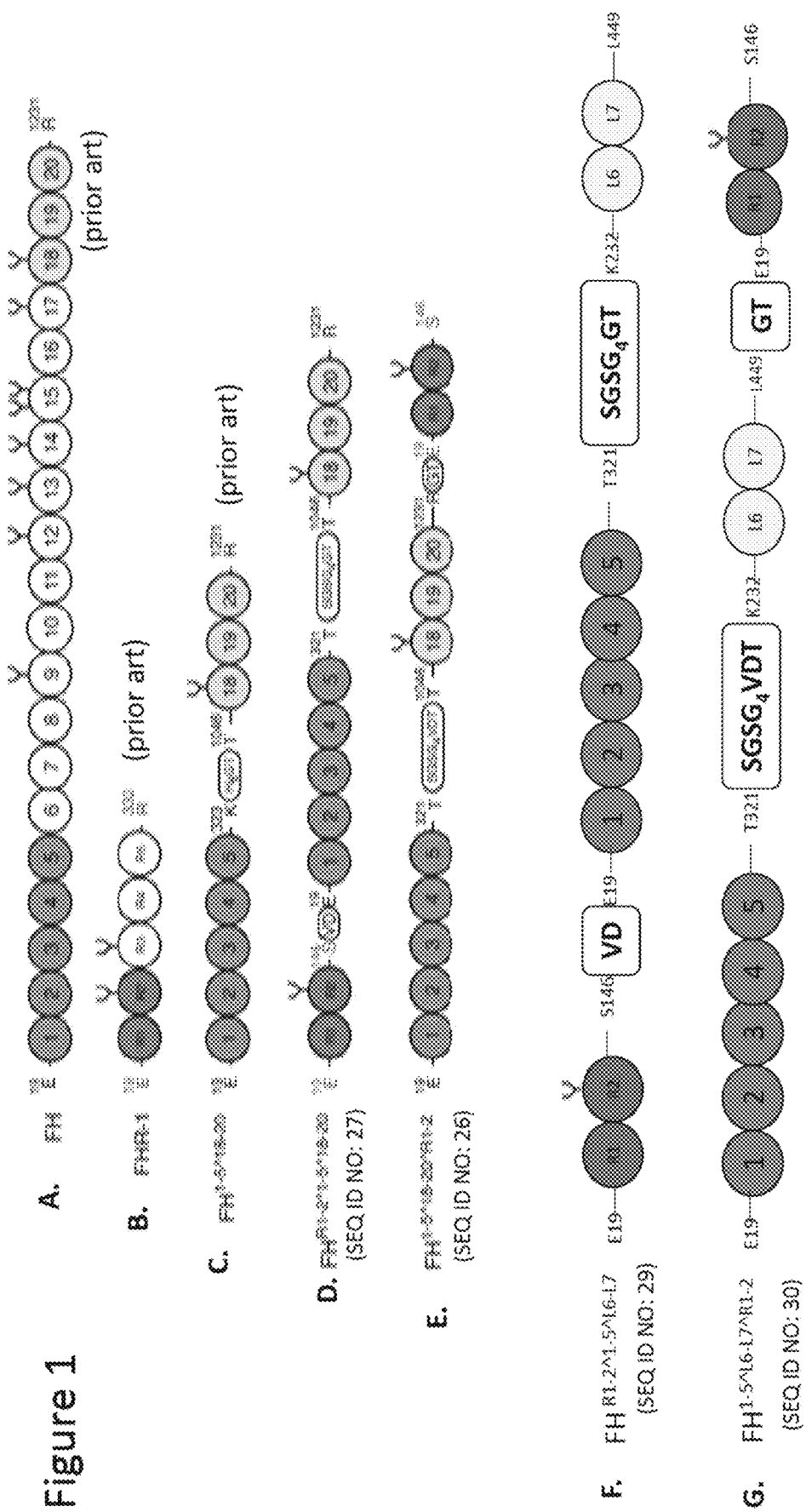
FIG. 1 illustrates schematic representations of the modular structure of:
A) an FH protein comprising CCP domains 1 to 20 (prior art);
B) an FHR1 protein comprising FHR1 CCP domains 1, 2, 3, 4, and 5 (R1, R2 etc.) (prior art);
C) a mini-FH protein comprising FH CCP domains 1, 2, 3, 4 and 5 and 18, 19 and 20 (referred to herein as $FH^{1-5\wedge 18-20}$) (prior art);
D) an embodiment of a complement regulator protein of the present invention comprising FHR1 CCP domains 1 (SEQ ID NO: 24) and 2 (SEQ ID NO: 25), FH CCP domains 1 (SEQ ID NO: 9), 2 (SEQ ID NO: 10), 3 (SEQ ID NO: 11), 4 (SEQ ID NO: 12) and 5 (SEQ ID NO: 13) and FH CCP domains 18 (SEQ ID NO:16), 19 (SEQ ID NO:17) and 20 (SEQ ID NO:18) (referred to herein as $FH^{R1-2\wedge 1-5\wedge 18-20}$) (SEQ ID NO: 27) (also referred herein as the "HDM-FH construct"),
E) an embodiment of a complement regulator protein of the present invention comprising FH CCP domains 1 (SEQ ID NO: 9), 2 (SEQ ID NO: 10), 3 (SEQ ID NO: 11), 4 (SEQ ID NO: 12) and 5 (SEQ ID NO: 13) and FH CCP domains 18 (SEQ ID NO: 16), 19 (SEQ ID NO: 17) and 20 (SEQ ID NO: 18) and FHR1 CCP domains 1 (SEQ ID NO: 24) and 2 (SEQ ID NO: 25) (referred to herein as $FH^{1-5\wedge 18-2\wedge R1-2}$) (SEQ ID NO: 26) (also referred to herein as the "HDM-FH construct"),
F) an embodiment of a complement regulator protein of the present invention comprising FHR1 CCP domains 1 (SEQ ID NO: 24) and 2 (SEQ ID NO: 25) and FH CCP domains 1 (SEQ ID NO: 9), 2 (SEQ ID NO: 10), 3 (SEQ ID NO: 11), 4 (SEQ ID NO:12) and 5 (SEQ ID NO: 13) and FHL-1 CCP domains 6 (SEQ ID NO: 22) and 7 (SEQ ID NO: 23) (also referred to herein as "ND-FHL1") (SEQ ID NO: 29),
G) an embodiment of a complement regulator protein of the present invention comprising FH CCP domains 1 (SEQ ID NO: 9), 2 (SEQ ID NO: 10), 3 (SEQ ID NO: 11), 4 (SEQ ID NO: 12) and 5 (SEQ ID NO: 13), FHL-1 CCP domains 6 (SEQ ID NO: 22) and 7 (SEQ ID NO: 23) and FHR1 CCP domains 1 (SEQ ID NO: 24) and 2 (SEQ ID NO: 25) (also referred to herein as "CD-FHL1") (SEQ ID NO: 28).

Referring to FIG. 1 a mini-FH protein not including a dimerization region is shown in C) (referred to as $FH^{1\text{-}5\wedge 18\text{-}20}$) which comprises a complement interaction region comprising FH CCP domains 1 to 5 linked via the amino acids Histidine, Histidine, Histidine, Histidine, Histidine, Histidine, Glycine and Threonine (denoted as $H_6GT$) to a fragment comprising FH CCP domains 18 to 20. A glycosylation site is shown on FH CCP domain 18.

The embodiment shown in D) (referred to as $FH^{R1\text{-}2\wedge 1\text{-}5\wedge 18\text{-}20}$) (SEQ ID NO: 27) comprises from N-terminal to C-terminal, a dimerization region comprising FHR1 CCP domains 1 (SEQ ID NO: 24) and 2 (SEQ ID NO: 25) (R1 and R2), this is shown linked via the amino acid residues Valine (V) and Aspartic acid (D) (denoted as VD) to a complement interaction region comprising FH CCP domains 1 to 5 (SEQ ID NOs: 9 to 13 respectively). The first FH fragment is further linked via the amino acid residues Serine, Glycine, Serine, Glycine, Glycine, Glycine, Glycine, Glycine and Threonine (denoted as $SGSG_4GT$, SEQ ID NO: 31) to a further FH fragment comprising FH CCP domains 18 to 20 (SEQ ID NOs: 16 to 18 respectively). Glycosylation sites are located on the FHR1 CCP domain 2 (SEQ ID NO: 25) (R2) and the FH CCP domain 18 (SEQ ID NO: 16).

The embodiment shown in E) (referred to as $FH^{1\text{-}5\wedge 18\text{-}20\wedge R1\text{-}2}$) (SEQ ID NO: 26) comprises from N-terminal to C-terminal a complement interaction region comprising FH CCP domains 1 to 5 (SEQ ID NOs: 9 to 13) linked via the amino acid residues $SGSG_4VDT$ (SEQ ID NO: 33) to a further FH fragment comprising FH CCP domains 18 to 20 (SEQ ID NOs: 16 to 18 respectively). The complement interaction region is further linked via the amino acid residues Glycine and Threonine (denoted GT) to a dimerization region comprising FHR1 CCP domains 1 (SEQ ID NO: 24) and 2 (SEQ ID NO: 25) (R1 and R2). Glycosylation sites are located on the FHR1 CCP domain 2 (SEQ ID NO: 25) (R2) and the FH CCP domain 18 (SEQ ID NO: 16).

The embodiment shown in F) (referred to as $FH^{R1\text{-}2\wedge 1\text{-}5\wedge L6\text{-}L7}$) (SEQ ID NO: 29) comprises from N-terminal to C-terminal, a dimerization region comprising FHR1 CCP domains 1 (SEQ ID NO: 24) and 2 (SEQ ID NO:25) (R1 and R2), this is shown linked via the amino acid residues Valine (V) and Aspartic acid (D) (denoted as VD) to a complement interaction region comprising FH CCP domains 1 to 5 (SEQ ID NOs: 9 to 13 respectively). The first FH fragment is further linked via the amino acid residues Serine, Glycine, Serine, Glycine, Glycine, Glycine, Glycine, Glycine and Threonine (denoted as $SGSG_4GT$, SEQ ID NO: 31) to an FHL fragment comprising FHL-1 CCP domains 6 (SEQ ID NO: 22) and 7 (SEQ ID NO: 23) (L6 and L7). A glycosylation site is located on the FHR1 CCP domain 2 (SEQ ID NO: 25) (R2).

The embodiment shown in G) (referred to as $FH^{1\text{-}5\wedge L6\text{-}L7\wedge R1\text{-}2}$) (SEQ ID NO: 28) comprises from N-terminal to C-terminal a complement interaction region comprising FH CCP domains 1 to 5 (SEQ ID NOs: 9 to 13) linked via the amino acid residues $SGSG_4VDT$ (SEQ ID NO: 33) to an FHL fragment comprising FHL-1 CCP domains 6 (SEQ ID NO: 22) and 7 (SEQ ID NO: 23) (L6 and L7). The complement interaction region is further linked via the amino acid residues Glycine and Threonine (denoted GT) to a dimerization region comprising FHR1 CCP domains 1 (SEQ ID NO: 24) and 2 (SEQ ID NO: 25) (R1 and R2). A glycosylation site is located on the FHR1 CCP domain 2 (R2) (SEQ ID NO: 25).

Methods

Complement Regulator Protein Construction

Two dimeric recombinant mini-FH expression vectors were generated by domain shuffling using the restriction sites planned in a pre-prepared pDR2EF1α-$FH^{1\text{-}5\wedge 18\text{-}20}$ vector. To produce recombinant FH$^{R1\text{-}2\char`\^1\text{-}5\char`\^18\text{-}20}$ (SEQ ID NO: 27), the DNA encoding the first two CCP domains of FHR-1 were amplified via Polymerase Chain Reaction (PCR) from a previously cloned and sequence verified pDR2EF1α-CFHR-1 expression vector, using PCR primers to introduce a XbaI restriction site at the 5' end and a SalI site at the 3' end (forward primer: 5'-GCTCTAGAATGTGGCTCCTGGTCAGTGTA-3' (SEQ ID NO: 34) and reverse primer: 5'-CGCGTCGACG-GAAGTGTCAGTGGACCTGC-3' (SEQ ID NO: 35, respectively). FH CCPs 1, 2, 3, 4 and 5 (SEQ ID NOs: 9 to 13 respectively) were amplified from a pDR2EF1α-P6LNK vector using a forward primer to introduce a SalI restriction site at the 5' end and a reverse primer to create site a KpnI at the 3' 5'-end (Forward primer: CGCGTCGACGAAGAT-TGCAATGAACTTCCTCC-3' (SEQ ID NO: 36) and reverse primer: 5'-GGGGTACCCC-CACCTCCTCCCGAAC-3' (SEQ ID NO: 37)). The two PCR products were then digested using restriction enzyme SalI and subsequently ligated using T4 DNA ligase.

After ligation a PCR was performed using primers to amplify the correctly ligated DNA fragment (forward primer: 5'-GCTCTAGAATGTGGCTCCTGGTC-3' (SEQ ID NO: 38) and reverse primer: 5'-GGGGTACCCC-CACCTCC-3' SEQ ID NO: 39). The amplified products were gel extracted, and then the DNA fragment with the correct size was double digested with XbaI and KpnI, and ligated with the double digested pDR2EF1α-FH$^{1\text{-}5\char`\^18\text{-}20}$ vector, consequently producing the pDR2EF1α-FH$^{R1\text{-}2\char`\^1\text{-}5\char`\^18\text{-}20}$ expression vector.

Using a similar cloning strategy and the same DNA templates, the DNA fusion for FH$^{1\text{-}5\char`\^18\text{-}20\char`\^R1\text{-}2}$ (SEQ ID NO: 26) was constructed. The cDNA of FHR-1 CCPs 1-2 was amplified by PCR using forward and reverse primers containing KpnI and NheI restriction sites (Forward primer: 5'GGGGTACCGAAGCAACATTTTGTGATTTTCCA-3' (SEQ ID NO: 40 and reverse primer: 5'-CTAGCTAGCT-TAGGAAGTGTCAGTGGACCTGC-3' (SEQ ID NO: 41)). A subsequent PCR was used to amplify the DNA of FH$^{1\text{-}5\char`\^18\text{-}20}$ utilizing 5' and 3' primers to introduce SalI and KpnI restriction sites, respectively (forward primer: 5'-CGCGTCGACACCACCTCCTCATGTGTGAAT-3' (SEQ ID NO: 42) and reverse primer: 5'-GGGGTACCTCTTTTTGCACAAGTTGGATACTC-3' (SEQ ID NO: 43)). The two amplified PCR products were digested with KpnI restriction enzyme and ligated by a ligation reaction, and then specially designed primers (forward primer: 5'-CGCGTCGACACCACCTC-3' (SEQ ID NO: 44) and reverse primer: 5'-CTAGCTAGCTTAG-GAAGTGTCAGTGGACC-3' SEQ ID NO: 45)) were used to amplify the ligated DNA fragment. Finally, the ligated DNA fragment and the pDR2EF1α-FH$^{1\text{-}5\char`\^18\text{-}20}$ vector were double digested with the restriction enzymes SalI and NheI and ligated, replacing the FH CCPs 18 to 20 DNA in the original vector with FH CCPS 18 to 20 and FHR1 CCPs 1 and 2 (18^20^R1-2).

All newly generated constructs had the sequence verified by DNA sequencing.

Expression and Purification of Complement Regulator Proteins

Newly generated DNA constructs were transfected into Chinese hamster ovary (CHO) cells using jetPEI (Polyplus; VWR, Leicestershire, UK) following the manufacture's protocols. CHO cells were cultured in Dulbecco's Modified Eagle's medium (DMEM) F-12 supplemented with 10% foetal bovine serum (FBS) (Biotech) and penicillin-streptomycin solution (1 in 100 dilution, Sigma Aldrich UK). Stable transfections were selected in the presence of 0.6 mg/ml Hygromycin B. A single clone of a stable expresser was picked for protein production, which was carried out in the absence of Hygromycin B for 10 days using the roller bottle method as described in U.S. Pat. No. 4,962,033 A which is incorporated herein by reference. Complement regulator proteins were purified from the over grown media using a 5 ml His-trap normal human serum (NHS) activated HP column (GE Healthcare, Buckinghamshire UK) coupled with the anti-Factor H OX-24 monoclonal antibody. Fractions were eluted using 0.1M Glycine pH7.2. Collected fractions were run on reducing and non-reducing sodium dodecyl sulphate polyacrylamide gels. Extinction coefficients and the theoretical molecular weights of monomeric FH$^{R1\text{-}2\char`\^1\text{-}5\char`\^18\text{-}20}$ (ε: 130160, MW: 72855.9 Da) and FH$^{1\text{-}5\char`\^18\text{-}20\char`\^R1\text{-}2}$ (ε: 130285, MW: 73704.9 Da) were calculated using ExPASy Protparam program (Swiss Institute of Bioinformatics, Lausanne, Switzerland). Concentration of proteins was determined by Nanodrop (Thermo Fisher, Waltham MA USA) as per the manufacturer's instructions.

Evaluation of Binding Properties by Enzyme Linked Immunosorbent Assay

The capability of FH, FH$^{1\text{-}5\char`\^18\text{-}20}$, FH$^{1\text{-}5}$ (FH CCPs 1 to 5), FH$^{R1\text{-}2\char`\^1\text{-}5\char`\^18\text{-}20}$ (SEQ ID NO: 27) and FH$^{1\text{-}5\char`\^18\text{-}20\char`\^R1\text{-}2}$ (SEQ ID NO: 26) to bind C3b, C3d and heparin was determined by Enzyme linked immunosorbent assay (ELISA). To measure the interaction with C3 activation products, C3b (0.5 μg/well) and C3d (0.5 μg/well) in carbonate buffer were coated onto respective Maxisorb plates. Plates were then incubated at 4° C. overnight, the plates were blocked with PBST (Phosphate Buffered Saline with 0.01% Tween-20) supplemented with 5% skimmed milk powder, after which a 100 μL dilution series of either FH, FH$^{1\text{-}5\char`\^18\text{-}20}$, FH$^{R1\text{-}2\char`\^1\text{-}5\char`\^18\text{-}20}$ (SEQ ID NO: 27) or FH$^{1\text{-}5\char`\^18\text{-}20\char`\^R1\text{-}2}$ (SEQ ID NO: 26) was applied in 1% milk PBST. The bound FH reagents (FH, FH$^{1\text{-}5\char`\^18\text{-}20}$, FH$^{R1\text{-}2\char`\^1\text{-}5\char`\^18\text{-}20}$ (SEQ ID NO: 27) or FH$^{1\text{-}5\char`\^18\text{-}20\char`\^R1\text{-}2}$ (SEQ ID NO: 26)) were detected by addition of a polyclonal goat anti-human FH antibody (Complement technologies, Tyler TX USA) diluted 1 in 10,000, followed by addition of a donkey anti-Sheep antibody conjugated to Horse radish peroxidase (HRP) (Stratech Scientific Ltd, Newmarket UK) diluted 1 in 20,000 in 5% milk PBST. Alternatively, ELISA plates were coated with 0.1 μg/well of heparin sulphate dissolved in PBS and the detection of bound FH reagents was performed as described above.

Fluid Phase Factor I (FI) Co-Factor Activity Assay

The complement regulatory activity of FH reagents was measured in a fluid phase FI co-factor activity assay. 0.7 μM of C3b and 20 nM of FI were briefly mixed with either FH, FH$^{1\text{-}5\char`\^18\text{-}20}$ FH$^{R1\text{-}2\char`\^1\text{-}5\char`\^18\text{-}20}$ (SEQ ID NO: 27) or FH$^{1\text{-}5\char`\^18\text{-}20\char`\^R1\text{-}2}$ (SEQ ID NO: 26) to a total volume of 16 UL in PBS buffer at 37° C. for 30 min. The proteolytic breakdown of C3b was accessed by a 10% SDS-PAGE gel followed by Coomassie staining.

Protection of Non-Self Surface Assay

Guinea pig erythrocytes (GRBCs) were washed with GV buffer (5 mM veronal, 145 mM NaCl, 0.1% (w/V) gelatin, pH7.4) and the cell concentration was adjusted to produce an $A_{405}$ reading of 0.5 when 100 μL of completely lysed cell supernatant was measured in a 96 well plate. The predetermined amount of GRBCs were then suspended in 25% (v/v) of NHS and were incubated with either FH, FH$^{1\text{-}5\char`\^18\text{-}20}$, FH$^{R1\text{-}2\char`\^1\text{-}5\char`\^18\text{-}20}$ (SEQ ID NO: 27) or FH$^{1\text{-}5\char`\^18\text{-}20\char`\^R1\text{-}2}$ (SEQ ID NO: 26) at a range of concentrations from 1 to 100 nM at 37° C. for 30 min. Complement activation of the GRBCs was restricted to the alternative pathway by adding $MgCl_2$ and EGTA to a final concentration of 7 mM and 10 mM. The amount of lysis was determined by measuring the absorbance at 405 nm ($A_{405}$), and was normalised using a $A_{405}$ measurement for when no FH reagents were present.

Determination of Decay Acceleration Properties and FI Co-Factor Activity of FH Reagents on Sheep Erythrocyte Surfaces Decay acceleration property and FI co-factor activity of FH reagents on sheep erythrocyte surfaces was assessed using a method described previously in (Tortajada 2009, Hum Mol. Genet September 15, 18 (18): 3452-61). To assess decay acceleration properties, antibody sensitized sheep erythrocytes were washed and suspended to a concentration of 2% (v/v) in Veronal Buffered Saline (VBS) buffer (5 mM veronal, 145 mM NaCl, pH 7.4) supplemented with 0.3 mM $CaCl_2$). C3b deposition on sheep erythrocyte surface was achieved by the addition of ΔFBΔFH-NHS (normal human serum subsequently depleted of FB and FH) to a final concentration of 8% (v/v) in the presence of 1 μM of Eculizumab. To form alternative pathway (AP) C3 convertase, 2% (v/v) C3b coated sheep erythrocytes were mixed with an identical volume of AP VBS buffer containing 42 μg/ml Factor B (FB) and 0.4 μg/ml Factor D (FD) and incubated at 37° C. for 15 min. A stock EDTA solution was then added at a final concentration of 10 mM to stop further C3 convertase assembly. The cells were washed, suspended to a concentration of 2% (v/v) in TPB (terminal pathway buffer, PBS supplemented with 20 mM EDTA). Subsequently aliquots (50 μL) of cells were incubated with 50 μL of either FH, $FH^{1-5^\wedge 18-20}$, $FH^{R1-2^\wedge 1-5^\wedge 18-20}$ (SEQ ID NO: 27) or $FH^{1-5^\wedge 18-20^\wedge R1-2}$ (SEQ ID NO: 26) in TPB at 25° C. for 10 min. Lysis was initiated by adding 50 ul of 4% ΔFBΔFH-NHS prepared in TPB at 37° C. for 20 min. To measure haemolysis, cells were pelleted by centrifugation (1500 g for 10 min), and the $A_{405}$ of the supernatant was measured.

To measure the FI cofactor activity, 50 μL of 2% (v/v) C3b coated sheep erythrocytes were mixed with an equal volume of serial diluted FH reagents each dilution containing 2.5 μg/ml FI. After 25 min incubation at 25° C., the washed cells were re-suspended with 100 μL of AP VBS buffer containing 35 μg/ml FB and 0.2 μg/ml FD and incubated at 37° C. for an additional 15 min. Finally, the functional C3 convertase was quantified using cell lysis level by adding 50 μL of 4% ΔFBΔFH-NHS prepared in TPB at 37° C. for 20 min. To express the cell lysis percentage, control samples included 100% lysed cells (cells in water) and 0% lysed cells (cells in buffer only). The percentage of inhibition from lysis was calculated as: $100-100\times((A_{405}$ test sample$-A_{405}$ 0% control$)/(A_{405}$ 100%$-A_{405}$ 0% control$))$.

Antibody Mediated Loss of FH Function Assay

The antibody mediated FH loss-of-function assay was carried out as previously described by Nichols 2015 (Kidney International, Dec. 9, 2015, Vol. 88, Issue 6, 1314-1322) with minor adjustments. Briefly prior to the experiment, Sheep erythrocytes were washed with GV buffer (5 mM veronal, 145 mM NaCl, 0.1% (w/v) gelatin) and the cell concentration was adjusted to produce an $A_{405}$ reading of 1.0 when the cells were completely lysed in water. To set up the reaction, sheep erythrocytes were suspended in 100 μL of 20% NHS (normal human serum) supplemented with the monoclonal anti-factor H antibody OX-24 (80 μg/ml), either FH, $FH^{1-5^\wedge 18-20}$ $FH^{R1-2^\wedge 1-5^\wedge 18-20}$ (SEQ ID NO: 27) or $FH^{1-5^\wedge 18-20^\wedge R1-2}$ (SEQ ID NO: 26) (at varying concentrations), $Mg^+$ (7 mM) and EGTA (10 mM) in GVB buffer. Haemolysis was detected after incubating the reaction mixture at 37° C. for 30 min, followed by the addition of 150 μL of quenching buffer (GVB supplemented with 10 mM EDTA). The cells were pelleted by centrifugation at 1500 g for 10 min, and $A_{405}$ of 100 μL of supernatant measured.

aHUS Model Haemolysis Assay aHUS model haemolysis assay was performed in a nearly identical protocol as described above for antibody mediated loss of FH function, however the OX-24 supplemented NHS was replaced by the addition of FH depleted serum (Comptech, Texas, USA) and recombinant FH mutant S1191L-V1197A-CFH (a non-functioning FH mutant) to the final concentrations of 20% and 50 nM.

Administration of Plasma Purified FH, $FH^{1-5^\wedge 18-20}$, $FH^{R1-2^\wedge 1-5^\wedge 18-20}$ (SEQ ID NO: 27) and $FH^{1-5^\wedge 18-20^\wedge R1-2}$ (SEQ ID NO: 26) to Cfh$^{-/-}$ Mice Mice were housed at the comparative biology centre, Newcastle University. All reagents were buffer exchanged into PBS and removed from lipopolysaccharide using a method described previously in Aida Y, Pabst M J. Removal of endotoxin from protein solutions by phase separation using Triton X-114. J Immunol Methods 1990; 132:191-195 which is incorporated herein by reference. 500 μl of plasma purified full-length FH (3 nmoles/400 μg), $FH^{1-5^\wedge 18-20}$ (6 nmoles/360 μg), $FH^{R1-2^\wedge 1-5^\wedge 18-20}$ (SEQ ID NO: 27) (3 nmoles of dimer/440 μg), $FH^{1-5^\wedge 18-20^\wedge R1-2}$ (SEQ ID NO: 26) (3 nmoles of dimer/442 μg) or PBS were administered intraperitoneally to Cfh$^{-/-}$ mice. 7 days before and at various time points during the experiment, blood samples were collected into EDTA via tail venesection and intermediately placed on ice, plasma was collected after centrifugation at 1000 g for 5 mins and stored at −80° C. At the end point of the experiment, mice were euthanized and the kidneys were collected and snap frozen in liquid nitrogen pre-chilled isopentane, before being stored at −80° C.

Measurement of Mouse Plasma C3 or FH Reagents by ELISA

Intact C3 and FH reagent levels in mouse serum samples were determined by ELISA. To determine mouse C3 levels, 50 μL of diluted sample (1 in 800 in Dulbecco's PBS) was used for analysis. 20 ng/well of monoclonal antibody 11H9 was immobilized on a NUNC Maxisorp flat-bottom ELISA plate in order to bind and capture mouse C3. The mouse C3 was then detected by an HRP-conjugated goat polyclonal anti-mouse C3 antibody (1 in 25000, MP Biomedicals, Santa Ana, CA catalog no. 0855557). The C3 concentrations were interpreted based on a standard curve generated using purified mouse C3 of known concentration. Similarly, to measure FH reagents' concentration, 100 μL of diluted serum sample was added to a ELISA plate coated with 0.5 μg/well of OX-24 monoclonal antibody, then 100 μl of polyclonal goat anti-human FH antibody (1 in 20000) was applied, followed by the detection of a donkey anti-Sheep HRP (1 in 20000). For each FH reagent, a standard curve was generated correspondingly using the purified protein at known concentration.

Immunostaining of Mouse Renal Sections for Murine C3

Seven micrometre cryosections from the kidneys of test mice were mounted on a SHANDON Colorfrost Plus microscope slide (Thermo Scientific), before fixing in 100% ice cold acetone before being stored at −80° C. To visualize glomerular C3 deposition, the thawed tissue sections were blocked for 1 hour with 60 μL of 20% (v/v) goat serum in PBS, then detected with application of FITC-conjugated goat polyclonal anti-mouse C3 antibody (MP Biomedicals, Santa Ana, CA catalog no. 0855500) for 30 minutes diluted 1 in 200 in PBS. After repetitive washes with PBS, the tissue sections were stained with DAPI (4',6-diamidino-2-phenylindole; Vector Laboratories; Burlingame) and covered with glass coverslips. Fluorescent images were taken at ×40 magnification using a Zeiss Axio imager II.

Results

Evaluation of Binding Properties of FH Reagents

The abilities of either FH, $FH^{1-5}$, $FH^{1-5\wedge 18-20}$, $FH^{R1-2\wedge 1-5\wedge 18-20}$ (SEQ ID NO: 27) or $FH^{1-5\wedge 18-20\wedge R1-2}$ (SEQ ID NO: 26) to bind to the plate immobilized plasma derived C3b (A), recombinant C3d (B) and heparin sulphate (C) are shown in FIG. 2. It can be seen in (A) and (B) that $FH^{R1-2\wedge 1-5\wedge 18-20}$ (SEQ ID NO: 27) and $FH^{1-5\wedge 18-20\wedge R1-2}$ (SEQ ID NO: 26) have higher $A_{450}$ values at lower concentrations in comparison to other FH reagents. This indicates that $FH^{R1-2\wedge 1-5\wedge 18-20}$ (SEQ ID NO: 27) and $FH^{1-5\wedge 18-20\wedge R1-2}$ (SEQ ID NO: 26) have improved C3b and C3d (complement activation/inactivation products) binding properties and/or avidity in comparison to FH, $FH^{1-5}$ and $FH^{1-5\wedge 18-20}$. In (C) it can be seen that $FH^{R1-2\wedge 1-5\wedge 18-20}$ (SEQ ID NO: 27) has a higher $A_{450}$ value for all concentrations in comparison to all other FH reagents indicating that $FH^{R1-2\wedge 1-5\wedge 18-20}$ (SEQ ID NO: 27) has improved heparin binding properties. $FH^{1-5\wedge 18-20\wedge R1-2}$ (SEQ ID NO: 26) has an $A_{450}$ value that is similar to that of FH for all concentrations indicating that $FH^{1-5\wedge 18-20\wedge R1-2}$ (SEQ ID NO: 26) maintains similar heparin binding properties as FH.

Evaluation of Fluid Phase Cofactor Activity

Disappearance of C3α'-110 kDa band and the appearances of C3α'-68, -46 and -43 kDa bands are indicative of the C3b proteolytic inactivation. It can be seen from FIG. 3 that in fluid phase $FH^{1-5\wedge 18-20\wedge R1-2}$ (SEQ ID NO: 26) (B) shows a higher functional concentration range in comparison to FH (A) and $FH^{1-5\wedge 18-20}$ (D) by the decrease in intensity of the C3α' band (complete degradation of C3b) at a lower concentration of complement regulator protein (100 nM for FH, 200 nM for $FH^{1-5\wedge 18-20}$ and 50 nM for $FH^{1-5\wedge 18-20\wedge R1-2}$) (SEQ ID NO: 26) indicating that $FH^{1-5\wedge 18-20\wedge R1-2}$ (SEQ ID NO: 26) has improved cofactor activity in comparison to FH and $FH^{1-5\wedge 18-20}$. A concentration of $FH^{R1-2\wedge 1-5\wedge 18-20}$ (SEQ ID NO: 27) similar to that of FH was required to completely degrade C3b indicating that $FH^{1-5\wedge 18-20\wedge R1-2}$ (SEQ ID NO: 27) has a similar FI cofactor activity as FH.

Protection of a "Non-Self" Surface

It can be seen from Figure that for $FH^{1-5\wedge 18-20}$, $FH^{R1-2\wedge 1-5\wedge 18-20}$ (SEQ ID NO: 27) and $FH^{1-5\wedge 18-20\wedge R1-2}$ (SEQ ID NO: 26) the percentage of cells lysed decrease at a lower concentration of the afore-mentioned FH reagents in comparison to FH. This indicates that $FH^{1-5\wedge 18-20}$, $FH^{R1-2\wedge 1-5\wedge 18-20}$ (SEQ ID NO: 27) and $FH^{1-5\wedge 18-20\wedge R1-2}$ (SEQ ID NO: 26) all have improved "non-self" protection from lysis properties in comparison to FH.

Cell Membrane Complement Regulatory Activity of FH Reagents

It can be seen from FIG. 5A that both $FH^{R1-2\wedge 1-5\wedge 18-20}$ (SEQ ID NO: 27) and $FH^{1-5\wedge 18-20\wedge R1-2}$ (SEQ ID NO: 26) provide a higher percentage of protection from lysis at lower concentrations, for all tested concentrations in comparison to FH and $FH^{1-5\wedge 18-20}$. This indicates that $FH^{R1-2\wedge 1-5\wedge 18-20}$ (SEQ ID NO: 27) and $FH^{1-5\wedge 18-20\wedge R1-2}$ (SEQ ID NO: 26) have improved decay acceleration of cell surface C3b activity in comparison to both FH and $FH^{1-5\wedge 18-20}$. It can also be seen from FIG. 5B that both $FH^{R1-2\wedge 1-5\wedge 18-20}$ (SEQ ID NO: 27) and $FH^{1-5\wedge 18-20\wedge R1-2}$ (SEQ ID NO: 26) also have improved cell surface FI co-factor activity in comparison to both FH and $FH^{1-5\wedge 18-20}$.

Antibody Mediated Loss of FH Function

It can be seen from FIG. 6A that plasma purified FH, $FH^{1-5\wedge 18-20}$, $FH^{R1-2\wedge 1-5\wedge 18-20}$ (SEQ ID NO: 27) and $FH^{1-5\wedge 18-20\wedge R1-2}$ (SEQ ID NO: 26) protect sheep red blood cells (SRBC) from lysis in human sera with deregulated complement AP. Referring to (A) it can be seen that the increasing concentrations of the relevant FH reagent, as indicated on the graph, protects SRBC from AP mediated lysis in OX24 containing Normal human serum (NHS) (an autoantibody model serum). $FH^{R1-2\wedge 1-5\wedge 18-20}$ (SEQ ID NO: 27) can be seen to have higher protective properties at lower concentrations indicating that it has improved protective properties in comparison to FH and $FH^{1-5\wedge 18-20}$ aHUS Model Haemolysis Assay It can be seen from FIG. 6B that the addition of increasing concentrations of FH reagents prevented SRBC lysis in FH depleted serum supplemented with recombinant human FH S1191A/V1197L FH (an aHUS model serum). It can be seen that both $FH^{R1-2\wedge 1-5\wedge 18-20}$ (SEQ ID NO: 27) and $FH^{1-5\wedge 18-20\wedge R1-2}$ (SEQ ID NO: 26) have higher protection against lysis at lower concentrations in comparison to FH indicating that $FH^{R1-2\wedge 1-5\wedge 18-20}$ (SEQ ID NO: 27) and $FH^{1-5\wedge 18-20\wedge R1-2}$ (SEQ ID NO: 26) have improved haemolytic lysis protective properties in comparison to FH.

Therapeutic Effectiveness of FH Reagents in Cfh$^{-/-}$ Mouse Model

It can be seen from FIG. 7A that plasma C3 levels increased steadily up to 24 hours after the injection of 3 nmoles of plasma purified FH or $FH^{1-5\wedge 18-20\wedge R1-2}$ dimer (SEQ ID NO: 26), and elevated C3 levels can still be observed at a 48-hour time point compared with the PBS treatment. Injection of 3 nmoles of $FH^{R1-2\wedge 1-5\wedge 18-20}$ dimer (SEQ ID NO: 27) partially restored C3 level up to 6 hours followed by a slow decline back to the background level over the next 42 hours. The injection of 6 nmoles of $FH^{1-5\wedge 18-20}$ only produced a short-lived increase in C3 level 2 hours after injection. This indicates that $FH^{1-5\wedge 18-20\wedge R1-2}$ dimer (SEQ ID NO: 26) and $FH^{R1-2\wedge 1-5\wedge 18-20}$ dimer (SEQ ID NO: 27) both have complement regulation activity for a period of time comparable to FH and greater than $FH^{1-5\wedge 18-20}$. It can be seen from FIG. 7B that FH and its derivatives were detected at comparable levels 2 hours after a single intraperitoneal injection. $FH^{1-5\wedge 18-20}$ falls sharply within 6 hours and becomes undetectable at 24 and 48 hours. FH, $FH^{R1-2\wedge 1-5\wedge 18-20}$ dimer (SEQ ID NO: 27) and $FH^{1-5\wedge 18-20\wedge R1-2}$ dimer (SEQ ID NO: 26) persisted at a similar level until 6 hour, FH then demonstrated a slow serum clearance rate but remained detectable at 48 hour, increased serum clearance rates were observed for $FH^{R1-2\wedge 1-5\wedge 18-20}$ dimer (SEQ ID NO: 27) and $FH^{1-5\wedge 18-20\wedge R1-2}$ dimer (SEQ ID NO: 26) in comparison to FH but both where still detectable at 24 hours. FIGS. 7A and 7B indicate that $FH^{R1-2\wedge 1-5\wedge 18-20}$ (SEQ ID NO: 27) and $FH^{1-5\wedge 18-20\wedge R1-2}$ dimers (SEQ ID NO: 26) have improved serum timescales for complement regulation and serum half-life in comparison to $FH^{1-5\wedge 18-20}$ Immunostaining of Mouse Renal Sections for Murine C3

It can be seen from FIG. 8 from the florescent intensity of C3 in the images that compared with PBS, FH, $FH^{1-5\wedge 18-20}$ and $FH^{R1-2\wedge 1-5\wedge 18-20}$ (SEQ ID NO: 27) caused significant reduction in C3 intensity at 48 hours. It can also be seen that $FH^{R1-2\wedge 1-5\wedge 18-20}$ (SEQ ID NO: 27) gives the lowest intensity of C3 after 48 hours indicating that $FH^{R1-2\wedge 1-5\wedge 18-20}$ (SEQ ID NO: 27) is the most effective of the three FH reagents at reducing glomerular C3.

Conclusion

It can be seen that both $FH^{R1-2\wedge 1-5\wedge 18-20}$ (SEQ ID NO: 27) and $FH^{1-5\wedge 18-20\wedge R1-2}$ (SEQ ID NO: 26) and their dimeric forms have overall improved complement regulation activity and properties in comparison to FH and a mini-FH ($FH^{1-5\wedge18-20}$) indicating that the complement regulator proteins described herein may exhibit improved complement regulation activity and serum half-life.

Example 2

Evaluation of HDM-FDH Constructs on C3 Deposition of Kidney Proximal Tubule Cells In Vitro Kidney proximal tubule cells (KTPC) from fresh normal human kidney (less than 12 hours ex vivo) were collected and grown on permeable filter HTS transwell membranes to generate fully functional differentiated monolayers. Briefly Normal human kidney tissue, which became available from nephrectomies not found propriate for renal allograft, was collected in sterile RPMI 1640 media supplemented with 5% fetal bovine serum and 2% penicillin/streptomycin at 4° C. Under sterile conditions, macroscopically normal tissue was de-capsulated, and the cortex and outer strip of the outer medulla (if present) were dissected, cut into pieces of approximately 1 mm$^3$, and digested in collagenase D solution (Roche, Ottweiler, Germany) to a final concentration of 0.67 mg/ml in RPMI1640 media. The suspension was shaken vigorously for 2 h at 37° C. and then passed through a 120-μm sieve. The resulting cell suspension was loaded on top of a discontinuous Percoll (Pharmacia, Uppsala, Sweden) gradient made up in RPMI 1640 media with densities of 1.04 and 1.07 g/ml. After centrifugation (3000 rpm, 25 min, 4° C.) in a 4×200-ml swing-out rotor, cells from the intersection were carefully aspirated, washed, and brought into culture as a mixed population of PTC and DTC seeded directly onto 6.5-mm 0.4-μm pore size permeable (polycarbonate) filter supports (Costar, New York, NY) at a density of 5×10$^4$ cells per filter. To obtain pure cultures of PTC, a subconfluent mixed culture was trypsinized and purified by flow cytometric sorting. Cells were incubated for 30 min at 4° C. with an anti-human leucine aminopeptidase (LAP) monoclonal antibody to identify PTC. Subsequently, phycoerythrin-labeled rabbit F(ab')$_2$ anti-mouse (Dako Denmark A/S, Glostrup, Denmark) secondary antibody was added to the cell suspension. Labeled cells were sorted using a FACSAria flow cytometer (BD Biosciences, San Diego, CA).

Pure cultures of PTC were grown until confluence (8-12 days) on semipermeable filter supports in α-MEM (Invitrogen, Carlsbad, CA) modified according to Gibson d'Ambrosio et al. (1987) supplemented with 10% fetal calf serum. Cell cultures grown on permeable filter supports were allowed to polarize and had a separated apical and basolateral compartment. Cell culture medium was replaced only once before performing the experiments (7-9 days after culturing of the cells).

$FH^{R1-2\wedge1-5\wedge18-20}$ (SEQ ID NO: 27) and $FH^{1-5\wedge18-20\wedge R1-2}$ (SEQ ID NO: 26) recombinant proteins (i.e., the HDM-FDH constructs shown in FIGS. 1D and E) were expressed and purified as described in Example 1. Normal human serum (NHS) or Heat inactivated normal human serum (HI NHS, control) were diluted 1:4 in Krebs solution. CD1 ($FH^{1-5\wedge18-20\wedge R1-2}$) (SEQ ID NO: 26) and ND2 ($FH^{R1-2\wedge1-5\wedge18-20}$) (SEQ ID NO: 27) were added to NHS at concentrations of 10 nM, 3.3 nM, 1 nM, 0.33 nM. Krebs alone was used as a negative control. Experiments were carried out on a 37° C. heating plate with 6 well plates left for 30 minutes to reacclimatise. Media on the top and bottom of transwells was removed and discarded Pre-warmed solutions (as above) were added to transwells (200 ul/well) in duplicate and incubated at 37° C. for 1 hr. Supernatant was carefully aspirated into a clean eppendorf and frozen at -80° C. Transwells were removed and rinsed in a pot of clean Krebs solution at 37° C. Using a scalpel blade the bottom membrane of the transwell was removed and immediately added to an Eppendorf containing 100 ul 1× Laemmli buffer. Eppendorfs were vortexed for 3×30 s, with 1 minute rest between each 30 sec vortex. Laemmli buffer was removed, transferred to a fresh tube, and stored at -20° C. until required for application (20 μl) to a 20% SDS-PAGE gel and western blotting. It can be seen from FIG. 23B that C3b is bound or deposited on KTPC cells as detected using a goat anti-human C3 polyclonal antibody (Comptech). C3 deposition is confirmed by the presence of C3 beta chain (70 kDa band) but very little C3 deposition and breakdown in heat inactivated (HI) serum or media only, that 10 nM of the proteins act to reduce C3 deposition on KTPC cells in vitro by between 80-90%. It can be seen by densitometry analysis of the western blots, FIG. 23C, that serum plus $FH^{R1-2\wedge1-5\wedge18-20}$ (SEQ ID NO: 27) and $FH^{1-5\wedge18-20\wedge R1-2}$ (SEQ ID NO: 26) leads to a significant reduction in C3b/iC3b deposition as compared to control serum alone. The analysis of endpoint C3a generation in the collected supernatant above the KTPC using the Quidel MicroVue human C3a ELISA kit (according to the manufacturer's instructions) confirms a ~80% reduction in complement activation on or immediately adjacent to the cell surface (FIG. 23D).

In summary, the experiments reveal that the HDM-FH constructs reduce C3 deposition on KTPC cells. Thus, the $FH^{R1-2\wedge1-5\wedge18-20}$ (SEQ ID NO: 27) and $FH^{1-5\wedge18-20\wedge R1-2}$ (SEQ ID NO: 26) recombinant proteins act to regulate complement function in kidney cells.

Evaluation of HDM-FDH Constructs in the EVNP System

An Ex-vivo Normothermic Perfusion (EVNP) system was developed (as described by Hosgood et al *Transplantation* 92:735-738, 2011; Hosgood et al *Am J Transplant* 16:3062, 2016; and Hosgood et al *Br J Surg* 102:1433-1440, 2015). Briefly, a pair of kidneys offered for research, after being deemed unsuitable for transplantation by the national organ allocation scheme, were used in this experiment. Discarded kidneys with an absolute contraindication to transplantation, such as malignancy, were excluded. Consent for the use of the organs for research was obtained from the donor family by the specialist nurses in organ donation before organ retrieval. Ethical approval was granted for the study by the National Research Ethics Committee in the UK. All kidneys were retrieved by one of the National Organ Retrieval teams. After transport to the study centre, kidneys were prepared for EVNP. In brief, the ex vivo kidney perfusion circuit was designed using paediatric cardiopulmonary bypass technology (Medtronic, Watford, UK) and consisted of a centrifugal blood pump (Bio-pump 560), a heat exchanger (Chalice Medical, Worksop, UK), a venous reservoir (Medtronic), ¼-inch PVC tubing and an Affinity membrane oxygenator (Medtronic). The hardware included a speed controller, a TX50P flow transducer and a temperature probe (Cole-Parmer, London, UK). Two Alaris infusion pumps (Carefusion, Basingstoke, UK) were also incorporated into the system. The circuit was primed with a perfusate solution (Ringer's solution; Baxter Healthcare, Borehamwood, UK) and supplements were added to provide a physiological environment. One unit of O-positive blood group packed red cells from the local blood bank was added to the priming solution. Kidneys were perfused at a set mean arterial pressure (70-75 mmHg). The plasma-free red cell-based perfusate was circulated from the venous reservoir through the centrifugal pump into the membrane oxygenator, where it was oxygenated and also warmed to 36° C. It then flowed through the arterial limb of the circuit to the renal artery.

Venous return from the renal vein was fed back into the reservoir. Renal blood flow was monitored continuously during EVNP and the total urine output was collected and recorded.

A 1:1 mixture of the HDM-FH constructs were injected (5 µg/ml) into the renal artery of the isolated kidney at 20 mins (indicated by arrow of FIG. 24A) and perfusate sampled. Analyse of the perfusate by HDM-FH specific sandwich ELISA (capture with anti-FHR1 (2 µg/ml) and detected with biotin-OX24 (1/1000) with SA-HRPO (1/000); standard wash and block solutions were used) reveals that $FH^{R1-2\wedge1-5\wedge18-20}$ (SEQ ID NO: 27) and $FH^{1-5\wedge18-20\wedge R1-2}$ (SEQ ID NO: 26) recombinant proteins are rapidly absorbed onto the kidney vascular and not excreted in urine.

Analysis of kidney biopsy section (carried out as per the method outline above for immunostaining of mouse Kidney with the exception that FIGS. 24B and C show that the HDM-FH proteins are present in the glomerulus of the kidney, and not present in control untreated kidney (FIGS. 24D and E). The urine produced during the experiment was diluted 1:1 in PBS and applied to an OX24 affinity column, concentrating both endogenous FH and the HDM-FH drugs. It can be seen from FIG. 24F, SDS-PAGE and subsequent densitometry analysis, that approximately 1% of the drug is lost over 6 hrs into urine, and endogenous FH is 10-fold more abundant in the urine. Western analysis of tissue lysates from the cortex (50 µg tissue in 200 µl 1% NP40/PBS including protease inhibitor cocktail, complete minitab from Roche) and artery (flushed with Laemmli buffer) of a HDM-FH treated (T) or control (C) untreated kidney shows the presence of significant quantities of HDM-FH, at least double endogenous FH by densitometry analysis (see FIG. 24G).

In summary, the experiments reveal that the HDM-FH constructs can be successfully applied to the EVNP system. The coating of cells in the vasculature of organs such as kidneys by HDM-FH may therefore act to prevent complement activation and rejection of organs following allografts.

Example 3

Methods
Construction and Purification of ND-FHL1 ($FH^{R1-2\wedge1-5\wedge L6-L7}$) (SEQ ID NO: 29) and CD-FHL1 ($FH^{1-5\wedge L6-L7\wedge R1-2}$) (SEQ ID NO: 28)

The N-/C-Termini Recombinant Homodimer Factor H like 1 proteins (ND FHL-1 and CD-FHL1, as shown in FIGS. 1F and G) were generated using a similar strategy to the constructs described in Example 1. In particular, CCP6 and CCP7 (also referred to herein as L6 and L7 or SCR 6 and 7) were amplified by PCR using the primers below:

| Name of primer | Support + restriction site + primer |
|---|---|
| N67F (N-terminal 6-7, Forward primer) | 5'- GG GGTACC ACC TTG AAA CCT TGT GAT TAT CC 3' (SEQ ID NO: 53) |
| N67R (N-terminal 6-7, Reverse primer) | 5'- CTA GCTAGC TCA GAG GGT AAA GCT GAC ACG 3' (SEQ ID NO: 54) |
| C67F (C-terminal 6-7, Forward primer) | 5'- ACGC GTCGAC ACC TTG AAA CCT TGT GAT TAT CC 3' (SEQ ID NO: 55) |
| C67R (C-terminal 6-7, Reverse primer) | 5'- GG GGTACC GAGGGT AAAGCTGACACGGAT 3' (SEQ ID NO: 56) |

The restriction sites used for the forward and reverse N terminal primers were KpnI and NheI respectively. The restriction sites used for the forward and reverse C terminal primers were SalI and KpnI respectively. An pDR2EF1α plasmid containing FHR-1 (SCR1 and SCR2), FH (SCR1-5) and FH (SCR18-20) was digested with restriction enzymes KpnI/NheI (for N-termini) and SalI/KpnI (for C-termini) to release the SCR18-20 fragment and the PCR amplified and purified SCR6-7 was inserted to generate ND/CD-FHL1. Plasmids and PCR products were restriction digested, and digested N/C-terminal PCR products and N/C parental plasmids ligated and transformed into *E. coli*.

ND-FHL1 (SEQ ID NO: 29) and CD-FHL1 (SEQ ID NO: 28) constructs had sequence verified by DNA sequencing, as described above. ND-FHL1 (SEQ ID NO: 29) and CD-FHL1 (SEQ ID NO: 28) were also expressed and purified, as described above.

Results
Evaluation of Binding Properties by Enzyme Linked Immunosorbent Assay

ND-FHL1 (SEQ ID NO: 29) and CD-FHL1 (SEQ ID NO: 28) binding to C3b (5 µg/ml) or recombinant human CRP (2 µg/ml; Abcam, UK) was evaluated by ELISA, as described above. The results shown in FIG. 25 illustrate that ND-FHL1 (SEQ ID NO: 29) and CD-FHL1 (SEQ ID NO: 28) bind to surface bound C3b, with the ND-FHL1 (SEQ ID NO: 29) construct binding markedly better than full length purified FH.

The results shown in FIG. 26 illustrate that ND-FHL1 (SEQ ID NO: 29) and CD-FHL1 (SEQ ID NO: 28) bind to surface bound CRP. FIG. 26 also reveals that ND-FHL1 (SEQ ID NO: 29) binds significantly better to CRP compared to the other regulators.

Increased avidity demonstrates specificity in binding to glycosaminoglycans (GAGs) found in the retina. In age-related macular degeneration (AMD), there's an increase of CRP at the surface of retinal epithelial cell (RPE) GAGs. The complement regulatory proteins described herein may therefore provide a therapeutic for AMD that will specifically bind to RPE GAGs and inactivate C3b.

Throughout the description and claims of this specification, the words "comprise" and "contain" and variations of them mean "including but not limited to" and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of the features and/or steps are mutually exclusive. The invention is not restricted to any details of any foregoing embodiments. The invention extends to any novel one, or novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A recombinant complement regulator protein, comprising;

a) at least one complement interaction region operable to regulate complement through the alternative complement pathway and bind the complement regulator protein to at least one target, the complement interaction region comprising at least one Factor H (FH) fragment, wherein the at least one FH fragment comprises at least one FH complement control protein domain (CCP) and at least one further FH CCP domain operable to bind the complement regulator protein to the at least one target and/or at least one further target; and b) at least one Factor H Related Protein (FHR) dimerization region operable to dimerize the complement regulator protein, wherein the dimerization region comprises two N-terminal CCP domains 1 and 2 of FHR1, FHR2 and/or FHR5, wherein the two FHR CCP domains are selected from a complement Factor H Related Protein 1 (FHR1) CCP1 domain, a FHR1 CCP2 domain, a complement Factor H Related Protein 2 (FHR2) CCP1 domain, a FHR2 CCP2 domain, a complement Factor H Related Protein 5 (FHR5) CCP1 domain, a FHR5 CCP2 domain and combinations thereof.

2. The complement regulator protein as claimed in claim 1, wherein the at least one FH fragment comprises one or more of a FH CCP1 domain (SEQ ID NO: 9), a FH CCP2 domain (SEQ ID NO: 10), a FH CCP3 domain (SEQ ID NO: 11), a FH CCP4 domain (SEQ ID NO: 12), a FH CCP5 domain (SEQ ID NO: 13), a FH CCP6 domain (SEQ ID NO: 14) and/or a FH CCP7 domain (SEQ ID NO: 15).

3. The complement regulator protein as claimed in claim 1, wherein the at least one FH fragment comprises a FH CCP1 domain (SEQ ID NO: 9), a FH CCP2 domain (SEQ ID NO: 10), a FH CCP3 domain (SEQ ID NO: 11) and a FH CCP4 domain (SEQ ID NO: 12) or the least one FH fragment comprises a FH CCP1 domain (SEQ ID NO: 9), a FH CCP2 domain (SEQ ID NO: 10), a FH CCP3 domain (SEQ ID NO: 11), a FH CCP4 domain (SEQ ID NO: 12) and a FH CCP5 domain (SEQ ID NO:13).

4. The complement regulator protein as claimed in claim 1, wherein the dimerization region comprises FHR1 CCP1 domain (SEQ ID NO: 24), and a FHR1 CCP2 domain (SEQ ID NO: 25).

5. The complement regulator protein as claimed in claim 1, wherein the dimerization region comprises a FHR1 CCP1 domain (SEQ ID NO: 24) and a FHR1 CCP2 domain (SEQ ID NO: 25).

6. The complement regulator protein as claimed in claim 1, wherein the at least one FH CCP domain and/or further FH CCP domain are human FH.

7. The complement regulator protein as claimed in claim 4, wherein the at least one further FH CCP domain comprises one or more of a FH CCP18 domain (SEQ ID NO: 16) and/or a FH CCP19 domain (SEQ ID NO: 17) and/or a FH CCP20 domain (SEQ ID NO: 18).

8. The complement regulator protein as claimed in 1, wherein the at least one complement interaction region further comprises at least one Factor H Related protein (FHR) fragment operable to bind the complement regulator protein to the at least one target and/or at least one further target, wherein the at least one FHR fragment comprises at least one FHR5 CCP domain.

9. The complement regulator protein as claimed in claim 5, wherein the at least one FHR5 CCP domain comprises one or more of a FHR5 CCP7 domain (SEQ ID NO: 19), a FHR5 CCP8 domain (SEQ ID NO: 20), and/or a FHR5 CCP9 domain (SEQ ID NO: 21).

10. The complement regulator protein as claimed in claim 5, wherein the at least one FHR fragment of the complement interaction region and/or the at least one FHR CCP domain of the dimerization region are each one or more human FHRs.

11. The complement regulator protein as claimed in claim 1 wherein the at least one complement interaction region further comprises at least one complement Factor H-Like protein (FHL) fragment operable to bind the complement regulator protein to the at least one target and/or at least one further target wherein the at least one FHL-1 CCP domain comprises one or more of a FHL-1 CCP6 domain (SEQ ID NO: 22) and/or a FHL-1 CCP7 domain (SEQ ID NO: 23).

12. The complement regulator protein as claimed in claim 1, further comprising at least one linker molecule.

13. The complement regulator protein as claimed in claim 12, wherein the at least one linker and/or further linker molecules are independently selected from one or more linker molecules comprising: an amino acid sequence as set forth in SEQ ID NO: 30; an amino acid sequence as set forth in SEQ ID NO: 31; an amino acid sequence as set forth in SEQ ID NO: 32; an amino acid sequence as set forth in SEQ ID NO: 33; Glycine and Threonine (GT); Valine and Aspartic acid (VD); and/or Valine, Aspartic acid and Threonine (VDT).

14. The complement regulator protein as claimed in claim 1, comprising from N-terminal to C-terminal, a FH CCP1 domain (SEQ ID NO: 9), a FH CCP2 domain (SEQ ID NO: 10), a FH CCP3 domain (SEQ ID NO: 11), a FH CCP4 domain (SEQ ID NO: 12), a FH CCP5 domain (SEQ ID NO: 13), optionally at least one linker molecule, a FH CCP18 domain (SEQ ID NO: 16), a FH CCP19 domain (SEQ ID NO: 17), a FH CCP20 domain (SEQ ID NO: 18), optionally at least one linker molecule, a FHR1 CCP1 domain (SEQ ID NO: 24) and a FHR1 CCP2 domain (SEQ ID NO: 25).

15. The complement regulator protein as claimed in claim 1, comprising an amino acid sequence, which has at least 80% sequence identity to the amino acid sequence as set forth in SEQ ID NO: 26.

16. The complement regulator protein as claimed in claim 1, comprising from N-terminal to C-terminal, a FHR1 CCP1 domain (SEQ ID NO: 24), a FHR1 CCP2 domain (SEQ ID NO: 25), optionally at least one linker molecule, a FH CCP1 domain (SEQ ID NO: 9), a FH CCP2 domain (SEQ ID NO: 10), a FH CCP3 domain (SEQ ID NO: 11), a FH CCP4 domain (SEQ ID NO: 12), a FH CCP5 domain (SEQ ID NO: 13), optionally at least one linker molecule, a FH CCP18 domain (SEQ ID NO: 16), a FH CCP19 domain (SEQ ID NO: 17) and a FH CCP20 domain (SEQ ID NO: 18).

17. The complement regulator protein as claimed in claim 1, comprising an amino acid sequence which has at least 80% sequence identity to the amino acid sequence as set forth in SEQ ID NO: 27.

18. The complement regulator protein as claimed in claim 1, comprising from N-terminal to C-terminal, a FH CCP1 domain (SEQ ID NO: 9), a FH CCP2 domain (SEQ ID NO: 10), a FH CCP3 domain (SEQ ID NO: 11), a FH CCP4 domain (SEQ ID NO: 12), a FH CCP5 domain (SEQ ID NO:13), optionally at least one linker molecule, a FHL-1 CCP6 domain (SEQ ID NO: 22), a FHL-1 CCP7 domain (SEQ ID NO: 23), optionally at least one linker molecule, a FHR1 CCP1 domain (SEQ ID NO: 24) and a FHR1 CCP2 domain (SEQ ID NO: 25).

19. The complement regulator protein as claimed in claim 1, comprising an amino acid sequence which has at least 80% sequence identity to the amino acid sequence as set forth in SEQ ID NO: 28.

20. The complement regulator protein as claimed in claim 1, comprising from N-terminal to C-terminal, a FHR1 CCP1 domain (SEQ ID NO: 24), a FHR1 CCP2 domain (SEQ ID NO: 25), optionally at least one linker molecule, a FH CCP1 domain (SEQ ID NO: 9), a FH CCP2 domain (SEQ ID NO: 10), a FH CCP3 domain (SEQ ID NO: 11), a FH CCP4 domain (SEQ ID NO: 12), a FH CCP5 domain (SEQ ID NO: 13), optionally at least one linker molecule, a FHL-1 CCP6 domain (SEQ ID NO: 22) and a FHL-1 CCP7 domain (SEQ ID NO: 23).

21. The complement regulator protein as claimed in claim 1, comprising an amino acid sequence which has at least 80% sequence identity to the amino acid sequence as set forth in SEQ ID NO: 29.

22. A complement regulator protein, comprising the general formula:

$$X_1\text{-}L1\text{-}X_2\text{-}L2\text{-}Y_1 \quad \text{Formula I}$$

wherein:
  $X_1$ is a molecule selected from a molecule comprising:
    FH CCP domains 1 (SEQ ID NO: 9), 2 (SEQ ID NO: 10), 3 (SEQ ID NO: 11) and 4 (SEQ ID NO: 12); FH CCP domains 1 (SEQ ID NO: 9), 2 (SEQ ID NO: 10), 3 (SEQ ID NO: 11), 4 (SEQ ID NO: 12) and 5 (SEQ ID NO: 13); FH CCP domains 1 (SEQ ID NO: 9), 2 (SEQ ID NO: 10), 3 (SEQ ID NO: 11), 4 (SEQ ID NO: 12), and 7 (SEQ ID NO: 15); or FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15);
  $L_1$ is at least one linker molecule or is absent;
  $X_2$ is a molecule selected from a molecule comprising:
    FH CCP domains 18 (SEQ ID NO: 16), 19 (SEQ ID NO: 17) and 20 (SEQ ID NO: 18); FH CCP domain 19 (SEQ ID NO: 17) and 20 (SEQ ID NO: 18); FHL-1 CCP domains 6 (SEQ ID NO: 22) and 7 (SEQ ID NO: 23); FHR5 CCP domains 7 (SEQ ID NO: 19), 8 (SEQ ID NO: 20) and 9 (SEQ ID NO: 21); FHR5 CCP domains 8 (SEQ ID NO: 20) and 9 (SEQ ID NO: 21); or is absent;
  $L_2$ is at least one linker molecule or is absent; and
  $Y_1$ is a molecule selected from a molecule comprising:
    FHR1 CCP domains 1 (SEQ ID NO: 24) and 2 (SEQ ID NO: 25).

23. A complement regulator protein comprising the general formula:

$$Y_1\text{-}L_2\text{-}X_1\text{-}L_1\text{-}X_2 \quad \text{Formula II}$$

wherein:
  $X_1$ is a molecule selected from a molecule comprising:
    FH CCP domains 1 (SEQ ID NO: 9), 2 (SEQ ID NO: 10), 3 (SEQ ID NO: 11) and 4 (SEQ ID NO: 12); FH CCP domains 1 (SEQ ID NO: 9), 2 (SEQ ID NO: 10), 3 (SEQ ID NO: 11), 4 (SEQ ID NO: 12) and 5 (SEQ ID NO: 13); FH CCP domains 1 (SEQ ID NO: 9), 2 (SEQ ID NO: 10), 3 (SEQ ID NO: 11), 4 (SEQ ID NO: 12), and 7 (SEQ ID NO: 15); or FH CCP domains 1 (SEQ ID NO: 9), 2 (SEQ ID NO: 10), 3 (SEQ ID NO: 11), 4 (SEQ ID NO: 12), 5 (SEQ ID NO: 13) and 7 (SEQ ID NO: 15);
  $L_1$ is at least one linker molecule or is absent;
  $X_2$ is a molecule selected from a molecule comprising:
    FH CCP domains 18 (SEQ ID NO: 16), 19 (SEQ ID NO: 17) and 20 (SEQ ID NO: 18); FH CCP domain 19 (SEQ ID NO: 17) and 20 (SEQ ID NO: 18); FHL-1 CCP domains 6 (SEQ ID NO: 22) and 7 (SEQ ID NO: 23); FHR5 CCP domains 7 (SEQ ID NO: 19), 8 (SEQ ID NO: 20) and 9 (SEQ ID NO: 21); FHR5 CCP domains 8 (SEQ ID NO: 20) and 9 (SEQ ID NO: 21); or is absent;
  $L_2$ is at least one linker molecule or is absent; and
  $Y_1$ is a molecule selected from a molecule comprising:
    FHR1 CCP domains 1 (SEQ ID NO: 24) and 2 (SEQ ID NO: 25).

24. A method of inhibiting complement activation on the surface of a cell, tissue or organ ex vivo, the method comprising administering a complement regulator protein according to claim 1 to the cell, tissue or organ ex vivo.

25. A nucleic acid molecule encoding the recombinant complement regulator protein of claim 1.

26. A nucleic acid molecule encoding a protein having at least 80% sequence identity to the amino acid sequence as set forth in SEQ ID NO: 26, 27, 28 or 29, 46, 47, 48 or 49.

* * * * *